US012661404B2

(12) United States Patent
Oklu et al.

(10) Patent No.: US 12,661,404 B2
(45) Date of Patent: Jun. 23, 2026

(54) METHODS AND MATERIALS FOR TISSUE ABLATION

(71) Applicants:Mayo Foundation for Medical Education and Research, Rochester, MN (US); President and Fellows of Harvard College, Cambridge, MA (US)

(72) Inventors: Rahmi Oklu, Chandler, AZ (US); Hassan Albadawi, Tempe, AZ (US); Samir Mitragotri, Lexington, MA (US)

(73) Assignees: Mayo Foundation for Medical Education and Research, Rochester, MN (US); President and Fellows of Harvard College, Cambridge, MA (US)

( * ) Notice: Subject to any disclaimer, the term of this patent is extended or adjusted under 35 U.S.C. 154(b) by 493 days.

(21) Appl. No.: 18/021,249

(22) PCT Filed: Aug. 16, 2021

(86) PCT No.: PCT/US2021/046109
§ 371 (c)(1),
(2) Date: Feb. 14, 2023

(87) PCT Pub. No.: WO2022/036309
PCT Pub. Date: Feb. 17, 2022

(65) Prior Publication Data
US 2023/0338537 A1 Oct. 26, 2023

Related U.S. Application Data

(60) Provisional application No. 63/066,024, filed on Aug. 14, 2020.

(51) Int. Cl.
*A61K 41/00* (2020.01)
*A61K 9/00* (2006.01)
(Continued)

(52) U.S. Cl.
CPC ........ *A61K 41/0052* (2013.01); *A61K 9/0019* (2013.01); *A61K 9/0024* (2013.01);
(Continued)

(58) Field of Classification Search
CPC .............. A61K 41/0052; A61K 9/0019; A61K 9/0024; A61K 31/201; A61K 31/704; A61K 47/02; A61K 49/0034; A61P 35/00
See application file for complete search history.

(56) References Cited

U.S. PATENT DOCUMENTS 5,614,204 A 3/1997 Cochrum
8,029,560 B2 10/2011 Bates et al.
(Continued)

FOREIGN PATENT DOCUMENTS

CN 109562137 4/2019
CN 111012947 * 4/2020 ............. A61L 27/16
(Continued)

OTHER PUBLICATIONS

McWilliams et al, Image-Guided Tumor Ablation: Emerging Technologies and Future Directions, 2010, Seminars in Interventional Radiology, vol. 27, No. 3, p. 302-313. (Year: 2010).*
(Continued)

*Primary Examiner* — Trevor Love
(74) *Attorney, Agent, or Firm* — PROCOPIO, CORY, HARGREAVES & SAVITCH LLP

(57) ABSTRACT

This document relates to methods and materials for tissue ablation. For example, methods for using a composition including one or more ionic liquids (e.g., a composition including a LATTE solution) for tissue ablation are provided. In some cases, a composition including one or more ionic liquids (e.g., a composition including a LATTE solution) can be used to ablate tumor tissue within a mammal having cancer (e.g., to treat the mammal).

20 Claims, 87 Drawing Sheets

(51) Int. Cl.

| | |
|---|---|
| *A61K 31/201* | (2006.01) |
| *A61K 31/704* | (2006.01) |
| *A61K 47/02* | (2006.01) |
| *A61K 49/00* | (2006.01) |
| *A61P 35/00* | (2006.01) |

(52) U.S. Cl.
CPC .......... *A61K 31/201* (2013.01); *A61K 31/704* (2013.01); *A61K 47/02* (2013.01); *A61K 49/0034* (2013.01); *A61P 35/00* (2018.01)

(56) References Cited

U.S. PATENT DOCUMENTS

| | | |
|---|---|---|
| 10,449,254 B2 | 10/2019 | Zakrewsky et al. |
| 2012/0039884 A1 | 2/2012 | Watson et al. |
| 2016/0030635 A1 | 2/2016 | Bhatia et al. |
| 2016/0144068 A1 | 5/2016 | Gaharwar et al. |
| 2018/0071446 A1 | 3/2018 | Yeh et al. |
| 2018/0093011 A1 | 4/2018 | Kellar et al. |
| 2019/0089124 A1 | 3/2019 | Bhatia et al. |
| 2019/0367884 A1 | 12/2019 | Satchi-Fainaro et al. |
| 2020/0390804 A1 | 12/2020 | Abdulijauwad et al. |
| 2023/0190648 A1 | 6/2023 | Oklu et al. |
| 2023/0321316 A1 | 10/2023 | Oklu et al. |
| 2023/0338537 A1 | 10/2023 | Oklu et al. |

FOREIGN PATENT DOCUMENTS

| | | |
|---|---|---|
| CN | 111246883 | 6/2020 |
| EP | 4196574 A2 | 6/2023 |
| WO | WO 1998/03203 | 1/1998 |
| WO | WO 2002/040501 | 5/2002 |
| WO | WO 2012/021860 | 2/2012 |
| WO | WO 2014/205261 | 12/2014 |
| WO | WO 2015/066647 | 5/2015 |
| WO | WO 2017/040864 | 3/2017 |
| WO | WO 2017/069822 | 4/2017 |
| WO | WO 2019/032431 | 2/2019 |
| WO | WO 2019/099837 | 5/2019 |
| WO | WO 2022/036309 | 2/2022 |

OTHER PUBLICATIONS

Partial Supplementary European Search Report in European Appln. No. 21856850.9, dated Aug. 13, 2024, 13 pages.

Torrecilla et al., "Estimation of toxicity of ionic liquids in Leukemia Rat Cell Line and Acetylcholinesterase enzyme by principal component analysis, neural networks and multiple lineal regressions," J. Hazard. Mater., May 2009, 164(1):182-194.

Bakhtiari et al., "PO323-TUE: Composition-dependent effects of nanoparticles on coagulation," Abstract, XXV Congress of the International Society on Thrombosis and Haemostasis, Jun. 2015, Toronto, Canada. Journal of Thrombosis and Haemostasis, 13(Suppl. 2):625.

De Almeida Barros Mourao et al., "Usefulness of platelet-rich fibrin as a hemostatic agent after dental extractions in patients receiving anticoagulant therapy with factor Xa inhibitors: a case series," Oral Maxillofac. Surg., Sep. 2019, 23(3):381-386.

Long et al., "Emerging Nanoclay Composite for Effective Hemostasis," Adv. Funct. Mater., Mar. 2018, 28(10):1704452.

Naik et al., "Role of Platelet rich fibrin in wound healing: A critical review," J. Conserv. Dent., Jul. 2013, 16(4):284-293.

Sammartino et al., "Prevention of hemorrhagic complications after dental extractions into open heart surgery patients under anticoagulant therapy: the use of leukocyte- and platelet-rich fibrin," J. Oral Implantol., Dec. 2011, 37(6):681-690.

Shang et al., "Zeolite-fibrin clot composite as a haemostatic agent for haemophilia A," J. Biomater. Appl., May 2019, 33(10):1427-1433 (Abstract Only).

Afewerki et al., "Gelatin-polysaccharide composite scaffolds for 3D cell culture and tissue engineering: Towards natural therapeutics," Bioeng. Transl. Med., Dec. 2018, 4(1):96-115.

Ajwani et al., "Comparative evaluation of platelet-rich fibrin biomaterial and open flap debridement in the treatment of two and three wall intrabony defects," J. Int. Oral Health, Apr. 2015, 7(4):32-37.

Albadawi et al., "Percutaneous liquid ablation agent for tumor treatment and drug delivery," Sci. Transl. Med., Feb. 2021, 13(580):eabe3889, 12 pages.

Altun et al., "Blood-Derived Biomaterial for Catheter-Directed Arterial Embolization," Adv. Mater., Dec. 2020, 32(52):e2005603.

Anderson et al., "Foreign body reaction to biomaterials," Semin. Immunol., Apr. 2008, 20(2):86-100.

Avery et al., "An injectable shear-thinning biomaterial for endovascular embolization," Sci. Transl. Med., Nov. 2016, 8(365):365ra156, 12 pages.

Bakshi et al., "Imidazolium-based ionic liquids cause mammalian cell death due to modulated structures and dynamics of cellular membrane," Biochim Biophys Acta Biomembr, Feb. 2020, 1862(2):183103.

Banerjee et al., "Ionic liquids for oral insulin delivery," Proc. Natl. Acad. Sci. U.S.A., Jul. 2018, 115(28):7296-7301.

Banerjee et al., "Transdermal Protein Delivery Using Choline and Geranate (CAGE) Deep Eutectic Solvent," Adv. Healthc. Mater., Aug. 2017, 6(15):1601411.

Bejleri et al., "Decellularized Extracellular Matrix Materials for Cardiac Repair and Regeneration," Adv. Healthc. Mater., Mar. 2019, 8(5):e1801217.

Bhattacharya et al., "Structural changes in cellular membranes induced by ionic liquids: From model to bacterial membranes," Chem. Phys. Lipids, Sep. 2018, 215:1-10.

Bracaglia et al., "Extracellular Matrix-Based Biohybrid Materials for Engineering Compliant, Matrix-Dense Tissues," Adv. Healthc. Mater., Nov. 2015, 4(16):2475-2487.

Bray et al., "Global cancer statistics 2018: GLOBOCAN estimates of incidence and mortality worldwide for 36 cancers in 185 countries," CA Cancer J. Clin., Nov. 2018, 68(6):394-424.

Bridges et al., "Chronic inflammatory responses to microgel-based implant coatings," J. Biomed. Mater. Res. A., Jul. 2010, 94(1):252-258.

Bruix et al., "Hepatocellular carcinoma: clinical frontiers and perspectives," Gut, May 2014, 63(5):844-855.

Bruix et al., "Insights into the success and failure of systemic therapy for hepatocellular carcinoma," Nat Rev Gastroenterol Hepatol, Oct. 2019, 16(10):617-630.

Bruix et al., "Management of hepatocellular carcinoma: an update," Hepatology, Mar. 2011, 53(3):1020-1022.

Brunel et al., "Polyamino geranic derivatives as new chemosensitizers to combat antibiotic resistant gram-negative bacteria," Bioorg. Med. Chem., Mar. 2013, 21(5):1174-1179.

Buell et al., "Optimizing the management of aneurysmal subarachnoid hemorrhage: Lessons learned and future directions," J Neurosci Rural Pract, Apr. 2014, 5(2):109-110.

Byrne et al., "Loco-regional therapies for patients with hepatocellular carcinoma awaiting liver transplantation: Selecting an optimal therapy," World J. Transplant., Jun. 2016, 6(2):306-313.

Castro et al., "Antimicrobial capacity of Leucocyte-and Platelet Rich Fibrin against periodontal pathogens," Sci. Rep., Jun. 2019, 9(1):8188.

Cescon et al., "Hepatocellular carcinoma locoregional therapies for patients in the waiting list. Impact on transplantability and recurrence rate," J. Hepatol., Mar. 2013, 58(3):609-618.

Chen et al., "Adipose-derived mesenchymal stem cells embedded in platelet-rich fibrin scaffolds promote angiogenesis, preserve heart function, and reduce left ventricular remodeling in rat acute myocardial infarction," Am. J. Transl. Res., May 2015, 7(5):781-803.

Chen et al., "Induction of VX2 carcinoma in rabbit liver: comparison of two inoculation methods, " Lab. Anim., Jan. 2004, 38(1):79-84.

Choi, "Inhibitory effects of geranic acid derivatives on melanin biosynthesis," J. Cosmet. Sci., Nov.-Dec. 2012, 63(6):351-358.

Choukroun et al., "Platelet-rich fibrin (PRF): a second-generation platelet concentrate. Part IV: clinical effects on tissue healing," Oral Surg Oral Med Oral Pathol Oral Radiol Endod, Mar. 2006, 101(3):e56-e60.

(56)     References Cited

OTHER PUBLICATIONS

Chuang et al., "Complications of coil embolization: prevention and management," AJR Am. J. Roentgenol., Oct. 1981, 137(4):809-813.

Clark, "Chemical ablation of liver cancer," Tech Vasc Interv Radiol, Mar. 2007, 10(1):58-63.

Couri et al., "Goals and targets for personalized therapy for HCC," Hepatol. Int., Mar. 2019, 13(2):125-137.

Delwatta et al., "Reference values for selected hematological, biochemical and physiological parameters of Sprague-Dawley rats at the Animal House, Faculty of Medicine, University of Colombo, Sri Lanka," Animal Model Exp Med, Nov. 2018, 1(4):250-254.

Desai et al., "Use of Platelet-Rich Fibrin over Skin Wounds: Modified Secondary Intention Healing," J Cutan Aesthet Surg, Jan. 2013, 6(1):35-37.

Dewhirst et al., "Transport of drugs from blood vessels to tumour tissue," Nat. Rev. Cancer, Dec. 2017, 17(12):738-750.

Di Veroli et al., "Combenefit: an interactive platform for the analysis and visualization of drug combinations," Bioinformatics, Sep. 2016, 32(18):2866-2868.

Dohan et al., "Platelet-rich fibrin (PRF): a second-generation platelet concentrate. Part I: technological concepts and evolution," Oral Surg Oral Med Oral Pathol Oral Radiol Endod, Mar. 2006, 101(3):e37-e44.

Dohan et al., "Platelet-rich fibrin (PRF): a second-generation platelet concentrate. Part II: platelet-related biologic features," Oral Surg Oral Med Oral Pathol Oral Radiol Endod, Mar. 2006, 101(3):e45-e50.

Dohan et al., "Platelet-rich fibrin (PRF): a second-generation platelet concentrate. Part III: leucocyte activation: a new feature for platelet concentrates?" Mar. 2006, 101(3):e51-e55.

El Hassouni et al., "To Combine or Not Combine: Drug Interactions and Tools for Their Analysis. Reflections from the EORTC-PAMM Course on Preclinical and Early-phase Clinical Pharmacology," Anticancer Res., Jul. 2019, 39(7):3303-3309.

Erezuma et al., "Nanoclay Reinforced Biomaterials for Mending Musculoskeletal Tissue Disorders," Adv. Healthc. Mater., Aug. 2021, 10(16):e2100217.

Extended European Search Report in European Appln. No. 21804674. 6, dated Oct. 18, 2023, 8 pages.

Faulk et al., "Decellularization and cell seeding of whole liver biologic scaffolds composed of extracellular matrix," J. Clin. Exp. Hepatol., Mar. 2015, 5(1):69-80.

Faustino-Rocha et al., "Estimation of rat mammary tumor vol. using caliper and ultrasonography measurements," Lab. Anim. (NY), Jun. 2013, 42(6):217-224.

Finn et al., "Pembrolizumab As Second-Line Therapy in Patients With Advanced Hepatocellular Carcinoma in Keynote-240: A Randomized, Double-Blind, Phase III Trial," J. Clin. Oncol., Jan. 2020, 38(3):193-202.

Forner et al., "Controversies in the management of hepatocellular carcinoma," JHEP Rep., Mar. 2019, 1(1):17-29.

Forner et al., "Hepatocellular carcinoma," Lancet, Mar. 2018, 391(10127):1301-1314.

Frantz et al., "The extracellular matrix at a glance," J. Cell. Sci., Dec. 2010, 123(24):4195-4200.

Gaharwar et al., "2D Nanoclay for Biomedical Applications: Regenerative Medicine, Therapeutic Delivery, and Additive Manufacturing," Adv. Mater., Jun. 2019, 31(23):e1900332.

Gaharwar et al., "Shear-thinning nanocomposite hydrogels for the treatment of hemorrhage," ACS Nano., Oct. 2014, 8(10):9833-9842.

Ghanaati et al., "Advanced platelet-rich fibrin: a new concept for cell-based tissue engineering by means of inflammatory cells," J. Oral Implantol., Dec. 2014, 40(6):679-689.

Gharaie et al., "Smart Shear-Thinning Hydrogels as Injectable Drug Delivery Systems," Polymers, Nov. 2018, 10(12):1317, 15 pages.

Gilpin et al., "Decellularization Strategies for Regenerative Medicine: From Processing Techniques to Applications," Biomed. Res. Int., 2017, 2017:9831534, 14 pages.

Gomez-Florit et al., "Natural-Based Hydrogels for Tissue Engineering Applications," Molecules, Dec. 2020, 25(24):5858, 29 pages.

Grandhi et al., "Hepatocellular carcinoma: From diagnosis to treatment," Surg. Oncol., Jun. 2016, 25(2):74-85.

Guo et al., "Highly malignant intra-hepatic metastatic hepatocellular carcinoma in rats," Am. J. Transl. Res., Nov. 2010, 3(1):114-120.

Hamid et al., "Intratumoral Immunotherapy—Update 2019," Oncologist, Mar. 2020, 25(3):e423-e438.

Han et al., "Mussel-inspired cryogels for promoting wound regeneration through photobiostimulation, modulating inflammatory responses and suppressing bacterial invasion," Nanoscale, Aug. 2019, 11(34):15846-15861.

Hasegawa et al., "Factors that predict intrahepatic recurrence of hepatocellular carcinoma in 81 patients initially treated by percutaneous ethanol injection," Cancer, Nov. 1999, 86(9):1682-1690.

Henderson et al., "AHPBA/AJCC consensus conference on staging of hepatocellular carcinoma: consensus statement," HPB (Oxford), 2003, 5(4):243-250.

Hickman et al., "Biomaterials and Advanced Technologies for Hemostatic Management of Bleeding," Adv. Mater., Jan. 2018, 30(4):10.1002/adma.201700859.

Hu et al., "Advances in Biomaterials and Technologies for Vascular Embolization," Adv. Mater., Aug. 2019, 31:e1901071, 52 pages.

Hu et al., "Bioactive-Tissue-Derived Nanocomposite Hydrogel for Permanent Arterial Embolization and Enhanced Vascular Healing," Adv. Mater., Jun. 2020, 32(33):e2002611, 13 pages.

Huleihel et al., "Macrophage phenotype in response to ECM bioscaffolds," Semin. Immunol., Feb. 2017, 29:2-13.

Ibsen et al., "Mechanism of Antibacterial Activity of Choline-Based Ionic Liquids (CAGE)," ACS Biomater. Sci. Eng., Jul. 2018, 4(7):2370-2379.

Idee et al., "Use of Lipiodol as a drug-delivery system for transcatheter arterial chemoembolization of hepatocellular carcinoma: a review," Crit. Rev. Oncol. Hematol., Dec. 2013, 88(3):530-549.

International Organization for Standardization, "Biological evaluation of medical devices—Part 5: Tests for in vitro cytotoxicity," ISO 10993-5, Jun. 2009, 42 pages.

International Preliminary Report on Patentability in International Appln. No. PCT/US2021/032772, mailed on Nov. 24, 2022, 10 pages.

International Preliminary Report on Patentability in International Appln. No. PCT/US2021/046109, mailed on Feb. 23, 2023, 10 pages.

International Search Report and Written Opinion in International Appln. No. PCT/US2021/032772, mailed on Oct. 14, 2021, 14 pages.

International Search Report and Written Opinion in International Appln. No. PCT/US2021/046109, mailed on Feb. 18, 2022, 15 pages.

Jain et al., "Role of platelet-rich-fibrin in enhancing palatal wound healing after free graft," Contemp Clin Dent, Sep. 2012 Sep, 3(Suppl. 2):S240-S243.

Jemal et al., "Global cancer statistics," CA Cancer J. Clin., Mar.-Apr. 2011, 61(2):69-90.

Jensen et al., "A dual-functional Embolization-Visualization System for Fluorescence image-guided Tumor Resection," Theranostics, Mar. 2020, 10(10):4530-4543.

Johnson et al., "Tailoring material properties of a nanofibrous extracellular matrix derived hydrogel," Nanotechnology, Dec. 2012, 22(49):494015.

Jouanneteau et al., "[Action of homologues of geranic and farnesic acids on the biogenesis of cholesterol in the rat]," C. R. Hebd. Seances Acad. Sci., Feb. 1961, 252:1380-1382, Considered to the extent in English (i.e. only Title).

Keane et al., "Scarring vs. functional healing: Matrix-based strategies to regulate tissue repair," Adv. Drug Deliv. Rev., Apr. 2018, 129:407-419.

Khan et al., "Prospective analysis of risk factors for early intrahepatic recurrence of hepatocellular carcinoma following ethanol injection," J. Hepatol., Feb. 2000, 32(2):269-278.

(56)        References Cited

OTHER PUBLICATIONS

Kirstein et al., "[Multimodal treatment of hepatocellular carcinoma]," Internist. (Berl)., Feb. 2020, 61(2):164-169 (with English Abstract).

Koda et al., "Predictive factors for intrahepatic recurrence after percutaneous ethanol injection therapy for small hepatocellular carcinoma," Cancer, Feb. 2000, 88(3):529-537.

Korga et al., "Inhibition of glycolysis disrupts cellular antioxidant defense and sensitizes HepG2 cells to doxorubicin treatment," FEBS Open Bio., May 2019, 9(5):959-972.

Kumari et al., "Sub-Toxic Concentrations of Ionic Liquids Enhance Cell Migration by Reducing the Elasticity of the Cellular Lipid Membrane," J Phys Chem Lett, Sep. 2020, 11(17):7327-7333.

Kwon, "Is percutaneous ethanol injection therapy still effective for hepatocellular carcinoma in the era of radiofrequency ablation?" Gut Liver, Sep. 2004, 4(Suppl. 1):S105-S112.

Lam et al., "Optimizing cell encapsulation condition in ECM-Collagen I hydrogels to support 3D neuronal cultures," J. Neurosci. Methods, Jan. 2020, 329: 108460, 8 pages.

Landen et al., "Transition from inflammation to proliferation: a critical step during wound healing," Cell Mol. Life Sci., Oct. 2016, 73(20):3861-3885.

Lang et al., "[3-dimensional sonography for volume determination of liver tumors—report of initial experiences]," Chirurg, March 1999, 70(3):246-250 (with English Abstract).

Lee et al., "Thermal Injury-induced Hepatic Parenchymal Hypoperfusion: Risk of Hepatocellular Carcinoma Recurrence after Radiofrequency Ablation," Radiology, Mar. 2017, 282(3):880-891.

Lencioni et al., "Lipiodol transarterial chemoembolization for hepatocellular carcinoma: A systematic review of efficacy and safety data," Hepatology, Jul. 2016, 64(1):106-116.

Lencioni, "Loco-regional treatment of hepatocellular carcinoma," Hepatology, Aug. 2010, 52(2):762-773.

Lin et al., "Local injection therapy for hepatocellular carcinoma," Hepatobiliary Pancreat Dis Int, Feb. 2006, 5(1):16-21.

Liu et al., "Injectable hydrogels for cartilage and bone tissue engineering," Bone Res., May 2017, 5:17014, 20 pages.

Liu et al., "Nanoparticle contrast-enhanced micro-CT: A preclinical tool for the 3D imaging of liver and spleen in longitudinal mouse studies," J. Pharmacol. Toxicol. Methods, Mar.-Apr. 2019, 96:67-77.

Liu et al., "Weaving of organic threads into a crystalline covalent organic framework," Science, Jan. 2016, 351(6271):365-369.

Llovet et al., "Hepatocellular carcinoma," Nat. Rev. Dis. Primers, Jan. 2021, 7(1):6.

Lubarsky et al., "Embolization agents-which one should be used when? Part 1: large-vessel embolization," Semin. Intervent. Radiol., Dec. 2009, 26(4):352-357.

Lundquist et al., "Bioactivity and stability of endogenous fibrogenic factors in platelet-rich fibrin," Wound Repair Regen, May-Jun. 2008, 16(3):356-363.

Lusic et al., "X-ray-computed tomography contrast agents," Chem. Rev., Mar. 2013, 113(3):1641-1666.

Mane et al., "Validation of immunoexpression of tenascin-C in oral precancerous and cancerous tissues using ImageJ analysis with novel immunohistochemistry profiler plugin: An immunohistochemical quantitative analysis," J Oral Maxillofac Pathol, May-Aug. 2017, 21(2): 211-217.

Marchand et al., "Extracellular matrix scaffolding in angiogenesis and capillary homeostasis"; Semin. Cell Dev. Biol., May 2019, 89:147-156.

Mattiuzzi et al., "Current Cancer Epidemiology," J. Epidemiol. Glob. Health, Dec. 2019, 9(4):217-222.

Mazzaferro et al., "Liver transplantation for the treatment of small hepatocellular carcinomas in patients with cirrhosis," N. Engl. J. Med., Mar. 1996, 334(11):693-699.

Mikhail et al., "Mapping Drug Dose Distribution on CT Images Following Transarterial Chemoembolization with Radiopaque Drug-Eluting Beads in a Rabbit Tumor Model, " Radiology, Nov. 2018, 289(2):396-404.

Minchinton et al., "Drug penetration in solid tumours," Nat. Rev. Cancer, Aug. 2006, 6(8):583-592.

Miron et al., "Injectable platelet rich fibrin (i-PRF): opportunities in regenerative dentistry?" Clin Oral Investig, Nov. 2017, 21(8):2619-2627.

Miron et al., "Platelet-Rich Fibrin and Soft Tissue Wound Healing: A Systematic Review," Tissue Eng Part B Rev, Feb. 2017, 23(1):83-99.

Mitra et al., "Surface Activities of a Lipid Analogue Room-Temperature Ionic Liquid and Its Effects on Phospholipid Membrane," Langmuir, Jan. 2020, 36(1):328-339.

Novikoff, "A transplantable rat liver tumor induced by 4-dimethylaminoazobenzene," Cancer Res., Nov. 1957, 17(10):1010-1027.

O'Connell et al., "Autologous platelet-rich fibrin matrix as cell therapy in the healing of chronic lower-extremity ulcers," Wound Repair Regen, Nov.-Dec. 2008, 16(6):749-756.

Peng et al., "Bioinspired, Artificial, Small-Diameter Vascular Grafts with Selective and Rapid Endothelialization Based on an Amniotic Membrane-Derived Hydrogel"; ACS Biomater. Sci. Eng., Mar. 2020, 6(3):1603-1613.

Petterino et al., "Clinical chemistry and haematology historical data in control Sprague-Dawley rats from pre-clinical toxicity studies," Exp Toxicol Pathol, Jan. 2006, 57(3):213-219.

Poursaid et al., "Polymeric materials for embolic and chemoembolic applications," J. Control Release, Oct. 2016, 240:414-433.

Qi et al., "Mechanistic study of transdermal delivery of macromolecules assisted by ionic liquids," J. Control. Release, Oct. 2019, 311-312:162-169.

Rawat et al., "Aspect ratio dependent cytotoxicity and antimicrobial properties of nanoclay," Appl. Biochem. Biotechnol., Oct. 2014, 174(3):936-944.

Reig et al., "Complete angiographic obliteration of intracranial AVMs with endovascular embolization: incomplete embolic nidal opacification is associated with AVM recurrence," J. Neurointerv. Surg., Sep. 2010, 2(3):202-207 (Abstract only).

Roy et al., "Platelet-rich fibrin matrix improves wound angiogenesis via inducing endothelial cell proliferation," Wound Repair Regen, Nov. 2011, 19(6):753-766.

Rujitanaroj et al., "Controlling fibrous capsule formation through long-term down-regulation of collagen type I (COL1A1) expression by nanofiber-mediated siRNA gene silencing," Acta. Biomater., Jan. 2013, 9(1):4513-4524.

Rungseevijitprapa et al., "Injectability of biodegradable in situ forming microparticle systems (ISM)," Eur. J. Pharm. Sci., Mar. 2009, 36(4-5):524-531.

Saldin et al., "Extracellular matrix hydrogels from decellularized tissues: Structure and function," Acta. Biomater., Feb. 2017, 49:1-15.

Sangro et al., "Diagnosis and management of toxicities of immune checkpoint inhibitors in hepatocellular carcinoma," J. Hepatol., Feb. 2020, 72(2):320-341.

Seer.Cancer.gov [online], "Cancer Stat Facts: Liver and Intrahepatic Bile Duct Cancer," available no later than Jun. 5, 2020, retrieved on Sep. 27, 2023, retrieved from URL<https://seer.cancer.gov/statfacts/html/livibd.html>, 3 pages.

Sheth et al., "Assessment of Image-Guided Intratumoral Delivery of Immunotherapeutics in Patients With Cancer," JAMA Netw. Open, Jul. 2020, 3(7):e207911, 9 pages.

Sheth et al., "Barriers to drug delivery in interventional oncology," J Vasc Interv Radiol, Aug. 2013, 24(8):1201-1207.

Sheth et al., "Role of Locoregional Therapy and Predictors for Dropout in Patients with Hepatocellular Carcinoma Listed for Liver Transplantation," J. Vasc. Interv. Radiol., Dec. 2015, 26(12):1761-1768.

Shin, "Recent update of embolization of upper gastrointestinal tract bleeding," Korean J. Radiol., Jan.-Feb. 2012, 13(Suppl 1):S31-S39.

Simon et al., "Relative cost comparison of embolic materials used for treatment of wide-necked intracranial aneurysms," J Neurointerv Surg, Jun. 2010, 2(2):163-167.

Singh et al., "Resveratrol and cancer: Challenges for clinical translation," Biochim. Biophys. Acta, Jun. 2015, 1852(6):1178-1185.

(56)　　　　References Cited

OTHER PUBLICATIONS

Sodhi et al., "The clinical profile, management, and overall outcome of aneurysmal subarachnoid hemorrhage at the neurosurgical unit of a tertiary care center in India," J Neurosci Rural Pract, Apr. 2014, 5(2):118-126.

Soyer et al., "Use of autologous platelet rich fibrin in urethracutaneous fistula repair: preliminary report," Int Wound J, Jun. 2013, 10(3):345-347.

Spada et al., "Hepatic intra-arterial chemotherapy in patients with advanced primary liver tumours," Ecancermedicalscience, 2012, 6:280, 12 pages.

Steenvoorde et al., "Use of autologous platelet-rich fibrin on hard-to-heal wounds," J. Wound Care, Feb. 2008, 17(2):60-63.

Strauss et al., "Effect of platelet-rich fibrin on cell proliferation, migration, differentiation, inflammation, and osteoclastogenesis: a systematic review of in vitro studies," Clin Oral Investig, Feb. 2020, 24(2):569-584.

Sun et al., "Direct implantation versus platelet-rich fibrin-embedded adipose-derived mesenchymal stem cells in treating rat acute myocardial infarction," Int. J. Cardiol., May 2014, 173(3):410-423.

Suzuki et al., "Gelatin gel as a carrier of platelet-derived growth factors," J. Biomater. Appl., Nov. 2013, 28(4):595-606.

Tanner et al., "Design Principles of Ionic Liquids for Transdermal Drug Delivery," Adv. Mater., Jul. 2019, 31(27):e1901103.

Tanner et al., "Transdermal insulin delivery using choline-based ionic liquids (CAGE)," J. Control. Release, Sep. 2018, 286:137-144.

Tarasconi et al., "Transcatheter arterial embolization versus surgery for refractory non-variceal upper gastrointestinal bleeding: a meta-analysis," World J. Emerg. Surg., Feb. 2019, 14:3.

Traverse et al., "First-in-Man Study of a Cardiac Extracellular Matrix Hydrogel in Early and Late Myocardial Infarction Patients," J. Am. Coll. Cardiol. Basic Trans. Science, Oct. 2019, 4(6):659-669.

Tummala et al., "Outcomes after aneurysm rupture during endovascular coil embolization," Neurosurgery, Nov. 2001, 49(5):1059-1066.

Uhlig et al., "Radiofrequency ablation versus surgical resection of hepatocellular carcinoma: contemporary treatment trends and outcomes from the United States National Cancer Database," Eur. Radiol., May 2019, 29(5):2679-2689.

Uquillas et al., "Modeling the electromobility of type-I collagen molecules in the electrochemical fabrication of dense and aligned tissue constructs," Ann. Biomed. Eng., Aug. 2012, 40(8):1641-1653.

Vaidya et al., "An overview of embolic agents," Semin. Intervent. Radiol., Sep. 2008, 25(3):204-215.

Vaidya et al., "Ionic liquid-mediated delivery of insulin to buccal mucosa," J. Control. Release, Nov. 2020, 327:26-34.

Varela et al., "Injectable platelet rich fibrin: cell content, morphological, and protein characterization," Clin Oral Investig, Mar. 2019, 23(3):1309-1318.

Varghese et al., "IHC Profiler: an open source plugin for the quantitative evaluation and automated scoring of immunohistochemistry images of human tissue samples," PLoS One, May 2014, 9(5):e96801.

Villalba-Rodriguez et al., "Nanoclay/Polymer-Based Hydrogels and Enzyme-Loaded Nanostructures for Wound Healing Applications," Gels, May 2021, 7(2):59.

Villanueva, "Hepatocellular Carcinoma," N. Engl. J. Med., Apr. 2019, 380(15):1450-1462.

Wang et al., "Effects of an injectable platelet-rich fibrin on osteoblast behavior and bone tissue formation in comparison to platelet-rich plasma," Platelets, Jan. 2018, 29(1):48-55.

Wang et al., "Emerging embolic agents in endovascular embolization: an overview," Prog. Biomed. Eng. (Bristol)., Sep. 2021, 2(1):012003, 20 pages.

Wolf et al., "A hydrogel derived from decellularized dermal extracellular matrix," Biomaterials, Oct. 2012, 33(29):7028-7038.

Wong et al., "Hepatocellular carcinoma: locoregional and targeted therapies," Gastroenterol. Clin. North Am., Sep. 2011, 40(3):599-610.

World Health Organization, "World Cancer Report 2014," Stewart et al. (ed)., 2014, 632 pages.

Xu, "Trends in Liver Cancer Mortality Among Adults Aged 25 and Over in the United States, 2000-2016," NCHS Data Brief, Jul. 2018, (314):1-8.

Yoo et al., "Molecular Mechanism of Ionic-Liquid-Induced Membrane Disruption: Morphological Changes to Bilayers, Multilayers, and Vesicles," Langmuir, May 2016, 32(21):5403-5411.

Yu et al., "Clinical Application of Platelet-Rich Fibrin in Plastic and Reconstructive Surgery: A Systematic Review," Aesthetic Plast Surg, Apr. 2018, 42(2):511-519.

Yu et al., "Label-Free Visualization of Early Cancer Hepatic Micrometastasis and Intraoperative Image-Guided Surgery by Photoacoustic Imaging," J. Nucl. Med., Jul. 2020, 61(7):1079-1085.

Zakrewsky et al., "Choline and Geranate Deep Eutectic Solvent as a Broad-Spectrum Antiseptic Agent for Preventive and Therapeutic Applications," Adv. Healthc. Mater., Jun. 2016, 5(11):1282-1289.

Zakrewsky et al., "Ionic liquids as a class of materials for transdermal delivery and pathogen neutralization," Proc. Natl. Acad. Sci. U.S.A., Aug. 2014, 111(37):13313-13318.

Zarrinpart et al., "Liver transplantation: past, present and future," Nat Rev Gastroenterol. Hepatol., Jul. 2013, 10(7):434-440.

Zhang et al., "Novel preparation of Au nanoparticles loaded Laponite nanoparticles/ECM injectable hydrogel on cardiac differentiation of resident cardiac stem cells to cardiomyocytes," J. Photochem. Photobiol. B., Mar. 2019, 192:49-54.

Zhang et al., "Radiopaque Highly Stiff and Tough Shape Memory Hydrogel Microcoils for Permanent Embolization of Arteries," Adv. Funct. Mater., Jan. 2018, 28(9):1705962.

Zhang et al., "Self-Adhesive Macroporous Carbon Electrodes for Efficient and Stable Perovskite Solar Cells," Adv. Funct. Mater., Aug. 2018, 28(39):1802985.

Zhou et al., "Novel Hydrogel Material as a Potential Embolic Agent in Embolization Treatments," Sci. Rep., Aug. 2016, 6:32145, 11 pages.

Zhu et al., "Endovascular Metal Devices for the Treatment of Cerebrovascular Diseases," Adv. Mater., Feb. 2019, 31(8):e1805452.

U.S. Appl. No. 17/925,520, filed Nov. 15, 2022, Rahmi Oklu, Published as U.S. Patent Application Publication No. 2023/0190648.

U.S. Appl. No. 18/044,357, filed Mar. 7, 2023, Rahmi Oklu, Published as U.S. Patent Application Publication No. 2023/0321316.

* cited by examiner

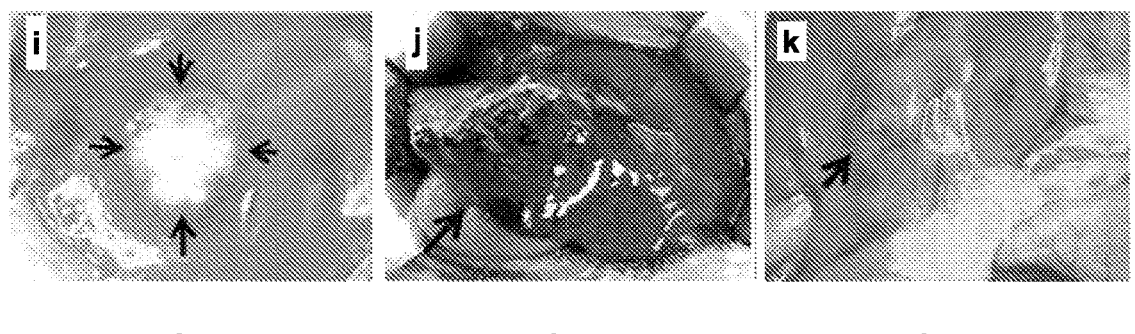
FIG. 1I          FIG. 1J          FIG. 1K
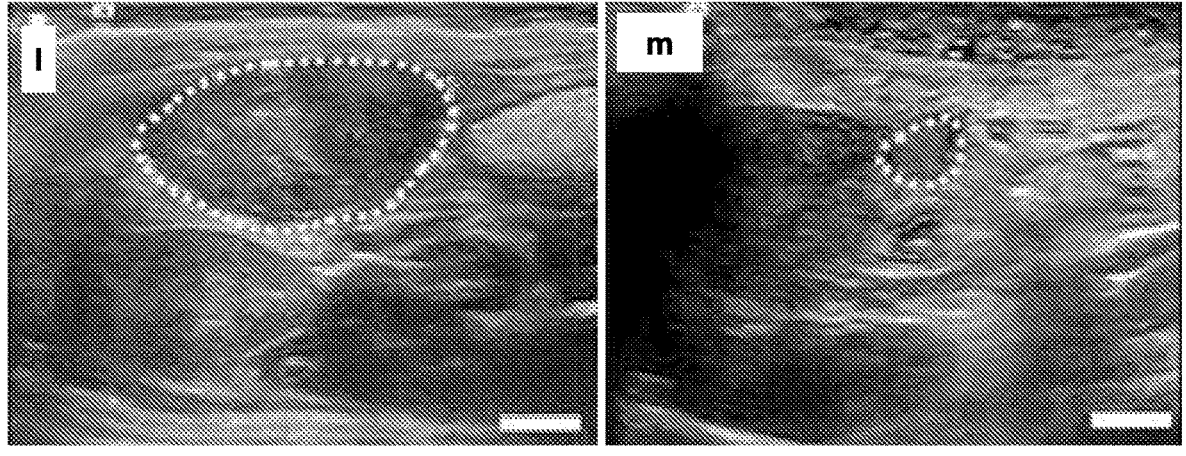
FIG. 1L                    FIG. 1M
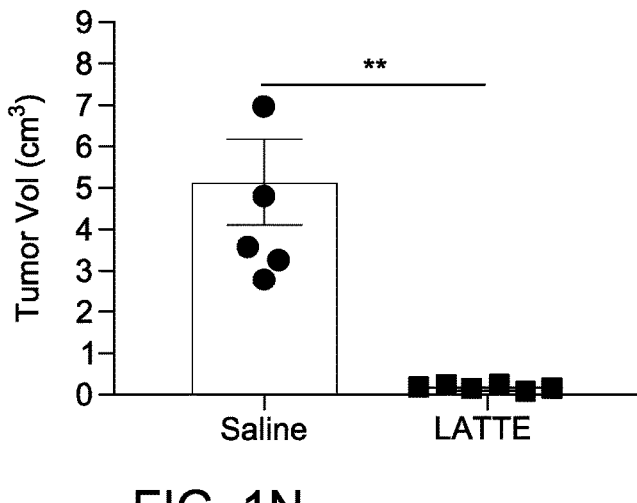
FIG. 1N Proliferation Proliferation Apoptosis Apoptosis Saline LATTE

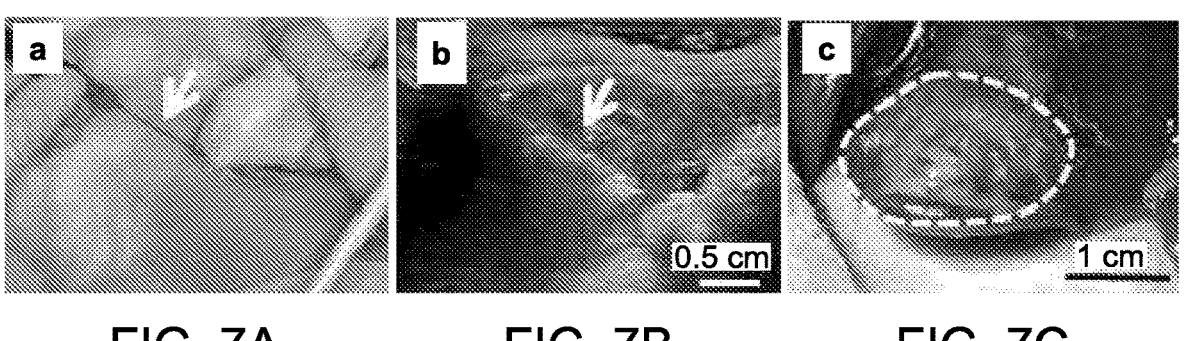
FIG. 7A          FIG. 7B          FIG. 7C
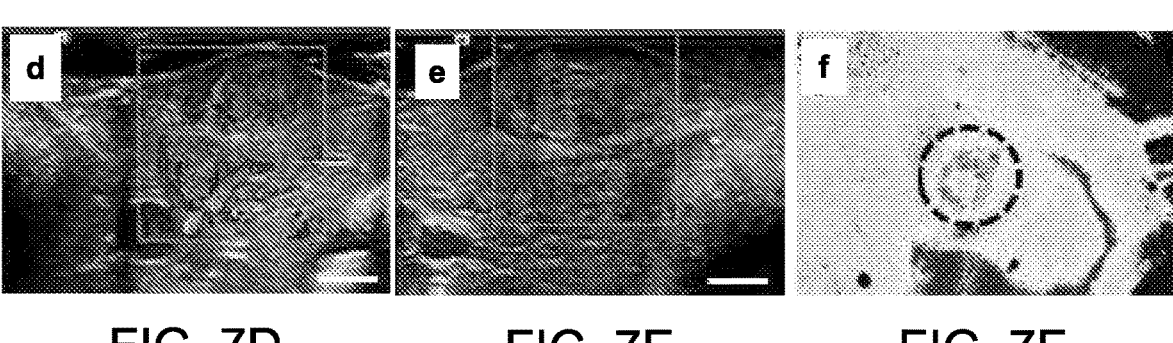
FIG. 7D          FIG. 7E          FIG. 7F
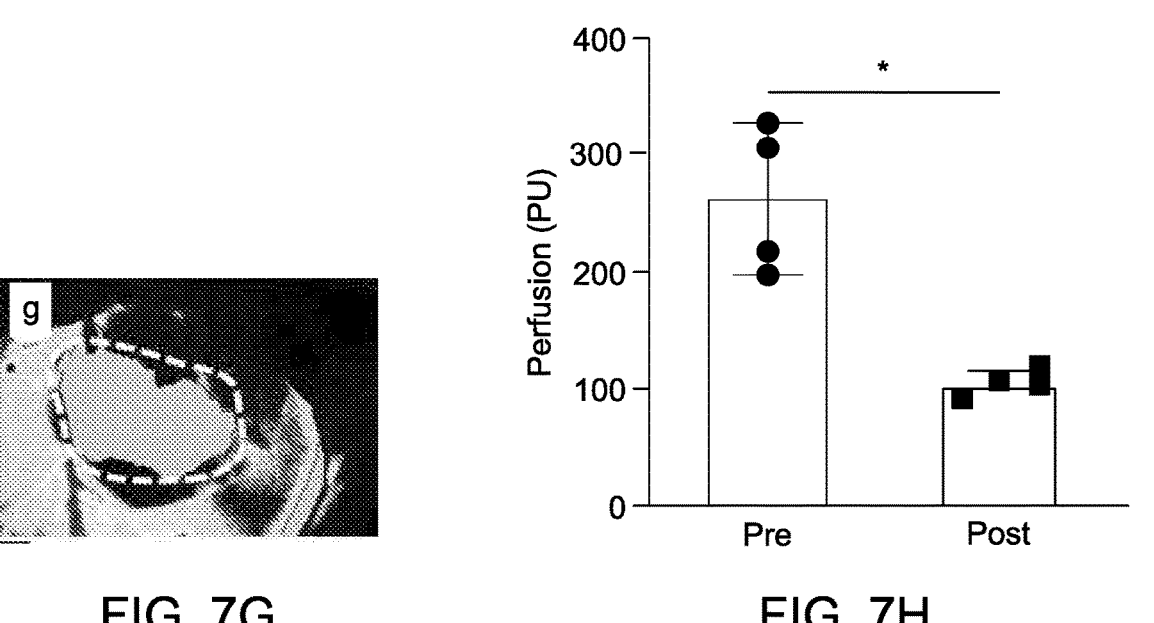
FIG. 7G                    FIG. 7H

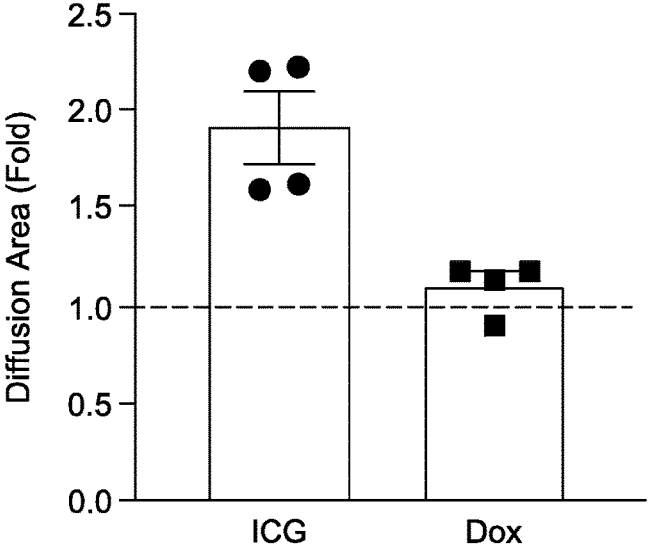
FIG. 7M
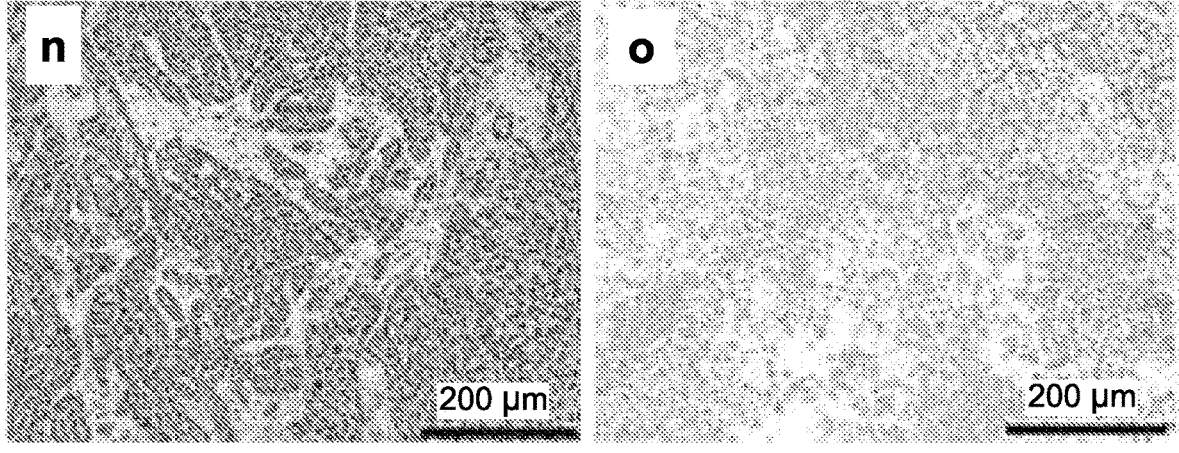
FIG. 7N                         FIG. 7O

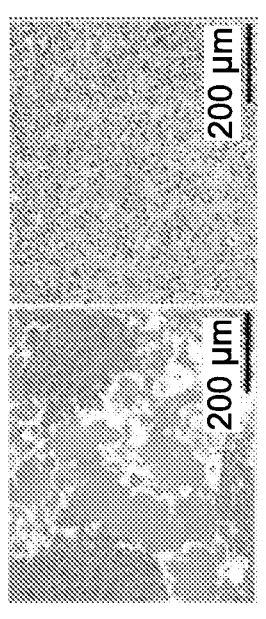
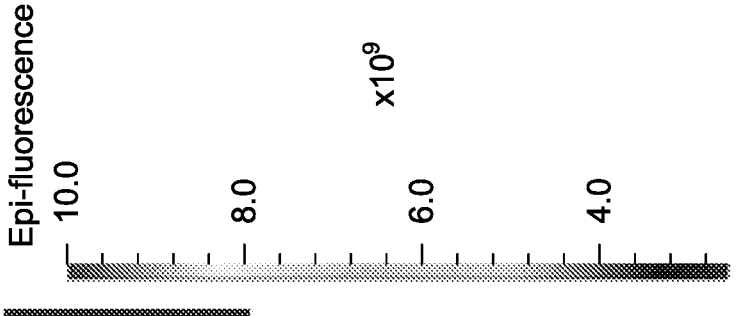
Epi-fluorescence
10.0
8.0
6.0
4.0
x10⁹
Radiant
(Efficiency)
Color Scal
Min = 2.50e8
Max = 1.40e9
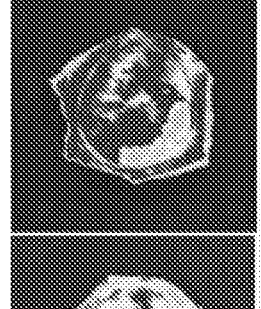
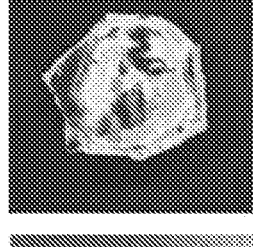
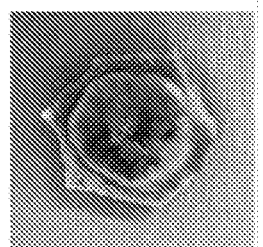
HCC
FIG. 8B

25% LATTE before    After

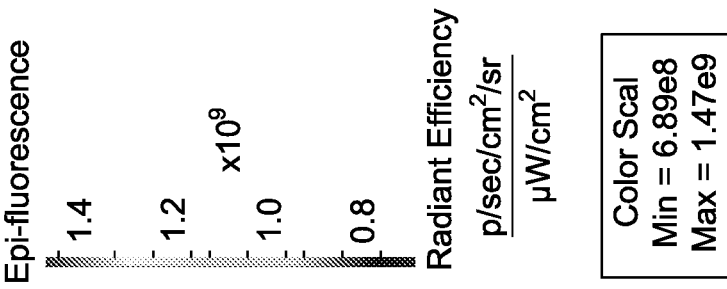
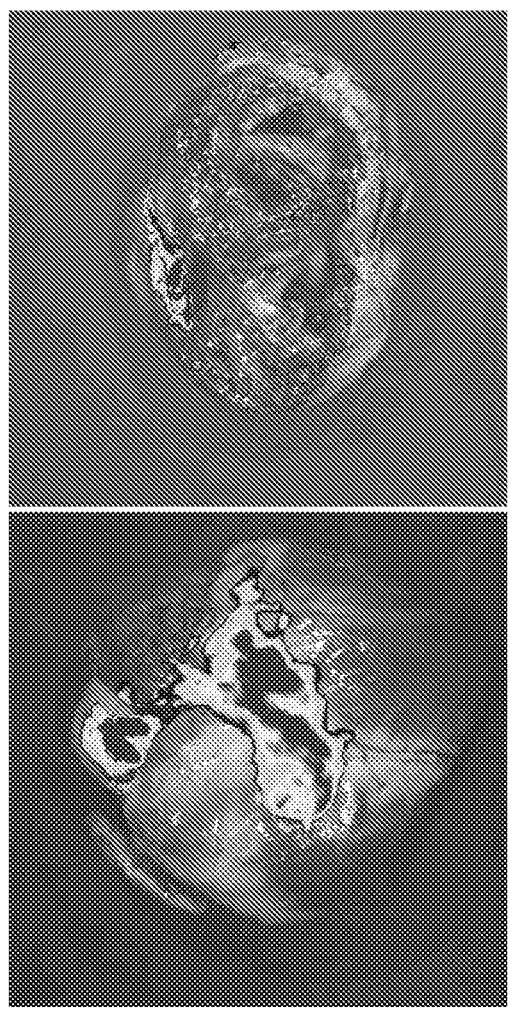
FIG. 14A

| Gel Formulation | IL [wt%] | NS [wt%] | Dox [wt%] | Nivo [wt%] | Iohexol [wt%] | Water [wt%] |
|---|---|---|---|---|---|---|
| NanoGel (NG) | 25 | 3 | 0 | 0 | 20 | 52 |
| NG + Dox | 25 | 3 | 0.125 | 0 | 20 | 51.875 |
| NG + Nivo | 25 | 3 | 0 | 0.25 | 20 | 51.75 |
| NG + Nivo + Dox | 25 | 3 | 0.125 | 0.25 | 20 | 51.625 |

FIG. 15G 3 mm 1 mm

NanoGel (2 Weeks)
Control (2 Weeks)
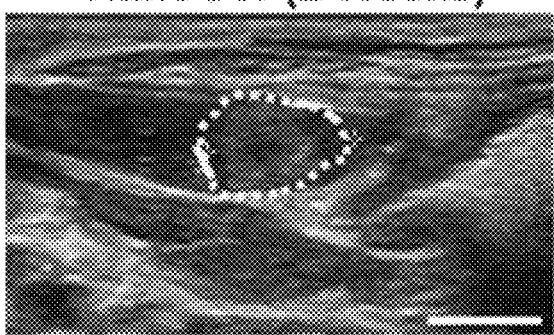
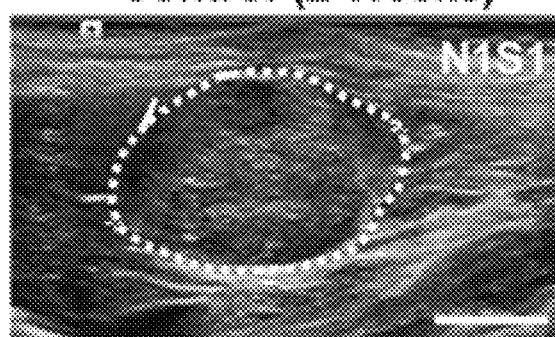
FIG. 27A
FIG. 27B
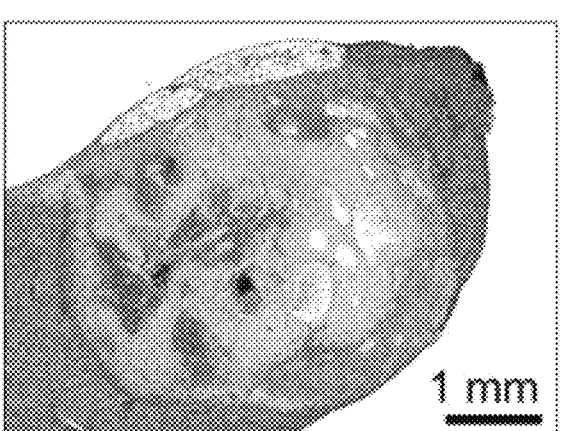
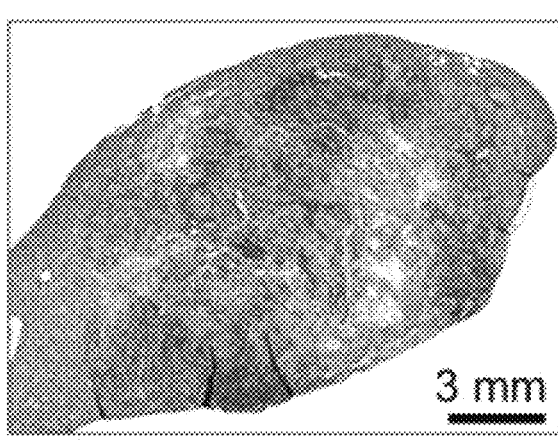
FIG. 27C
FIG. 27D
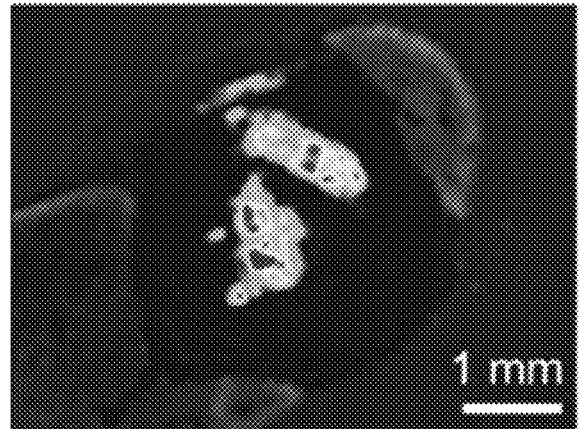
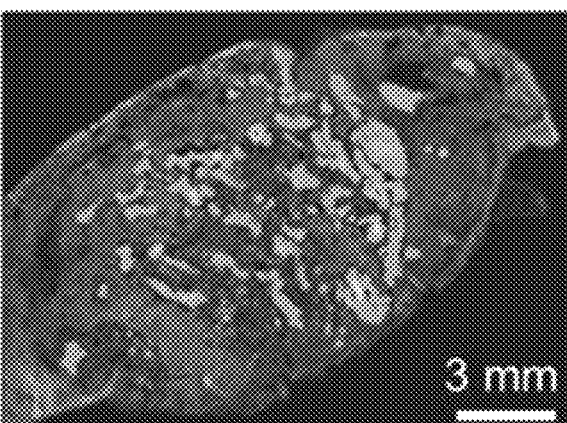
FIG. 27E
FIG. 27F

Tissue Ablation

1 mm

Delivery of Immunotherapy

1 mm

Enhancement of T-Lymphocytes Recruitment

1 mm

150 µm

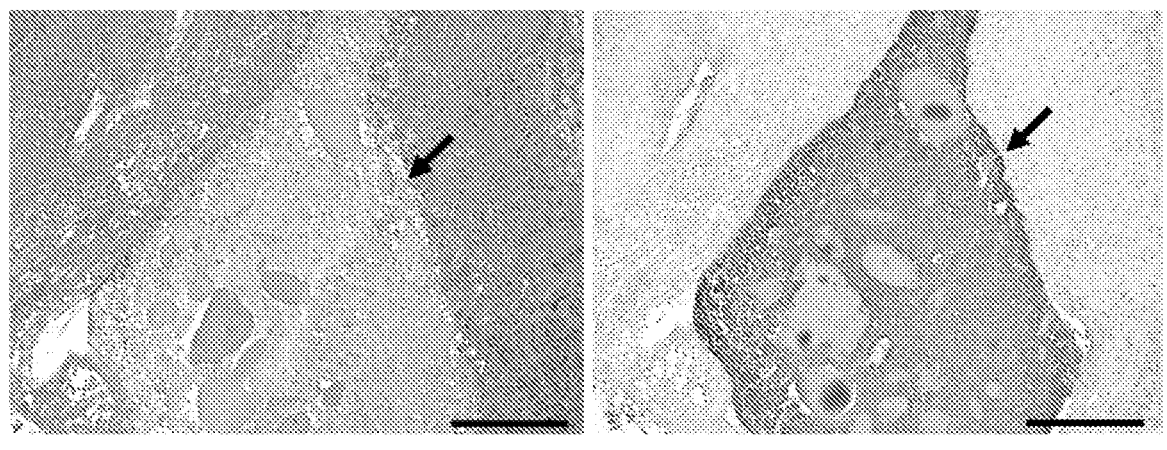
FIG. 29F                    FIG. 29G

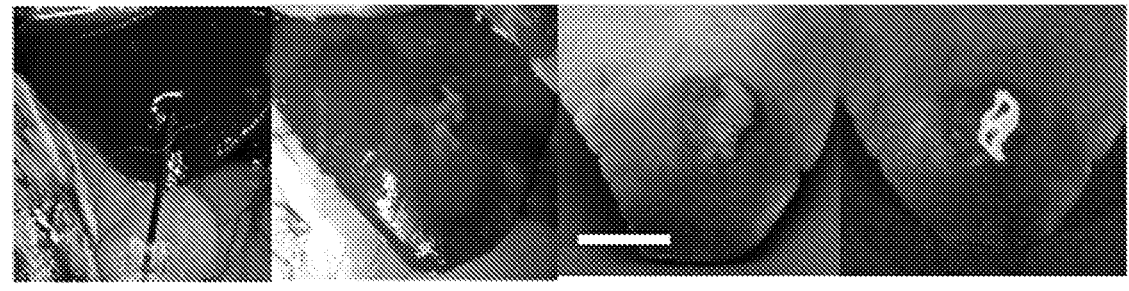
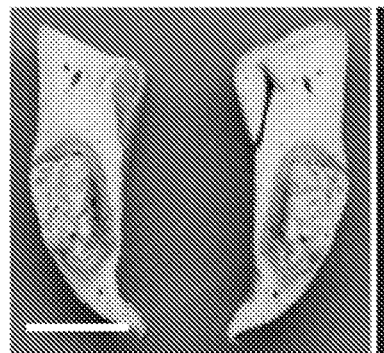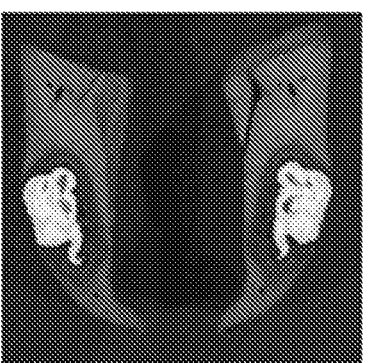
FIG. 30

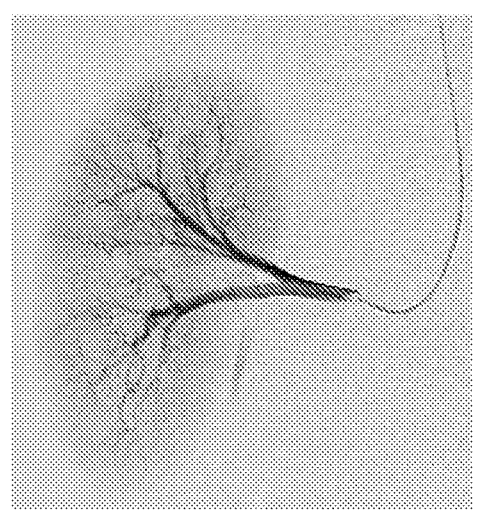
FIG. 32A                              FIG. 32B

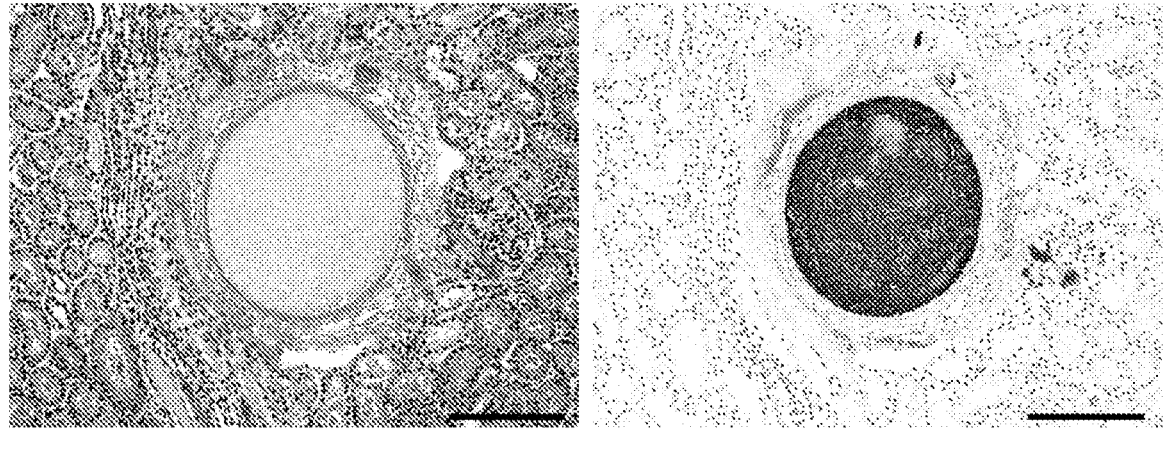
FIG. 33A                 FIG. 33B
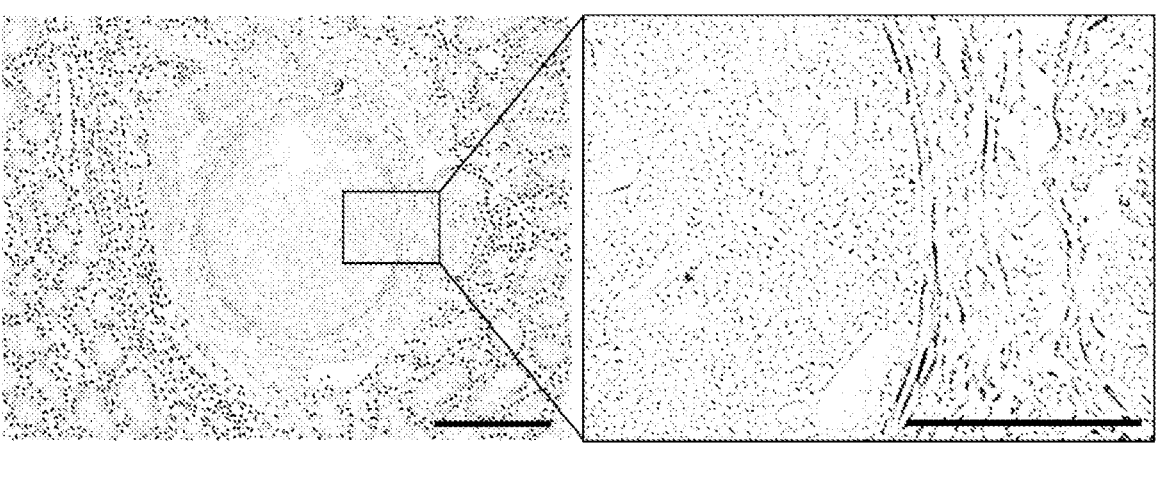
FIG. 33C                 FIG. 33D

METHODS AND MATERIALS FOR TISSUE ABLATION

CROSS-REFERENCE TO RELATED APPLICATIONS

This application claims the benefit of U.S. Patent Application Ser. No. 63/066,024, filed on Aug. 14, 2020. The disclosure of the prior application is considered part of (and is incorporated by reference in) the disclosure of this application.

STATEMENT REGARDING FEDERAL FUNDING

This invention was made with government support under EP024403 awarded by the National Institutes of Health. The government has certain rights in the invention.

TECHNICAL FIELD

This document relates to methods and materials for tissue ablation. For example, a composition including one or more ionic liquids can be used to ablate one or more tissues within a mammal. In some cases, a composition including one or more ionic liquids can be used to ablate tumor tissue within a mammal having cancer (e.g., to treat the mammal).

BACKGROUND INFORMATION

Cancer is a leading cause of morbidity and mortality with an estimated annual rate of 10 million deaths worldwide (World Cancer Report 2014, (World Health Organization, 2014)) costing>$200 billion annually in the US alone (Mattiuzzi et al., *J Epidemiol Glob Health* 9:217-222 (2019)). Hepatocellular carcinoma (HCC) is the most common type of liver cancer. Once diagnosed, 5-year survival for regional or metastatic liver cancer is 9% and 3%, respectively.

SUMMARY

Systemic chemotherapy has been the cornerstone to cancer treatment. However, its inability to achieve uniform drug delivery in tumors, collateral toxicity to non-cancerous liver, and systemic side-effects have limited the progress in the development of novel therapies for liver cancer. Despite significant world-wide efforts, both systemic and locoregional therapies (LRTs) such as percutaneous microwave ablation or endovascular embolization have not led to a change in the over-all survival of these patients.

This document provides methods and materials for tissue ablation. For example, this document provides ionic liquids (e.g., compositions including one or more ionic liquids) and methods for using such ionic liquids for tissue ablation. In some cases, a composition including one or more ionic liquids a (e.g., a composition including a locally-active agent for tumor treatment and eradication (LATTE) solution) can be used to ablate tumor tissue (e.g., to treat cancer) within a mammal. As demonstrated herein, a composition including a LATTE solution can uniformly spread in a circumferential fashion while destroying tumor tissue. When a composition including a LATTE solution is administered together with a chemotherapeutic agent such as doxorubicin, the chemotherapeutic agent can remain within the ablation zone up to 28 days. Also as demonstrated herein, a composition including a LATTE solution can be used to ablate fat tissue, cardiac tissue, blood clots, and to deplete blood of nucleated cells. Accordingly, a composition including one or more ionic liquids (e.g., a composition including a LATTE solution) can be used as a therapeutic agent (e.g., as an anticancer agent) to ablate tissue (e.g., tumor tissue) within a mammal (e.g., a human).

In general, one aspect of this document features methods for ablating at least a portion of a tissue within a mammal. The methods can include, or consist essentially of, percutaneously injecting a composition comprising an ionic liquid into a tissue within a mammal, where the ionic liquid comprises: (a) a cationic component including a cation selected from the group consisting of choline, benzyl pyridinium, benzyl dimethyl dodecyl ammonium, phosphonium, tetraalkylphosphonium, benzethonium, imidazolium, pyridinium, piperidinium, quinolinium, morpholinium, quaternary phosphonium, and quaternary ammonium; and (b) an anionic component comprising an anion selected from the group consisting of geranate, bistriflimide, oleate, hexanoate, dodecyldimethyl ammonia propane sulfonate, N-lauryl sarcosinate, geraniolate, tetrafluoroborate, hexafluorophosphate, methyl sulfate, octyle sulfate, acesulfame, halides, bis(trifluoromethylsulfonyl)amide, bis(trifluoromethyl)amide, dicyanamide, and trifluoromethanesulfonate; where the composition can be effective to create an ablation zone within the tissue, and where the composition can be effective to reduce the number of cells within the ablation zone. The mammal can be a human. The tissue can be fat tissue, cardiac tissue, connective tissue, bone tissue, synovial tissue, abscess tissue, or cysts. The percutaneously injecting step can include a guided injection. The composition also can include a contrast agent. The contrast agent can be indocyanine green, a radiodense contrast agent, iohexol tantalum nanoparticles, tantalum microparticles, gold nanoparticles, gadolinium, indium$^{111}$, or microbubbles. The ablation zone can be from about 0.1 cm to about 4 cm. The composition can be in the form of a hydrogel. The hydrogel can include a nanosilicate. The hydrogel can include from about 1% (w/v) to about 10% (w/v) of the nanosilicate. The nanosilicate can include a smectite clay.

In another aspect, this document features methods for treating a mammal having cancer. The methods can include, or consist essentially of, percutaneously injecting a composition including an ionic liquid into a tumor tissue within a mammal, where the ionic liquid comprises: (a) a cationic component comprising a cation selected from the group consisting of choline, benzyl pyridinium, benzyl dimethyl dodecyl ammonium, phosphonium, tetraalkylphosphonium, benzethonium, imidazolium, pyridinium, piperidinium, quinolinium, morpholinium, quaternary phosphonium, and quaternary ammonium; and (b) an anionic component comprising an anion selected from the group consisting of geranate, bistriflimide, oleate, hexanoate, dodecyldimethyl ammonia propane sulfonate, N-lauryl sarcosinate, geraniolate, tetrafluoroborate, hexafluorophosphate, methyl sulfate, octyle sulfate, acesulfame, halides, bis(trifluoromethylsulfonyl)amide, bis(trifluoromethyl)amide, dicyanamide, and trifluoromethanesulfonate; where the composition can be effective to create an ablation zone within said tumor tissue, and where the composition can be effective to reduce the number of cancer cells within the ablation zone. The mammal can be a human. The cancer can be a liver cancer, a bile duct cancer, a pancreatic cancer, a colorectal cancer, a renal cancer, an ovarian cancer, a breast cancer, a prostate cancer, a colon cancer, a bladder cancer, a lung cancer, a thyroid cancer, a melanoma, a brain cancer, a stomach cancer, a cervical cancer, a uterine cancer, a skin cancer, a synovial cancer, an appendiceal cancer, or an adrenal cancer. When the cancer is a liver cancer, the liver cancer can be a hepatocellular carcinoma (HCC).

When the cancer is a bile duct cancer, the bile duct cancer can be a cholangiocarcinoma. When the cancer is a colorectal cancer, the colorectal cancer can be a colorectal cancer liver metastasis (CRCLM). The composition also can include a chemotherapy agent and/or a radioactive agent. The chemotherapy agent can be doxorubicin, cisplatin, paclitaxel, olaparib, everolimus, mitomycin, atezolizumab, bevacizumab, cabozantinib-s-malate, ramucirumab, pembrolizumab, lenvatinib mesylate, sorafenib tosylate, nivolumab, pemigatinib, pembrolizumab, ramucirumab, regorafenib, or abemaciclib. The radioactive agent can be Y90. The method can be effective to deliver the chemotherapy agent and/or the radioactive agent to the ablation zone. The method can be effective to maintain the chemotherapy agent and/or the radioactive agent within the ablation zone for from about 1 day to about 30 days. The method can be effective to reduce the size of the cancer by at least 2-fold. The method can include identifying the mammal as having the cancer. The composition can be in the form of a hydrogel. The hydrogel can include a nanosilicate. The hydrogel can include from about 1% (w/v) to about 10% (w/v) of the nanosilicate. The nanosilicate can include a smectite clay.

In another aspect, this document features methods for treating a mammal having a disease or disorder associated with fat accumulation. The methods can include, or consist essentially of, percutaneously injecting a composition including an ionic liquid into a fat tissue within a mammal, where the ionic liquid comprises: (a) a cationic component comprising a cation selected from the group consisting of choline, benzyl pyridinium, benzyl dimethyl dodecyl ammonium, phosphonium, tetraalkylphosphonium, benzethonium, imidazolium, pyridinium, piperidinium, quinolinium, morpholinium, quaternary phosphonium, and quaternary ammonium; and (b) an anionic component comprising an anion selected from the group consisting of geranate, bistriflimide, oleate, hexanoate, dodecyldimethyl ammonia propane sulfonate, N-lauryl sarcosinate, geraniolate, tetrafluoroborate, hexafluorophosphate, methyl sulfate, octyle sulfate, acesulfame, halides, bis(trifluoromethylsulfonyl)amide, bis(trifluoromethyl)amide, dicyanamide, and trifluoromethanesulfonate; where the composition can be effective to create an ablation zone within said fat tissue, and where the composition can be effective to reduce the number of adipocytes cells within said ablation zone. The mammal can be a human. The disease or disorder associated with fat accumulation can be obesity, lipedema, a lipid storage disease, or a cancer having a fat laden tumor. The method can include identifying the mammal as having the disease or disorder associated with fat accumulation. The composition can be in the form of a hydrogel. The hydrogel can include a nanosilicate. The hydrogel can include from about 1% (w/v) to about 10% (w/v) of the nanosilicate. The nanosilicate can include a smectite clay.

In another aspect, this document features methods for treating a mammal having a heart disease or disorder. The methods can include, or consist essentially of, percutaneously injecting a composition including an ionic liquid into atrophied cardiac muscle within a mammal, where the ionic liquid comprises: (a) a cationic component comprising a cation selected from the group consisting of choline, benzyl pyridinium, benzyl dimethyl dodecyl ammonium, phosphonium, tetraalkylphosphonium, benzethonium, imidazolium, pyridinium, piperidinium, quinolinium, morpholinium, quaternary phosphonium, and quaternary ammonium; and (b)

an anionic component comprising an anion selected from the group consisting of geranate, bistriflimide, oleate, hexanoate, dodecyldimethyl ammonia propane sulfonate, N-lauryl sarcosinate, geraniolate, tetrafluoroborate, hexafluorophosphate, methyl sulfate, octyle sulfate, acesulfame, halides, bis(trifluoromethylsulfonyl)amide, bis(trifluoromethyl)amide, dicyanamide, and trifluoromethanesulfonate; where the composition is effective to create an ablation zone within said atrophied cardiac muscle, and where the composition can be effective to reduce the number of atrophied cardiomyocytes within the ablation zone. The mammal can be a human. The heart disease or disorder can be hypertrophic cardiomyopathy, an arrhythmia, or atrial fibrillation foci. The method can include identifying the mammal as having the heart disease or disorder. The composition can be in the form of a hydrogel. The hydrogel can include a nanosilicate. The hydrogel can include from about 1% (w/v) to about 10% (w/v) of the nanosilicate. The nanosilicate can include a smectite clay.

In another aspect, this document features methods for treating a mammal having a disease or disorder associated with a blood clot. The methods can include, or consist essentially of, percutaneously injecting a composition including an ionic liquid into said blood clot within a mammal, where the ionic liquid comprises: (a) a cationic component comprising a cation selected from the group consisting of choline, benzyl pyridinium, benzyl dimethyl dodecyl ammonium, phosphonium, tetraalkylphosphonium, benzethonium, imidazolium, pyridinium, piperidinium, quinolinium, morpholinium, quaternary phosphonium, and quaternary ammonium; and (b) an anionic component comprising an anion selected from the group consisting of geranate, bistriflimide, oleate, hexanoate, dodecyldimethyl ammonia propane sulfonate, N-lauryl sarcosinate, geraniolate, tetrafluoroborate, hexafluorophosphate, methyl sulfate, octyle sulfate, acesulfame, halides, bis(trifluoromethylsulfonyl)amide, bis(trifluoromethyl)amide, dicyanamide, and trifluoromethanesulfonate; where the composition is effective to reduce the size of the blood clot. The mammal can be a human. The disease or disorder associated with the blood clot can be acute deep vein thrombosis, chronic deep vein thrombosis, antiphospholipid syndrome, arteriosclerosis, atherosclerosis, or pulmonary embolism. The method can include identifying the mammal as having the disease or disorder associated with the blood clot. The composition can be in the form of a hydrogel. The hydrogel can include a nanosilicate. The hydrogel can include from about 1% (w/v) to about 10% (w/v) of the nanosilicate. The nanosilicate can include a smectite clay.

In another aspect, this document features methods for treating a mammal having an infected tissue. The methods can include, or consist essentially of, percutaneously injecting a composition including an ionic liquid into an infected tissue within a mammal, where the ionic liquid comprises: (a) a cationic component comprising a cation selected from the group consisting of choline, benzyl pyridinium, benzyl dimethyl dodecyl ammonium, phosphonium, tetraalkylphosphonium, benzethonium, imidazolium, pyridinium, piperidinium, quinolinium, morpholinium, quaternary phosphonium, and quaternary ammonium; and (b) an anionic component comprising an anion selected from the group consisting of geranate, bistriflimide, oleate, hexanoate, dodecyldimethyl ammonia propane sulfonate, N-lauryl sarcosinate, geraniolate, tetrafluoroborate, hexafluorophosphate, methyl sulfate, octyle sulfate, acesulfame, halides, bis(trifluoromethylsulfonyl)amide, bis(trifluoromethyl)amide, dicyanamide, and trifluoromethanesulfonate; where the composition can be effective to create an ablation zone within the infected tissue, and where the composition can be effective to reduce the number of infected cells within the ablation zone. The mammal can be a human. The infected tissue can be at a wound site. The wound can be a diabetic wound or a surgical wound. The method can include identifying the mammal as having the infected tissue. The composition can be in the form of a hydrogel. The hydrogel can include a nanosilicate. The hydrogel can include from about 1% (w/v) to about 10% (w/v) of the nanosilicate. The nanosilicate can include a smectite clay.

In another aspect, this document features methods for delivering a therapeutic agent to a tissue within a mammal. The methods can include, or consist essentially of, percutaneously injecting a composition comprising (a) an ionic liquid and (b) a therapeutic agent about 0.1 picometers ($\mu$m) to about 12 pm of a tissue within a mammal; where the ionic liquid comprises: (a) a cationic component comprising a cation selected from the group consisting of choline, benzyl pyridinium, benzyl dimethyl dodecyl ammonium, phosphonium, tetraalkylphosphonium, benzethonium, imidazolium, pyridinium, piperidinium, quinolinium, morpholinium, quaternary phosphonium, and quaternary ammonium; and (b) an anionic component comprising an anion selected from the group consisting of geranate, bistriflimide, oleate, hexanoate, dodecyldimethyl ammonia propane sulfonate, N-lauryl sarcosinate, geraniolate, tetrafluoroborate, hexafluorophosphate, methyl sulfate, octyle sulfate, acesulfame, halides, bis(trifluoromethylsulfonyl)amide, bis(trifluoromethyl) amide, dicyanamide, and trifluoromethanesulfonate; where the ionic liquid can be effective to create an ablation zone within the tissue, and where the method can be effective to maintain the therapeutic agent within the ablation zone. The mammal can be a human. The tissue can be fat tissue, cardiac tissue, connective tissue, bone tissue, synovial tissue, abscess tissue, or cysts. The tissue can be a tumor tissue. The therapeutic agent can be a chemotherapeutic agent, a radioactive agent, an antibody, an angiogenic factor, a therapeutic polypeptide, nucleic acid encoding a therapeutic polypeptide, or an immune modulator. The ablation zone can be from about 0.1 cm to about 4 cm. The method can be effective to maintain the therapeutic agent within the ablation zone for from about 1 day to about 30 days. The percutaneously injecting step can include a guided injection. The composition also can include a contrast agent. The contrast agent can be indocyanine green, a radiodense contrast agent, iohexol tantalum nanoparticles, tantalum microparticles, gold nanoparticles, gadolinium, indium$^{111}$, or microbubbles. The composition can be in the form of a hydrogel. The hydrogel can include a nanosilicate. The hydrogel can include from about 1% (w/v) to about 10% (w/v) of the nanosilicate. The nanosilicate can include a smectite clay.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 1A-1W. Assessing permeation and ablation effects following intrahepatic injection of LATTE into rat liver using micro-computed tomography and ultrasound imaging. FIGS. 1A-1B. Photograph of rat liver during and at 24 hours after injection showing LATTE treatment zone.

FIGS. 1I, 1J, and 1K. Respective photographs showing N1S1 rat liver tumor, immediately after, and at 2 weeks following intratumoral injection of 25% LATTE demonstrating tumor regression on gross examination. FIGS. 1L and 1M. Respective ultrasound scans of N1S1 rat liver lesions obtained at two weeks after direct intratumoral injection of saline or LATTE (dashed yellow outline, scale bar, 0.5 cm). FIGS. 1N and 1O. Respective plots of N1S1 tumor volume and relative change in lesion volume measured with ultrasound in saline or LATTE injected rats (p=0.002). FIG. 1V. Plot showing higher tissue ICG diffusion in the LATTE injected tumors compared to saline (p=0.002). FIG. 1W. Summary of fluorescent intensity in transected livers showing substantially higher intensity in the LATTE treated lesions (p=0.002). Data presented as mean±SEM with n=6 in each group. Statistical significance between three groups was assessed using one-way ANOVA and Tukey's post-hoc test whereas comparison between two groups was calculated using Mann-Whitney test.

FIG. 2A. Plot of rheometry study assessing viscosity of 6.25, 25, 35, 50%, or 100% LATTE concentrations following dilution in 0.9 w/v saline compared to neat LATTE (100%) showing concentration dependent change on viscosity. FIG. 2B. graph comparing viscosity forces of 6.25%, 25% and 50% LATTE concentrations at shear rate of 50 l/s illustrating substantially higher viscosity of the 50% LATTE compared to 6.25% or 25% (n=3). FIG. 2C. Graphic summary of time-dependent assessment of viscosity of different LATTE concentrations measured at 0, 10 or 20 days after dilution showing stability of each solution. FIG. 2D. Injection force testing of 25%, 35%, 50% and 100% LATTE on a 1 mL syringe that was injected through a 21 gauge percutaneous access needle showing concentration dependent injection forces with similar forces generated with 25% compared to 35% LATTE. Data represent the mean±SEM with * p<0.05, **** p<0.0001 calculated using ANOVA with Tukey's post hoc test (n=3).

FIGS. 3A and 3B. Representative micrographs of H&E stained N1S1 tissue sections obtained at two weeks after saline or LATTE injection respectively showing diminished cellularity and degenerated structures in the LATTE treatment tumor compared to saline. FIG. 3C. Graph summarizing morphometric analysis of cross-sectional tumor lesion at two weeks after treatment showing significantly smaller lesion in the LATTE treated tumors compared to saline. FIGS. 3D and 3E. Representative micrographs of PCNA stained rat liver sections obtained from saline or LATTE treated N1S1 tumors respectively. FIG. 3F. Summary of nuclei counts within each N1S1 tumor boundaries of saline or LATTE injected tumors respectively. FIGS. 3G and 3H. Respective images of immune-stained tissue section visualizing cleaved-Caspase-3 cells in Saline or LATTE treated N1S1 tumors. FIG. 3I. Quantitative analysis Graphic summary of the average proliferating (PCNA expressing) or apoptotic (Caspase-3 positive) counted cells within the tumor boundaries of N1S1 tumors showing markedly diminished proliferation with parallel to increase in apoptotic cells detected in the LATTE treated tumors compared to saline. Statistical significance was calculated using Mann-Whitney tests (** and ++p<0.01). Data represented as the mean±SEM with n=6 in each group. Scale bars, 100 μm.

FIGS. 4A and 4B. Representative immuno-staining to identify CD3 T-Lymphocytes in N1S1 tumors tissue sections obtained at two weeks after injection with saline or LATTE respectively. FIG. 4C. Quantitative analysis of CD3 expressing cell count in tumor tissue sections showing higher infiltration of CD3+ within the boundaries in the LATTE injected tumors ( p–0.002 using unpaired Mann-Whitney test). FIGS. 4D and 4E. Representative micrographs of CD68 expressing cells in saline or LATTE treated N1S1 tumors. FIG. 4F. Quantitative analysis of CD68 bearing cells count in tumor tissue sections showing higher infiltration in the LATTE injected tumors. FIGS. 4G and 4I**. Representative fluorescent micrograph showing CD8 expressing lymphocytes in the LATTE treated tumors. Data expressed as mean±SEM, n=6 in each group). Scale bare, 100 μm.

FIG. 5A. Summary of fractional cell viability dose response plotted using water-soluble tetrazolium-1 (WST-1) outputs curves to LATTE treatment in human hepatocellular carcinoma (Hep-G2), Cholangiocarcinoma (SNU-478), or pancreas ductal adenocarcinoma (Panc-1) cells at 24 hours after incubation resulted in effective dose (EC50) of 0.19%, 0.2% or 0.3% respectively. FIG. 5B. Fractional viability dose response curves of Doxorubicin against HepG2 cells that were incubated with serially diluted Doxorubicin concentrations of 80-0.156 μM in growth media resulted in EC50 of 1.63 μM at 24 hours after treatment. FIGS. 5C and 5D. Synergy matrices based on the Loewe model were generated at 24 and 48 hours after incubation using selected concentrations close to the EC50 values of individual compound with all possible combination of LATTE and Doxorubicin mixtures of 0.05%-0.78% for LATTE and 1.25-10 μM for Doxorubicin revealed synergistic cytotoxic effects against HepG2 cells observed with 0.39% LATTE and 5 μM Doxorubicin at 24 hours (FIG. 5C) and 0.19% LATTE and 1.25 μM Doxorubicin at 48 hours (FIG. 5D). Results represent replicates of three independent experiments with n=12.

FIGS. 6A-6O. Time-dependent evaluation of chemotherapy drug diffusion and retention following LATTE injection in rat liver. The lateral lobe of Sprague Dawley rats was injected with 50 μL volume of 25%-LATTE mixed with ICG, whereas the medial site received 50 μL of 25% LATTE and ICG in addition to 50 μg doxorubicin followed by survival period of 1, 7, or 28 days after injection (n=10). FIGS. 6A, 6B, and 6C. Post necropsy, near-infrared fluorescent scans (NIRF) showing ICG retention at the two injection sites. FIGS. 6I-6O. Representative micrographs of H&E stained tissue sections obtained from LATTE treated sites at 1, 7, and 28 days respectively showing maximum necrosis at the center of the treated zone with lesser necrosis towards the peripheral boundary at 1 and 7 days after injection with evidence of tissue remodeling associated with fibrous formation by 28 days after injection. FIGS. 6L, 6M, and 6N**. Corresponding Picrosirius red stained histologic sections demonstrated enhanced collagen staining in the LATTE treatment zone at 28 days after injection (black arrows).

FIG. 7A. Photograph depicts percutaneous ultrasound guided injection into VX2 tumor in rabbit liver. FIG. 7W. Follow up NIRF scan of the injected pig liver displaying ICG diffusion in the affected zone.

FIGS. 8A-8G. Ex vivo injection of LATTE into explanted human cancer tissue. FIGS. 8A-8E. Panels of resected solid tumor including; (FIG. 8A) colorectal cancer liver metastasis (CRCLM), (FIG. 8B) hepatocellular carcinoma (HCC), (FIG. 8C) cholangiocarcinoma (CAA), (FIG. 8D) breast cancer (BC), and (FIG. 8E) renal cancer. Each panel (left to right) contains a photograph of tumor tissue, NIRF scans obtained at 10 minutes after LATTE injection, NIRF at 24 hours after LATTE injection, H&E stained sections from ablated and not ablated tumors respectively. Scale bar, 200 µm. FIG. 8F. Graphic summary of fluorescent intensity assessed at showing substantial increase at 10 minutes and 24 hours after LATTE injection compared to baseline (BL). FIG. 8G. Plot of ICG diffusion area assessed at 10 minutes and 24 hours following LATTE injection. Data represent the mean±SEM with  p<0.01, ** p<0.0001 calculated using repeated measures ANOVA (n=12).

FIG. 10A. Fat from pig. FIG. 10B. Fat removed from pig following placement in LATTE solution. After 1 hour, fat was depleted from the adipocytes.

FIG. 12A. Normal blood smear showing blood cells throughout the microscope field.

FIG. 12B. No blood cells are detectable in the blood sample that received the LATTE ablation agent treatment.

FIG. 13A. Image of coagulated blood in a multi-well plate that was overlayed with saline. FIG. 13B. Image of coagulated blood that was overlayed with LATTE in the multi-wells showing clot was dissolved. FIG. 13C. Image of blood clot formed in the tube in a petri dish showing complete lysis following incubation with LATTE. These images indicate that LATTE is able to dissolve blood clots; these data imply that LATTE may be used to lyse or dissolve clots, enabling treatment of both arterial and venous clot in diseased conditions including stroke, myocardial infarction, deep vein thrombosis and ischemic leg or organs.

FIGS. 14A-14B. Effect of an ablation agent on pig heart tissue. FIG. 14A. In a living Yorkshire pig weighing 50-55 kg, a syringe connected to a 21 gauge 7 cm needle was guided through the skin into the myocardium using handheld ultrasound guidance. On necropsy, 14A shows near-infrared image of pig cardiac muscle following injection with LATTE mixed with indocyanine green showing intense signal. FIG. 14B. Stained histology image of cardiac muscle showing extensive cardiac muscle ablation at the treated zone following direct percutaneous image guided injection of 25% LATTE.

FIGS. 15A-15G. Characterizing the mechanical properties of a hydrogel containing LATTE (NanoGel). FIG. 15A. Representative flow curves of hydrogels containing 3 wt %, 4.5 wt %, 6 wt %, or 9 wt % of nanosilicate (NS) demonstrating shear-thinning behavior. FIG. 15B. Graph showing the effect of increasing NS ratio on storage modulus (G') generated by hydrogels containing 3 wt %, 4.5 wt %, 6 wt %, or 9 wt % NS. FIG. 15C. A graph summarizing the rheometry results showing concentration dependent increase in G' in the NanoGel containing 1.25 wt % or 25 wt % IL compared to NS alone (as shown in FIG. 15B) whereas 50 wt % IL results in a much higher G'. FIGS. 15D and 15E. Representative flow curves and graph of NS hydrogel, NanoGel (NG), NG containing 0.25% mg/mL ICG (NG+ICG), 1.25 mg/mL Doxorubicin (Dox) (NG+Dox), 1 mg/mL Nivo (Nivolumab) (NG+Nivo), or NG+Dox+Nivo as indicated. FIG. 15F. A graph displaying the injection force generated by different NanoGel formulations loaded in a 1 cc syringe and injected through a 110 cm 2.8 F microcatheter at 1 mL per min-1 injection rate. FIG. 15G. A table showing examples of different NG formulation to incorporate Dox, nivolumab (Nivo; a PD-1 IgG), iohexol contrast agent to be added in single component or in combination as indicated for different testing purposes. Data in graphs are means±SEM. Statistical analyses were calculated by one-way ANOVA with Tukey's multiple comparison post hoc tests (n=6 for each test). ns; not significant, * p<0.05, and **** p<0.0001.

FIG. 16A. Images showing examples of NanoGel containing 3 wt % NS, 25 wt % IL, 1 mg/mL Nivo, and 0.25 mg/mL ICG, loaded into a clinical grade syringe fitted with 21-gauge vascular access needle for direct intratumoral or intravascular injection. FIG. 16B. Image showing NanoGel injection through the needle exhibiting shear-thinning behavior evident by maintaining coherence upon exiting the needle tip. FIGS. 16C to 16F. To demonstrate the effect of IL or Nivo on hydrogel appearance on microscale level, scanning electron microscope imaging of nanosilicate hydrogel (NS), NS mixed with Nivo (NS+Nivo), Nanogel alone (NG), or NanoGel mixed with 1 mg/mL Nivo (NG+Nivo) respectively displaying porus microstructure in the NS and NS+Nivo hydrogels compared to less porus and mesh-like microstructure in the NanoGel containing ionic liquid or NG+Nivo suggesting that IL alters the interactions of the nanocomposites in the NS hydrogel which may explain the changes seen in its mechanical proprieties. Scale bar, 200 µm.

FIG. 17A. Stained blood smears prepared from pig blood treated with IL at the concentrations of 0% (control), 0.78 wt %, 1.56 wt % and 3.12 wt % exhibited concentration dependent changes in morphology and a decrease in white blood cell detection starting at 1.56% IL with evidence of complete hemolysis observed at 3.12 wt % IL. Scale bar, 100 µm. FIG. 17B. Representative rheometry flow curves to assess the effect of IL treatment on thrombus generation and modulus in aliquots of pig blood treated with IL at concentrations of 0% (control), 0.78%, 1.56%, and 3.12% wt % IL. The control and 0.78 wt % IL treated pig blood showed consistent G' and G" modulus profile, whereas 1.56% IL treated blood displayed a delayed clotting lag time with lower G' and G" (modulus) levels compared to control blood (n=5). The 3.12 wt % IL treated blood failed to coagulate during the 30 minutes testing period (n=5).

FIG. 17C. Quantitative analysis of blood coagulation initiation lag time (tlag) showing a slight increase in lag time at 0.78% IL and significantly extended lag time with 1.56 wt % IL treatment. FIG. 17D. Summary graph of storage modulus (G') at 30 minutes following treatment with 0 wt %, 0.78 wt %, 1.56 wt %, or 3.12 wt % IL showing a ~20% decrease in storage modulus at 0.78% IL compared to 95% drop in modulus at 1.56 wt % IL and 100 wt % decrease at 3.12 wt % IL suggesting concentration dependent anti-coagulation effect of IL. FIG. 17E. Hemolysis test in pig blood treated with 0 wt %, 0.78%, 1.56%, 3.12%, 6.25%, 12.5 wt % and 25 wt % IL exhibiting a significant increase in hemolysis (****p<0.0001). FIGS. 17F to 17J. Graphs showing complete blood count performed on fresh blood aliquots treated with increasing concentrations of 0.78 wt %, 1.56 wt %, and 3.12 wt % IL illustrating concentration dependent decrease in the total counts of red blood cells (RBC, FIG. 17F), and white blood cells (WBC, FIG. 17G) counts, that paralleled a similar decrease in granulocytes (FIG. 17J), and monocytes (FIG. 17I) counts. However, there was no change in lymphocytes count (FIG. 17H) in the same aliquots compared to control suggesting resistance to IL treatment at the tested concentrations (n=6). Blood count data are expressed as a percent of the control values (0 wt % IL) of the same blood pool. Data are mean±SEM. Statistical analyses were performed using one-way ANOVA with Tukey's post hoc tests (*p<0.05, p<0.01, *p<0.001, and ****p<0.0001).

FIG. 18A. Fluorescent images showing radiant diffusion of the naturally fluorescencing anticancer drug agent, Dox. Dox was incorporated into NS hydrogel (control hydrogel without ionic liquid), or into NanoGel containing 6.25%-IL or 25%-IL for 24 hours after loading equal aliquots to the center of designated wells at the center of a 2% agarose casted within a multi-well plate to assess radial diffusion at 37° C. over a 24 hours period. FIG. 18B. A plot showing serial measurements of Dox fluorescence in NS+Dox, NG+Dox 6.25%-IL, or NG+Dox with 25%-IL showing significantly enhanced area of diffusion in the NG+Dox 25%-IL compared to NG+Dox 6.25%-IL and NS+Dox (n=4). FIGS. 18C and 18D. Fluorescence images and plots showing serial detection and measurements of Dox fluorescence (FIG. 18C) or ICG (FIG. 18D) incorporated into NanoGel or NS hydrogel respectively showing persistent enhancement of Dox (FIG. 18C) or ICG (FIG. 18D) over a 56 days period compared to diminished detection in the NS hydrogel (n=4). : p<0.01, *: p<0.001, ****: p<0.0001. Statistical differences were calculated using ANOVA and Turkey's post-hoc tests. Data in all graphs are the means±SEM.

FIG. 19A. A plot showing cumulative Dox release from NanoGel (NG) mixed with 0.25 mg/mL Dox then incubated for 7 days under physiologic (pH=7.4) or acidic (pH=5.0) conditions demonstrating sustained Doxorubicin release (n=3). FIG. 19B. Fractional viability of HepG2 cells at 24 hours post treatment with serially diluted NG extract resulting in an $IC_{50}$ at an IL concentration of 0.14% suggesting preserved cytotoxic effect of NG. FIG. 19C. A plot demonstrating enhanced cytotoxicity of HepG2 post incubation with NG extract containing 0.25 mg/mL Dox (NG+Dox) compared to Nanosilicate extract containing similar amount of Dox (NS+Dox) suggesting synergistic effect. NS alone did not show cytotoxic effect. FIG. 19D. A plot showing sterility of NG, or NG+Dox post incubation for 24 hours, or 2 months in LB broth at 37° C. LB broth inoculated with E. coli bacteria was used as a positive control (n=6). ns: not significant, *: p<0.001, **: p<0.0001. Statistical differences were calculated using ANOVA and Turkey's post-hoc tests. Data in all graphs are means±SEM.

FIG. 20A. Ultrasound scan of NanoGel loaded inside a latex sleeve then placed inside a human phantom displaying high echogenicity suggesting compatibility and visibility with ultrasound. FIGS. 20B and 20C. Representative in vivo ultrasound images during direct injection of NanoGel inside the liver parenchyma of a rat demonstrating the feasibility of percutaneous injection directly into targeted tissue (arrow in FIG. 20B; indicate injection needle, outline in FIG. 20C showing highly echogenic NanoGel after injection). FIGS. 20D and 20E. Graph and corresponding transverse views of T1 (FIG. 20D) and T2 (FIG. 20E) weighted MR images of syringes loaded with different formulation of NS, or NG alone, or syringes loaded with NS, or NG that contained 0.25 mg/mL Dox, or 1 mg/mL Nivo, or a combination of Dox+ Nivo showing 2-3-fold enhancement on T1 weighted images and 4-8-fold enhancement on T2 weighted images compared to the human liver or the aorta (n=6). *: p<0.5, ***: p<0.01 using ANOVA.

FIGS. 21A-21I. Assessing Tissue Ablation and Drug diffusion and Retention Capacity Following NanoGel Injection in rats. 3D rendered reconstructed microCT and ICG fluorescence analysis of rat livers showing tissue ablation in each injection site that received 50 µL injection of NS, NG, or NG+Dox at Day-1, Day-14, or Day-28 respectively as shown in the 3D rendered image in FIG. 21A, FIG. 21C, and FIG. 21E. FIGS. 21B, 21D, and 21F. Representative near infrared images of explanted rat liver showing the ICG-enhanced fluorescence area at each injection site at Day-1, Day-14, or Day-28 post injection with NS, NG, or NG+Dox, and graphs showing the diffusion area at 28 days post injection with NG and NG+Dox compared to NS suggesting higher diffusion and retention of ICG in the presence of IL in the NanoGel formulation (n=5). FIGS. 21G to 21I. *: p<0.5, ***: p<0.01. Statistical analysis was calculated using one-way ANOVA with Tukey's post hoc test. Scale bars in FIGS. 21A, 21C, and 21E are 0.5 cm.

FIG. 22A. Graph and corresponding transverse views of T2 weighted MRI images of syringes loaded with NS or NS-IL hydrogel showing signal enhancement compared to liver or aorta. FIG. 22B. Plot showing NS-IL and NS-IL-Dox sterility at 24 hours and 2 months after incubation.

FIGS. 23A, 23B, and 23C. Different ionized channels of Dox molecules showing identical retention time at 4.1 minutes. FIG. 23D. Plot of LC-MS/MS quantitative analysis of Dox levels showing linearity (R2=0.99).

FIGS. 24A-24D. Representative US images of N1S1 tumors at baseline prior to intratumoral injection (FIGS. 24A and 24B) and their corresponding US images at 2 weeks (FIGS. 24C and 24D) after intratumoral injection of control NS-Dox-PD-1 antibody hydrogel (FIGS. 24A and 24C) or NanoGel (NS-Dox-IL-PD-1 antibody hydrogel) treated N1S1 tumor (FIGS. 24B and 24D). Scale bars, 0.5 cm. FIGS. 20E and 20F. H&E stained histology sections of control (FIG. 24E) or NanoGel treated tumors (FIG. 24F). FIGS. 24G and 24H. Histology sections of control (FIG. 24G) or NanoGel treated N1S1 tumors (FIG. 24H) showing PD-1 antibody immunostaining (brown; Black arrow). n=3.

FIGS. 25A and 25B. Histology sections of rat liver tissues immunostained for myeloperoxidase (MPO) bearing inflammatory cells (FIG. 25A) or CD3+T-lymphocytes (FIG. 25B) at Day-1, Day-14 or Day-28 following injection with NS, NG, or NG+Dox. FIG. 25C. Graph summarizing the area of ablation in the rat liver sections at Day-1, Day-14, and Day-28 after injection with NS, NG, or NG+Dox showing significantly larger ablation area in the NG and the NG+Dox injected sites compared to NS injected site at Day-1, Day-14. FIG. 25D. Graph showing morphometric analysis of MPO positive cells illustrating early MPO positive cells recruitment at Day-1 that was gradually decreased by Day-14 and Day-28 suggesting a transient acute pro-inflammatory response (n=4). FIG. 25E. Histologic analysis of the number of immunostained CD3+ cells counted within each injection site showing significantly higher CD3+ cells in the NG+Dox site compared to NS or NG injection sites showed higher number of T-lymphocytes recruitment in the NG+Dox injection site up to and a higher number of CD3+ cells up to 28 days after injection (n=4). Statistical analysis was calculated using two-way ANOVA with post hoc test. Ns, not significant, *: $p<0.05$, : $p<0.01$, **: $p<0.0001$. Scale bars in A and B histology panels=1 mm in the stitched images, and 75 μm in the high-power images to the right.

FIG. 26A. Gross view image of a subcutaneously inoculated with MC38 colon adenocarcinoma cells (colorectal cancer cells) showing a tumor in the right lower flank of an immune competent C57BL6 mouse (as indicated in the image with a arrow). FIG. 26B. Ultrasound image of an MC38 tumor obtained during direct intratumoral injection of NanoGel showing high echogenic needle inside a hypoechogenic tumor lesion (dotted outline). FIGS. 26C and 26D. NanoGel treated tumor at 49 days post Nanogel injection showing complete treatment response leaving a small scar on the mouse skin (FIG. 26C) that was visible on ultrasound (FIG. 26D). FIGS. 26E and 26F. Gross view and corresponding ultrasound images of MC38 tumor bearing mouse showing tumor progression that reached ~2 cm$^2$ at 21 days post injection with saline (Control, arrow in gross image; FIG. 26E and, dotted outline in US; FIG. 26F). Scale bars, 5 mm. FIG. 26G. Survival curves of MC38 tumor bearing mice post ultrasound guided intratumoral injection of NanoGel or control. p=0.0003. FIG. 26H. Graph displaying MC38 tumor growth curves of individual tumors assessed by ultrasound in NanoGel (black, n=7) or control (red, n=7) showing early tumor progression in the control compared to consistently lower tumor volume in the NanoGel injected tumors suggesting a tumor response to treatment. Scale bars=5 mm. FIG. 26I. Graph of average change in tumor volume measured before intratumoral injection of NanoGel or Control and at the end of the survival period in each group. n=7 mice in each group.  p<0.1. Statistical analysis was calculated using unpaired t test. FIG. 26J**. Histology section of MC38 tumor at 1 hour after injection with NanoGel showing tumor cell ablation in the high-power image. FIG. 26K. Histology section of MC38 tumor at 48 days after intratumoral injection of NanoGel showing reduced lesion size, cell ablation, and evidence of fibrous formation. FIG. 26L. Histology section of control, untreated, MC38 tumor showing substantially larger tumor area and evidence of actively proliferating tumor cells.

FIGS. 27A-27J. The effect of intratumoral injection of NanoGel into the N1S1 rat model of hepatocellular carcinoma. FIG. 27A. Representative US image of ablated N1S1 tumor at two weeks post intratumoral injection with NanoGel mixed with 1 mg/mL Nivo, and 0.25 ng/mL of the anti-cancer drug, Dox. FIG. 27B. Representative US images of N1S1 tumor at 2 weeks post intratumoral injection with NS hydrogel (Control) mixed with Nivo, and Doxorubicin without IL. FIGS. 27C and 27D. Corresponding stained histology sections of N1S1 tumors at two weeks after injection with NanoGel or Control hydrogel, respectively. Scale bars in US images, 0.5 cm. FIGS. 27G and 27H. Infrared correlation maps of N1S1 tumor sections on gold slides showing silicate oxide (Si—O, a derivative of nano-silicate) distribution using reflection mode at two weeks after injection with NanoGel (FIG. 27E) or Control (FIG. 27F). FIGS. 27G and 27H. Corresponding fluorescence imaging of N1S1 tissue sections in FIGS. 27E and 27F. FIGS. 27I and 27J. Histology sections showing substantial Nivo detected within the N1S1 tumor lesion (brown staining, black arrow) at two weeks after injection with NanoGel containing Dox and Nivo (FIG. 27A) compared to diminished detection of Nivo in the tumor that received NS hydrogel containing Dox and Nivo (FIG. 27B). n=3 in each group.

FIGS. 28A and 28B. Histology sections showing tissue ablation and substantial Nivo distribution detected within the N1S1 tumor lesion (brown staining, black arrow) at two weeks after injection with NanoGel containing Dox and Nivo. FIGS. 28C and 28D. Representative immunostained histology sections of N1S1 tumor at two weeks after intratumoral injection with Nano-Gel displaying extensive lymphocytes infiltration (CD3+ cells in brown) at the interface between the ablated tumor area and the adjacent liver as shown in FIG. 28C and in the higher magnification image, FIG. 28D. The high magnification image in FIG. 28D, correspond to the area marked with the black box in FIG. 28C (n=3).

FIGS. 29A-29G. Image-guided intratumoral injection of NanoGel into the VX2 liver cancer model in rabbits. FIG. 29A. Ultrasound scan of rabbit liver showing VX2 tumor denoted with the white dotted outline. FIGS. 29B and 29C. Images demonstrating ultrasound-guided injection of Nano-Gel using a standard 21-gauge vascular access needle (outline showing tumor, arrow indicate needle). FIG. 29D. Image of transected VX2 tumor at 1 hour after injection of NG mixed with 1.25 mg/mL Dox, and 1 mg/mL Nivo showing the red Dox material distributed throughout the transected tumor (arrow). FIG. 29E. Ex vivo fluorescence image of transected VX2 tumor from FIG. 29D showing Dox fluorescence throughout the treated zone at 1 hour after injection of NG+Dox+Nivo. FIGS. 29F and 29G. Representative histology sections localizing the area of ablation in the H&E-stained section (FIG. 29D) to the PD-1 antibody (Nivo) immunostained section (FIG. 29G) at 1 hour post intratumoral injection of NG+Dox+Nivo. Scale bar in ultrasound images (FIGS. 29A and 29C), 1 cm. Scale bars in histology sections (FIGS. 29F and 29G), 200 μm.

FIG. 30. Representative normal rabbit liver treated with NanoGel (NG) containing 1.25 mg/mL Doxorubicin (Dox) and 1 mg/mL Nivolumab (Nivo).

FIGS. 32A-32G. Endovascular chemoembolization and drug delivery in swine renal artery. FIGS. 32A and 32B. Representative fluoroscopic images before and post renal artery embolization with 2-3 cc of NG containing 0.25 mg/mL ICG and 20% iohexol contrast agent to provide imaging enhancements on fluorescence and x-ray-based imaging platforms such as CT or fluoroscopy. FIG. 32C. Gross view of an explanted and transected kidney at one hour after embolization with NG. FIG. 32D. Near infrared fluorescence image of swine kidney at 1 hour post embolization with NG showing diffuse fluorescence enhancement of ICG throughout the renal cortex and medulla. FIGS. 32E and 32F. Gross view and near-infrared fluorescence imaging of harvested and transected kidney swine at one hour post embolization with NS hydrogel containing 0.25 mg/mL, and 20% iohexol demonstrating diminished fluorescence enhancement of ICG that was limited to the vascular network of the renal. FIG. 32G. Graph showing enhanced fluorescence intensity of ICG in transected renal tissues harvested at one post embolization with NG+ICG compared or renal artery embolization with NS+ICG. ****$p<0.0001$ using unpaired student t test, n=4 in each group. Data reported as the mean±SEM. Scale bar=10 mm.

FIGS. 33A-33D. Histological Assessment of Transarterial Diffusion of Immunotherapy Post Transcatheter Embolization with NanoGel containing Nivolumab. FIG. 33A. H&E-stained histology section of renal artery branch at the renal cortex region showing complete casting of the artery at one hour following renal artery embolization with NanoGel demonstrating the ability of the NG to reach smaller arterial branches. FIG. 33B. High-power image showing immuno-histochemistry detection of Nivo in a sequential serial section in FIG. 33A. Nivo was localized inside the renal artery and in the surrounding area suggesting transarterial drug delivery. FIGS. 33C and 33D. Images of hematoxylin-stained histology section showing diminished nuclear staining in the arterial wall suggesting successful transarterial delivery of IL and ablation following embolization with NG. Scale bar=150 um in A-C. Scale bar=50 μm in FIG. 33D.

DETAILED DESCRIPTION

Figures 1A, 1B:
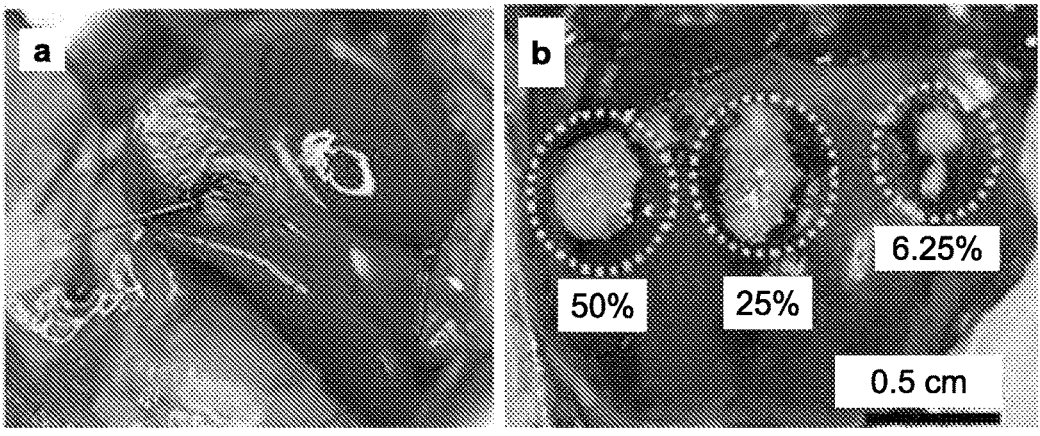

This document provides methods and materials for tissue ablation. For example, this document provides ionic liquids having a cationic component and an anionic component (e.g., a composition containing one or more ionic liquids having a cationic component and an anionic component) and methods for using such ionic liquids for tissue ablation. In some cases, a composition including one or more ionic liquids (e.g., a composition including a LATTE solution) can be used to ablate (e.g., to scar and/or destroy) at least a portion of a tissue within a mammal. For example, a composition including one or more ionic liquids (e.g., a composition including a LATTE solution) can be used to ablate tumor tissue within a mammal (e.g., to treat a mammal having cancer). For example, a composition including one or more ionic liquids (e.g., a composition including a LATTE solution) can be used to ablate fat tissue within a mammal (e.g., to treat a mammal having a disease or disorder associated with fat accumulation). In some cases, a composition including one or more ionic liquids (e.g., a composition including a LATTE solution) can be used to ablate cardiac tissue within a mammal (e.g., to treat a mammal having a heart disease or disorder). In some cases, a composition including one or more ionic liquids (e.g., a composition including a LATTE solution) can be used to ablate one or more blood clots within a mammal (e.g., to treat the mammal).

In some cases, a composition provided herein (e.g., a composition including one or more ionic liquids such as a LATTE solution) can be sterile.

In some cases, a composition provided herein (e.g., a composition including one or more ionic liquids such as a LATTE solution) can be anti-bacterial.

A composition including one or more ionic liquids can include any appropriate ionic liquid(s). In some cases, an ionic liquid can be a eutectic ionic liquid (e.g., a deep eutectic solvent (DES)). For example, when an ionic liquid is a eutectic ionic liquid (e.g., a DES), the eutectic ionic liquid can have a melting temperature that is lower than the melting point of the cationic component and is lower than the melting point of the anionic component.

An ionic liquid can include any appropriate cationic component. In some cases, a cationic component can be an organic cationic component. In some cases, a cationic component can be a non-organic cationic component. Examples of cations that can be included in a cationic component of an ionic liquid include, without limitation, choline (e.g., a choline cation), benzyl pyridinium, benzyl dimethyl dodecyl ammonium, phosphonium, tetraalkylphosphonium, benze-thonium, imidazolium, pyridinium, piperidinium, quino-linium, morpholinium, quaternary phosphonium, and qua-ternary ammonium. In some cases, a cationic component can be in the form of a salt (e.g., choline bicarbonate).

An ionic liquid can include any appropriate anionic component. Examples of anions that can be included in an anionic component of an ionic liquid include, without limi-tation, geranate, bistriflimide, oleate, hexanoate, dodecyldi-methyl ammonia propane sulfonate, N-lauryl sarcosinate, geraniolate, tetrafluoroborate, hexafluorophosphate, methyl sulfate, octyle sulfate, acesulfame, halides, bis(trifluorom-ethylsulfonyl)amide, bis(trifluoromethyl)amide, dicyana-mide, and trifluoromethanesulfonate.

When an ionic liquid is a eutectic ionic liquid (e.g., a DES), the eutectic ionic liquid can include one or more hydrogen bond donors. In some cases, a hydrogen bond donor can provide a hydroxyl group (e.g., a —OH group). In some cases, a hydrogen bond donor can provide an amine group (e.g., a secondary amino such as a —NH group). A hydrogen bond donor can be any type of molecule (e.g., alcohols, fatty acids, and amines). Examples of hydrogen bond donors that can be included in a eutectic ionic liquid include, without limitation, imidazolium, and chloride ions.

In some cases, an ionic liquid can have a cationic com-ponent including choline and can have an anionic compo-nent including geranate.

In some cases, an ionic liquid can be as described else-where (see, e.g., U.S. Pat. No. 10,449,254 at, e.g., column 4, line 2 to column 6, line 52; and column 11, line 6 to column 14, line 66).

An ionic liquid can include any appropriate ratio of a cationic component to an anionic component. In some cases, an ionic liquid can include from about 1:2 (cation:anion) to about 2:1 (cation:anion). For example, an ionic liquid can include a ratio of 1:1, 1:2, 2:1, 1:3, 3:1, 2:3, or 3:2 of the cationic component to the anionic component.

In some cases, an ionic liquid (e.g., a LATTE solution) can be in the form of a solution (e.g., an aqueous solution) or a suspension.

In some cases, an ionic liquid (e.g., a LATTE solution) can be in the form of (e.g. can be incorporated into) a hydrogel (e.g., a shear-thinning hydrogel). For example, a shear-thinning hydrogel including an ionic liquid can include one or more nanosilicates, one or more gelatins, and an ionic liquid.

When a composition provided herein (e.g., a composition including one or more ionic liquids such as a LATTE solution) is incorporated into a hydrogel, the composition can be incorporated into any appropriate hydrogel. Examples of hydrogels that a composition provided herein can be incorporated into can include, without limitation, nanosilicate hydrogels, tantalum microparticle hydrogels, gelatin-based hydrogels, alginate hydrogels, gelatin methacrylate hydrogels, extracellular matrix-based hydrogels, self-assembled peptide-based hydrogels, polyethylene glycol hydrogels, and chitosan hydrogels. In some cases, a hydrogel that a composition provided herein can be incorporated into can be as described elsewhere (see, e.g., Altun et al., *Adv. Mater.*, 32(52):e2005603 (2020); Hu et al., *Adv. Mater.*, 32(33):e2002611 (2020); Albadawi et al., *Adv. Sci.*, 8(1):2003327 (2020); and Avery et al., *Sci. Transl. Med.*, 8(365):365ra156 (2016)).

In some cases, a composition provided herein can be incorporated into a hydrogel including one or more nanosilicates. A hydrogel can include any appropriate type of nanosilicate(s). In some cases, a hydrogel can include a single type of nanosilicate. In some cases, a hydrogel can include two or more (e.g., two, three, four, or more) types of nanosilicates. In some cases, a nanosilicate can be a synthetic nanosilicate. Examples of nanosilicates that can be included in a hydrogel that can be used in a hydrogel composition provided herein include, without limitation, smectite clays (e.g., synthetic smectite clays such as LAPONITE™, LAPONITE® XLG; LAPONITE® XLS, and LAPONITE® XL21).

When a composition provided herein (e.g., a composition including one or more ionic liquids such as a LATTE solution) is incorporated into a hydrogel including one or more nanosilicates, the hydrogel can include any amount of nanosilicate(s). For example, a composition provided herein (e.g., a composition including one or more ionic liquids such as a LATTE solution) can be incorporated into a hydrogel including from about 1% (w/v) to about 10% (w/v) nanosilicates (e.g., from about 1% (w/v) to about 9% (w/v), from about 1% (w/v) to about 8% (w/v), from about 1% (w/v) to about 7% (w/v), from about 1% (w/v) to about 5% (w/v), from about 1% (w/v) to about 3% (w/v), from about 2% (w/v) to about 10% (w/v), from about 3% (w/v) to about 10% (w/v), from about 4% (w/v) to about 10% (w/v), from about 5% (w/v) to about 10% (w/v), from about 7% (w/v) to about 10% (w/v), from about 9% (w/v) to about 10% (w/v), from about 2% (w/v) to about 9% (w/v), from about 3% (w/v) to about 8% (w/v), from about 4% (w/v) to about 7% (w/v), from about 5% (w/v) to about 6% (w/v), from about 1% (w/v) to about 4% (w/v), from about 3% (w/v) to about 7% (w/v), or from about 5% (w/v) to about 8% (w/v) nanosilicates). In some cases, a composition provided herein (e.g., a composition including one or more ionic liquids such as a LATTE solution) can be incorporated into a hydrogel including from about 3% (w/v) to about 9% (w/v) nanosilicates (e.g., synthetic smectite clays).

When a composition provided herein (e.g., a composition including one or more ionic liquids such as a LATTE solution) is incorporated into a hydrogel, the hydrogel composition including one or more ionic liquids (e.g., a LATTE solution) can include any amount of the ionic liquid(s). In some cases, a hydrogel composition can include from about 3% by weight (w/w or wt %) to about 50% (w/w) of one or more ionic liquids (e.g., from about 3% by weight (w/w or wt %) to about 40% (w/w), from about 3% by weight (w/w or wt %) to about 30% (w/w), from about 3% by weight (w/w or wt %) to about 25% (w/w), from about 3% by weight (w/w or wt %) to about 20% (w/w), from about 3% by weight (w/w or wt %) to about 15% (w/w), from about 3% by weight (w/w or wt %) to about 10% (w/w), from about 10% by weight (w/w or wt %) to about 50% (w/w), from about 20% by weight (w/w or wt %) to about 50% (w/w), from about 25% by weight (w/w or wt %) to about 50% (w/w), from about 30% by weight (w/w or wt %) to about 50% (w/w), from about 35% by weight (w/w or wt %) to about 50% (w/w), from about 40% by weight (w/w or wt %) to about 50% (w/w), from about 5% by weight (w/w or wt %) to about 40% (w/w), from about 10% by weight (w/w or wt %) to about 30% (w/w), from about 5% by weight (w/w or wt %) to about 15% (w/w), from about 10% by weight (w/w or wt %) to about 20% (w/w), from about 15% by weight (w/w or wt %) to about 25% (w/w), from about 20% by weight (w/w or wt %) to about 30% (w/w), from about 25% by weight (w/w or wt %) to about 35% (w/w), from about 30% by weight (w/w or wt %) to about 40% (w/w), or from about 35% by weight (w/w or wt %) to about 45% (w/w) of one or more ionic liquids). For example, a hydrogel including one or more ionic liquids (e.g., a LATTE solution) can include about 3.25% (w/w) of one or more ionic liquids. For example, a hydrogel including one or more ionic liquids (e.g., a LATTE solution) can include about 12.5% (w/w) of one or more ionic liquids. For example, a hydrogel including one or more ionic liquids (e.g., a LATTE solution) can include about 25% (w/w) of one or more ionic liquids. For example, a hydrogel including one or more ionic liquids (e.g., a LATTE solution) can include about 50% (w/w) of one or more ionic liquids.

When a composition provided herein (e.g., a composition including one or more ionic liquids such as a LATTE solution) is incorporated into a hydrogel, the hydrogel can be a shear-thinning hydrogel composition. For example, a viscosity of a hydrogel that a composition provided herein can be incorporated into can decrease under a shear rate of from about 0.1 l/s to about 1000 l/s (e.g., from about 0.1 l/s to about 750 l/s, from about 0.1 l/s to about 500 l/s, from about 0.1 l/s to about 250 l/s, from about 0.1 l/s to about 100 l/s, from about 0.1 l/s to about 75 l/s, from about 0.1 l/s to about 50 l/s, from about 0.1 l/s to about 25 l/s, from about 0.1 l/s to about 10 l/s, from about 10 l/s to about 1000 l/s, from about 50 l/s to about 1000 l/s, from about 100 l/s to about 1000 l/s, from about 250 l/s to about 1000 l/s, from about 500 l/s to about 1000 l/s, from about 750 l/s to about 1000 l/s, from about 10 l/s to about 800 l/s, from about 50 l/s to about 600 l/s, from about 100 l/s to about 500 l/s, from about 200 l/s to about 300 l/s, from about 100 l/s to about 300 l/s, from about 300 l/s to about 500 l/s, from about 400 l/s to about 600 l/s, from about 500 l/s to about 700 l/s, from about 600 l/s to about 800 l/s, or from about 700 l/s to about 900 l/s).

In some cases, an ionic liquid (e.g., a LATTE solution) can be incorporated into microparticles or nanoparticles.

Any appropriate method can be used to obtain an ionic liquid (e.g., a LATTE solution). In some cases, an ionic liquid can be synthesized by combining a cationic component and an anionic component in the presence of a solute.

An example of a solute that can be used to synthesize an ionic liquid includes, without limitation, acetone. When an ionic liquid is a eutectic ionic liquid (e.g., a DES), the eutectic ionic liquid can be synthesized using salt metathesis of a cationic component and an anionic component in the presence of a hydrogen bond donor. For example, a LATTE solution can be synthesized using salt metathesis at 1:1 molar ratio of choline bicarbonate and geranic acid). In some cases, an ionic liquid can be synthesized as described in Example 1. In some cases, an ionic liquid can be synthesized as described elsewhere (see, e.g., U.S. Pat. No. 10,449,254 at, e.g., column 11, line 6 to column 14, line 66). When an ionic liquid is incorporated into a hydrogel, the hydrogel including an ionic liquid can be synthesized as described in Example 5. In some cases, a hydrogel including an ionic liquid can be synthesized as described elsewhere (see, e.g., Albadawi et al., *Adv. Sci.,* 8(1):2003327 (2020); and Avery et al., *Sci. Transl. Med.,* 8(365):365ra156 (2016)).

A composition including one or more ionic liquids (e.g., a composition including a LATTE solution) can include any amount of the ionic liquid(s). In some cases, a composition including one or more ionic liquids can include from about 6% by weight (wt %) to about 100 wt % (e.g., from about 6 wt % to about 100 wt %, from about 10 wt % to about 100 wt %, from about 20 wt % to about 100 wt %, from about 30 wt % to about 100 wt %, from about 40 wt % to about 100 wt %, from about 50 wt % to about 100 wt %, from about 60 wt % to about 100 wt %, from about 70 wt % to about 100 wt %, from about 80 wt % to about 100 wt %, from about 90 wt % to about 100 wt %, from about 6 wt % to about 90 wt %, from about 6 wt % to about 80 wt %, from about 6 wt % to about 70 wt %, from about 6 wt % to about 60 wt %, from about 6 wt % to about 50 wt %, from about 6 wt % to about 40 wt %, from about 6 wt % to about 30 wt %, from about 6 wt % to about 20 wt %, from about 6 wt % to about 10 wt %, from about 10 wt % to about 90 wt %, from about 20 wt % to about 80 wt %, from about 30 wt % to about 70 wt %, from about 40 wt % to about 60 wt %, from about 10 wt % to about 30 wt %, from about 20 wt % to about 40 wt %, from about 30 wt % to about 50 wt %, from about 40 wt % to about 60 wt %, from about 50 wt % to about 70 wt %, from about 60 wt % to about 80 wt %, or from about 70 wt % to about 90 wt %) of one or more ionic liquids. For example, a composition including one or more ionic liquids (e.g., a composition including a LATTE solution) can include about 6.25 wt % of one or more ionic liquids. For example, a composition including one or more ionic liquids (e.g., a composition including a LATTE solution) can include about 25 wt % of one or more ionic liquids. For example, a composition including one or more ionic liquids (e.g., a composition including a LATTE solution) can include about 35 wt % of one or more ionic liquids. For example, a composition including one or more ionic liquids (e.g., a composition including a LATTE solution) can include about 50 wt % of one or more ionic liquids. For example, a composition including one or more ionic liquids (e.g., a composition including a LATTE solution) can include 100 wt % of one or more ionic liquids.

In some cases, a composition including one or more ionic liquids (e.g., a composition including a LATTE solution) can include one or more therapeutic agents. For example, a composition including one or more ionic liquids (e.g., a composition including a LATTE solution) can be used to deliver one or more therapeutic agents to an ablation zone created by the composition. Examples of therapeutic agents that can be included in a composition including one or more ionic liquids (e.g., a composition including a LATTE solution) include, without limitation, chemotherapeutic agents (e.g., doxorubicin, cisplatin, and paclitaxel), radioactive agents, antibodies (e.g., antibodies targeting a specific cell type such as a cancer cell), angiogenic factors (e.g., factors that can inhibit angiogenesis or factors that can stimulate angiogenesis), therapeutic polypeptides, nucleic acid encoding a therapeutic polypeptide (e.g., a vector such as a viral vector or an expression plasmid encoding a therapeutic polypeptide), immune modulators (e.g., factors that can enhance an immune response or factors that can inhibit an immune response including, without limitation, immune checkpoint inhibitors (e.g., anti-PD-1, anti PD-L1, and anti CTLA-4 antibodies) and immuno stimulators (e.g., interleukins and interferons)), hormones, antibiotics, and blood thinners (e.g., lovenox, coumadin, and FactorXA inhibitors). In some cases, a therapeutic agent can be conjugated to a nanoparticle. In some cases, a therapeutic agent can be contained within a nanoparticle.

When a composition including one or more ionic liquids (e.g., a composition including a LATTE solution) includes one or more therapeutic agents, the composition can include any amount of the therapeutic agent(s). In some cases, a composition provided herein (e.g., a composition including one or more ionic liquids such as a LATTE solution) can include from about 50 µg of therapeutic agent(s) per mL of composition (µg/mL) to about 2000 µg/mL of therapeutic agent(s) (e.g., from about 50 µg/mL to about 1500 µg/mL, from about 50 µg/mL to about 1000 µg/mL, from about 50 µg/mL to about 700 µg/mL, from about 50 µg/mL to about 500 µg/mL, from about 50 µg/mL to about 300 µg/mL, from about 50 µg/mL to about 200 µg/mL, from about 50 µg/mL to about 100 µg/mL, from about 100 µg/mL to about 2000 µg/mL, from about 200 µg/mL to about 2000 µg/mL, from about 300 µg/mL to about 2000 µg/mL, from about 500 µg/mL to about 2000 µg/mL, from about 700 µg/mL to about 2000 µg/mL, from about 1000 µg/mL to about 2000 µg/mL, from about 1200 µg/mL to about 2000 µg/mL, from about 1500 µg/mL to about 2000 µg/mL, from about 100 µg/mL to about 1500 µg/mL, from about 200 µg/mL to about 1200 µg/mL, from about 400 µg/mL to about 1000 µg/mL, from about 500 µg/mL to about 800 µg/mL, from about 200 µg/mL to about 500 µg/mL, from about 500 µg/mL to about 700 µg/mL, from about 700 µg/mL to about 1000 µg/mL, from about 1000 µg/mL to about 1300 µg/mL, from about 1300 µg/mL to about 1500 µg/mL, or from about 1500 µg/mL to about 1800 µg/mL of therapeutic agent(s)). For example, a composition provided herein (e.g., a composition including one or more ionic liquids such as a LATTE solution) that is included in a hydrogel can include from about 1 mg/mL to about 2 mg/mL (e.g., 1.25 mg/mL) of therapeutic agent(s) (e.g., doxorubicin).

In some cases, a composition including one or more ionic liquids (e.g., a composition including a LATTE solution) can include one or more contrast agents. In some cases, a contrast agent can be a radiodense contrast agent. In some cases, a contrast agent can be an earth metal-based contrast agent. In some cases, a contrast agent can be compatible with magnetic resonance imaging. In some cases, a contrast agent can be compatible with nuclear imaging. In some cases, a contract agent can be compatible with ultrasound imaging. In some cases, a contract agent can be compatible with fluorescent imaging. Examples of contrast agents that can be included in a composition including one or more ionic liquids include, without limitation, indocyanine green, ExiTron™, Lipiodol®, iohexol tantalum nanoparticles, tantalum microparticles, gold nanoparticles, gadolinium, indium[111], iodine, and microbubbles.

When a composition including one or more ionic liquids (e.g., a composition including a LATTE solution) includes one or more contrast agents, the composition can include any amount of the contrast agent(s). In some cases, a composition provided herein (e.g., a composition including one or more ionic liquids such as a LATTE solution) can include from about 10% (w/w) to about 30% (w/w) contrast agent(s) (e.g., from about 10% (w/w) to about 25% (w/w), from about 10% (w/w) to about 20% (w/w), from about 10% (w/w) to about 15% (w/w), from about 15% (w/w) to about 30% (w/w), from about 20% (w/w) to about 30% (w/w), from about 25% (w/w) to about 30% (w/w), from about 12% (w/w) to about 27% (w/w), from about 15% (w/w) to about 25% (w/w), from about 18% (w/w) to about 22% (w/w), from about 15% (w/w) to about 20% (w/w), or from about 20% (w/w) to about 25% (w/w) contrast agent(s)). For example, a composition provided herein (e.g., a composition including one or more ionic liquids such as a LATTE solution) that is included in a hydrogel can include about 20% (w/w) contrast agent(s).

When a composition including one or more ionic liquids (e.g., a composition including a LATTE solution) includes an additional agent (e.g., one or more therapeutic agents such as one or more therapeutic agents conjugated to a nanoparticle or contained within a nanoparticle, or a contrast agent), the additional agent can be any appropriate size. In some cases, an additional agent included in a composition including one or more ionic liquids (e.g., a composition including a LATTE solution) can be up to about 110 nm in size (e.g., across a longest dimension). For example, an additional agent included in a composition including one or more ionic liquids (e.g., a composition including a LATTE solution) can be from about 1 nm to about 110 nm (e.g., from about 1 nm to about 100 nm, from about 1 nm to about 90 nm, from about 1 nm to about 80 nm, from about 1 nm to about 70 nm, from about 1 nm to about 60 nm, from about 1 nm to about 50 nm, from about 1 nm to about 40 nm, from about 1 nm to about 30 nm, from about 10 nm to about 110 nm from about 20 nm to about 110 nm, from about 30 nm to about 110 nm, from about 40 nm to about 110 nm, from about 50 nm to about 110 nm, from about 60 nm to about 110 nm, from about 70 nm to about 110 nm from about 80 nm to about 110 nm, from about 90 nm to about 110 nm, from about 10 nm to about 100 nm, from about 20 nm to about 90 nm from about 30 nm to about 80 nm, from about 40 nm to about 70 nm, from about 10 nm to about 40 nm, from about 20 nm to about 50 nm, from about 30 nm to about 60 nm, from about 40 nm to about 70 nm, from about 50 nm to about 80 nm, from about 60 nm to about 90 nm, or from about 70 nm to about 100 nm) in size.

When a composition including one or more ionic liquids (e.g., a composition including a LATTE solution) includes one or more therapeutic agents and/or one or more contrast agents, the therapeutic agent(s) and/or contrast agent(s) can remain within the ablation zone for up to about 28 days (e.g., up to about 30 days, up to about 1 month, up to about 6 weeks, up to about 2 months, up to about 3 months, up to about 4 months, up to about 5 months, or up to about 6 months). In some cases, when a composition including one or more ionic liquids (e.g., a composition including a LATTE solution) includes one or more therapeutic agents, the therapeutic agent(s) and/or contrast agent(s) can remain within the ablation zone for from about 1 day to about 30 days (e.g., from about 1 day to about 30 days, from about 1 day to about 28 days, from about 1 day to about 25 days, from about 1 day to about 22 days, from about 1 day to about 20 days, from about 1 day to about 15 days, from about 1 day to about 12 days, from about 1 day to about 10 days, from about 1 day to about 8 days, from about 1 day to about 5 days, from about 5 days to about 30 days, from about 7 days to about 30 days, from about 10 days to about 30 days, from about 12 days to about 30 days, from about 15 days to about 30 days, from about 18 days to about 30 days, from about 20 days to about 30 days, from about 22 days to about 30 days, from about 25 days to about 30 days, from about 27 days to about 30 days, from about 5 days to about 10 days, from about 10 days to about 15 days, from about 15 days to about 20 days, from about 20 days to about 25 days, or from about 25 days to about 30 days).

In some cases, a composition including one or more ionic liquids (e.g., a composition including a LATTE solution) can include one or more additional components. In some cases, an additional component can be a stabilizing agent. Examples of additional components that can be included in a hydrogel composition provided herein include, without limitation, polysorbates, surfactants, organic solvents (e.g., dimethylsulfoxide (DMSO)), and detergents (e.g., sodium dodecyl sulfate (SDS)).

A composition including one or more ionic liquids (e.g., a composition including a LATTE solution) can be administered to a mammal (e.g., a human) by any appropriate route. In some cases, a composition including one or more ionic liquids (e.g., a composition including a LATTE solution) can be administered to a mammal (e.g., a human) by a percutaneous injection; e.g., intramuscular injection, subcutaneous injection, intratumoral injection, intraparenchymal injection, intradermal, intrathecal, transcatheter, intravascular, intraosseous, and intra-articular. For example, a composition including one or more ionic liquids (e.g., a composition including a LATTE solution) can be administered to a mammal (e.g., a human) by percutaneous injection directly to the tissue to be ablated. For example, a composition including one or more ionic liquids (e.g., a composition including a LATTE solution) can be administered to a mammal (e.g., a human) by percutaneous injection within from about 0.1 μm to about 12 μm (e.g., from about 0.1 μm to about 10 μm, from about 0.1 μm to about 9 μm, from about 0.1 μm to about 7 μm, from about 0.1 μm to about 5 μm, from about 0.1 μm to about 3 μm, from about 0.5 μm to about 12 μm, from about 3 μm to about 12 μm, from about 5 μm to about 12 μm, from about 8 μm to about 12 μm, from about 10 μm to about 12 μm, from about 0.5 μm to about 10 μm, from about 2 μm to about 8 μm, from about 3 μm to about 7 μm, from about 4 μm to about 6 μm, from about 1 μm to about 4 μm, from about 2 μm to about 5 μm, from about 3 μm to about 6 μm, from about 4 μm to about 7 μm, from about 5 μm to about 8 μm, from about 6 μm to about 9 μm, from about 7 μm to about 10 μm, or from about 8 μm to about 11 μm) of the tissue to be ablated. In some cases, a composition including one or more ionic liquids (e.g., a composition including a LATTE solution) can be administered to a mammal (e.g., a human) without the need for any anesthesia (e.g., without the need for general anesthesia). In some cases, a composition including one or more ionic liquids (e.g., a composition including a LATTE solution) can be administered to a mammal (e.g., human) using a guided injection (e.g., using ultrasound guidance). In some cases, when a composition is administered to a mammal (e.g., a human) by a percutaneous injection, a single injection can be used to administer the composition. In some cases, when a composition is administered to a mammal (e.g., a human) by a percutaneous injection, two or more (e.g., two, three, four, five, or more) injections can be used to administer the composition. For example, a multi-hole injection or a multiprong injection can be used to administer two or more (e.g., two, three, four, five, or more) injections to a mammal. In some cases, a composition including one or more ionic liquids (e.g., a composition including a LATTE solution) can be administered to a mammal (e.g., a human) by a topical application; e.g., sprayed on to tissue.

A composition including one or more ionic liquids (e.g., a composition including a LATTE solution) can used to ablate at least a portion of one or more tissues within any appropriate mammal. Examples of mammals within which one or more tissues can be ablated as described herein include, without limitation, humans, non-human primates such as monkeys, horses, bovine species, porcine species, dogs, cats, horses, cows, pigs, sheep, mice, rabbit, and rats.

A composition including one or more ionic liquids (e.g., a composition including a LATTE solution) can used to ablate at least a portion of any type of tissue. Examples of tissues that can be ablated using an ionic liquid (e.g., a composition including a LATTE solution) include, without limitation, fat tissue, cardiac tissue, connective tissue (e.g., blood), bone tissue, synovial tissue, abscess tissue, and cysts. In some cases, a tissue can be a tumor tissue (e.g., can include one or more cancer cells). A tumor tissue can be a benign tumor tissue or a malignant tumor tissue. In some cases, a composition including one or more ionic liquids (e.g., a composition including a LATTE solution) can be used to create an ablation zone within a mammal (e.g., a human). For example, a composition including one or more ionic liquids (e.g., a composition including a LATTE solution) can spread (e.g., can spread from a site of administration) in a circumferential fashion to create an ablation zone within a mammal (e.g., a human). An ablation zone can be any appropriate size. In some cases, a composition including one or more ionic liquids (e.g., a composition including a LATTE solution) can create an ablation zone of up to about 5 cm (e.g., across a longest dimension) within a mammal. For example, a composition including one or more ionic liquids (e.g., a composition including a LATTE solution) can create an ablation zone having a dimeter of from about 0.1 cm to about 5 cm (e.g., from about 0.1 cm to about 4.5 cm, from about 0.1 cm to about 4 cm, from about 0.1 cm to about 3.5 cm, from about 0.1 cm to about 3 cm, from about 0.1 cm to about 2.5 cm, from about 0.1 cm to about 2 cm, from about 0.1 cm to about 1.5 cm, from about 0.1 cm to about 1 cm, from about 0.1 cm to about 0.5 cm, from about 0.5 cm to about 4 cm, from about 1 cm to about 4 cm, from about 1.5 cm to about 4 cm, from about 2 cm to about 4 cm, from about 2.5 cm to about 4 cm, from about 2.8 cm to about 4 cm, from about 3 cm to about 4 cm, from about 3.2 cm to about 4 cm, from about 3.5 cm to about 4 cm from about 0.5 cm to about 3.8 cm from about 1 cm to about 3.5 cm, from about 2 cm to about 3 cm, or from about 1 cm to about 2 cm) within a mammal.

In some cases, a composition including one or more ionic liquids (e.g., a composition including a LATTE solution) can be used to reduce the number of cells within an ablation zone. For example, a composition including one or more ionic liquids (e.g., a composition including a LATTE solution) can be administered to a mammal (e.g., a human) to reduce the number of cells within an ablation zone created by the composition by, for example, 10, 20, 30, 40, 50, 60, 70, 80, 90, 95, or more percent.

In some cases, a composition including one or more ionic liquids (e.g., a composition including a LATTE solution) can be used to induce an inflammatory reaction within an ablation zone created by the composition. For example, a composition including one or more ionic liquids (e.g., a composition including a LATTE solution) can be administered to a mammal (e.g., a human) to recruit T-cells (e.g., activated T-cells) to an ablation zone created by the composition.

In some cases, a composition including one or more ionic liquids (e.g., a composition including a LATTE solution) can be used to treat a mammal (e.g., a human) having a disease or disorder that could benefit from the ablation of at least a portion of a tissue within the mammal. For example, a composition including one or more ionic liquids (e.g., a composition including a LATTE solution) can be used to ablate tumor tissue within a mammal having cancer (e.g., to treat the mammal). In some cases, a composition including one or more ionic liquids (e.g., a composition including a LATTE solution) can be used to ablate fat tissue within a mammal having a disease or disorder associated with fat accumulation (e.g., to treat the mammal). In some cases, a composition including one or more ionic liquids (e.g., a composition including a LATTE solution) can be used to ablate cardiac tissue within a mammal having a heart disease or disorder (e.g., to treat the mammal). In some cases, a composition including one or more ionic liquids (e.g., a composition including a LATTE solution) can be used to ablate one or more blood clots within a mammal (e.g., to treat the mammal). In some cases, a composition including one or more ionic liquids (e.g., a composition including a LATTE solution) can be used to ablate one or more infected tissues within a mammal (e.g., to treat the mammal).

When treating a mammal (e.g., a human) having cancer as described herein (e.g., by administering a composition including one or more ionic liquids such as a LATTE solution), the composition can be effective to reduce the size of the cancer in the mammal (e.g., to reduce the number of cancer cells in the mammal and/or to reduce the volume of one or more tumors in the mammal). For example, a composition including one or more ionic liquids (e.g., a composition including a LATTE solution) can be administered to a mammal (e.g., a human) in need thereof (e.g., a human having cancer) as described herein to reduce the size of the cancer by, for example, 10, 20, 30, 40, 50, 60, 70, 80, 90, 95, or more percent. In some cases, a composition including one or more ionic liquids (e.g., a composition including a LATTE solution) can be administered to a mammal (e.g., a human) in need thereof (e.g., a human having cancer) as described herein to reduce the size of the cancer by at least 2-fold (e.g., by 2-fold, 3-fold, 4-fold, 5-fold, or more).

In some cases, when treating a mammal (e.g., a human) having cancer as described herein (e.g., by administering a composition including one or more ionic liquids such as a LATTE solution), the composition can be effective to facilitate entry of one or more T cells (e.g., activated T cells) into a tumor (e.g., to increase the amount of one or more T cells in the tumor) within the mammal. For example, a composition including one or more ionic liquids (e.g., a composition including a LATTE solution) can be administered to a mammal (e.g., a human) in need thereof (e.g., a human having cancer) as described herein to increase the amount of one or more T cells in a tumor within the mammal by, for example, 10, 20, 30, 40, 50, 60, 70, 80, 90, 95, or more percent. Examples of T cells that can be increased in a tumor following administration of a composition including one or more ionic liquids (e.g., a composition including a LATTE solution) can include, without limitation, CD4+ T cells, CD8+ T cells, and natural killer T cells.

In some cases, when treating a mammal (e.g., a human) having cancer as described herein (e.g., by administering a composition including one or more ionic liquids such as a LATTE solution), the composition can be effective to induce an inflammatory reaction within an ablation zone created by the composition. For example, a composition including one or more ionic liquids (e.g., a composition including a LATTE solution) can be administered to locally accessible cancerous lesion (e.g., a locally accessible metastatic lesion such as a lesion on the skin or a peritoneal surface) on a mammal (e.g., a human) in need thereof (e.g., a human having cancer) as described herein to recruit T-cells (e.g., activated T-cells) to treat the locally accessible cancerous lesion. For example, a composition including one or more ionic liquids (e.g., a composition including a LATTE solution) can be administered to locally accessible cancerous lesion (e.g., a locally accessible metastatic lesion such as a lesion on the skin or a peritoneal surface) on a mammal (e.g., a human) in need thereof (e.g., a human having cancer) as described herein to recruit T-cells (e.g., activated T-cells) to treat other inaccessible cancerous lesions within the mammal.

When treating a mammal (e.g., a human) having cancer as described herein (e.g., by administering a composition including one or more ionic liquids such as a LATTE solution), the cancer can be any type of cancer. In some cases, a cancer can include one or more solid tumors. For example, a cancer can include one or more fat laden solid tumors. In some cases, a cancer can be a blood cancer. In some cases, a cancer can be a primary cancer. In some cases, a cancer can be a metastatic cancer. In some cases, a cancer can be a cancer that has escaped and/or has been non-responsive to chemotherapy (e.g., a chemoresistant cancer). Examples of cancers that can be treated as described herein (e.g., with a composition including one or more ionic liquids such as a LATTE solution) include, without limitation, liver cancers (e.g., HCCs), bile duct cancers (e.g., cholangiocarcinoma), pancreatic cancers (e.g., pancreatic adenocarcinomas), colorectal cancers (e.g., colorectal cancer liver metastasis (CRCLM)), renal cancers, ovarian cancers, breast cancers, prostate cancers, colon cancers, bladder cancers, lung cancers, thyroid cancers, melanomas, brain cancers, stomach cancers, cervical cancers, uterine cancers, skin cancers, synovial cancers, appendiceal cancers, adrenal cancers, sarcomas, and lymphomas.

In some cases, methods of treating a mammal having cancer described herein (e.g., by administering a composition including one or more ionic liquids such as a LATTE solution) also can include identifying a mammal as having cancer. Examples of methods for identifying a mammal as having cancer include, without limitation, physical examination, laboratory tests (e.g., blood and/or urine), biopsy, imaging tests (e.g., X-ray, PET/CT, MRI, and/or ultrasound), nuclear medicine scans (e.g., bone scans), endoscopy, and/or genetic tests.

In some cases, when a composition including one or more ionic liquids (e.g., a composition including a LATTE solution) is used to treat a mammal (e.g., a human) having cancer, a composition including one or more ionic liquids (e.g., a composition including a LATTE solution) can include the ionic liquid(s) as the sole active agent used to treat the cancer.

In some cases when a composition including one or more ionic liquids (e.g., a composition including a LATTE solution) is used to treat a mammal (e.g., a human) having cancer, a composition including one or more ionic liquids can include one or more (e.g., one, two, three, four, five or more) additional therapeutic agents used to treat the cancer. In some cases, a therapeutic agent used to treat cancer can be a chemotherapy agent. In some cases, a therapeutic agent used to treat cancer can be a radioactive agent. In some cases, a therapeutic agent used to treat cancer can be an immunotherapy agent (e.g., an immune checkpoint inhibitor such as anti-PD-1 antibodies and/or anti-PD-L1 antibodies). In some case, a therapeutic agent used to treat cancer can be a stimulator of interferon (IFN) gene (STING) agonist. Examples of therapeutic agents used to treat a cancer that can be administered to a mammal having cancer together with a composition including one or more ionic liquids (e.g., a composition including a LATTE solution) include, without limitation, doxorubicin, cisplatin, paclitaxel, olaparib, everolimus, mitomycin, radioactive isotopes (e.g., yttrium Y-90, lutetium-177, actinium, fluorine-18, gallium-67, krypton-81m, rubidium-82, nitrogen-13, technetium-99m, indium-111, iodine-123, xenon-133, and thallium-201), atezolizumab, bevacizumab, cabozantinib-s-malate, ramucirumab, pembrolizumab, lenvatinib mesylate, sorafenib tosylate, nivolumab, pemigatinib, pembrolizumab, ramucirumab, regorafenib, and abemaciclib. In some cases, the one or more additional therapeutic agents can be administered together with the composition including one or more ionic liquids (e.g., a composition including a LATTE solution). In some cases, the one or more additional therapeutic agents can be administered independent of the composition including one or more ionic liquids (e.g., a composition including a LATTE solution). When the one or more additional therapeutic agents are administered independent of the composition including one or more ionic liquids (e.g., a composition including a LATTE solution), the composition including one or more ionic liquids (e.g., a composition including a LATTE solution) can be administered first, and the one or more additional therapeutic agents administered second, or vice versa.

In some cases, methods for treating a mammal (e.g., a human) having cancer as described herein (e.g., by administering a composition including one or more ionic liquids such as a LATTE solution) also can include subjecting the mammal to one or more (e.g., one, two, three, four, five or more) additional treatments (e.g., therapeutic interventions) that are effective to treat cancer. Examples of additional treatments that can be used as described herein to treat cancer include, without limitation, radiation to therapy, surgery, percutaneous tumor ablation, transcatheter embolization, and cancer immunotherapy. In some cases, the one or more additional treatments that are effective to treat cancer can be performed at the same time as the administration of the composition including one or more ionic liquids (e.g., a composition including a LATTE solution). In some cases, the one or more additional treatments that are effective to treat cancer can be performed before and/or after the administration of the composition including one or more ionic liquids (e.g., a composition including a LATTE solution).

When treating a mammal (e.g., a human) having a disease or disorder associated with fat accumulation as described herein (e.g., by administering a composition including one or more ionic liquids such as a LATTE solution), the composition can be effective to reduce the number of adipocytes within the mammal. For example, a composition including one or more ionic liquids (e.g., a composition including a LATTE solution) can be administered to a mammal (e.g., a human) in need thereof (e.g., a human having cancer) as described herein to reduce the number of adipocytes within the mammal by, for example, 10, 20, 30, 40, 50, 60, 70, 80, 90, 95, or more percent.

When treating a mammal (e.g., a human) having a disease or disorder associated with fat accumulation as described herein (e.g., by administering a composition including one or more ionic liquids such as a LATTE solution), the disease or disorder associated with fat accumulation can be any disease or disorder associated with fat accumulation. Examples of diseases and disorders associated with fat accumulation that can be treated as described herein (e.g., with a composition including one or more ionic liquids such as a LATTE solution) include, without limitation, being overweight (e.g., obesity), lipedema, lipid storage diseases (e.g., glycogen storage disease), and cancers characterized by fat laden tumors.

In some cases, methods of treating a mammal (e.g., a human) having a disease or disorder associated with fat accumulation as described herein (e.g., by administering a composition including one or more ionic liquids such as a LATTE solution) also can include identifying a mammal as having a disease or disorder associated with fat accumulation. Examples of methods for identifying a mammal as having a disease or disorder associated with fat accumulation include, without limitation, physical examination, laboratory tests (e.g., blood and/or urine), CT imaging, and/or MRI.

In some cases, when a composition including one or more ionic liquids (e.g., a composition including a LATTE solution) is used to treat a mammal (e.g., a human) having a disease or disorder associated with fat accumulation, a composition including one or more ionic liquids (e.g., a composition including a LATTE solution) can include the ionic liquid(s) as the sole active agent used to treat the disease or disorder associated with fat accumulation.

In some cases, when a composition including one or more ionic liquids (e.g., a composition including a LATTE solution) is used to treat a mammal (e.g., a human) having a disease or disorder associated with fat accumulation, a composition including one or more ionic liquids (e.g., a composition including a LATTE solution) can include one or more (e.g., one, two, three, four, five or more) additional therapeutic agents used to treat the disease or disorder associated with fat accumulation. Examples of therapeutic agents used to treat a disease or disorder associated with fat accumulation that can be administered to a mammal having a disease or disorder associated with fat accumulation together with a composition including one or more ionic liquids (e.g., a composition including a LATTE solution) include, without limitation, orlistat, phentermine, topiramate, bupropion, naltrexone, liraglutide, and combinations thereof. In some cases, the one or more additional therapeutic agents can be administered together with the composition including one or more ionic liquids (e.g., a composition including a LATTE solution). In some cases, the one or more additional therapeutic agents can be administered independent of the composition including one or more ionic liquids (e.g., a composition including a LATTE solution). When the one or more additional therapeutic agents are administered independent of the composition including one or more ionic liquids (e.g., a composition including a LATTE solution), the composition including one or more ionic liquids (e.g., a composition including a LATTE solution) can be administered first, and the one or more additional therapeutic agents administered second, or vice versa.

In some cases, methods for treating a mammal (e.g., a human) having a disease or disorder associated with fat accumulation as described herein (e.g., by administering a composition including one or more ionic liquids such as a LATTE solution) also can include subjecting the mammal to one or more (e.g., one, two, three, four, five or more) additional treatments (e.g., therapeutic interventions) that are effective to treat a disease or disorder associated with fat accumulation. Examples of additional treatments that can be used as described herein to treat a disease or disorder associated with fat accumulation include, without limitation, dietary changes (e.g., dietary changes to reducing calories), increased activity levels, endoscopic procedures used for weight loss, bariatric surgery, vagal nerve blockade, and left gastric artery embolization. In some cases, the one or more additional treatments that are effective to treat a disease or disorder associated with fat accumulation can be performed at the same time as the administration of the composition including one or more ionic liquids (e.g., a composition including a LATTE solution). In some cases, the one or more additional treatments that are effective to treat a disease or disorder associated with fat accumulation can be performed before and/or after the administration of the composition including one or more ionic liquids (e.g., a composition including a LATTE solution).

When treating a mammal (e.g., a human) having a heart disease or disorder as described herein (e.g., by administering a composition including one or more ionic liquids such as a LATTE solution), the composition can be effective to reduce the amount of cardiac tissue (e.g., to reduce the number of atrophied cardiomyocytes and/or hypertrophied cardiomyocytes within cardiac muscle) within the mammal. For example, a composition including one or more ionic liquids (e.g., a composition including a LATTE solution) can be administered to a mammal (e.g., a human) in need thereof (e.g., a human having cancer) as described herein to reduce the number of atrophied cardiomyocytes within the mammal by, for example, 10, 20, 30, 40, 50, 60, 70, 80, 90, 95, or more percent.

When treating a mammal (e.g., a human) having a heart disease or disorder as described herein (e.g., by administering a composition including one or more ionic liquids such as a LATTE solution), the heart disease or disorder can be any heart disease or disorder. Examples of heart diseases and disorders that can be treated as described herein (e.g., with a composition including one or more ionic liquids such as a LATTE solution) include, without limitation, hypertrophic cardiomyopathy, arrhythmias, and atrial fibrillation foci.

In some cases, methods of treating a mammal (e.g., a human) having a heart disease or disorder as described herein (e.g., by administering a composition including one or more ionic liquids such as a LATTE solution) also can include identifying a mammal as having a heart disease or disorder. Examples of methods for identifying a mammal as having a disease or disorder associated with fat accumulation include, without limitation, physical examination, and/or laboratory tests (e.g., blood and/or urine).

In some cases, when a composition including one or more ionic liquids (e.g., a composition including a LATTE solution) is used to treat a mammal (e.g., a human) having a heart disease or disorder, a composition including one or more ionic liquids (e.g., a composition including a LATTE solution) can include the ionic liquid(s) as the sole active agent used to treat the heart disease or disorder.

In some cases, when a composition including one or more ionic liquids (e.g., a composition including a LATTE solution) is used to treat a mammal (e.g., a human) having a heart disease or disorder, a composition including one or more ionic liquids (e.g., a composition including a LATTE solution) can include one or more (e.g., one, two, three, four, five or more) additional therapeutic agents used to treat the heart disease or disorder. In some cases, a therapeutic agent used to treat a heart disease or disorder can be an anticoagulant. In some cases, a therapeutic agent used to treat a heart disease or disorder can be an ACE Inhibitor. In some cases, a therapeutic agent used to treat a heart disease or disorder can be a beta blocker. In some cases, a therapeutic agent used to treat a heart disease or disorder can be a calcium channel blocker. In some cases, a therapeutic agent used to treat a heart disease or disorder can be a cholesterol-lowering medication. Examples of therapeutic agents used to treat a heart disease or disorder that can be administered to a mammal having a heart disease or disorder together with a composition including one or more ionic liquids (e.g., a composition including a LATTE solution) include, without limitation, captopril, enalapril, fosinopril, lisinopril, perindopril, quinapril, ramipril, trandolapril, and combinations thereof. In some cases, the one or more additional therapeutic agents can be administered together with the composition including one or more ionic liquids (e.g., a composition including a LATTE solution). In some cases, the one or more additional therapeutic agents can be administered independent of the composition including one or more ionic liquids (e.g., a composition including a LATTE solution). When the one or more additional therapeutic agents are administered independent of the composition including one or more ionic liquids (e.g., a composition including a LATTE solution), the composition including one or more ionic liquids (e.g., a composition including a LATTE solution) can be administered first, and the one or more additional therapeutic agents administered second, or vice versa.

In some cases, methods for treating a mammal (e.g., a human) having a heart disease or disorder as described herein (e.g., by administering a composition including one or more ionic liquids such as a LATTE solution) also can include subjecting the mammal to one or more (e.g., one, two, three, four, five or more) additional treatments (e.g., therapeutic interventions) that are effective to treat a heart disease or disorder. Examples of additional treatments that can be used as described herein to treat a heart disease or disorder include, without limitation, dietary changes (e.g., dietary changes to reducing calories), and increased activity levels. In some cases, the one or more additional treatments that are effective to treat a heart disease or disorder can be performed at the same time as the administration of the composition including one or more ionic liquids (e.g., a composition including a LATTE solution). In some cases, the one or more additional treatments that are effective to treat a heart disease or disorder can be performed before and/or after the administration of the composition including one or more ionic liquids (e.g., a composition including a LATTE solution).

When treating a mammal (e.g., a human) having one or more blood clots as described herein (e.g., by administering a composition including one or more ionic liquids such as a LATTE solution), the composition can be effective to reduce the size of the blood clot(s) in the mammal (e.g., reduce the number of blood clots in the mammal and/or the volume of one or more blood clots in the mammal). For example, a composition including one or more ionic liquids (e.g., a composition including a LATTE solution) can be administered to a mammal (e.g., a human) in need thereof (e.g., a human having one or more blood clots) as described herein to reduce the size of the blood clot(s) by, for example, 10, 20, 30, 40, 50, 60, 70, 80, 90, 95, or more percent.

When treating a mammal (e.g., a human) having one or more blood clots as described herein (e.g., by administering a composition including one or more ionic liquids such as a LATTE solution), the mammal can have a disease or disor-der associated with one or more blood clots. Examples of diseases and disorders associate with one or more blood clots that can be treated as described herein (e.g., with a composition including one or more ionic liquids such as a LATTE solution) include, without limitation, deep vein thrombosis (e.g., acute deep vein thrombosis and chronic deep vein thrombosis), antiphospholipid syndrome, arterio-sclerosis, atherosclerosis, embolism (e.g., pulmonary embo-lism), stroke, and arterial thrombosis.

In some cases, methods of treating a mammal having one or more blood clots described herein (e.g., by administering a composition including one or more ionic liquids such as a LATTE solution) also can include identifying a mammal as having one or more blood clots. Examples of methods for identifying a mammal as having one or more blood clots include, without limitation, physical examination, and/or imaging tests (e.g., venography and/or MRI).

In some cases, when a composition including one or more ionic liquids (e.g., a composition including a LATTE solu-tion) is used to treat a mammal (e.g., a human) having one or more blood clots, a composition including one or more ionic liquids (e.g., a composition including a LATTE solu-tion) can include the ionic liquid(s) as the sole active agent used to treat the blood clot(s).

In some cases, when a composition including one or more ionic liquids (e.g., a composition including a LATTE solu-tion) is used to treat a mammal (e.g., a human) having one or more blood clots, a composition including one or more ionic liquids (e.g., a composition including a LATTE solu-tion) can include one or more (e.g., one, two, three, four, five or more) additional therapeutic agents used to treat the blood clot(s). In some cases, a therapeutic agent used to treat blood clot(s) can be an anticoagulant. In some cases, a therapeutic agent used to treat blood clot(s) can be a thrombolytic. Examples of therapeutic agents used to treat blood clot(s) that can be administered to a mammal having cancer together with a composition including one or more ionic liquids (e.g., a composition including a LATTE solution) include, without limitation, heparin, warfarin, dabigatran, apixaban, and rivaroxaban. In some cases, the one or more additional therapeutic agents can be administered together with the composition including one or more ionic liquids (e.g., a composition including a LATTE solution). In some cases, the one or more additional therapeutic agents can be administered independent of the composition including one or more ionic liquids (e.g., a composition including a LATTE solution). When the one or more additional thera-peutic agents are administered independent of the compo-sition including one or more ionic liquids (e.g., a composi-tion including a LATTE solution), the composition including one or more ionic liquids (e.g., a composition including a LATTE solution) can be administered first, and the one or more additional therapeutic agents administered second, or vice versa.

In some cases, methods for treating a mammal (e.g., a human) having one or more blood clots as described herein (e.g., by administering a composition including one or more ionic liquids such as a LATTE solution) also can include subjecting the mammal to one or more (e.g., one, two, three, four, five or more) additional treatments (e.g., therapeutic interventions) that are effective to treat one or more blood clots. Examples of additional treatments that can be used as described herein to treat one or more blood clots include, without limitation, thrombectomy, thrombolytic therapy, and inferior vena cava filter. In some cases, the one or more additional treatments that are effective to treat one or more blood clots can be performed at the same time as the administration of the composition including one or more ionic liquids (e.g., a composition including a LATTE solution). In some cases, the one or more additional treatments that are effective to treat one or more blood clots can be performed before and/or after the administration of the composition including one or more ionic liquids (e.g., a composition including a LATTE solution).

When treating a mammal (e.g., a human) having one or more infected tissues as described herein (e.g., by administering a composition including one or more ionic liquids such as a LATTE solution), the composition can be effective to reduce the number of infected cells within the mammal. For example, a composition including one or more ionic liquids (e.g., a composition including a LATTE solution) can be administered to a mammal (e.g., a human) in need thereof (e.g., a human having cancer) as described herein to reduce the number of infected cells within the mammal by, for example, 10, 20, 30, 40, 50, 60, 70, 80, 90, 95, or more percent.

When treating a mammal (e.g., a human) having one or more infected tissues as described herein (e.g., by administering a composition including one or more ionic liquids such as a LATTE solution), the infected tissue(s) can be any type of tissue. In some cases, an infected tissue can be at a wound site (e.g., a diabetic wound or a surgical wound). Examples of tissues that can be infected and that can be treated as described herein (e.g., with a composition including one or more ionic liquids such as a LATTE solution) include, without limitation, skin, abscess cavities, and enterocutaneous fistulas.

In some cases, methods of treating a mammal (e.g., a human) having one or more infected tissues as described herein (e.g., by administering a composition including one or more ionic liquids such as a LATTE solution) also can include identifying a mammal as having an infected tissue. Examples of methods for identifying a mammal as having an infected tissue include, without limitation, physical examination, and/or laboratory tests (e.g., blood and/or urine).

In some cases, when a composition including one or more ionic liquids (e.g., a composition including a LATTE solution) is used to treat a mammal (e.g., a human) having one or more infected tissues, a composition including one or more ionic liquids (e.g., a composition including a LATTE solution) can include the ionic liquid(s) as the sole active agent used to treat the infected tissue(s).

In some cases, when a composition including one or more ionic liquids (e.g., a composition including a LATTE solution) is used to treat a mammal (e.g., a human) having one or more infected tissues, a composition including one or more ionic liquids (e.g., a composition including a LATTE solution) can include one or more (e.g., one, two, three, four, five or more) additional therapeutic agents used to treat the infected tissue(s). Examples of therapeutic agents used to treat an infected tissue that can be administered to a mammal having one or more infected tissues together with a composition including one or more ionic liquids (e.g., a composition including a LATTE solution) include, without limitation, antibiotics, antifungals, and combinations thereof. In some cases, the one or more additional therapeutic agents can be administered together with the composition including one or more ionic liquids (e.g., a composition including a LATTE solution). In some cases, the one or more additional therapeutic agents can be administered independent of the composition including one or more ionic liquids (e.g., a composition including a LATTE solution). When the one or more additional therapeutic agents are administered independent of the composition including one or more ionic liquids (e.g., a composition including a LATTE solution), the composition including one or more ionic liquids (e.g., a composition including a LATTE solution) can be administered first, and the one or more additional therapeutic agents administered second, or vice versa. The invention will be further described in the following examples, which do not limit the scope of the invention described in the claims.

EXAMPLES

Example 1: Percutaneous Liquid Ablation Agent for Tumor Treatment and Drug Delivery A formulation of a eutectic ionic liquid was developed that can be used to ablate liver tumor tissue and, concurrently, to deliver drugs uniformly throughout the ablation zone. The choline-geranate (CAGE) ionic liquid formulation referred to herein as LATTE was prepared, and a needle based delivery of the formulation was tested in normal rat, rabbit and pig liver tissues; diffusion capability was monitored by microCT and real-time MRI imaging, and drug carrying capability was monitored by infrared imaging. Subsequently, ablation capability was demonstrated in a rat liver tumor model, rabbit VX2 liver tumor model and, finally, in 12 human tumors ex vivo.

LATTE was synthesized using salt metathesis at 1:1 molar ratio of choline bicarbonate and geranic acid creating deep eutectic ionic liquid as reported elsewhere (Banerjee et al., *Adv Healthc Mater* 6:1601411 (2017)). Briefly, a neat choline and geranate ionic liquid was first prepared using salt metathesis. For this purpose, one equivalent of neat geranic acid (Sigma Aldrich, St. Louis, MO) was recrystallized 5 times at −70° C. in acetone, in a 500-mL round bottom flask and added to one equivalent volume of choline bicarbonate (80 wt % solution, Sigma Aldrich, St. Louis, MO). The mixture was stirred at room temperature until $CO_2$ evolution ceased. Residual $H_2O$ was removed by rotary evaporation at 60° C. for 2 hours and drying in a vacuum oven for 96 hours at 60° C. A variety of LATTE mixtures were prepared by mixing neat LATTE (100%) with 0.25 mg/mL indocyanine green normal saline solution (ICG, Sigma-Aldrich, St. Louis, MO) at predetermined ratios. For example, a 6.25%-LATTE solution was prepared by mixing 6.25 wt % neat LATTE and 93.75 wt % of ICG solution. Using this approach, 25%-LATTE, 50%-LATTE, and 100%-LATTE (neat) were also prepared for characterization. The liver of healthy rats received three sub-capsular injections of 50%, 25%, or 6.25%-LATTE solution containing an equivalent amount of indocyanine green (ICG) and the radiodense nanoparticle contrast agent, Exitron (FIG. 1a,b). The inclusion of a contrast agent allows tracking during and after the intervention by standard computed tomography (CT) imaging, and in the case of Exitron, to demonstrate LATTE's capability to cotransport nanoparticles (i.e., 110 nm) throughout the ablation zone.

Figure 1C:
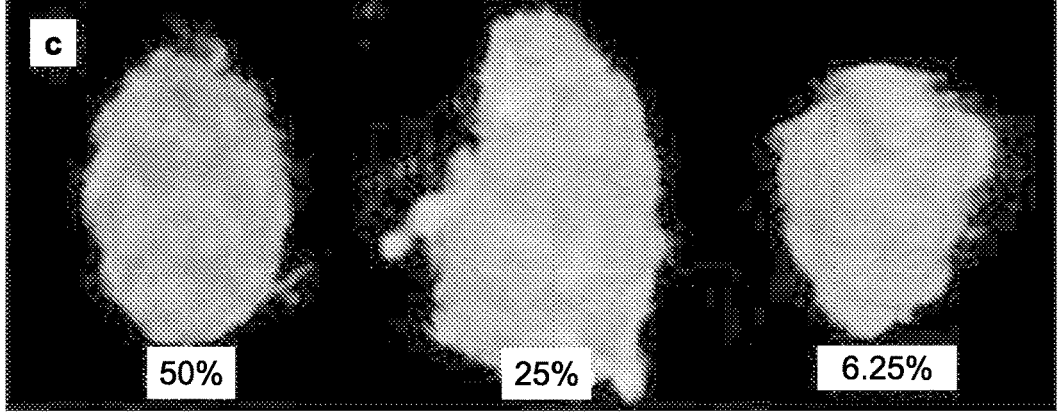
FIGS. 1C-1D. Representative micro-CT image and graphic representation of 3D volume analysis showing higher diffusion volume induced by 25% LATTE concentration (*p=0.03, **p=0.004, n=5).
Figure 1D:
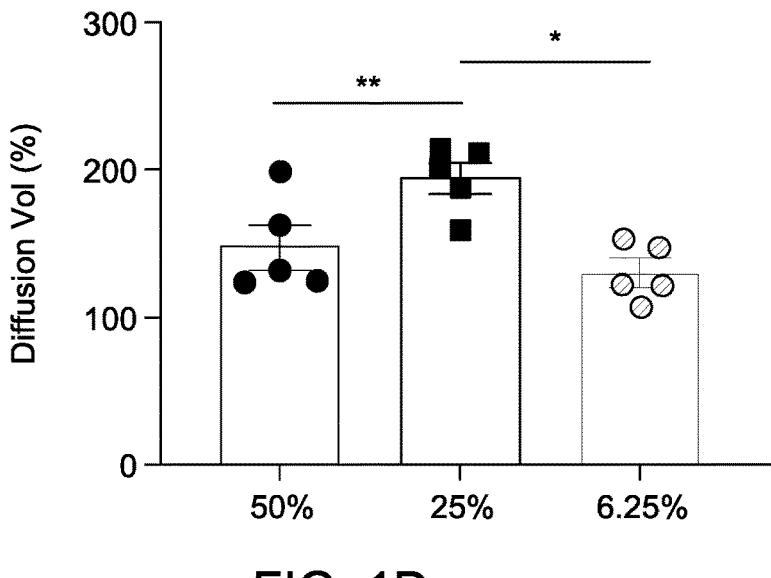
Figures 1E, 1F, 1G:
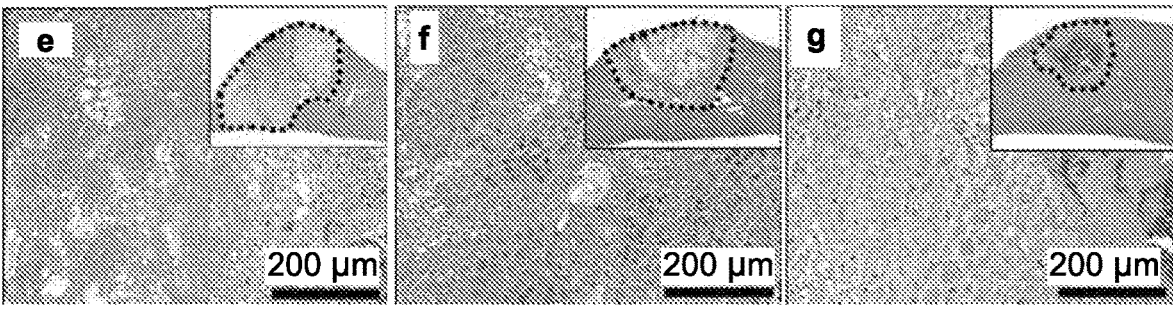
FIGS. 1E, 1F, and 1G. Micrographs of H&E-stained rat liver sections obtained at 24 hours after intraparenchymal injection of 50%, 25%, or 6.25% LATTE respectively showing necrotic area (dashed outline, scale bar, 200 $\mu$m).
Figure 1H:
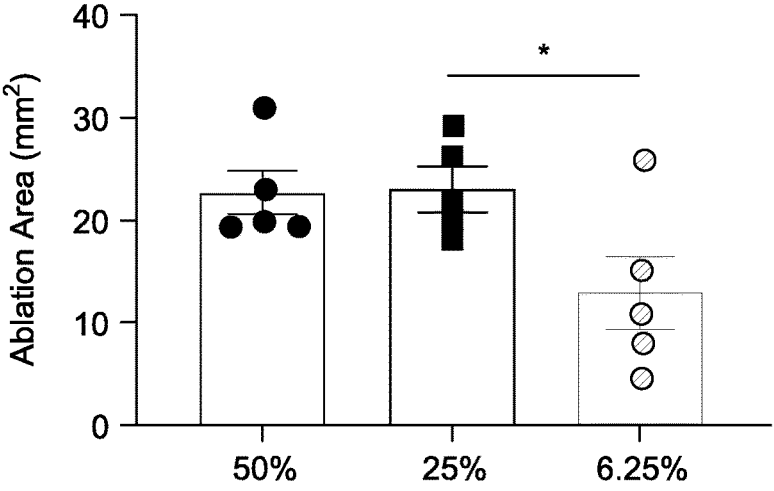
FIG. 1H. Morphometric analysis of necrotic area induced by 50, 25 or 6.25% LATTE revealed larger affected area in the 50% and 25% LATTE compared 6.25% LATTE injected site (* p=0.048, n=5).
Figure 1O:
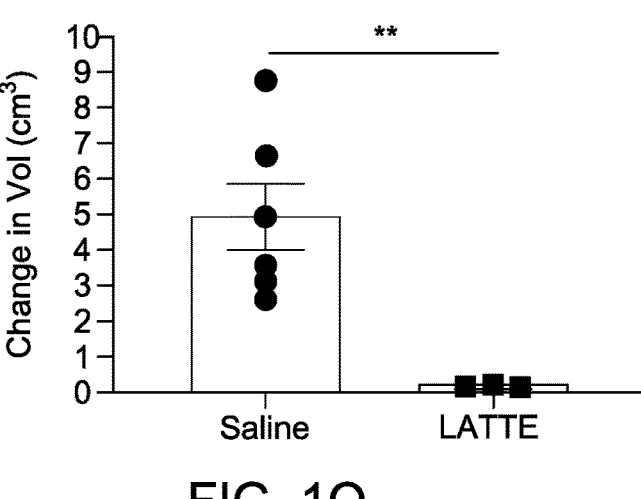

Following injection, LATTE showed immediate localized effects as it spread rapidly within the liver parenchyma, creating a well-demarcated ablation zone that remained visible at 24 hours without breaching the liver capsule (FIG. 1b). 3D reconstructed and segmented in vivo micro-CT images showed uniform enhancement in each treated site, whereas saline containing a similar amount of Exitron showed no enhancement (FIG. 1c). High resolution micro-CT analysis revealed larger diffusion volume with 25%-LATTE compared to 6.25% or 50% (FIG. 1d); this is likely the result of lower viscosity of 25%-LATTE compared to 50%-LATTE since liquid viscosity directly impacted its

Figure 2A:
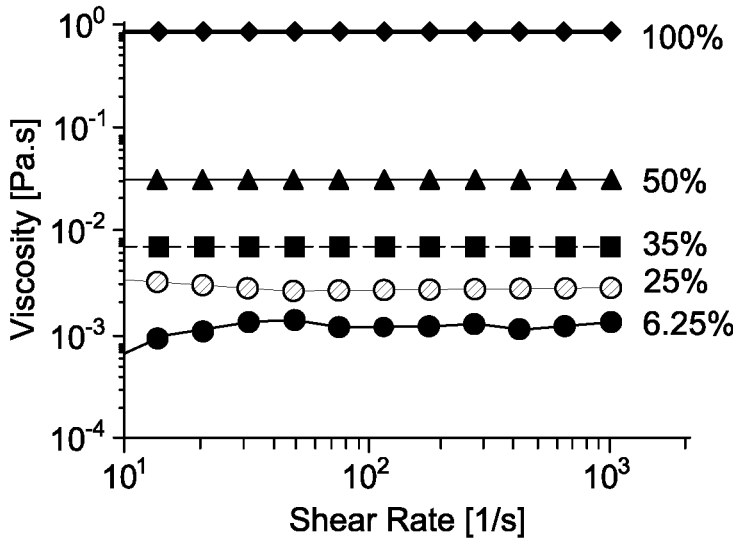
FIGS. 2A-2D. LATTE Viscosity and injection force testing.
Figure 2B:
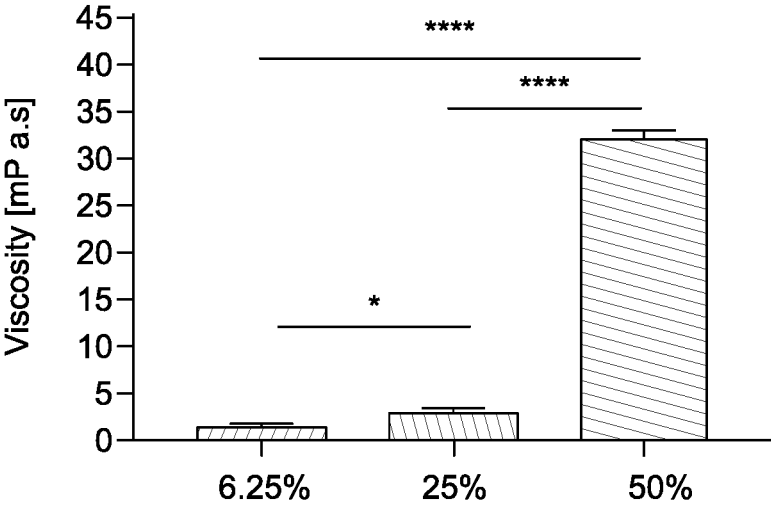
Figure 2C:
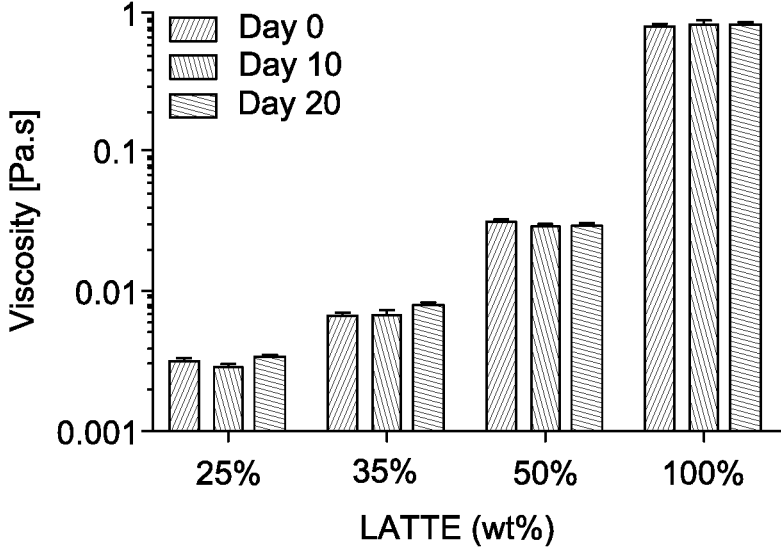
Figure 2D:
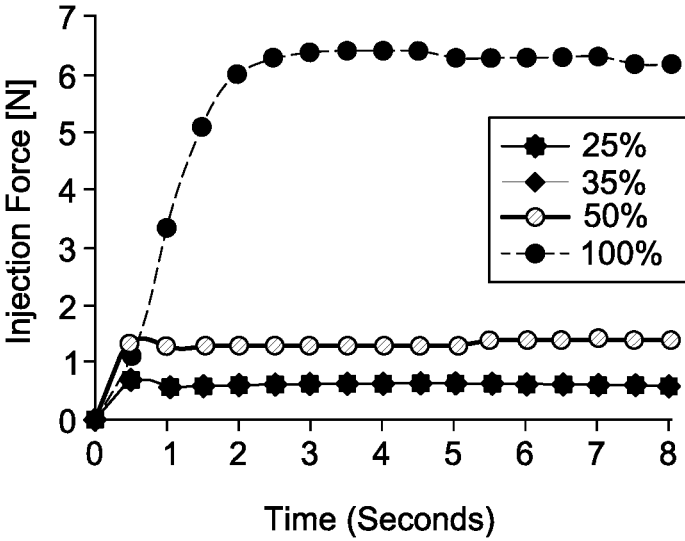

33 permeation and diffusion profile within tissues (FIG. 2a-c). In addition, 25%-LATTE demonstrated comfortable injection forces by hand to facilitate percutaneous needle-based intratumoral delivery (FIG. 2d). Histologic evaluation of the treated tissue sections revealed a similar ablation area caused by 50%-LATTE and 25%-LATTE, which were significantly greater than the size of the ablated liver parenchyma that received 6.25%-LATTE (FIG. 1e-h). The ablated zone showed necrosis associated with nuclear loss, scattered pooling of erythrocytes, and granulocyte infiltration which abruptly transitions to interstitial edema and cellular swelling along the periphery. These data suggested that LATTE possesses unique ability to transport and retain solubilized molecules while exerting potent tissue destruction effects throughout the treatment zone. Based on the favorable mechanical, micro-CT and histologic findings, 25%-LATTE was used in subsequent experiments.

Figures 1P, 1Q:
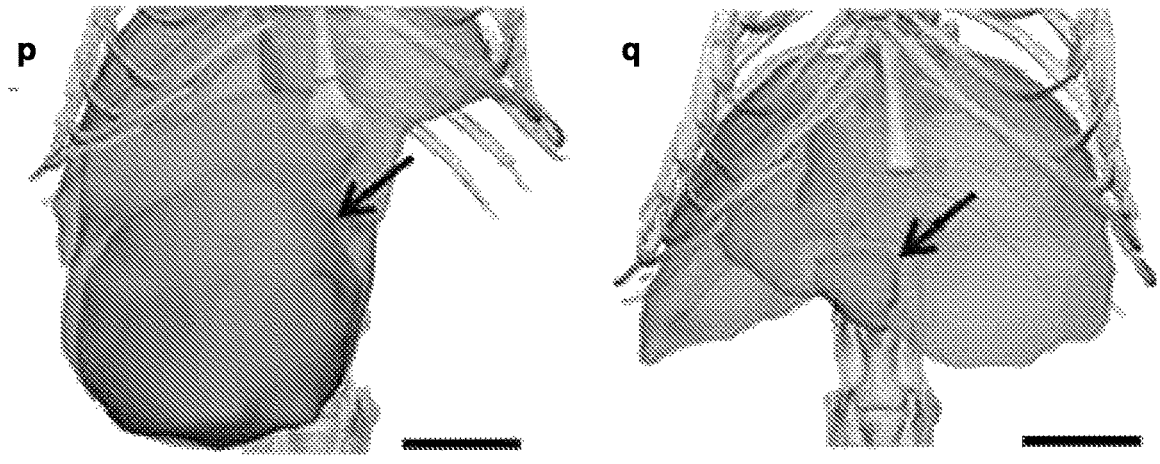
FIGS. 1P and 1Q. 3D rendered images of in vivo micro-CT scans following segmentation of normal rat liver from hypodense N1S1 tumor lesion (black arrow) at two weeks after direct injection with saline or LATTE respectively (scale bar, 1 cm).
Figure 1R:
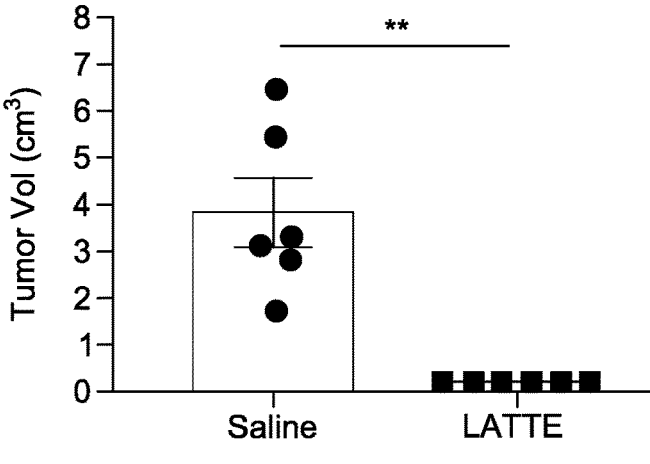
FIG. 1R. Quantitative micro-CT analysis of N1S1 tumor volume demonstrated markedly diminished lesions at two weeks after LATTE injection compared to saline (p=0.002).
Figure 1S:
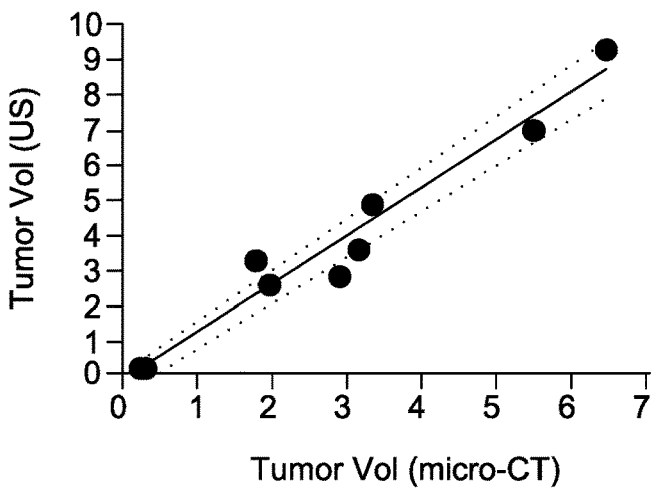
FIG. 1S. Linear regression plot of corresponding tumor volume determined by ultrasound (US) and micro-CT illustrating a linear relationship and significant correlation between the two-imaging modality (Pearson r=0.96, p<0.0001).
Figure 1T:
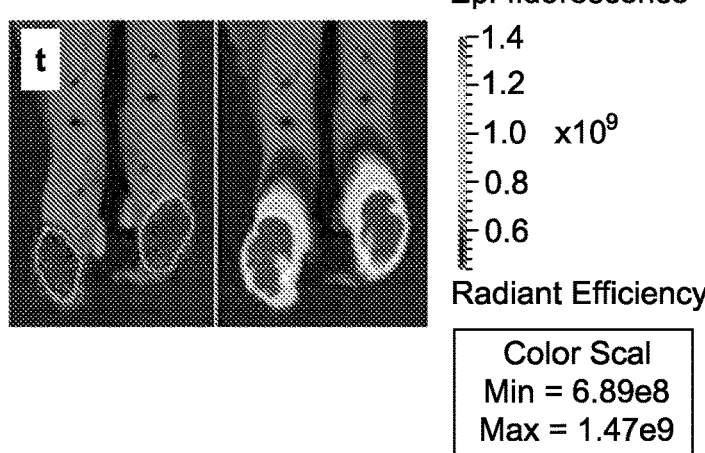
FIGS. 1T and 1U. NIRF scans of explanted rat liver bearing N1S1 tumors at two weeks after direct intratumoral injection with 25% LATTE or saline respectively.
Figure 1U:
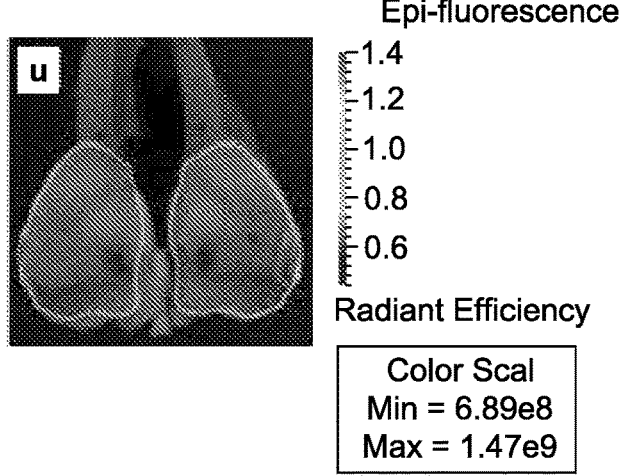
Figures 1V, 1W:
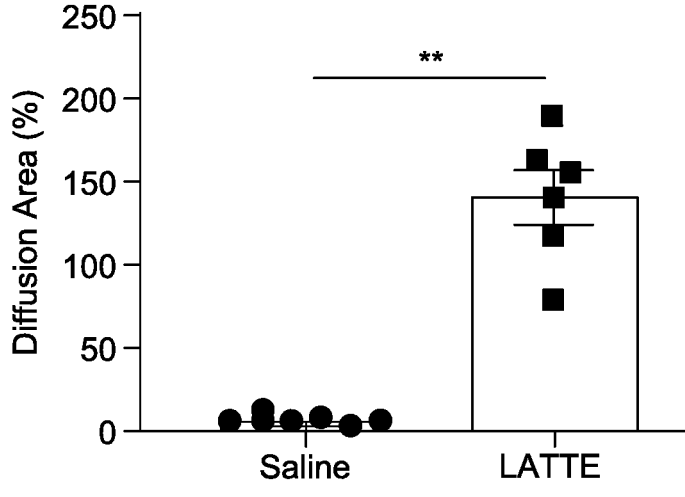
Figure 3A:
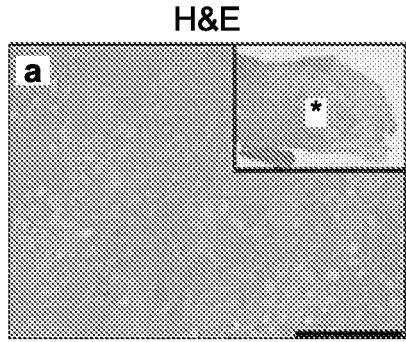
FIG. 3A-3I. Evaluating ablation effect and drug retention in N1S1 tumor injected with LATTE.
Figure 3B:
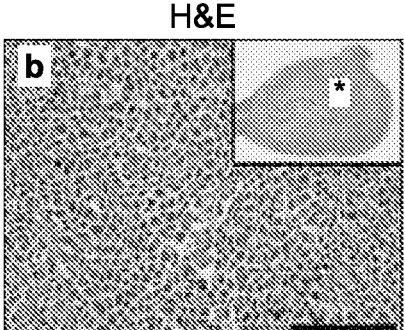
Figure 3C:
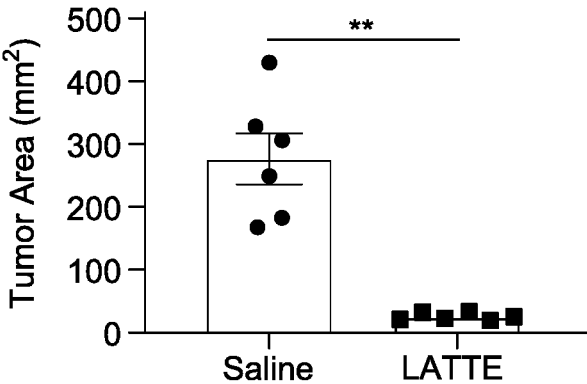
Figure 3D:
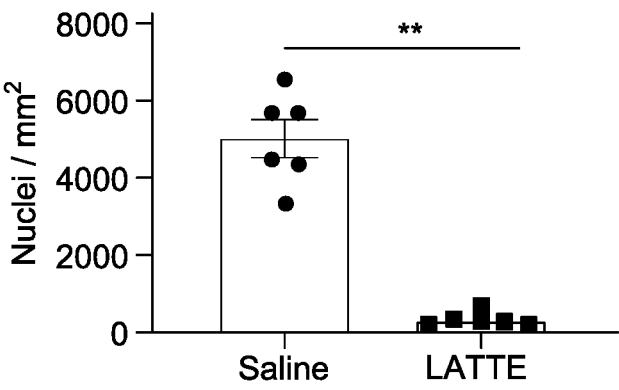
Figure 3E:
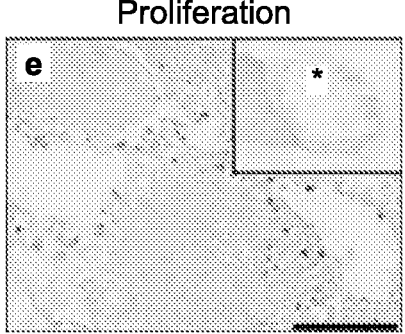
Figure 3F:
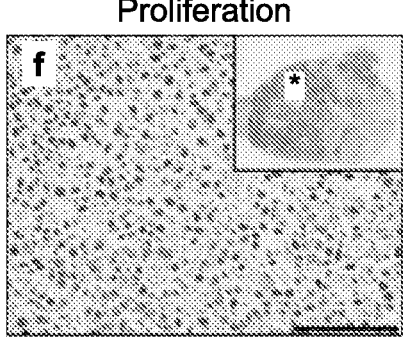
Figure 3G:
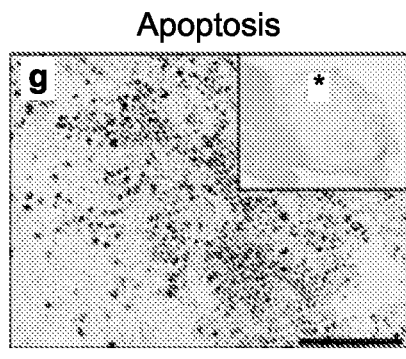
Figure 3H:
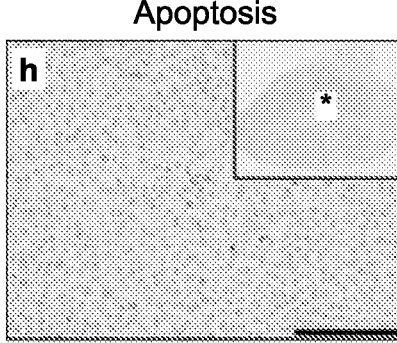
Figure 3I:
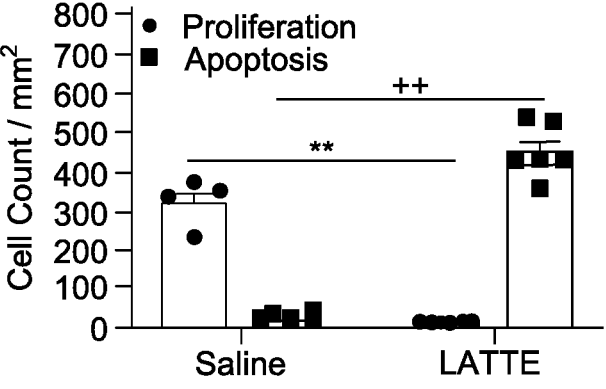
Figures 4A, 4B:
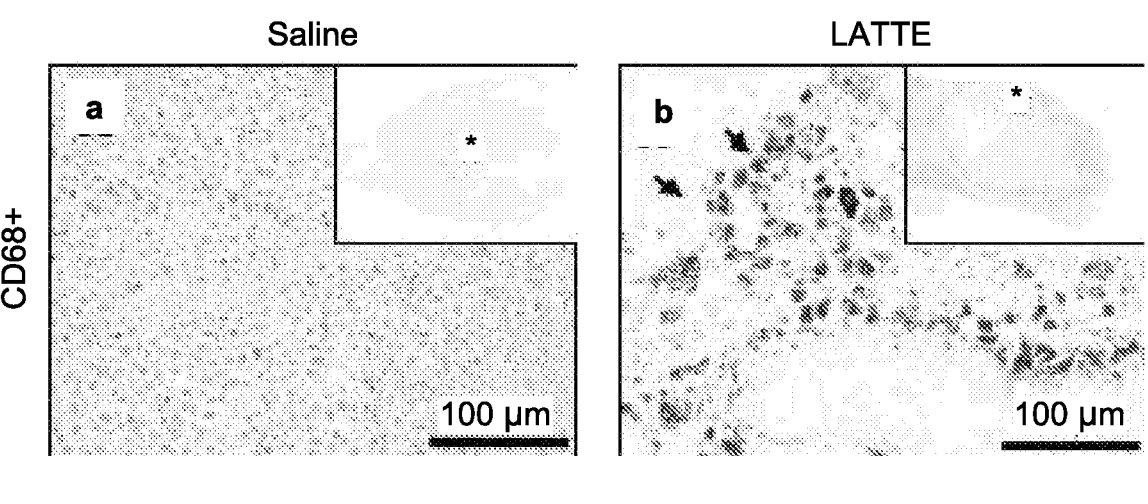
FIGS. 4A-4I. Effect of intratumoral injection of LATTE on T-lymphocyte and macrophage recruitment.
Figure 4C:
Figures 4D, 4E:
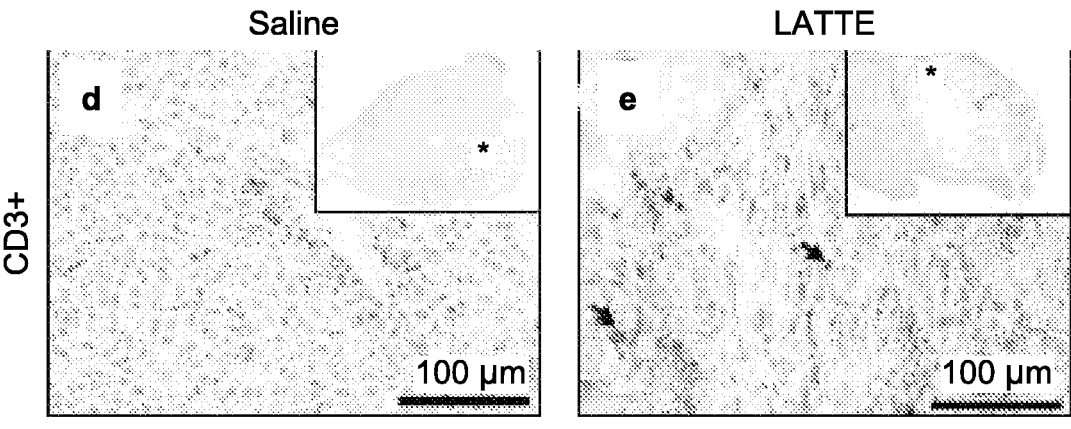
Figure 4F:
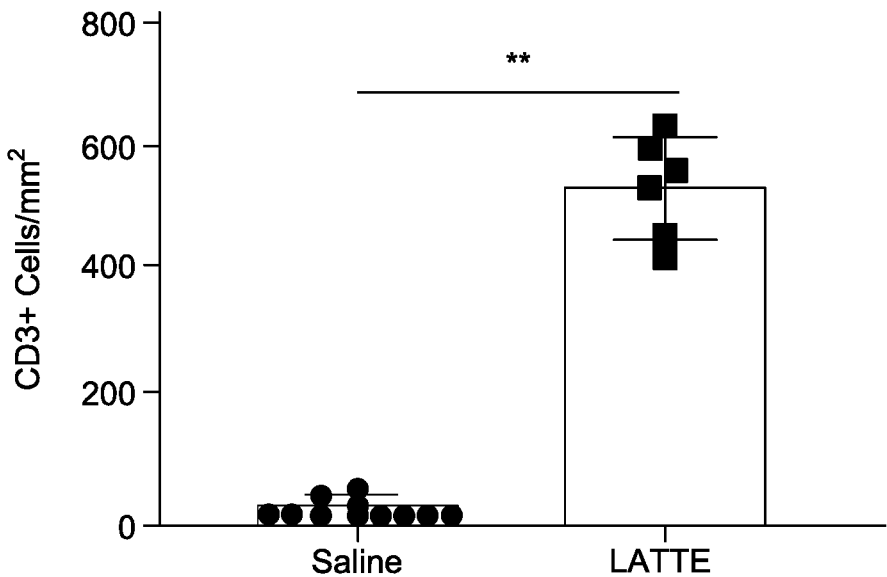
Figures 4G, 4H, 4I:
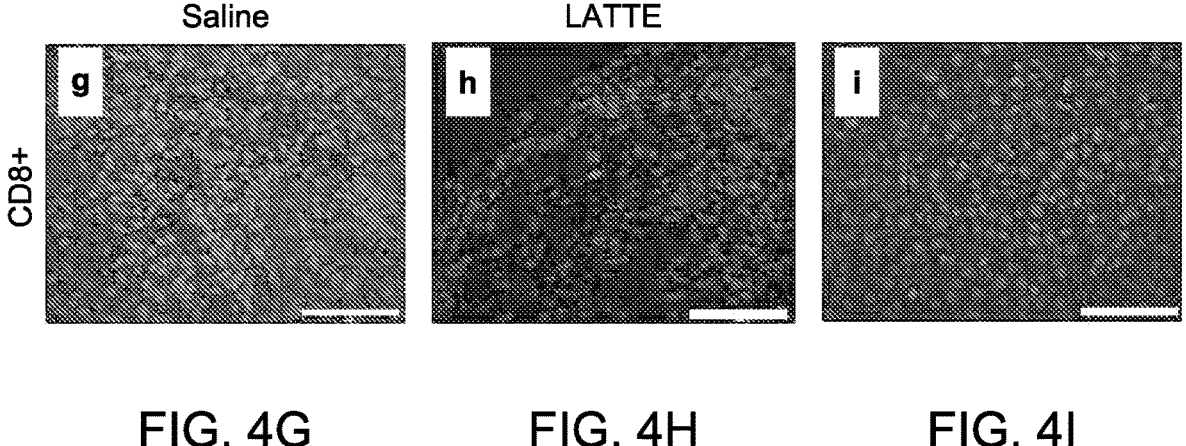

Next, in vivo experiments in immunocompetent rats bearing the highly malignant orthotropic N1S1 liver tumors were ablated using LATTE. Percutaneous injection of LATTE was performed and assessment also included CT imaging to mimic the clinical scenario. Gross examination revealed that 25%-LATTE injection into tumor resulted in marked tumor ablation at two weeks (FIG. 1i-k). Gray-scale US images showed a much larger tumor mass in the saline injected group compared to the 5-fold smaller tumors that received LATTE (FIG. 1l-o). These tumors also received high-resolution in vivo micro-CT imaging following intravenous injection of Exitron contrast agent to allow accurate segmentation of the liver tumors (FIG. 1p-q). Analysis of the micro-CT images produced results similar to ultrasound findings showing a substantially smaller tumor volumes in the LATTE treated animals at 2 weeks post-treatment (FIG. 1r). A linear relationship between the tumor volume assessed by ultrasound and micro-CT was established confirming the consistency and reproducibility of these measurements (FIG. 1s). Harvested tissues from the LATTE injected tumors revealed uniformly distributed robust fluorescent signal from ICG that extended to the margins of the tumor whereas the saline group had undetectable ICG signal in significantly larger tumors (FIG. 1t-u). Quantitative analysis of ICG diffusion and fluorescent intensity yielded a relatively 28 fold larger diffusion area and substantially higher fluorescent intensity in the LATTE treated group compared to the control, saline group (FIG. 1v-w). These data imply that LATTE can successfully ablate the highly malignant N1S1 liver tumor and uniformly distribute and retain the co-administered ICG. On review of the micro-CT images by a board-certified radiologist, LATTE treated tumors would be characterized as complete treatment response by size criteria alone. These tumors at two-weeks were also harvested and evaluated by histology. LATTE treated N1S1 tumors demonstrated complete tumor necrosis with absence of nuclear staining; saline treated tumors, however, showed hypercellularity, loss of normal tissue architecture and marked N1S1 tumor-cell infiltration (FIG. 3a-b). Morphometric analysis showed significant reduction in tumor size and cell count in the LATTE injected tumors (FIG. 3c-d). Quantitative analysis of proliferating (FIG. 3e-f) or apoptotic cells (FIG. 3g-h) showed markedly reduced number of proliferating cells associated with a 24 fold higher number of apoptotic cells in the LATTE group compared to the control, saline group (FIG. 3l). Additionally, LATTE treated samples demonstrated 16-fold increase in CD68-expressing macrophages (FIG. 4a-c) and enhanced CD3+T-lymphocyte infiltration within the treated tumor margin (FIG. 4d-f). Immunostaining identified that many of the CD3+ cells are CD8+ subpopulation (FIG. 2g-i). These data show that LATTE treatment leads to significant tumor destruction while effectively inhibiting cell proliferation and inciting a robust immune response in the tumor area, suggesting that LATTE may potentially enhance immunotherapy. Furthermore, analysis of serum samples collected at two weeks following treatment showed normal liver and renal function and no evidence for a systemic response and absence of injury to non-cancerous liver suggesting treatment safety (Table 1).

TABLE 1

Serum blood chemistry in rats: Serum levels of alkaline phosphatase (ALP) and alanine aminotransferase (ALT), creatinine (Cre), blood urea nitrogen (BUN), glucose (Glu) were measured in serum aliquots using DRI-CHEM 4000 analyzer. Whereas, C-Reactive protein (CRP) was measured using quantitative ELISA. Changes in ALP and ALT are typically used as an indication of altered liver function whereas increased creatinine levels suggest deficient renal function. Results showed marginal difference in ALP and BUN levels compared to control, however all serum values are within the normal limits of healthy Sprague Dawley rats (n = 6).

| | LATTE | Saline | Control | P Value | Normal Range |
|---|---|---|---|---|---|
| ALP U/L | *211 ± 29 | *199 ± 42 | 227 ± 15 | *p = 01 | 0-260 |
| ALT U/L | 57 ± 13 | 51 ± 10 | 48 ± 10 | 0.4 | 10-190 |
| CRE mg/dL | 0.3 ± 0.04 | 0.3 ± 0.05 | 0.2 ± 0 | 0.2 | 0.5-1.6 |
| CRP ng/mL | 459 ± 38 | 472 ± 39 | 425 ± 58 | 0.76 | 300-600 |
| BUN mg/dL | **25 ± 2.4 | **25 ± 4.2 | 18 ± 1.5 | **0.003 | 20-26 |
| GLU mg/dL | 268 ± 75 | 220 ± 54 | 196 ± 17 | 0.2 | 190-280 |
| Total Protein g/dL | 5.2 ± 0.3 | 5.5 ± 0.6 | 5.7 ± 0.3 | 0.28 | 5-7 |

Figure 5A:
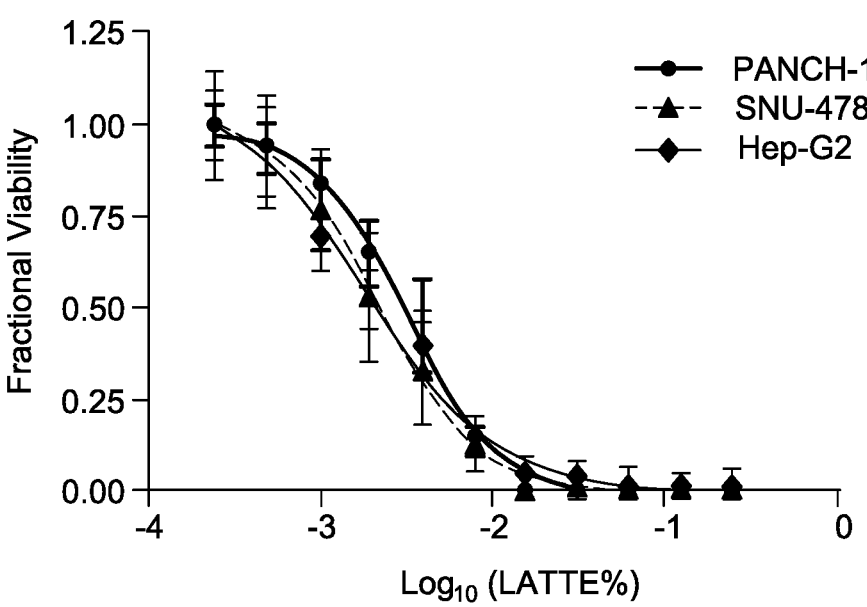
FIGS. 5A-5D. LATTE Cytotoxicity and synergistic interaction with chemotherapy against human cancer cells.
Figure 5B:
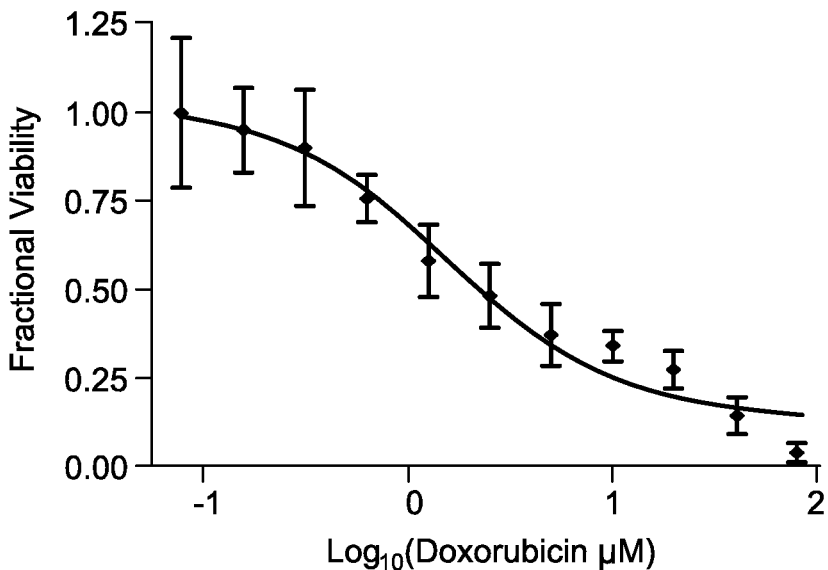
Figures 5C, 5D:
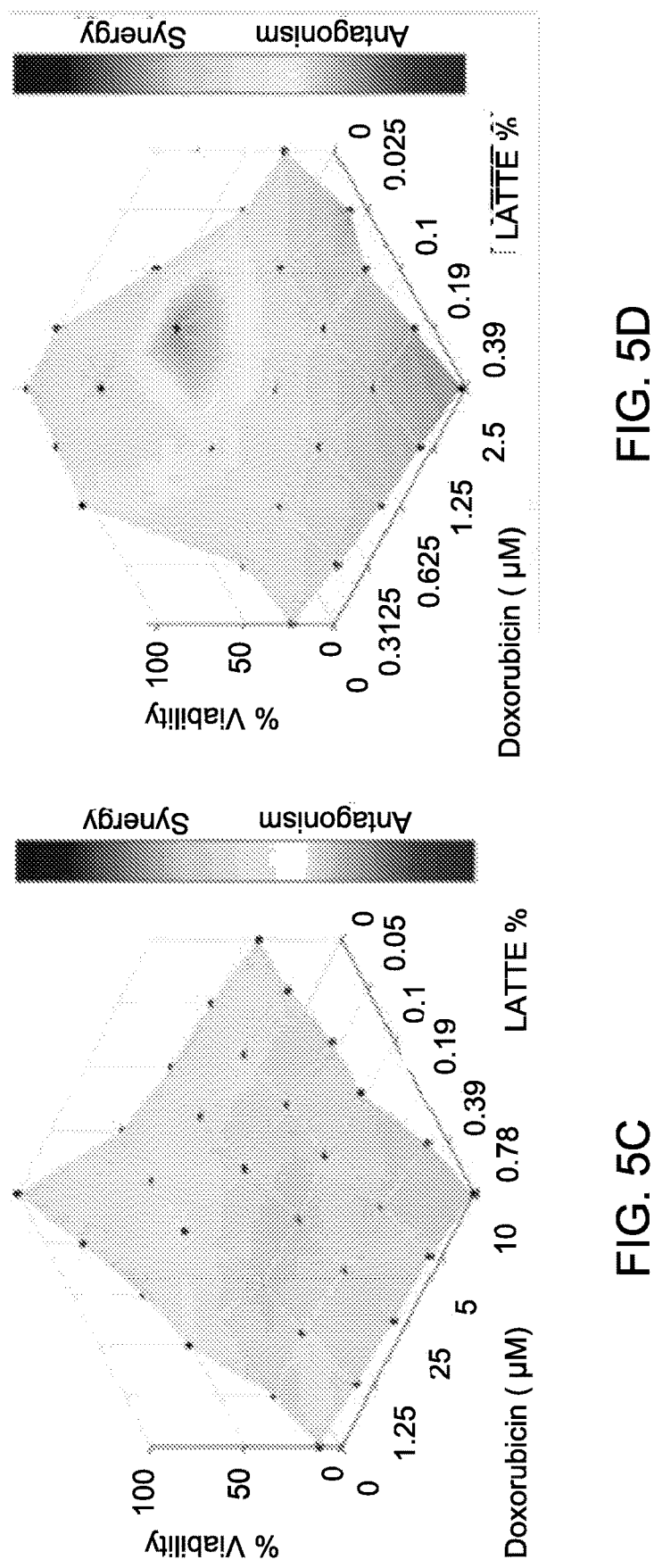
Figures 6A, 6B, 6C:
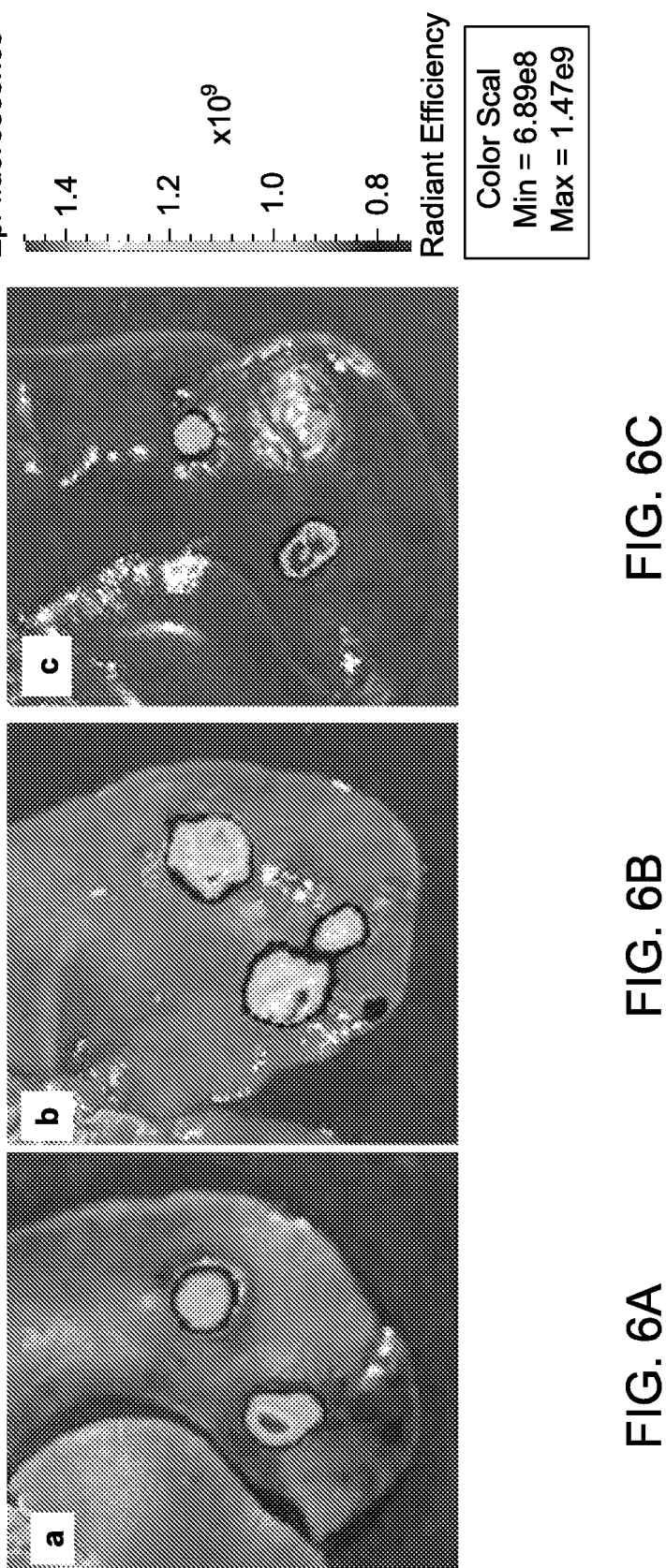
Figures 6D, 6E, 6F:
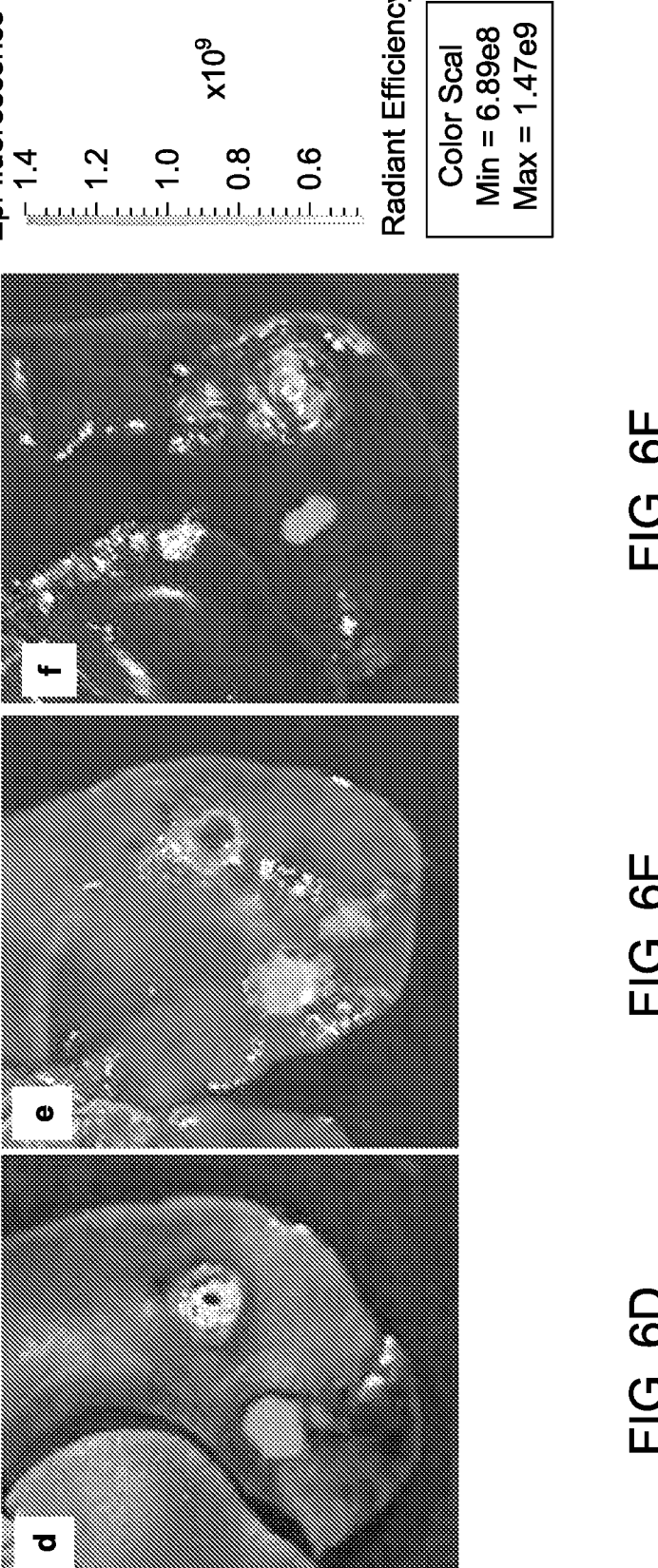
FIGS. 6D, 6E, and 6F. Fluorescent scans visualizing Doxorubicin at the medial location of the same liver.
Figure 6G:
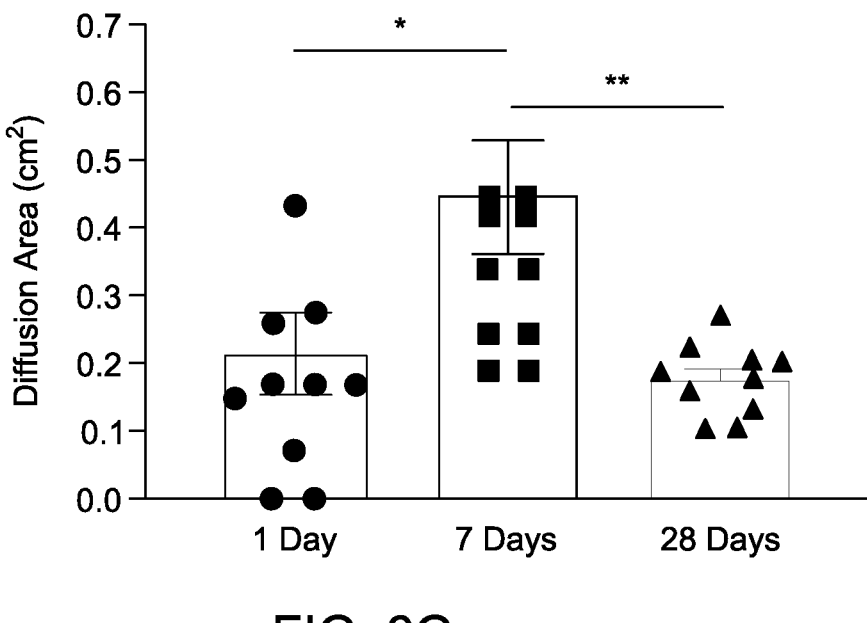
FIG. 6G. Graphic summary of ICG diffusion Doxorubicin fluorescent intensity in each injection site showing diffusion peaked at 7 days (* p=0.015,  p=0.001).
Figure 6H:
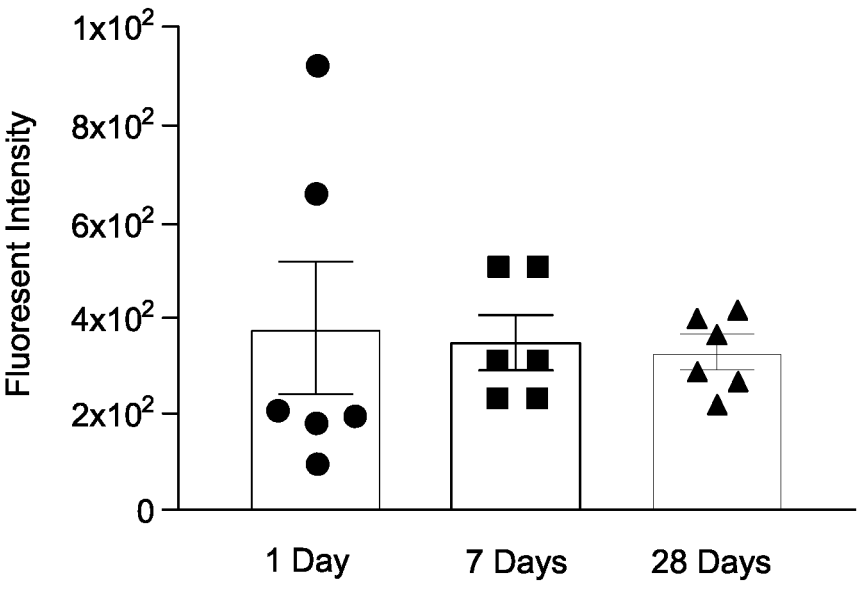
FIG. 6H. Quantitative analyses showed consistent fluorescent intensities for Doxorubicin at 1, 7 and 28 days after injection.
Figures 6I, 6J, 6K, 6L, 6M, 6N, 6O:

To determine synergy and the concentration of a chemotherapy agent such as doxorubicin to co-administer with LATTE, cell culture experiments were performed. To examine whether LATTE exerts cytotoxic effects on human cancer cells, concentration-dependent cytotoxicity dose-response curves were obtained by incubating patient derived cholangiocarcinoma, pancreas adenocarcinoma cell lines and HepG2 hepatocellular carcinoma cells with serially diluted LATTE (25-0.048% w/v) for 24 or 48 hours. Fractional viability showed an effective concentration that causes 50% cell death ($EC_{50}$) of 0.18-0.3% (FIG. 5a), suggesting that LATTE provokes a robust cytotoxic effect on cancer cells even at very low concentrations. To examine whether a dual treatment with LATTE and chemotherapy results to augment anticancer effect, extensive synergy analysis was performed by incubating Hep-G2 cells with LATTE and doxorubicin using selected concentrations derived from the assessed fractional viability $EC_{50}$ (FIG. 5a-b). Synergy plots demonstrated significantly enhanced synergistic cytotoxicity with the maximum effect observed with 0.19-0.39% for LATTE and 2.5-5 μM for Doxorubicin respectively at 24 and 48 hours (FIG. 5c-d). This data implies that LATTE can be used not only to induce cancer cell death but also maintains the functionality of chemotherapy drugs such as doxorubicin leading to synergy to maximize tumor response and potentially to widen the treatment margins.

Next, doxorubicin and ICG were solubilized in 25%-LATTE then injected into rat liver. NIRF imaging and histopathology of explanted rat liver at 3, 7, and 28 days after injection showed persistent doxorubicin retention throughout the affected zone up to 28 days period (FIG. 6a-h). This novel capability to retain chemotherapy within the ablation zone is highly desirable suggesting that it may help prevent tumor recurrence which commonly occurs in the clinical setting along the pen-ablation zone.

Figure 7I:
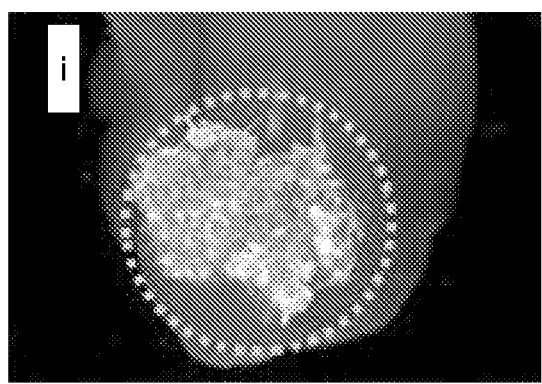
FIG. 7I. Micro-CT maximum intensity projection of explanted rabbit liver at 1 hour after LATTE injected illustrating effective distribution and retention of Exitron throughout the VX2 lesion.
Figure 7J:
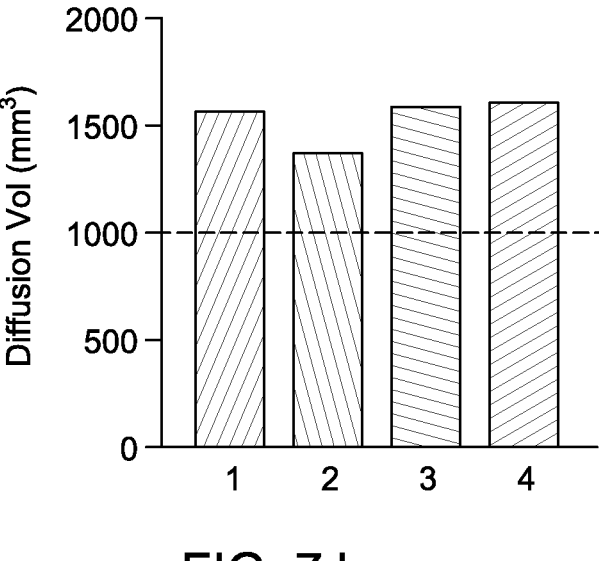
FIG. 7J. Volumetric micro-CT analysis of LATTE injected VX2 tumors showing an average of 150% Exitron diffusion in the four VX2 tumors exceeding the 1 mL LATTE injected volume.
Figures 7K, 7L:
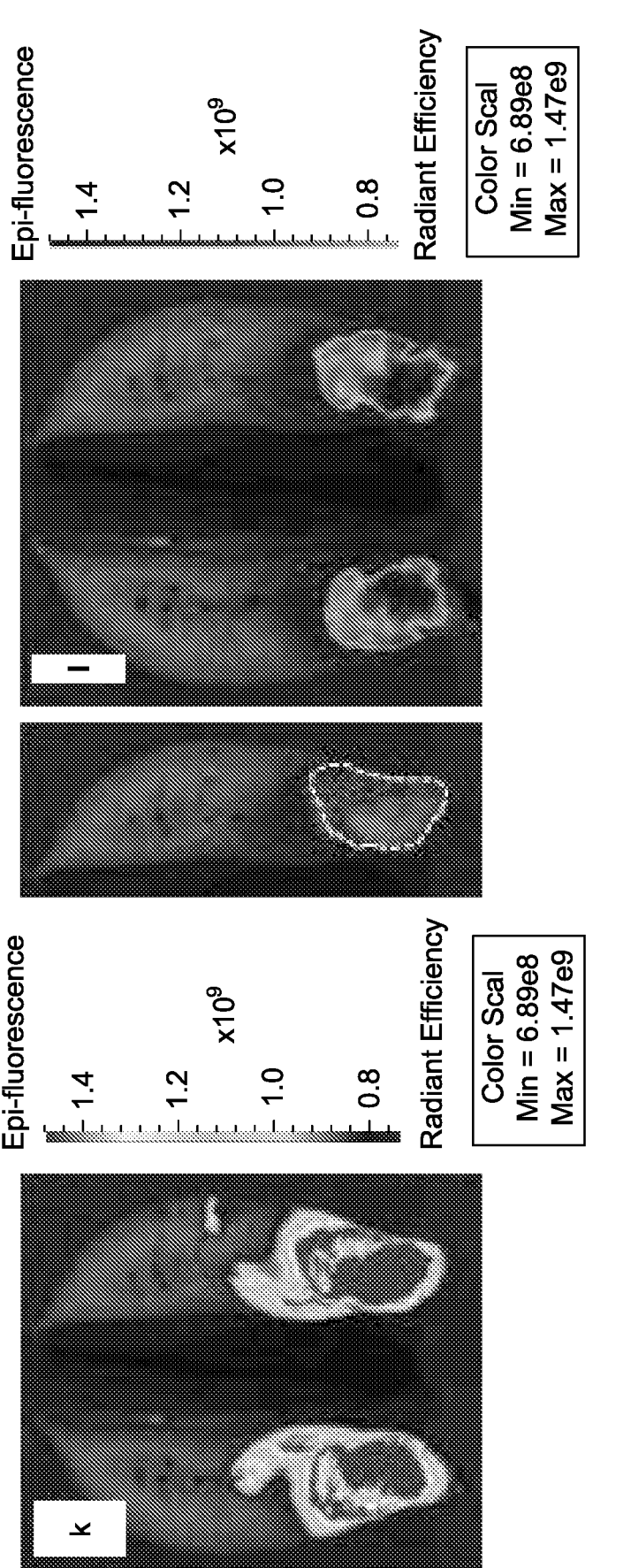
FIG. 7K. Respective images showing transected VX2 tumor in gray (white dotted outline) and NIRF image visualized ICG diffusion beyond the tumor zone whereas, fluorescent image (FIG. 7I) show Doxorubicin retention throughout the tumor.
Figure 7P:
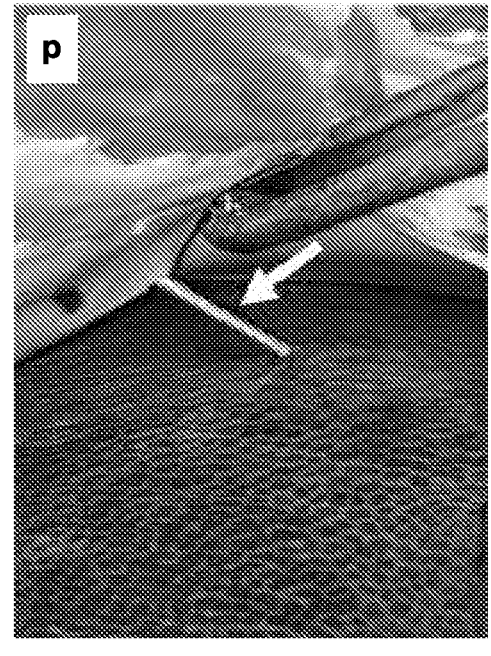
FIG. 7P. Photograph and ultrasound image illustrating percutaneous image-guided LATTE injection into pig liver showing access needle advanced inside the liver parenchyma with the needle track (white arrow) and the accumulated LATTE (yellow dashed outline) were visible in the US image after injection.
Figure 7Q:
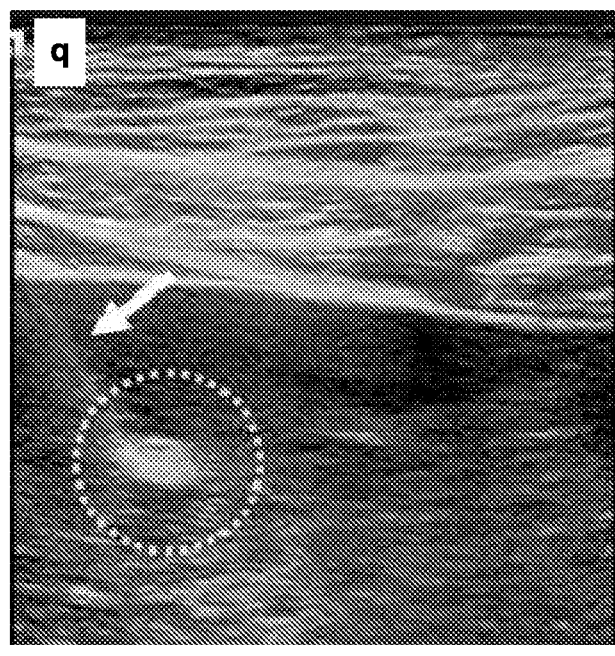
FIGS. 7A-7W. Image guided injection of LATTE into VX2 tumor in rabbit or normal pig liver.
FIG. 7B. Representative ultrasound image after intratumoral injection of 25% LATTE mixture into VX2 tumor showing needle track (white arrow).
FIG. 7C. Gross view of VX2 tumor immediately after injection of 25% LATTE mixture with ICG showing visible LATTE solution in the subcapsular space within the tumor lesion.
FIGS. 7D and 7E. Representative color Doppler ultrasound scans of rabbit liver before and after LATTE injection visualizing flow in the region of the hypoechoic VX2 tumor.
FIGS. 7F and 7G. Respective laser speckle perfusion scans showing diminished perfusion following LATTE injection into VX2 tumor.
FIG. 7H. Summary of laser speckle image analysis in the VX2 bearing liver illustrating a marked decrease in perfusion following LATTE injection.
FIG. 7M. Graphic summary of ICG and Doxorubicin diffusion revealed larger area of diffusion compared to tumor area.
FIGS. 7N-7O. H&E stained sections obtained from untreated or treated VX2 tumors respectively (scale bar, 200 μm).
FIG. 7R. NIRF scan of explanted pig liver lobe showing robust ICG signal in the affected zone.
FIGS. 7S-7T. NIRF and microscope images of pig liver tissue sections obtained from the injection site showing intense signal that corresponded to the area of necrosis in the stained section.
FIG. 7U. Representative T1-weighted MR axial image showing attenuation at the center of the affected zone and enhancement due to LATTE diffusion towards the periphery.
FIG. 7V. MRI volumetric analysis revealed 2.8 fold increase in diffusion volume within 90 minutes following LATTE injection (* p=0.038 using paired t test, n=4).
Figure 7R:
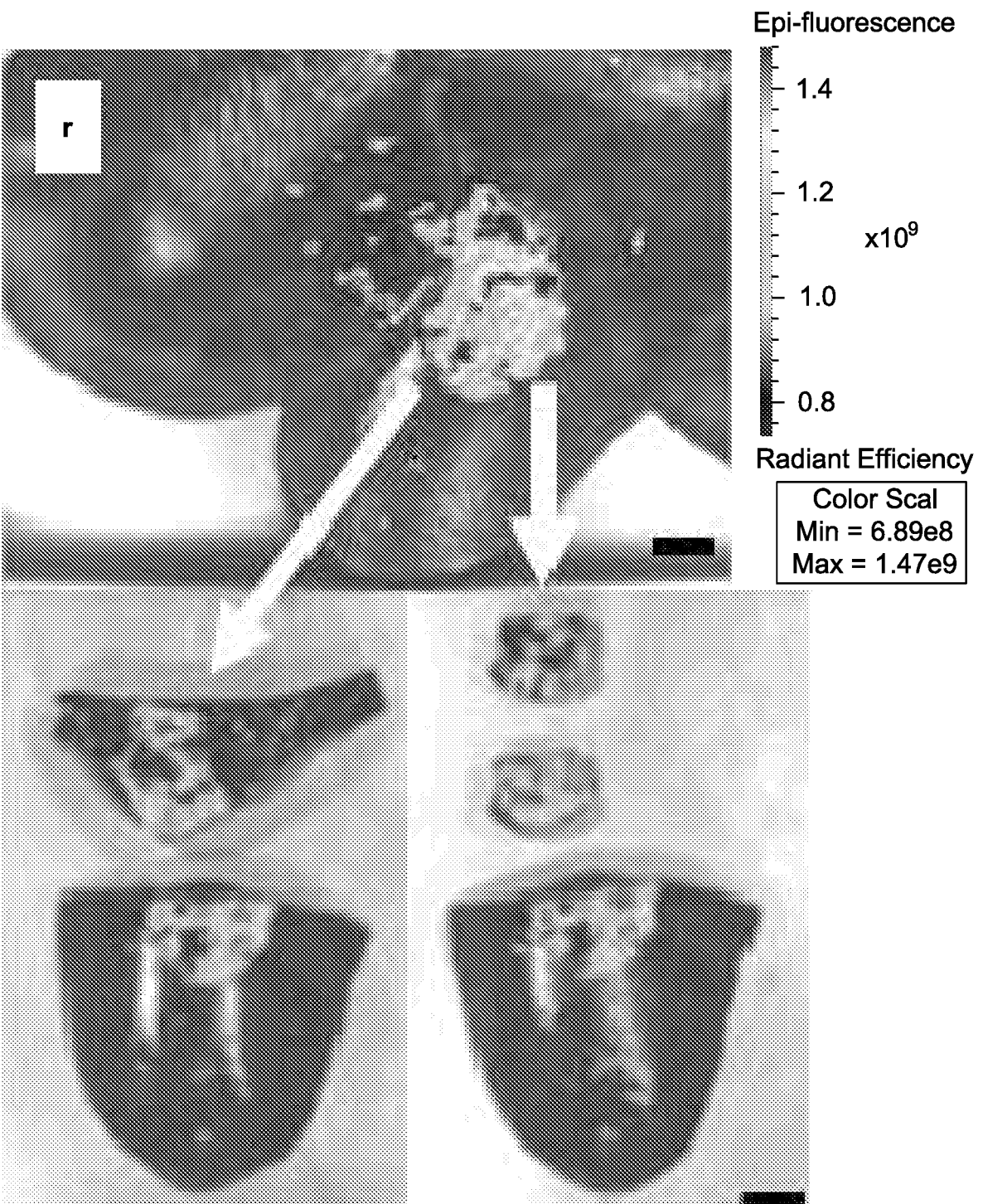
Figure 7S:
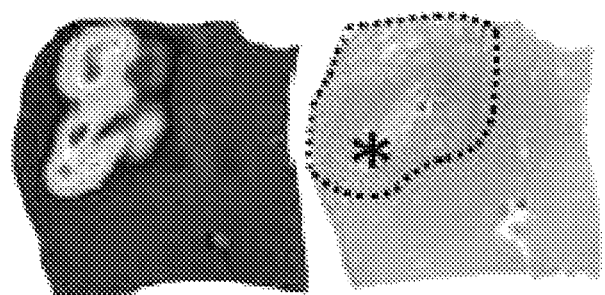
Figure 7T:
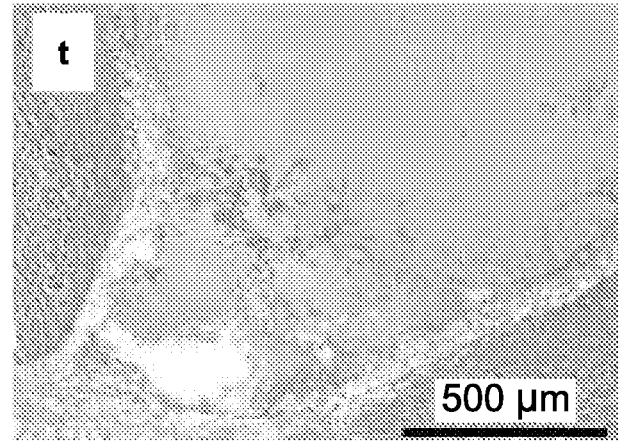

25%-LATTE mixed with 184 µM doxorubicin was injected into a rabbit liver tumor under US guidance. The rabbit VX2 liver tumor model was used because it is a commonly used cancer model to test preclinical interventional technologies. Intratumoral injection of 1 mL of 25% LATTE in a syringe containing doxorubicin, ICG, and exitron was performed using a 21 gauge vascular access needle (FIG. 7a-b). At 1 hour after injection, the rabbit liver was exposed and examined, showing subcapsular accumulation of the LATTE mixture, similar to what was observed in the rat N1S1 tumor injections (FIG. 7c, dashed outline). In vivo ultrasound Doppler imaging (FIG. 7d, e) and laser speckle perfusion scanning (FIG. 7f-h) demonstrated markedly diminished perfusion in the tumor following LATTE injection. Micro-CT imaging using the Exitron contrast imaging showed uniform distribution of the contrast agent throughout the tumor and demonstrated that LATTE had the unique capability to transport a nanoparticle measuring 110 nm throughout the tumor tissue (FIG. 7i-j). Furthermore, consistent with micro-CT findings, NIRF imaging of explanted rabbit liver VX2 lesions showed ICG (FIG. 7k), and Doxorubicin (FIG. 7l) retention detected throughout the tumor lesion that spread beyond the tumor margins similar to what was observed in the N1S1 tumors in rats (FIG. 1m). Histologic evaluation of the LATTE injected VX2 tumors revealed consistent tissue ablation with extensive necrosis compared to saline injected tumors (FIGS. 7n and 7o). Similar to the rabbit experiment, the feasibility of transcutaneous ablation in pigs was also performed to demonstrate the practicality of image guided LATTE delivery and consistency in liver parenchyma diffusion and ablation. FIG. 7p shows the injection of 2 mL of 25% LATTE mixed with ICG; FIG. 7q shows the needle and the echogenic appearance of LATTE within the liver tissue allowing it to be tracked in real-time. Following necropsy, near-infrared fluorescent scanning of the explanted liver lobe showed a robust fluorescent signal corresponding to the location of the LATTE injection (FIG. 7r). The injected site was harvested and histology slides were imaged with the fluorescence scanner before undergoing hematoxylin and eosin staining, which localized the fluorescent area to the ablation zone (FIG. 7s), indicating that LATTE mixture permeated and helped retain ICG throughout the ablation zone. Histologic examination showed total destruction of tissue architecture with interstitial edema and loss of nuclear staining consistent with the rat and rabbit tissue (FIG. 7t). This data implied that transcutaneous injection of LATTE in pigs is possible and causes a similar ablation effect capable of achieving up to 4 cm ablation zone.

Figure 7U:
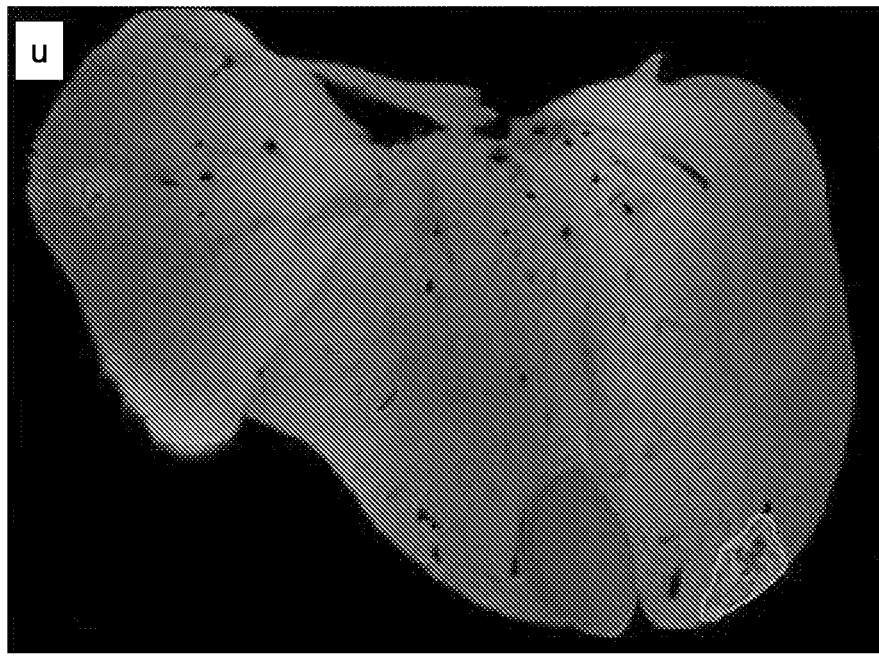
Figure 7V:
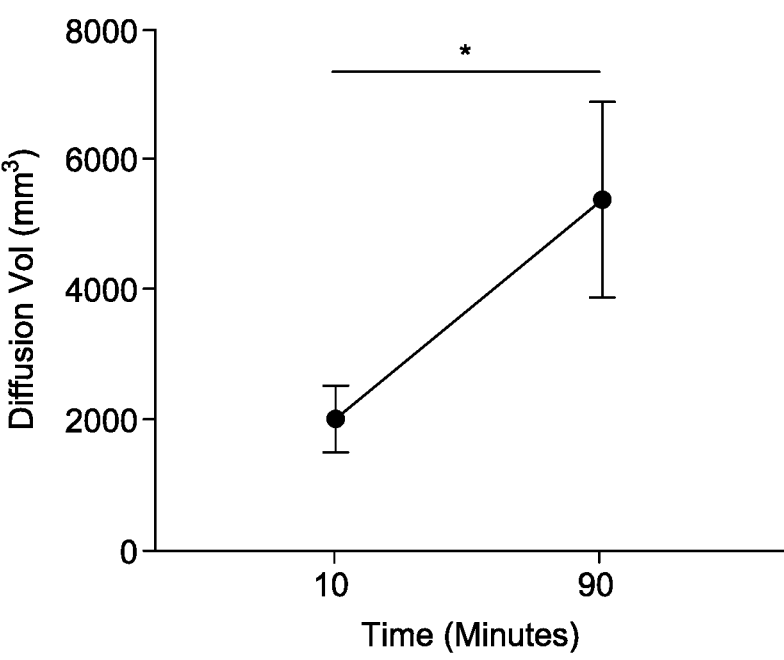
Figure 7W:
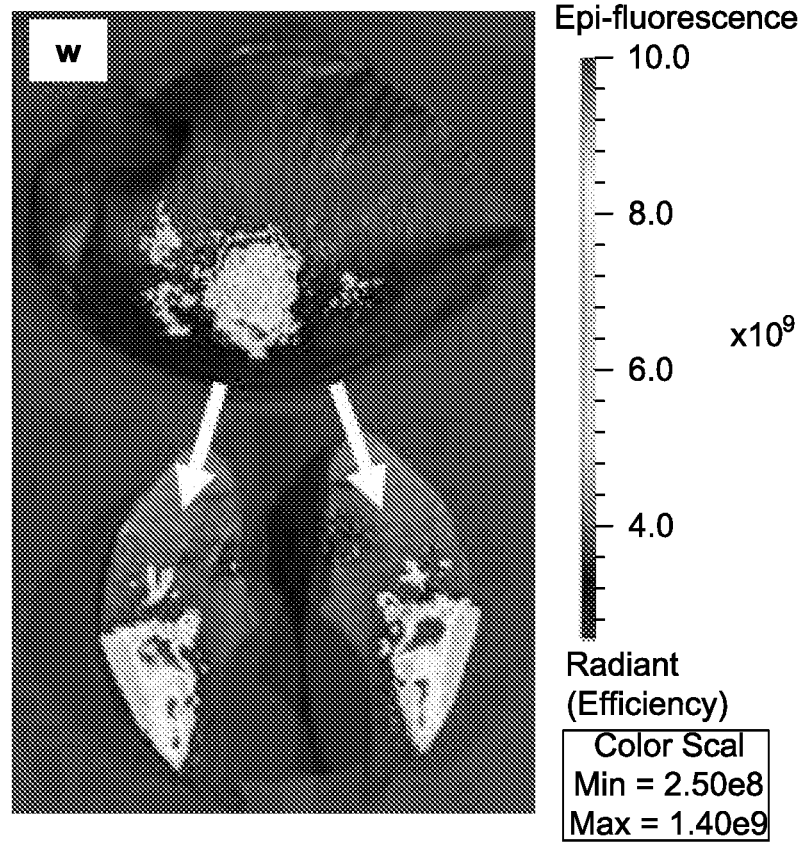
Figure 8A:
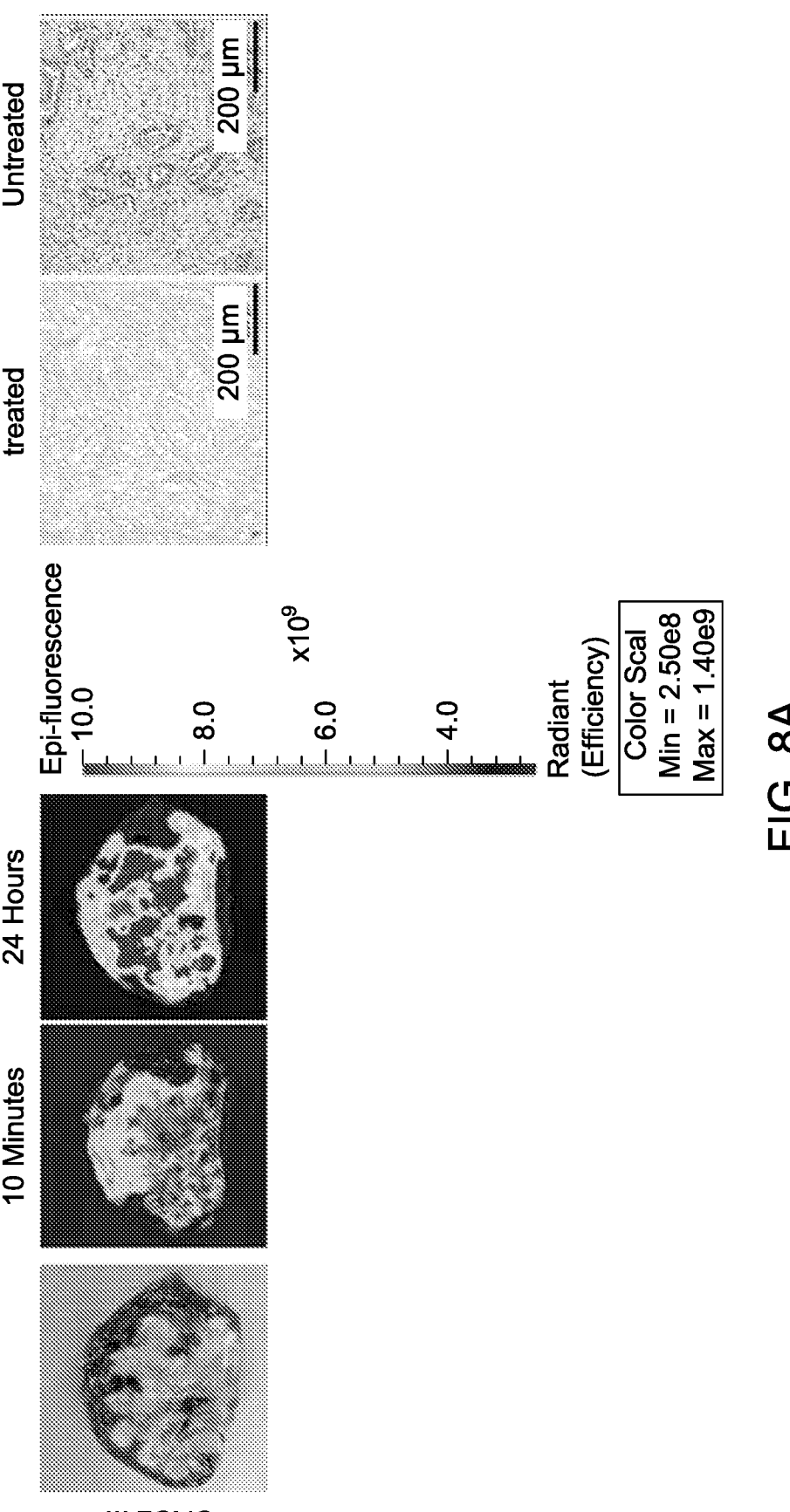
Figure 8C:
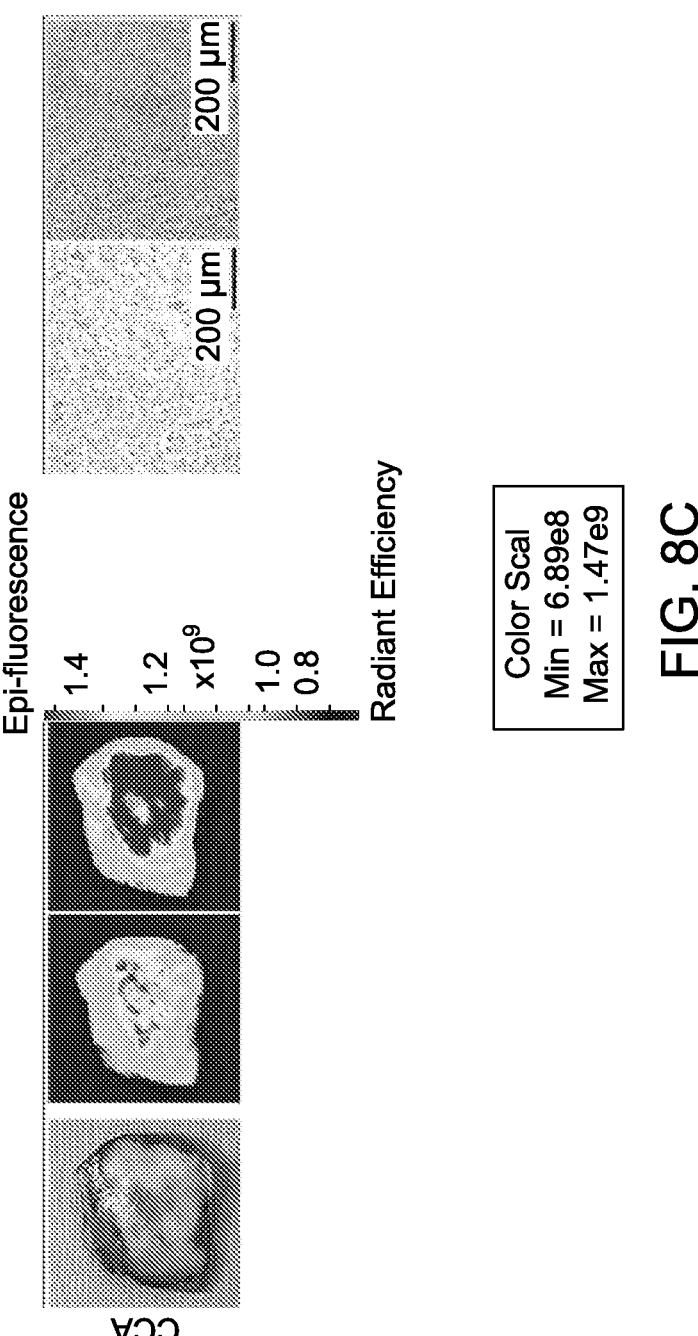
Figure 8D:
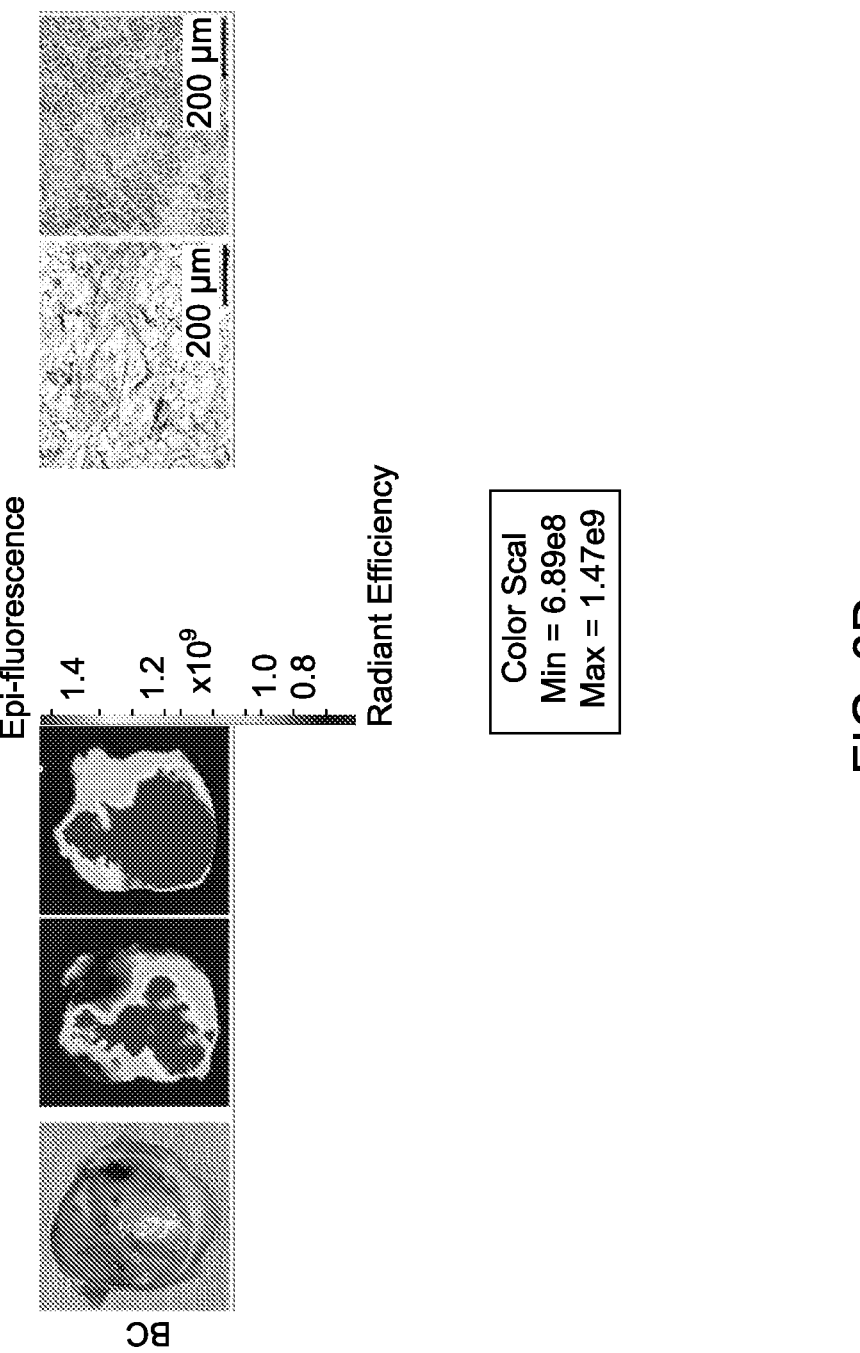
Figure 8E:
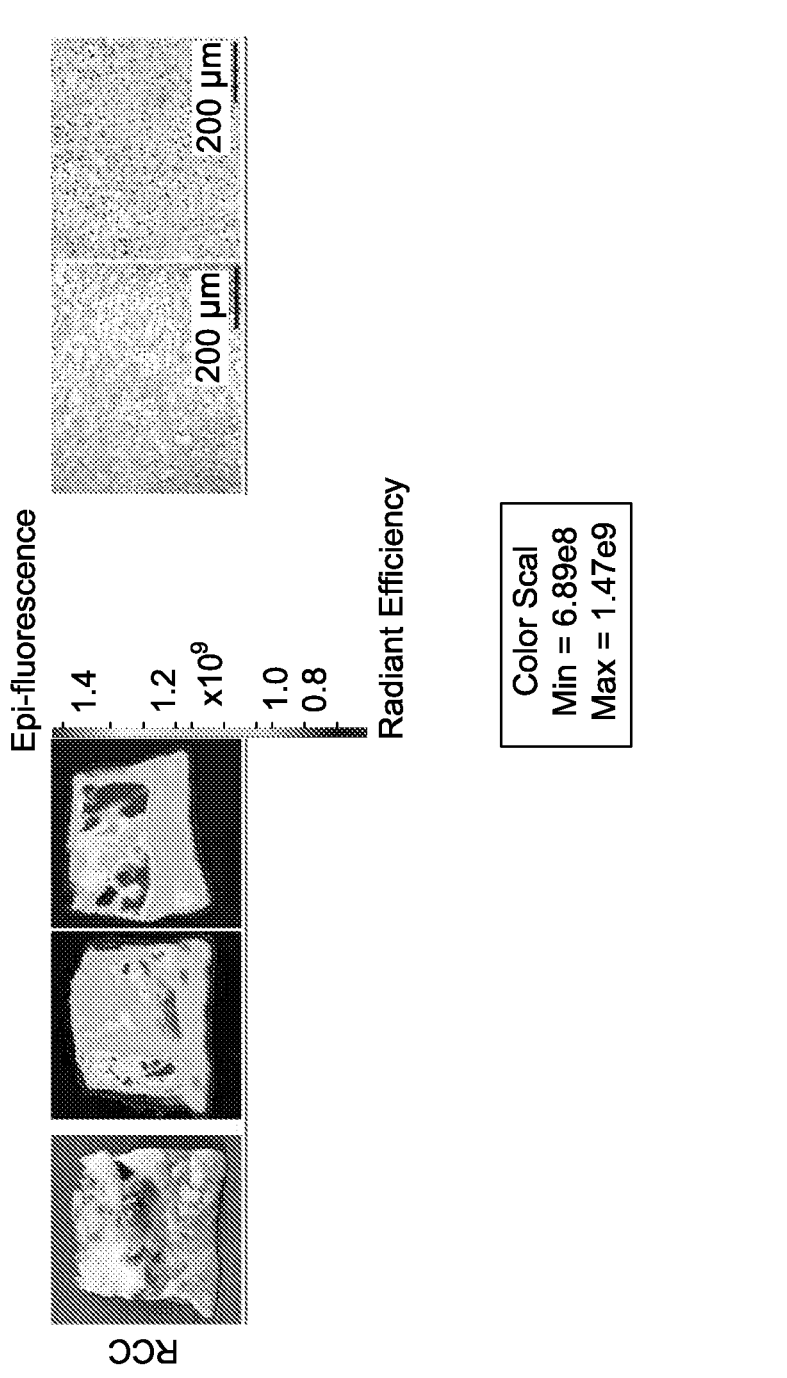
Figure 8G:
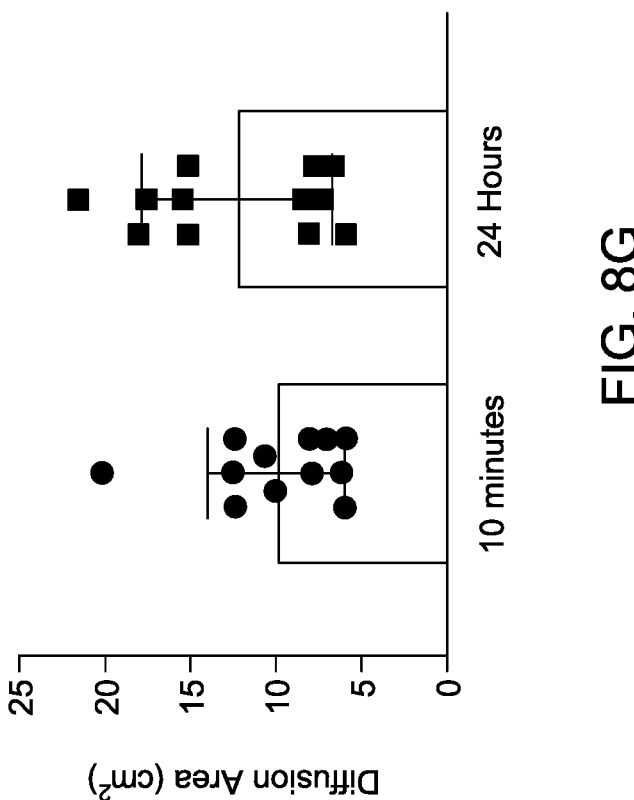
Figure 8F:
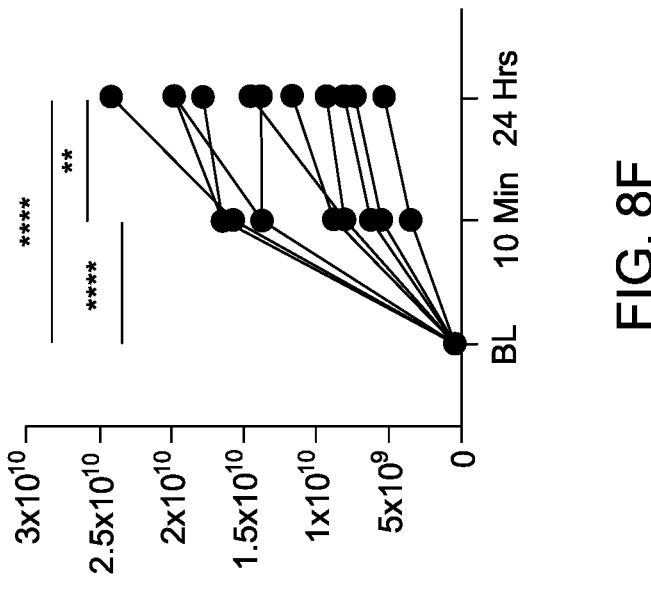

Since intrahepatic injection of LATTE results in quick diffusion, creating a clear volume of tissue destruction, the change in the volume of the ablation zone over time was examined in pig liver using real-time magnetic resonance imaging (MRI) in a clinical interventional MRI suite. T1-weighted MR imaging sequences showed 2.8 fold increase in the circumferential diffusion of LATTE within 90 minutes following injection (FIG. 7u-w). This data identified an early period of rapid diffusion of LATTE within a few seconds following intraparenchymal injection, followed by a gradual diffusion period of 90 minutes.

Finally, to show whether LATTE can ablate human tumors, 12 consecutive freshly resected human tumors were collected and kept in RPMI media; within 1 hour of resection, the ex vivo tumors received 25%-LATTE mixed with ICG. Tumor tissues were photographed, and NIRF images were obtained at 10 minutes after injection, then incubated for 24 hours at 37° C. inside a humidified tissue culture chamber in RPMI media. At 24 hours, fluorescent scanning was repeated, and tissues were processed for histologic evaluation. The fluorescent intensity and diffusion area were calculated using similar parameters for all tissues. Representative images of different types of human tumor tissues and their corresponding fluorescent scans at 10 minutes and 24 hours are displayed in FIG. 8. Analysis of the results show significant diffusion of LATTE throughout the tumor tissue peaking at 24 hours with marked tissue destruction, consistent with the results obtained from rat, rabbit and pig liver (FIG. 8). LATTE was able to ablate a variety of highly malignant human tumors.

In summary, LATTE represents a new class of LRT that can be easily delivered under US guidance. While LATTE can efficiently ablate tissue, it can also be used as a drug carrier in free-form or within nanoparticles to deliver chemotherapy and remain within the ablation zone up to 28 days. LATTE also induces significant immune response at the tumor margins, and in combination with immunotherapy drugs, may represent an effective way to activate T-cells and improve solid tumor response. LATTE treatment has the potential to improve HCC survival outcomes by enabling more patients to bridge to liver transplantation.

Materials and Methods

LATTE Synthesis and Formulation

Neat choline and geranate ionic liquid was first prepared using salt metathesis. For this purpose, one equivalent of neat geranic acid (Sigma Aldrich, St. Louis, MO) was recrystallized 5 times at −70° C. in acetone, in a 500-mL round bottom flask and added to one equivalent of choline bicarbonate (80 wt % solution, Sigma Aldrich, St. Louis, MO). The mixture was stirred at room temperature until $CO_2$ evolution ceased. Residual $H_2O$ was removed by rotary evaporation at 60° C. for 2 hours and drying in a vacuum oven for 96 hours at 60° C.

A variety of LATTE mixtures were prepared by mixing neat LATTE (100%) with 0.25 mg/mL indocyanine green normal saline solution (ICG, Sigma-Aldrich, St. Louis, MO) at predetermined ratios. For example, a 6.25%-LATTE solution was prepared by mixing 6.25 wt % neat LATTE and 93.75 wt % of ICG solution. Using this approach, 25%-LATTE, 50%-LATTE and 100%-LATTE (neat) were also prepared for characterization.

Viscosity was measured using an Anton Paar MCR 302 rheometer using a 25 mm diameter 1° aluminum plate. The gap between the upper and bottom plates was kept at 0.048 mm. LATTE was placed on the bottom plate and equilibrated at 25° C. for 10 minutes before experiments were conducted. Flow curves were performed over the shear rates between 10 and 1000 $s^{-1}$ for each LATTE formulation. The viscosity tests were run in triplicate. In addition, the viscosity of each variant of LATTE was measured at day 0, day 10 and day 20 to assess its stability.

The injectability of LATTE was tested using a mechanical tester (Instron, Model 5942). The injection force generated by different LATTE formulations loaded into a 1 mL syringe (Becton-Dickinson, Franklin Lakes, NJ) through a 7 cm 21-gauge access needle (COOK Medical, Bloomington, IN) at a flow rate of 10 µL/s was recorded. Each test was repeated five times.

Intraparenchymal Injection of LATTE into Normal Rat Liver

Intrahepatic injections or LATTE mixtures were performed in Sprague Dawley rats via laparotomy. Anesthetized rats were placed in a supine position on a warming platform. The abdominal hair was removed with an electric shaver and scrubbed to disinfect the skin with triple applications of povidone-iodine alternating with 70% alcohol. After preparing and draping the abdomen in a standard surgical fashion, a vertically oriented subxiphoid mini-laparotomy incision was made with a 15-blade, and blunt dissection was used to expose the peritoneum through the avascular linea alba. The careful division of the peritoneal wall with retractors allowed visualization of the liver. Care was taken to avoid tearing of the liver capsule, and the exposed organ will be kept moist with wet gauze. Cotton tipped applicator dipped in sterile saline, and blunt tweezers were used to expose and position the left lower liver lobe. Two injections in each lobe with 1 cm apart were done using 28 gauge needle syringes to deliver 100 microliter volume of LATTE mixtures. The medial injection site received 100 μL of 25% LATTE and 65 μg indocyanine green (ICG, Sigma-Aldrich) in normal saline while the lateral injection site received 100 μL of 25% v/v LATTE, 65 μg ICG and 100 μg doxorubicin in normal saline. After the injection is achieved, the subcutaneous tissues were reapproximated with 5-0 vicryl suture in a running fashion, and the final dermis layer was approximated using 5-0 vicryl subcuticular sutures. Subgroups of rats survived for 1, 3, 7, or 28 days following injections. At the end of the survival periods, explanted livers were fixed, and ex vivo fluorescent imaging was performed to detect ICG and Doxorubicin at the two injection sites and to calculate the area of diffusion and fluorescent intensity based on average radiant efficiency.

Evaluating Tumor Response to LATTE Treatment in an N1S1 Rat Model of Liver Cancer All procedures were approved by the institutional animal care and use committee and performed according to institutional guidelines. Eighteen male Sprague Dawley rats (Envigo, CA) weighting initially 300-325 grams were used to induce liver cancer. N1S1 rat hepatoma cells (ATCC, CRL-1604, Manassas, VA) were cultured in Iscove's Modified Dulbecco's Medium (IMDM, ATCC, Manassas, VA) supplemented with 10% heat-inactivated bovine calf serum (SH30072.03HI, HyClone, UT). N1S1 cells were maintained in suspension in a 75 cm$^2$ culture flasks at 37° C. in a 5% CO$_2$ humidified chamber. N1S1 cell viability of over 95% was documented with trypan blue exclusion before tumor inoculation procedure. To prepare the cells for inoculation, N1S1 cell aliquots were rinsed and suspended in plain IMDM (without antibiotics or serum) to yield 2×10$^6$ cells in 100 μL of fresh aliquots for each inoculation. The rat liver was surgically exposed through upper midline laparotomy under isoflurane anesthesia followed by subcapsular inoculation of N1S1 cells into the left liver lobe. Gentle compression with gauze for hemostasis was used to prevent cell reflux. The abdominal incision was closed using interrupted Vicryl sutures for abdominal muscle and subcuticular suture for the skin, followed by the application of Vetbond tissue adhesive (3M, St. Paul, MN) followed by recovery from anesthesia. Intratumoral injection of the ionic liquid mixture was performed in three groups of rats bearing 0.5 cm$^3$ N1S1 tumor lesions measured with ultrasound. Intratumoral injections consisted of the following mixtures; 25% (w/v) LATTE, normal saline, or 100% ethanol. All solutions contained 0.25 mg/mL indocyanine green (ICG, Sigma-Aldrich, St. Louis, MO) solubilized in normal saline. Following intratumoral injections, treated rats were allowed to survive for 2 weeks after treatment, and tumor volume was documented using ultrasound. N1S1 tumor progression and treatment response was assessed using percutaneous ultrasonography. Selected focal zone depth, gain, and tissue harmonic settings were optimized during the acquisition of the initial imaging at baseline, and the same parameters were applied during acquisition after intratumoral injection of LATTE mixture. Serial ultrasound examinations were performed on rat livers following N1S1 inoculation to confirm tumor formation and assess tumor volume. Rats were anesthetized using a gas mixture of 2-3% isoflurane in 100% oxygen via a nose cone. Rats were secured in a supine position on an electronically controlled warming platform to maintain the temperature at 37° C. during the imaging procedure. The abdominal area was shaved and prepped with depilatory cream (Nair, Church& Dwight Co. INC). Initially, abdominal sonography was performed to delineate tumor mass boundaries in grayscale (B-mode) using ACU-SON 52000 system (Siemens Inc., Germany) and a multi-frequency linear transducer (9L4, 9.0 MHz). The transducer was positioned to obtain 2D scans via the subcostal window to document liver tumors and measure lesion diameter. Maximum diameters based on tumor lesion echogenicity in the superior-inferior (SI), lateral-medial (LM), and anterior-posterior (AP) planes were measured. Tumor volumes were calculated as following: V=(4/3)×π×(1/2) SI×(1/2)LM×1/2 AP. Color Doppler images were also acquired to detect the distribution of the tumor blood flow weekly.

Measuring Tumor Volume Using Micro-Computed Tomography

Micro-computed tomography (μCT) was performed in rats in vivo or ex vivo on fixed liver tissues explanted from rats or rabbits following direct injection using the SkyScan-1276 (Bruker, Kontich, Belgium). To visualize normal liver parenchyma on CT imaging, rats received a bolus injection of 400 μL of the alkaline earth metal-based nanoparticle suspension, Exitron nano 12000 (Miltenyi Biotec, Auburn, CA) two hours prior to micro-CT scanning. Rats were anesthetized using inhalation of 2-3% isoflurane in 100% 02 at a constant flow rate of 2 L/minute and placed on a cassette equipped with a warming system and continuous gas exchange and integrated real-time motion detection camera. Fixed rat tissues were placed and immobilized using styrofoam beads inside a humidified plastic chamber. In vivo micro-CT scans of the upper abdominal region were acquired following flat field correction using a 0.25 aluminum filter and the following parameters; 85 kVp, 200 μA, 275 ms exposure, 20 μm pixel size, 360° rotation at 0.6° rotation steps whereas fixed liver tissues scanning protocol consisted of 40 kVp, 200 μA, 288 ms exposure, 20 μm pixel size and 360° rotation at 0.4° rotation steps, with 2 frames averaging without using a filter. The 3D image stacks were reconstructed using NRecon software and InstaRecon CBR Server (version: 1.7.4.6, Bruker, Kontich, Belgium) following adjustment of random movements, beam-hardening correction, and ring artifact reduction and smoothing. 3D volume rendering was visualized using CTVox software (version: 3.3. 0 r1383, Bruker, Kontich, Belgium). The stacks were virtually rotated and axially oriented to yield transverse projections of select volume of interest (VOI) using Data Viewer software (Bruker, Kontich, Belgium). 3D morphometric analysis of the segmented VOI was performed to measure tumor volume in vivo and ex vivo using CTAn software (version: 1.18.8.0, Bruker, Belgium). Segmentation was done by applying a global thresholding procedure followed by a series of morphological operations to separate the highly opaque healthy liver from the hypodense tumor volume. Tumor volume data are expressed in cubic centimeters as mean±SEM (* indicates p<0.05, **p indicates <0.01, n=6 in each group).

Fluorescence Imaging of Explanted Rat Livers

To assess differences in ICG or doxorubicin spreading and retention following intrahepatic injections, ex vivo spectral fluorescence imaging was performed on fixed liver tissues using the IVIS 200 system (PerkinElmer, Inc. USA). Transverse sections of each tumor lesion were cut using a scalpel and positioned inside the imaging system. Cross-sectional images were acquired following near-infrared illumination at the excitation wavelength of 750 nm, while fluorescent emission was acquired at 850 nm to visualize indocyanine green (ICG); Doxorubicin was detected at an excitation wavelength of 460 nm and an emission wavelength of 560 nm. Bright-field photographs were also obtained for each imaging sequence. All fluorescent images were acquired using 1 second-exposure time (f/stop=2) and displayed using the same scale of fluorescent intensity. Fluorescent intensity was quantified in the region of interest (ROI) of each tissue. Identical illumination settings (lamp voltage, filters, f/stop, the field of views, binning) were used for acquiring all images, and the fluorescence emission intensities were normalized to photons per second per centimeter square per steradian ($p/s/cm^2/sr$) in the quantitative analysis.

In Vitro Evaluation of LATTE Cytotoxicity and Synergy with Chemotherapy

HepG2 human liver cancer cell line (ATCC CRL10741; American Type Culture Collection, Manassas, VA, USA) were cultured in 75 $cm^2$ flasks using growth medium consisting of low glucose Dulbecco's Modified Eagle Medium (DMEM, ThermoFisher) and 10% heat-inactivated bovine serum that was supplemented with 100 IU penicillin and 10 µg/mL streptomycin (Thermo Fisher Scientific). Cells were incubated inside a 5% $CO_2$ incubator at 37° C. until it reached confluency cells; it was subsequently detached using 0.05% Trypsin-EDTA solution (Millipore-Sigma) and seeded into 96 multi-well replicate plates at $5 \times 10^3$ cell density per well for 24 hours. The anticancer activity of LATTE on HepG2 was determined using WST-1 reagent (2-(4-Iodophenyl)-3-(4-nitrophenyl)-5-(2,4-disulfophenyl)-2H-tetrazolium sodium) assay as an indication of viability/cytotoxicity treatment. WST-1 viability assay is based on the reduction of tetrazolium salt, WST-1 to an insoluble formazan dye by electron transport across the plasma membrane in viable cells that alter the optical density of the media. Following the 24 hours seeding period, the growth medium was replaced with a 200 µL of fresh growth medium containing a serially diluted LATTE or Doxorubicin into designated replicate wells. Cells were incubated for 24 or 48 hours following treatment. At the end of the incubation period, the medium was discarded, and the wells were rinsed three times with DPBS solution followed by addition of 100 µL growth medium and 10 µL of freshly prepared WST-1 reagent into each well and then incubated for 2 hours inside the 5% $CO_2$ incubator at 37° C. After the incubation period, the optical percent density was measured using a microplate reader at a wavelength of 450 nm (SpectraMax iD5, Molecular Devices, San Jose, CA). Cell viability was calculated relative to control wells that received the growth medium alone. Viability rate was calculated as follows: Viability (%)=(1−$OD_{treatment}$/$OD_{control}$)×100%.

The fractional viability dose-response curve for LATTE or Doxorubicin was used to calculate the concentrations that cause cytotoxicity in 50% of the HepG2 cells (EC50) at 24 or 48 hours was determined to determine the synergy score of LATTE and Doxorubicin treatment combination in vitro, using statistical software (Prizm Software, ver. 7, GraphPad, San Diego, CA). To establish a cytotoxic synergy of combined LATTE and Doxorubicin at low concentrations, HepG2 cells were incubated with single-agent using 4-5 concentrations spanning the $EC_{50}$ of LATTE or Doxorubicin, respectively. Subsequently, pairwise treatments of all possible combinations were generated to yield a 4-by-5 matrix for each singly tested drug; (C) the values of the pairwise concentrations were interpolated from the fitted Hill curves of each single treatment dose-response curve using the Loewe model, and Loewe synergy score as calculated and plotted using Combenefit software. Graphical outputs consist of single-agent dose-response data and its fitting, the combination dose-response, and graphic mapping of the synergy distribution onto the dose-response surface. All reported values are the means of three replicate experiments with each study having 8 wells per dose level. Plots of the log concentration versus fractional viability for each drug were generated for each study.

Inducing VX2 Liver Cancer in Rabbits

A preserved VX2 tumor tissue slurry aliquots preserved in liquid nitrogen obtained from an anesthetized donor rabbit were freshly thawed and suspended in 1 mL DMEM tissue culture medium then injected into the calf muscle of a donor New Zealand white female rabbit using a 16 gauge needle. Following tumor growth, muscle tissue containing the VX2 tumor lesion was harvested and placed in ice-cold DMEM then minced into 1 $mm^3$. Two fragments of freshly harvested and minced tumor tissues were surgically implanted into a small incision made in the left medial lobe liver through an upper abdominal exposure using aseptic techniques. The liver incision was gently compressed for three minutes using an absorbable gelatin sponge (Ethicon, Inc., Summerville, NJ) to control bleeding. The VX2 tumor-bearing rabbits confirmed by ultrasound were injected with 2 mL LATTE formulation under ultrasound guidance or following surgical exposure. One hour after injection, ultrasound imaging was repeated, then rabbits were euthanized following by liver harvesting and fixation.

Percutaneous Injection of LATTE Mixture Under Ultrasound-Guided into Rabbit and Pig Liver Ultrasound-guided injection of LATTE solution was performed in euthanized pigs or rabbits. 2 mL of 25%-LATTE and 0.25 mg/mL Indocyanine green (ICG) mixture loaded into a syringe (Becton-Dickenson, Franklin Lakes, NJ) on a 7 cm 21-gauge access needle (COOK Medical, Bloomington, IN). Ultrasonography was used to visualize the left liver lobe parenchyma using a high-frequency transducer (A 9-MHz multi-frequency linear probe, ACUSON 52000, Siemens, Germany). The access site position was marked on the skin and a scalpel blade was used to create a small incision in the center of the marked line. The access needle was advanced through the skin incision in front of the transducer parallel its long axis until it reached the desired location then the LATTE mixture was slowly injected over one minute. At 10 minutes post-injection, the liver tissue was harvested and subjected to near-infrared fluorescent imaging (NIRF) (IVIS 200, PerkinElmer, Inc. Waltham, MA) followed by fixation and histologic evaluation.

Magnetic resonance imaging of pig liver following subcapsular injection of LATTE Solution MR imaging was performed on explanted pig liver was performed after subcapsular injection of 2 mL solution comprises of 25% LATTE aqueous solution containing 0.25 mg/ml indocyanine green on a 21 gauge vascular access needle. Injection Images were acquired at 0 and 90 minutes after injection. Pig livers were scanned with a 3T MAGNE-TOM Skyra MRI (Siemens Healthcare, Erlangen, Germany) with an 18 channel anterior coil in combination with a 32 channel posterior spine coil. Following MR scan were performed: Coronal T2 single-shot fast spin-echo (HASTE) with FOV 300×300 mm, resolution 448×310, slice thickness 1.3 mm, TR 800 ms, TE 120 ms, BW 620 Hz/Px, 4 NEX, scan time 3:15 minutes; this was performed for anatomical reference. High resolution coronal 3D T1 fast gradient echo volumetric scan (MPRAGE) with FOV 320×320 mm, resolution 512×512, slice thickness 0.6 mm, TR 1350 ms, TE 2.34 ms, Flip angle 9 deg, TI 900 ms, BW 390 Hz/Px, scan time 6 min resulting in 0.6×0.6×0.6 mm 3D volumetric resolution; this sequence was performed to visualize the liver parenchyma. High resolution coronal 3D T2 fast spin-echo volumetric scan (SPACE) with FOV 300×300 mm, resolution 320×320, slice thickness 0.9 mm, TR 1700 ms, TE 105 ms, Flip angle 135 deg, BW 600 Hz/Px, NEX 1.4, scan time 9:24 minutes resulting in 0.9×0.9×0.9 mm 3D volumetric resolution; this sequence was performed to visualize vessels. Coronal T2 cine fast steady-state free precession (TRUFI) scan was performed with FOV 380×380 mm, resolution 256×256, slice thickness 5 mm, TR 630 ms, TE 11.77 ms, Flip angle 60 deg, BW 1300 Hz/Px, scan time 3:09 minutes resulting in a temporal resolution of approximately 1.5 frames/sec. Scans were acquired at 0 and 90 minutes after injection. Segmentation and volume calculations were acquired using the Materialise 3-Matic and Mimics 3D image processing software (Materialise, Belgium).

Human Cancer Tissue Processing

Explanted human cancer tissues were collected following surgical resection and placed in RPMI medium for preservation. 25% LATTE mixture was injected in the core of the tumor mass using a 25 gauge needle. Near-infrared fluorescent imaging (NIRF) was performed at 5 minutes after injection. Treated tissues were incubated inside a humidified chamber for 24 hours partially submerged in tissue culture media. NIRF was repeated at 24 hours after LATTE injection. Tissues were transected to reveal the ablated zone were fixed in 10% buffered formalin, embedded in paraffin, then sectioned and subsequently stained with hematoxylin and eosin for microscopic evaluation.

Histopathology and Immunohistochemistry

At necropsy, liver tissues were harvested and fixed in 10% buffered formaldehyde and transected axially to expose the core of the treatment zone. Fluorescent scans of each liver were acquired before and after transection, and subsequently, tissues were embedded in paraffin then serially sectioned to generate 4-μm-thick sections. Serial sections were stained with hematoxylin and eosin (H&E) to visualize tissue morphology and cellular infiltration or underwent immunohistochemistry (IHC) staining. To identify actively proliferating cells and cells undergoing apoptosis tissue sections were incubated with 1:250 dilution of rabbit IgG specific for proliferating cell nuclear antigen (PCNA, AB13847, Abcam) or an IgG that recognizes cleaved caspase-3 (1:250, AB13847, Abcam, MA) respectively. Rat anti-mouse CD3 IgG3,κ (1:20, 550295, BD Pharmingen,) was used to visualize naïve T-cells; and polyclonal rabbit anti-CD68 IgG (1:250, AB125212, Abcam) was used to recognize local monocytes and macrophages and those used to characterize infiltration by neutrophils granulocytes included rabbit monoclonal to myeloperoxidase IgG (MPO, 1:250, AB208670, Abcam). Sections were then incubated with goat anti-rabbit horseradish peroxidase-conjugated IgG HL (1:300, AB97051, Abcam) secondary antibodies at room temperature for 30 minutes. Specific proteins were detected using the 3,3'-diaminobenzidine (DAB, Dako) reagent, and Hematoxylin was used for counterstaining. Sections were dehydrated, and coverslips applied using Richard-Allen mounting medium (ThermoFisher Scientific). EVOS FL Auto microscope was used to obtain stitched digital micrographs. Appropriate thresholds and particle size were set to count the number of positive cells per field, and limited concentric radial measurements of each cross-sectional area of all tumor samples were compared. Data were expressed as the mean of positive cells per cubic millimeter.

Statistical Analysis

All results were analyzed using Prism software version.7 (GraphPad, San Diego, CA) to evaluate statistical differences between groups. Data are reported as mean±standard error of the mean (SEM) or percentage (%) as appropriate for the categorical variable. Comparisons between different treatments were performed using the Mann-Whitney test (U-test) for differences between two groups or analysis of variance (ANOVA) for continuous variable comparison among the three groups. Linear regression plot for in vivo measurements of tumor size determined by ultrasound US or micro-CT imaging were compared by Pearson factor for analysis of correlation of values obtained using the two imaging modality. A p-value of <0.05 for each comparison indicates statistical significance.

Taken together, these results demonstrate that the LATTE composition can be used, alone or in combination with a chemotherapeutic agent, to ablate tumor tissue to treat cancer.

Example 2: Effect of Ablation Agent on Fat

To demonstrate the ability of LATTE to ablate fat tissues, subcutaneous injection with 25% LATTE mixture was performed in pigs.

Figure 9:
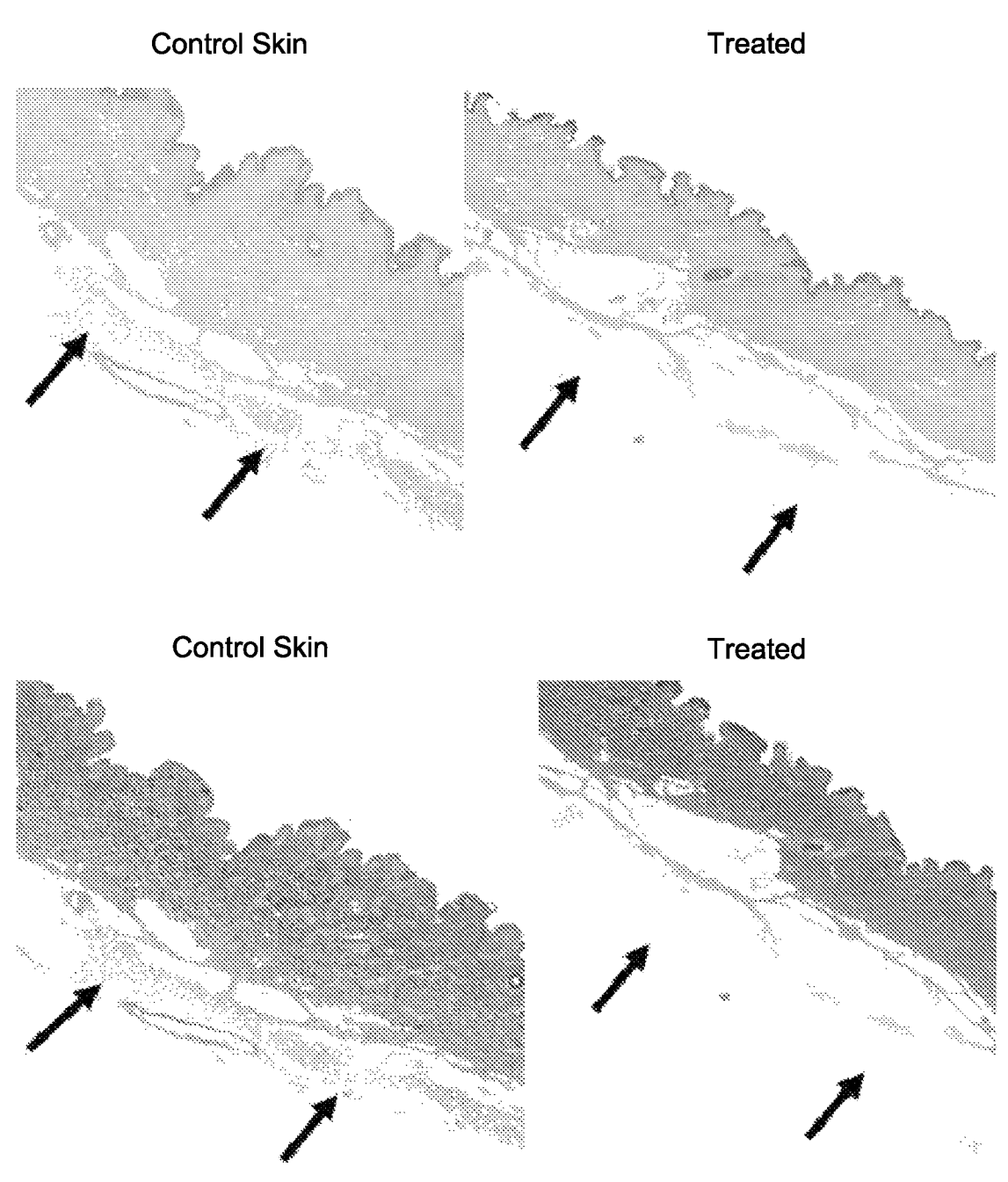
FIG. 9. Ablation of fat tissue from skin. Control skin: Arrows indicate subcutaneous fat. Treated skin: There is significantly reduced subcutaneous fat in pigs treated with LATTE liquid ablation agent as shown in the H&E stained (top) and trichrome stained (bottom) histology section.
Figure 10:
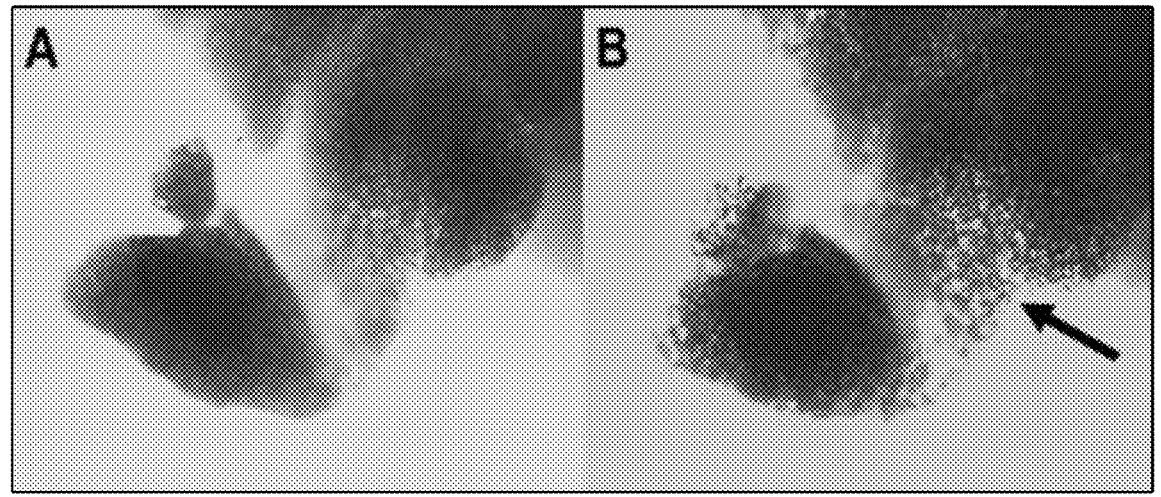
FIGS. 10A-10B. Ablation of fat from adipocytes.
Figure 11:
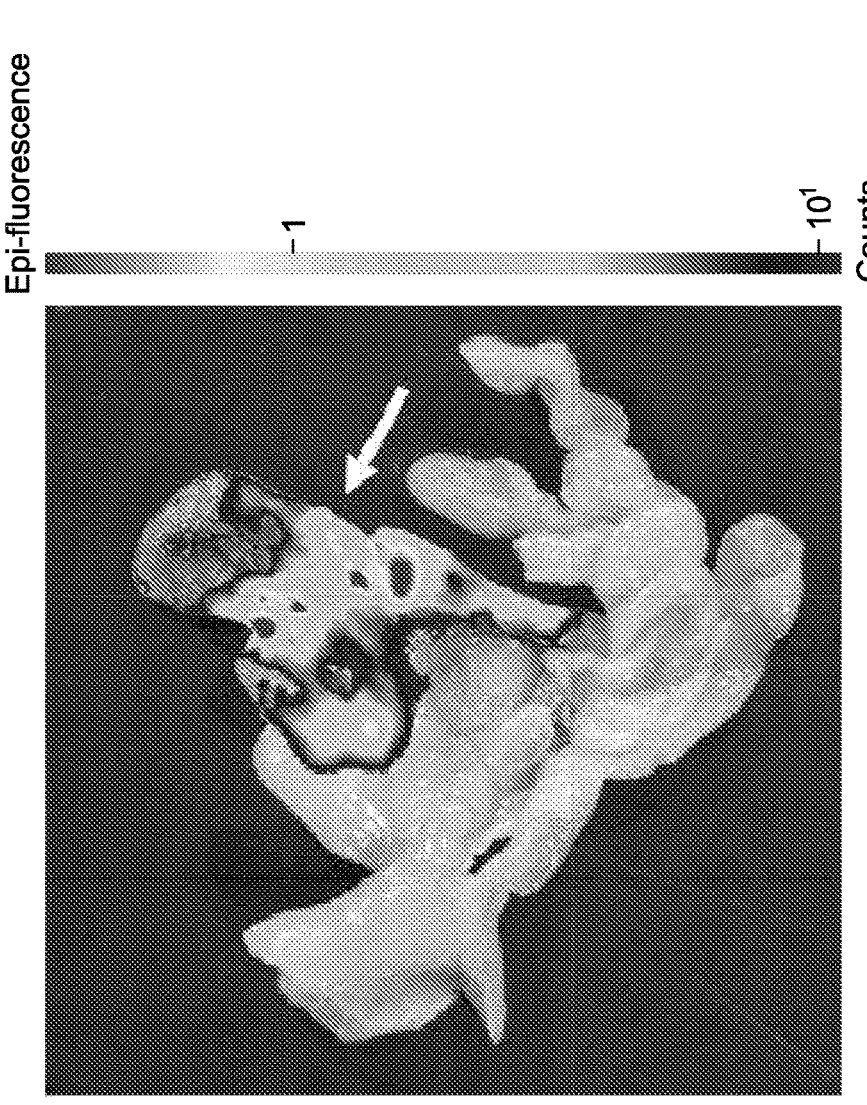
FIG. 11. Imaging during fat tissue ablation. Fat from pig was treated with LATTE liquid ablation agent mixed with indocyanine green (ICG). 1 cc of the mixture was injected. After 1 hour spreading of the LATTE liquid ablation agent is shown using near-infrared fluorescent imager showing the distribution of ICG enhanced fluorescence.

Skin tissues were harvested for histologic evaluation showed complete ablation of the adipocytes (fat cells) in the treated zone (FIG. 9), and demonstrate that LATTE is able to dissolve subcutaneous fat tissue without significant inflammatory reaction. Additional experiments were performed on explanted fat tissue obtained from the groin area from pig in a petri dish submersed in saline (FIG. 10). The explanted fat tissue was subsequently incubated with 25% LATTE and showed complete lysis of fat cells within 10-15 minutes following incubation. LATTE mixed with indocyanine green was injected into fat tissue showed clear enhanced fluorescence in the ablated area using near-infrared imaging (FIG. 11).

Taken together, these results demonstrate that the LATTE composition can be used to ablate fat tissue to treat obesity.

Example 3: Effect of Ablation Agent on Blood

Figures 12A, 12B:
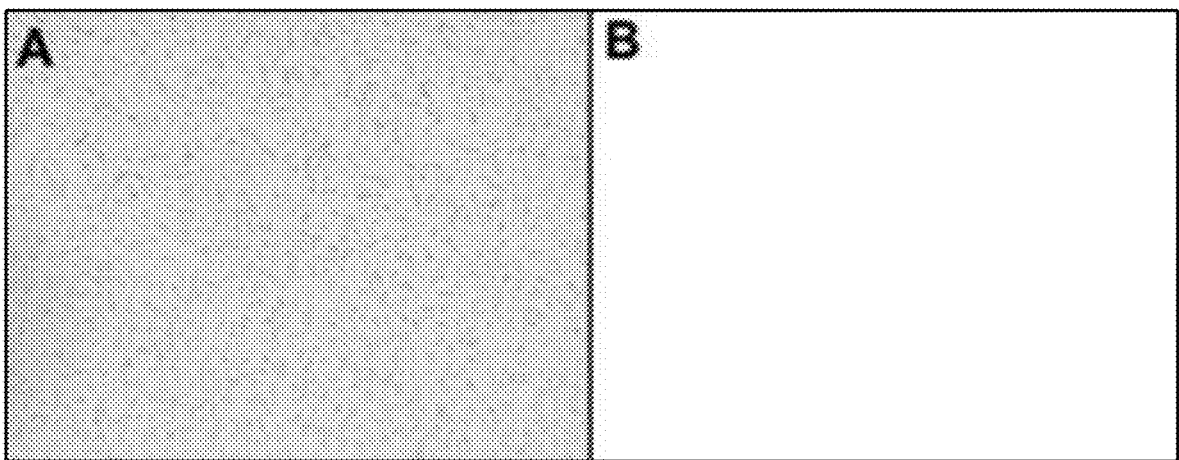
FIGS. 12A and 12B. Effect of an ablation agent on human blood.
Figure 13:
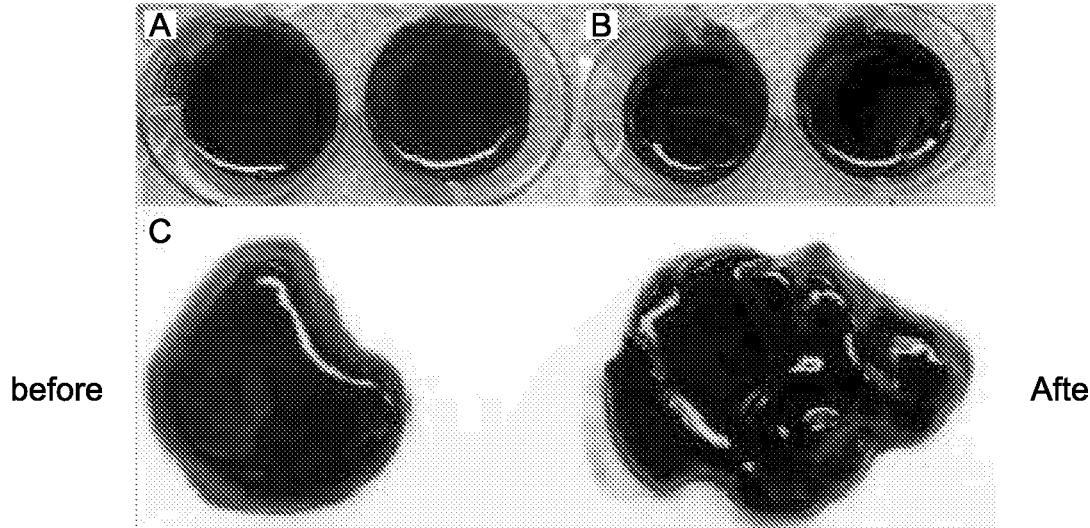
FIGS. 13A-13C. Effect of an ablation agent on human blood clot.

To demonstrate the ability of LATTE to lyse cells in human blood, whole blood was placed in a slide chamber after dilution normal saline then observed and photographed under a brightfield microscope (FIG. 12A). Following incubation with 25% LATTE solution all blood cells were undetectable in the slide demonstrating complete cell (FIG. 12B). In a separate experiment blood coagulation was induced in uncougulated human. A blood volume of 4 mL citrated blood loaded into a polypropylene tube and mixed with 400 µL of 0.2 M calcium chloride ($CaCl_2$) for 10 seconds. Aliquouts of 100 µL were deposited into multiple wells on a 96 well plate and the remaining blood volume was kept in the tube. Coagulation was initiated by incubating the samples at 37° C. for 10 minutes. Once coagulation is completed 100 µL of 25% LATTE was overlayed over of the coagulated blood in the multi-wells whereas the control wells were overlayed with similar volume of saline as shown in in FIGS. 13A and 13B respectively. Additionally, the blood clot that was formed in the tube was removed into a petri dish then submerged in 25% LATTE as shown in FIG. 13C which caused thrombolysis.

In real time, LATTE causes blood clot to dissolve. This can be a potential acute and chronic deep vein thrombosis treatment.

Taken together, these results demonstrate that the LATTE composition can be used to ablate blood clots to treat disease and disorders associate with clot clots.

Example 4: Effect of Ablation Agent on Cardiac Tissue

Figure 14B:
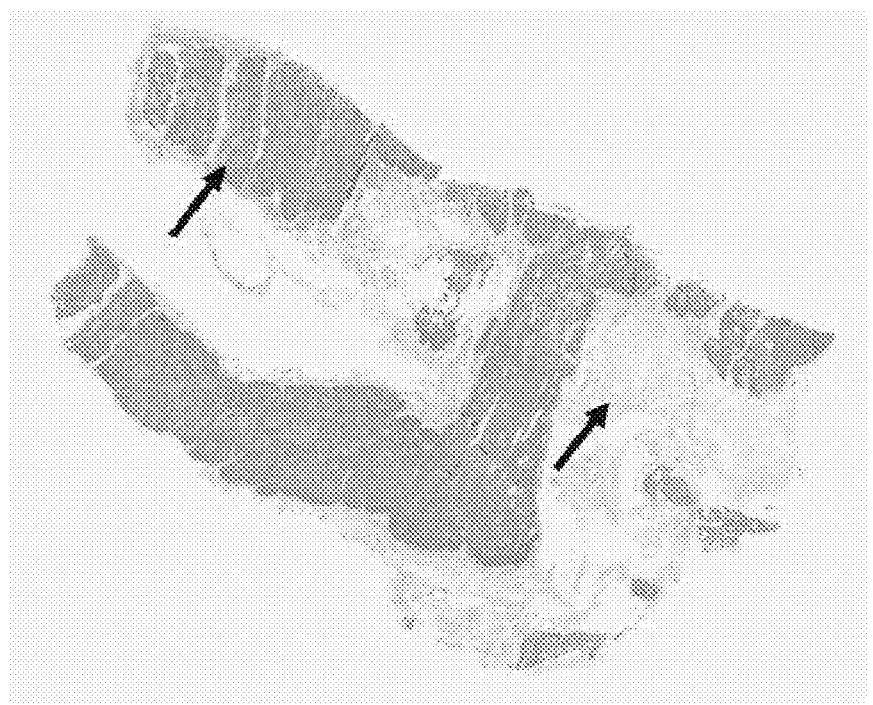

Pig heart tissue septum received 1 cc injection of LATTE mixture with ICG under ultrasound guidance. Cardiac muscle was removed after 1 hour for near-infrared imaging (NIRF) and histology was performed. NIRF imaging showed localized fluorescent enhancement in the cardiac muscle at the injected site (FIG. 14A). Histology section of the injected site demonstrated marked ablation of the cardiac myofibers limited to the treated zone (FIG. 14B).

Taken together, these results demonstrate that the LATTE composition can be used to ablate cardiac tissue to treat heart diseases and disorders.

Example 5: NanoGel Formulations for Effective Tissue Ablation and Drug Delivery This Example describes the synthesis and characterization of choline based ionic liquids (ILs). Selected ILs were used to make hydrogels containing LATTE (NanoGel formulations) with doxorubicin (Dox), immune checkpoint inhibitors (ICIs), and/or imaging agents. NanoGel material properties (e.g., viscosity, elastic modulus, injectability, and sterility), cytotoxicity profile, and drug release kinetics were assessed in vitro. Tissue ablation, drug diffusion/delivery, and retention were also evaluated in vivo in normal rat livers.

Methods

NanoGel Preparation and Characterization

A stock of neat CAGE IL was prepared using salt metathesis reaction as described elsewhere (see, e.g., Zakrewsky et al., *Adv. Healthc. Mater.*, 5(11):1282-9 (2016); Banerjee et al., *Adv. Healthc. Mater.*, 6(15) (2017)). Briefly, geranic acid (Sigma Aldrich, St. Louis, MO) will be recrystallized 5 times at −70° C. in acetone, in a 500-mL round bottom flask and added to molar equivalent of choline bicarbonate (80 wt % solution, Sigma Aldrich, St. Louis, MO). The mixture is stirred at room temperature until $CO_2$ evolution ceases. Residual $H_2O$ is removed by rotary evaporation at 60° C. for 2 hours and drying in a vacuum oven for 96 hours at 60° C. Long-term IL stability was verified using NMR following incubation at 4° C. or 65° C. Any IL that did not meet optimum physical properties or long-term stability was excluded. To make NanoGel, a nanosilicate (NS) hydrogel was prepared using LAPONITE® XLG, (BYK) by physically mixing LAPONITE® powder in ice cold water as described elsewhere (see, e.g., Albadawi et al., *Adv. Sci.*, 2020; 8(1):2003327 (2020); Avery et al., *Sci. Transl. Med.*, 8(365):365ra156 (2016)). An aliquot of freshly made NS hydrogel was combined with consistent weight ratio of Dox, ICIs, or ExiTron nano 12000 (Miltenyi Biotec, Germany) and efficiently mixed using a SpeedMixer (DAC-150.1, FlackTek Inc). A variety of NanoGel formulations were prepared by combining an aliquot of NS hydrogel containing Dox or species-specific ICIs, to a relevant amount of neat IL (100%) at predetermined weight ratios to generate NanoGels with a range of IL concentrations (6.25, 12.5, 25, and 50 wt % of IL). Anti-PD1 (LSBio, anti-rabbit PD1, LS-055247), anti-PDL1 (Biorbyt, anti-rabbit PDL1, orb228661) were used as ICI candidates.

The physical properties of each NanoGel formulation were analyzed to determined viscosity and injectability (rheometry and injection force testing), molecular integrity, conductivity, and density.

NanoGel viscosity variable ratios of NS (2-6 wt %) were tested to generate a NanoGel with easy injectability (rheology), and stability following injection.

Drug-Release Kinetics of NanoGel

To understand the interactions between anti-cancer agents with NS and IL as well as any possible interactions between anti-cancer agents, the release kinetics of synergistic IL/Dox/ICI-loaded NanoGel formulations were compared with the release profile of individually prepared Dox-loaded hydrogel and ICI-loaded hydrogels. Dox and ICI were applied to the NS hydrogel in the same way (fabricating NS first and then adding dox or ICI later). To assess the release profile, NanoGel was synthesized and 200 mg aliquots of different formulations, as well as IL, Dox, or ICI was aliquoted into transwell inserts fitted with polyethylene terephthalate filter and incubated for up to 30 days at 37° C. Release kinetics of Dox or/and ICIs was serially analyzed at different time-points using fluorescent intensity of Dox or ICI-specific ELISA, and liquid chromatography with tandem mass spectrometry (LC-MS/MS). Additionally, to assess ILs, ICI, and Dox chemical structure stability and functionality, samples were analyzed using FTIR, and nuclear magnetic resonance (NMR). A zeta potential analyses (Malvern Panalytical) was also performed for each formulation to analyze any change in surface charge, corresponding to possible interactions and their effect on release profile. In addition, injection force (Instron), viscosity, storage/loss modulus (Rheometer), and injectability test (Instron), were analyzed as described elsewhere (Albadawi et al., *Adv. Sci.*, 2020; 8(1):2003327 (2020); Avery et al., *Sci. Transl. Med.*, 8(365):365ra156 (2016)).

Determine NanoGel Cytotoxicity and Synergy with Chemotherapy

Cytotoxicity effect of selected NanoGel formulations was evaluated in different human liver cancer cell lines including human hepatocellular carcinoma (CRL10741, American Type Culture Collection, Manassas, VA), and cholangiocarcinoma (SNU-478). Additionally, selected NanoGel formulations were tested against animal cancer cell lines including: rat hepatocellular carcinoma cell line, N1S1 (ATCC, CRL-1604), and the mouse colorectal adeno carcinoma cell line, MC38. Both cell lines were used to create the cancer models for in vivo testing. Fractional viability ($IC_{50}$) of different cancer cell lines were determined following incubation with NanoGels extracts which were compared to cells treated with individual components using WST-1 assay (Cayman Chemicals, Ann Arbor, MI) and microplate reader (SpectraMax iD5, Molecular Devices, San Jose, CA) as described elsewhere (Albdawi et al., *Sci. Transl. Med.*, 13(580) (2021)). To assess the effect of NanoGel on energy metabolism of cancer cells, the steady state level of ATP, NAD/NADH ratio, and lactate was measured using chemiluminescence assays (Promega, Madison, WI) as described elsewhere (Albdawi et al., *Sci. Transl. Med.*, 13(580) (2021)). To determine the effect of NanoGel on Dox intracellular uptake and nuclear localization, confocal microscopy was performed on cells grown on microscope slide chambers. To quantify the amount of Dox uptake in the cellular, nuclear, or mitochondrial compartments were isolated and then suspended in 0.5 mL ethanol/0.3N HCl. The amount of the retained Dox was determined using fluorescence plate reader and extrapolated from a calibration curve. To evaluate the ICI-loaded NanoGel in vitro, HepG2 cells were also be used for testing ex vivo immunogenicity. The primary isolated rabbit or human splenocytes (Zen-Bio) was pre-activated for 2-4 days with different concentration of ICI-loaded NanoGel coated well plate to stimulate antitumor sensitivity. Then, activated splenocytes were co-cultured with HepG2 at the ratio of 1:20, 1:40 times in the commercially available ELISPOT module (MABTECH, IgG (#3865-2H), IFN-γ (#3321-2H), TNF-α (#3511-2H)) for 48 hours.

Rheological Testing

Rheological evaluation of NanoGel or Ns hydrogel was performed using an Anton Paar MCR 302 rheometer (Anton Paar USA Inc., Torrance, CA). A sandblasted 25 mm diameter aluminum upper plate and an aluminum lower plate, with a 500 μm gap in between, were used for all measurements. Flow curves and amplitude sweeps (at 10 rad s$^{-1}$) were obtained at 25 and 37° C. For tests at 37° C., the solvent trap was used, and the edge of the solvent trap was filled with water to provide a humidified environment. Data were acquired at least in triplicates for each experiment.

Injectability

The injectability of NS hydrogels, or NG through clinical catheters was investigated using a mechanical tester (Instron, Norwood, MA). The force required for NG or NS gels (loaded into a 1 cc BD syringe) to pass a 2.8 F, 110 cm catheter (Terumo Medical Corporation, Somerset, NJ) at a flow rate of 1 mL min$^{-1}$ was recorded using Bluehill version 3 Software (Instron, Norwood, MA, US). Subsequently, injection force of each samples was acquired.

Scanning Electron Microscopy (SEM)

A scanning electron microscopy (JCM-6000Plus) was used to visualize the microstructures of NanoGel or NS hydrogel following freezing at −80° C., followed by lyophilization (Labconco, 0.120 mBar, and −50° C.). All prepared specimens were then sputter-coated with 7 nm gold/palladium (Leica EM ACE200) and imaged using SEM.

Fluorescence Imaging of NanGel In Vitro

In vitro spectral fluorescence imaging was performed on 250 μL aliquots of NanoGel or NS hydrogel containing 1.25 mg/mL Dox or 0.25 mg/mL ICG loaded into 96 well plates to assess differences in Doxorubicin or ICG after intratumoral injection of NanoGel or NS hydrogel using the IVIS 200 system (PerkinElmer Inc., Waltham, MA). Fluorescence images for doxorubicin were acquired using an excitation wavelength of 460 nm and an emission wavelength of 560 nm. Whereas near-infrared illumination at the excitation wavelength of 750 nm, and emission wavelength of 850 nm were used to visualize ICG. Fluorescent images in different experimental specimens were acquired using an identical setting of 1-s exposure time (f/stop=2) and displayed using the same scale in each group. Each plate was incubated at 37° C. humidified chamber and was serially imaged up to 56 days. Fluorescence intensities in the wells were quantified using radiance values in the region of interest and normalized to photons per second per square centimeter per steradian (p/s/cm$^2$/sr), and the area of fluorescence enhancement in each specimen was also calculated after applying a standardized threshold value.

Cytotoxicity

Cytotoxicity of the human liver cancer cell line, HepG2 (CRL10741, American Type Culture Collection, Manassas, VA), was evaluated following incubation with serially diluted NanoGel extract under growth conditions consisting of Dulbecco's Modified Eagle Medium (DMEM, ThermoFisher Scientific, Waltham, MA) and 10% heat-inactivated bovine serum that was supplemented with 100 IU penicillin and 10 μg/mL streptomycin (Thermo Fisher Scientific, Waltham, MA). Cells were seeded into 96 multi-well replicate plates at 5,000 cell density per well for 24 hours. Following 24 hour seeding period, the medium was replaced with 200 μL of fresh growth medium containing a serially diluted NanoGel extract into designated replicate wells and subsequently incubated for 24 hours. At the end of the incubation period, the medium was removed, and the wells were rinsed three times with Dulbecco's modified phosphate buffer (DPBS, Sigma-Aldrich, Saint Louis, MO) followed by the addition of 100 μL growth medium. Cytotoxicity of NanoGel was determined by adding 10 μL of freshly prepared solution of the water soluble 2-(4-Iodophenyl)-3-(4-nitrophenyl)-5-(2,4-disulfophenyl)-2H-tetrazolium sodium reagent (WST-1, Cayman Chemicals, Ann Arbor, MI) into each well followed by 2-hour incubation inside a 5% CO$_2$ humidified incubator at 37° C. WST-1 output was assessed by measuring the optical density at a wavelength of 450 nm using a microplate reader (SpectraMax iD5, Molecular Devices, San Jose, CA). Cell viability was calculated relative to control wells that received aliquots of growth medium alone. Viability rate was calculated as follows:

Viability (%)=(1−ODtreatment/ODcontrol)×100%. The fractional viability dose-response plots was used to calculate the concentrations that induce cytotoxicity in 50% of the HepG2 cells (IC$_{50}$) at 24 hours using the Prism Software ver. 8 (GraphPad, San Diego, CA).

Assessing Sterility

Sterility of NS, or NG was tested using *Escherichia coli* (*E. coli*) according to an established protocol with minor modifications. A 10 mL *E. coli* suspension with a concentration of $10^7$ CFU mL-1 was added on top of the 1 mL gel to reach a final concentration of $10^8$ CFU per milliliter gel was used as a positive control. Samples of pain Luria-Bertani (LB) broth were used as negative controls. The All groups were incubated for 24 hours at 37° C. at 180 rpm in a shaker incubator. The optical density of the suspension was measured at 600 nm using a microplate reader. Each suspension was measured three times, and each test was conducted three times independently.

Results

Figure 15A:
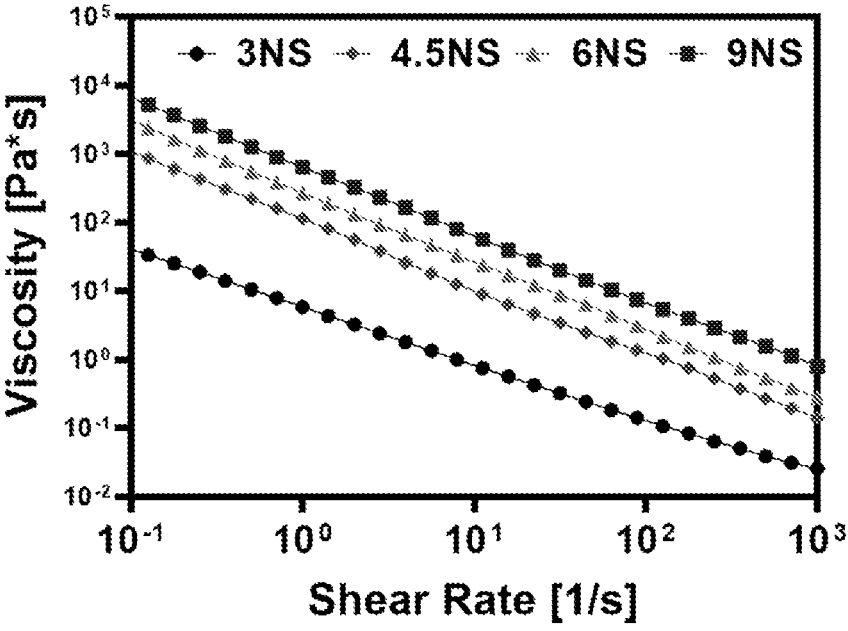
Figure 15B:
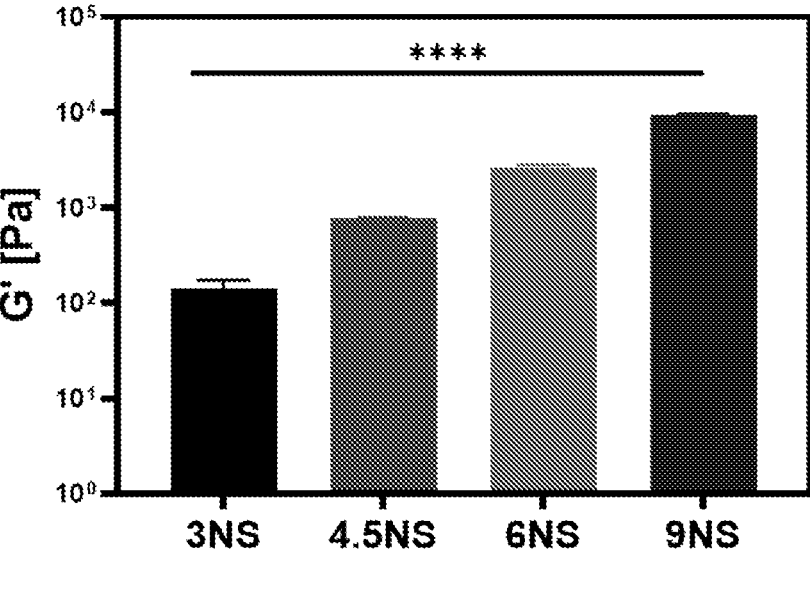
Figure 15C:
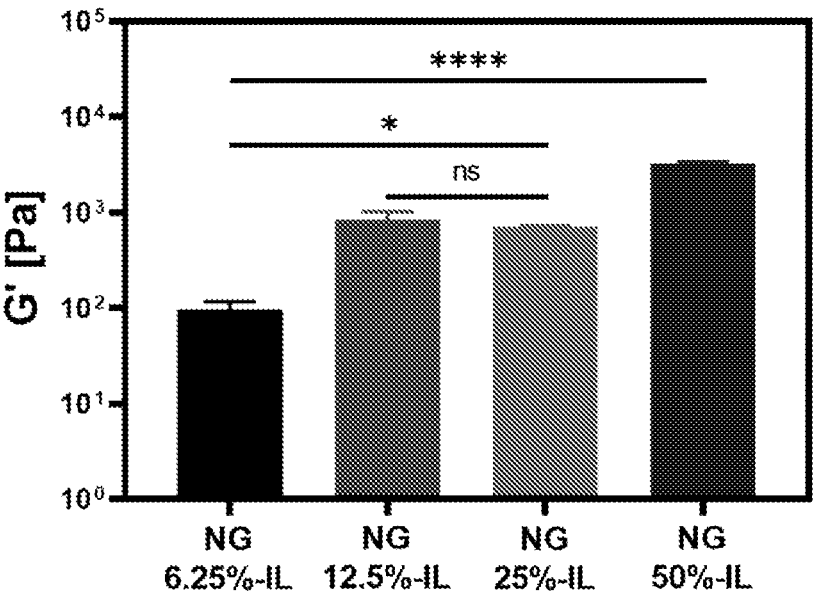

The mechanical properties of NG were characterized. To provide shear-thinning and drug carrying properties for NG and allow its injection through needles directly into tumor lesions or through catheters into the tumor feeding vessels to cause embolization, NS was used. Experiments were initially performed to evaluate the shear-thinning properties of hydrogels containing different ratios of NS. Hydrogels containing 3 wt %, 4.5 wt %, 6 wt %, or 9 wt % of NS demonstrated shear-thinning behavior (FIG. 15A). The effect of increasing NS ratio on storage modulus (G') generated by hydrogels containing 3 wt %, 4.5 wt %, 6 wt %, or 9 wt % NS is shown in FIG. 15B. 3 wt % NS provided sufficient storage modulus with the least amount of solid material in the hydrogel formulation and therefore it was chosen for further characterization. To assess the effect of incorporating different concentrations of ionic liquid (IL) in the hydrogel formulation, NGs containing 3 wt % NS and 6.25 wt %, 12.5 wt %, 25 wt %, or 50 wt % IL were made and tested by rheometry to assess their mechanical properties. Rheometry results showed concentration dependent increase in G' in the NanoGel containing 1.25 wt % or 25 wt % IL compared to NS alone (FIG. 15C, as compared to FIG. 15B), whereas 50 wt % IL results in a much higher G'. Since 25 wt % IL was proven effective in tissue ablation in previous Examples, a NG formulation containing 25 wt % IL was generated for further testing.

Figure 15D:
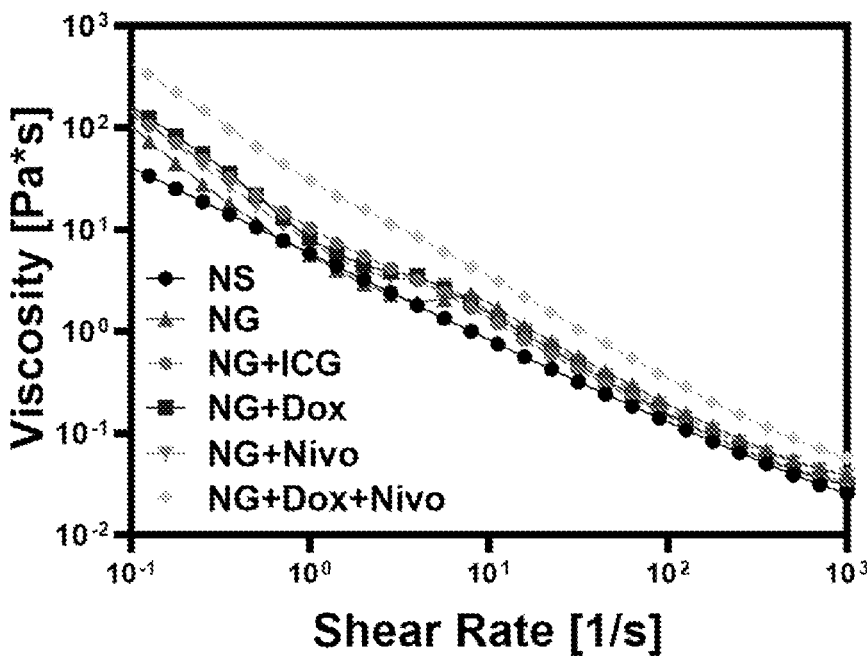
Figure 15E:
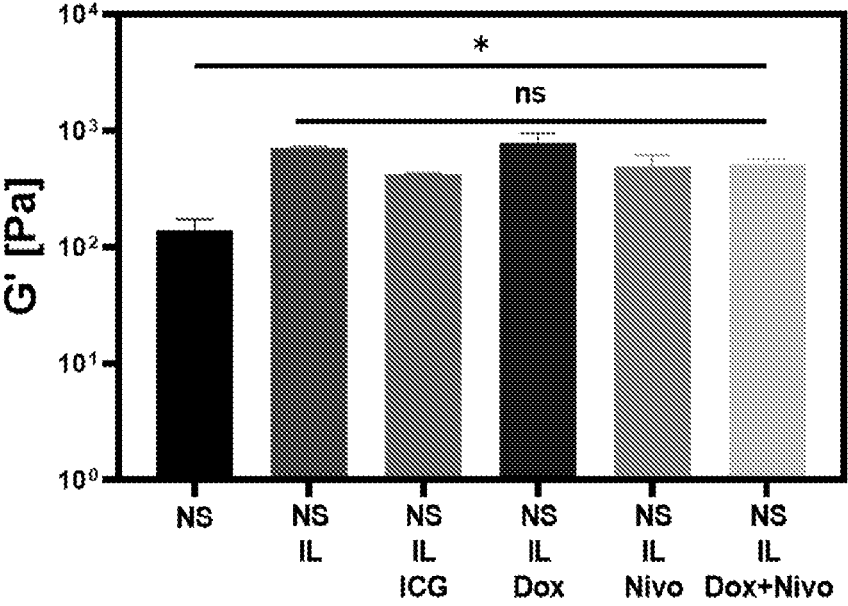

The effect of incorporating additional components, such as anti-cancer drugs, on mechanical properties of the NG was next investigated. NG containing 3 wt % NS and 25 wt % IL was mixed with 1.25 mg/mL of the anticancer drug Doxorubicin, 1 mg/mL of the immunotherapy agent Nivolumab (an anti PD-1 antibody), or 0.25 mg/mL of the near-infrared fluorescent agent ICG which has been used to track drug delivery in in vivo studies. A significant increase in G' was observed with different NG formulations compared to NS (FIG. 15D). An insignificant effect on viscosity and G' values by the added components was observed compared to NG alone (FIG. 15E).

Figure 15F:
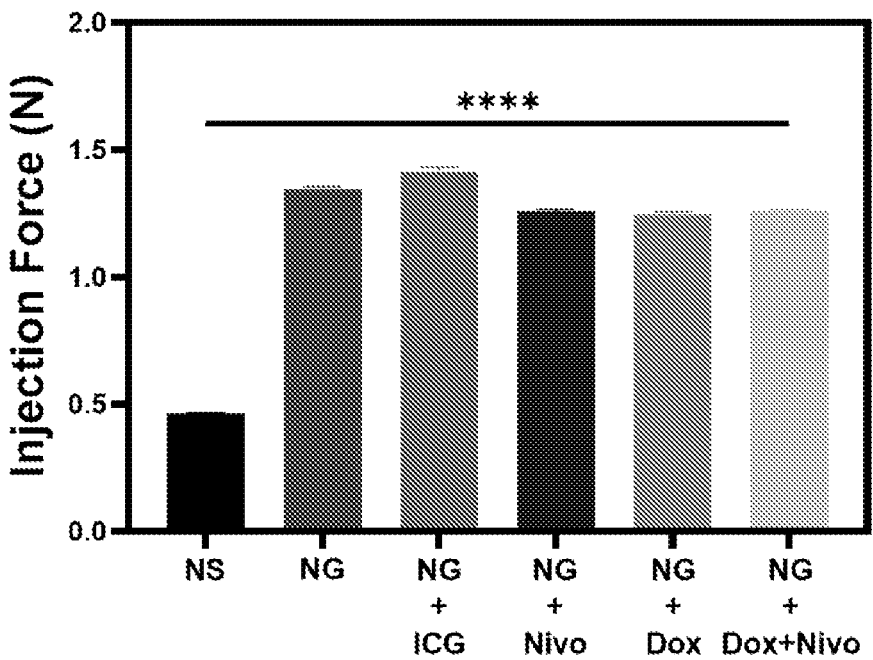

To verify whether NG could be comfortably injected through angiographic catheters, injection force testing was performed. The injection force generated by different NG formulations loaded in a 1 cc syringe and injected through a 110 cm 2.8 F microcatheter at 1 mL per min$^{-1}$ injection rate suggested comfortable injection by an average human hand and no effect of adding these components to NG on injection force values (FIG. 15F). (G) Exemplary NG formulations incorporating doxorubicin, nivolumab, or iohexol are shown in FIG. 15G.

Figure 16A:
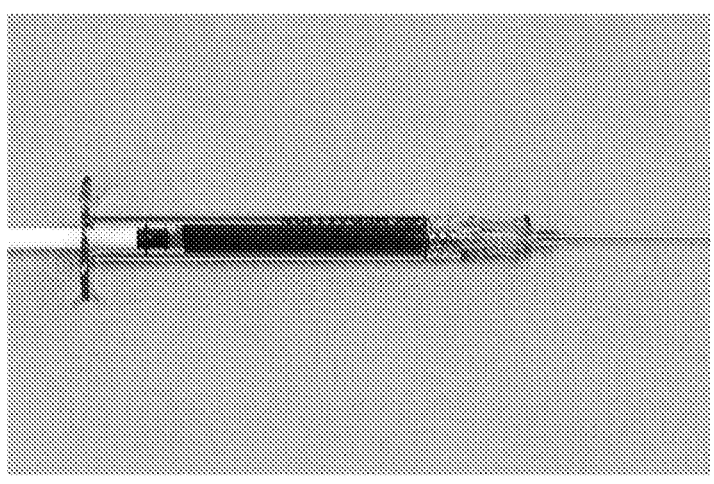
FIGS. 16A-16F. Assessing the microarchitectural appearance of NanoGel.
Figure 16B:
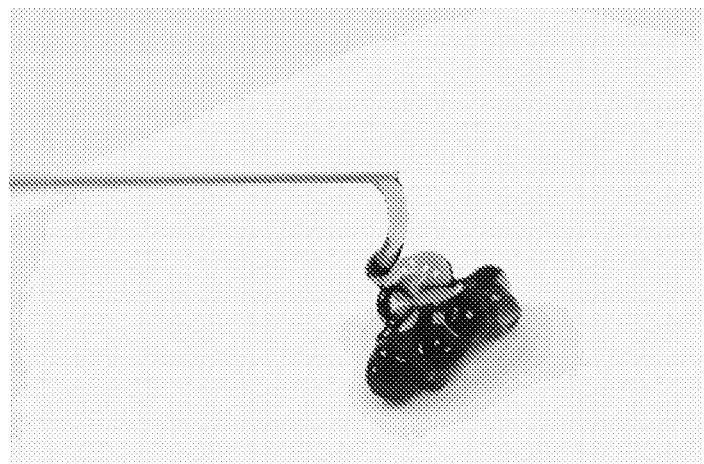
Figure 16C:
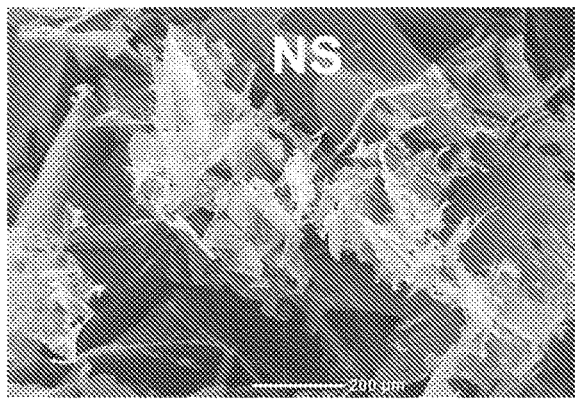
Figure 16D:
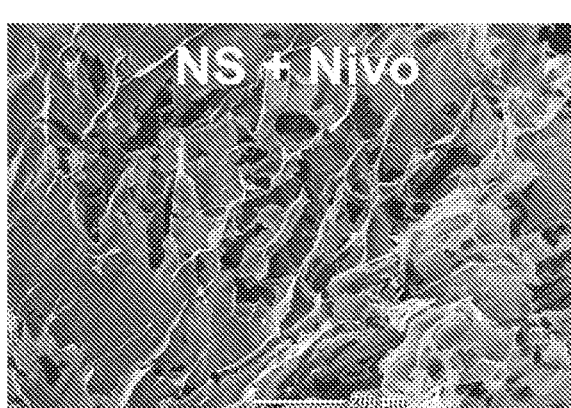
Figure 16E:
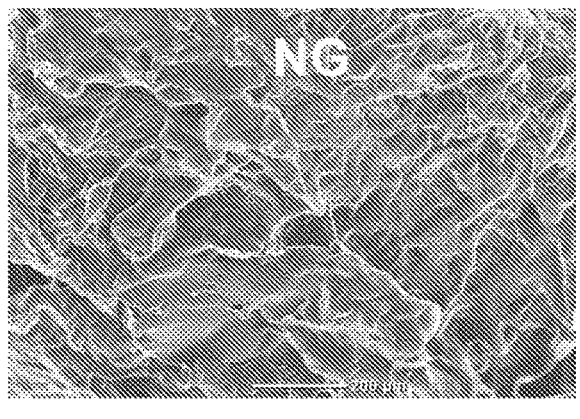
Figure 16F:
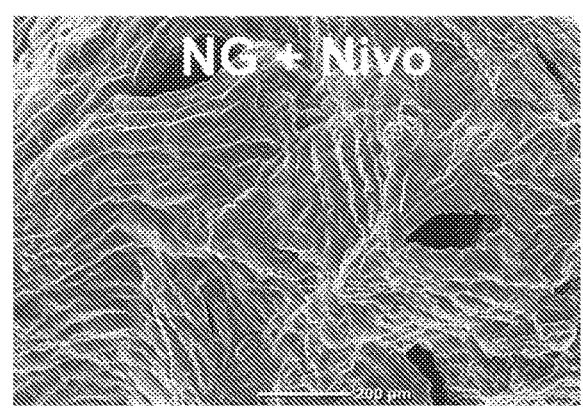

The microarchitectural appearance of NG was assessed. NGs containing 3 wt % NS, 25 wt % IL, 1 mg/mL nivolumab, or 0.25 mg/mL ICG were loaded into a clinical grade syringe fitted with 21-gauge vascular access needle for direct intratumoral or intravascular injection (FIG. 16A). Image showing NG was injected through the needle exhibiting shear-thinning behavior evident by maintaining coherence upon exiting the needle tip (FIG. 16B). Microscale level, SEM images of NS, NS mixed with Nivo (NS+Nivo), NG alone, and NG mixed with 1 mg/mL Nivo (NG+Nivo) are shown in FIGS. 16A to 16F, respectively, and show a porus microstructure in the NS and NS+Nivo hydrogels compared to less porus and mesh-like microstructure in the NanoGel containing ionic liquid or NG+Nivo. These data suggest that IL alters the interactions of the nanocomposites in the NS hydrogel.

Figure 17A:
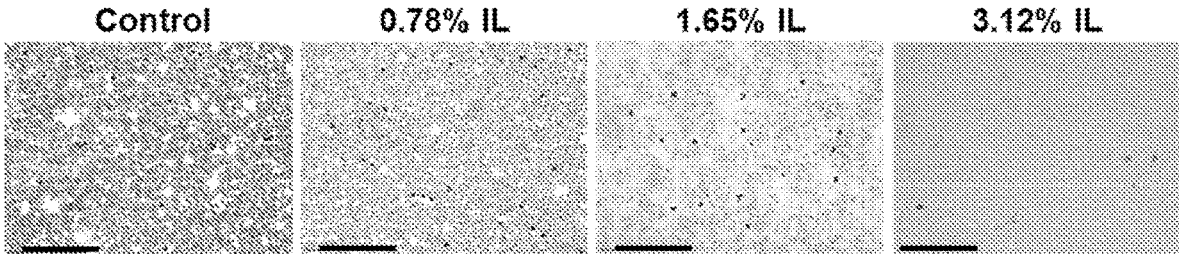
FIGS. 17A-17J. Effect of IL on coagulation and cell death in blood.
Figure 17B:
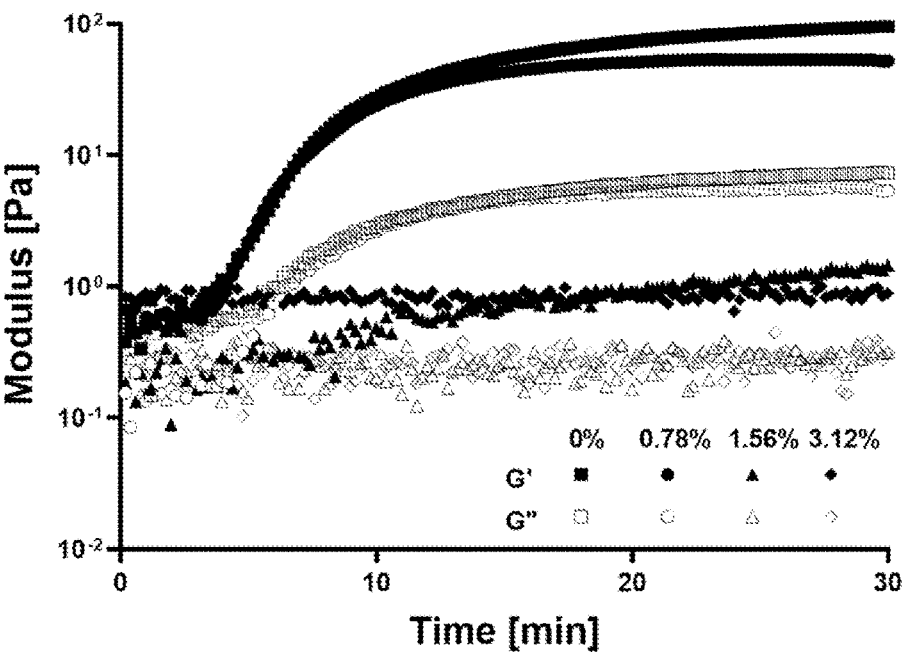
Figure 17C:
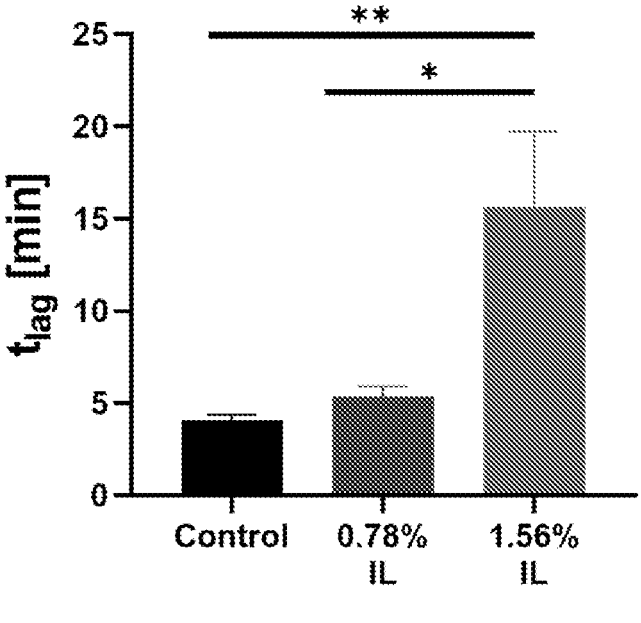
Figure 17D:
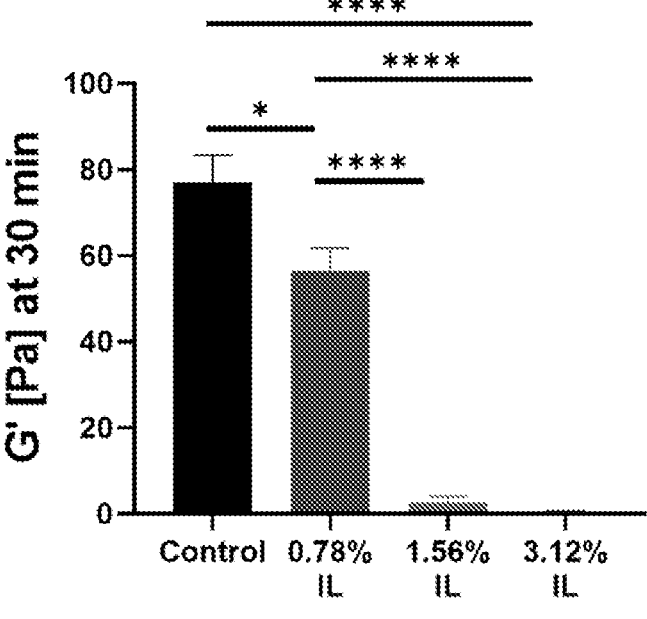
Figure 17E:
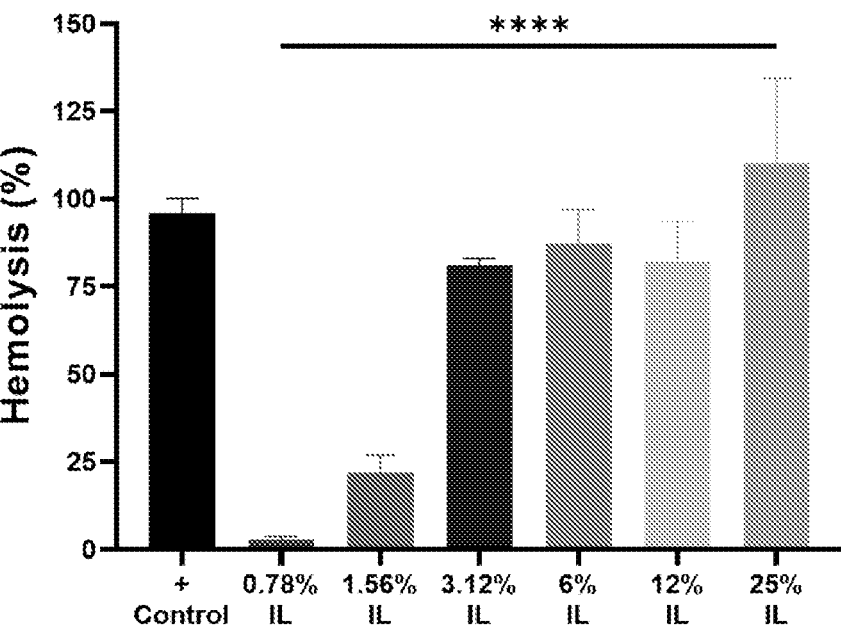
Figure 17F:
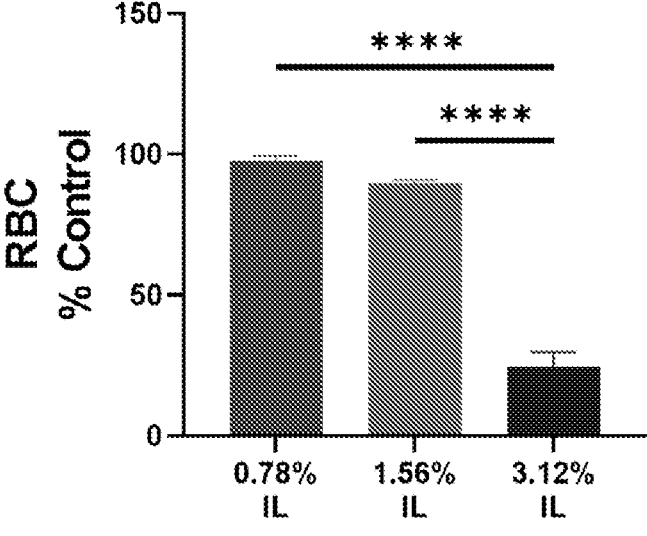
Figure 17G:
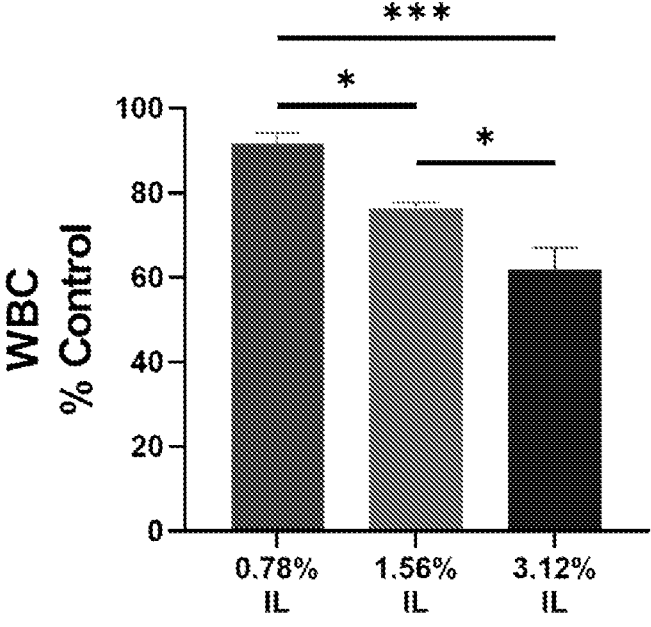
Figure 17H:
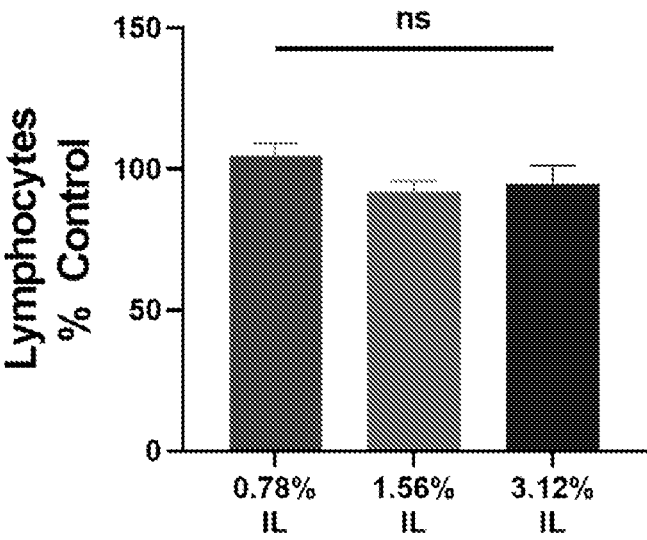
Figure 17I:
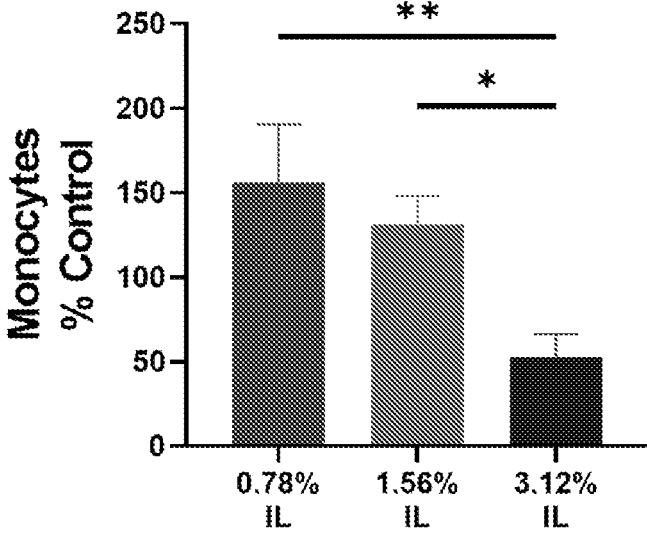
Figure 17J:
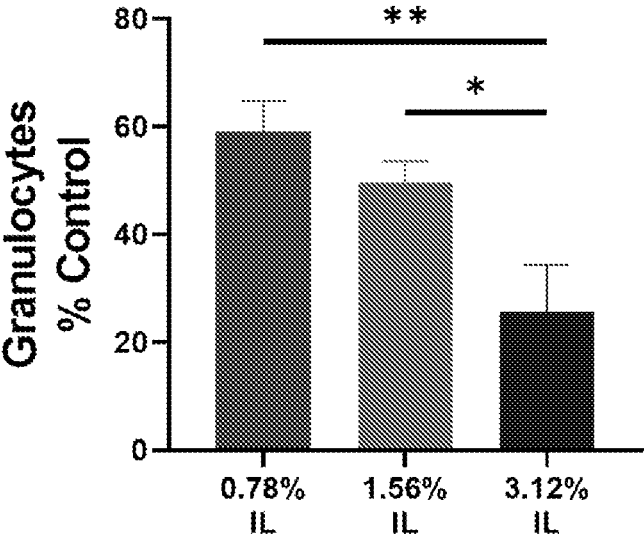

The effect of IL on coagulation and cell death in blood was evaluated in vitro. To evaluate the effect of cell death along the margins of the ablation zone, specifically on the effect of IL on inflammatory cells, blood treated with low concentrations of IL was used to simulate concentrations along the ablation margins. To analyze the effect of the ionic liquid on blood coagulation, RBC hemolysis, and immune cells, analyses including rheometry, hemolyses assay, complete blood counts were performed on blood smears following incubation of pig blood aliquots with various concentrations of IL. Stained blood smears prepared from pig blood treated with IL exhibited concentration dependent changes in morphology, a decrease in white blood cell detection, and exhibited evidence of complete hemolysis (FIG. 17A). The control and 0.78 wt % IL treated pig blood showed consistent G' and G" modulus profiles, whereas 1.56% IL treated blood displayed a delayed clotting lag time with lower G' and G" (modulus) levels compared to control blood (FIG. 17B). The 3.12 wt % IL treated blood failed to coagulate during the 30 minutes testing period (FIG. 17B). Since 3.12 wt % IL resulted in no coagulation, higher concentrations were not tested by rheometry. Quantitative analysis of blood coagulation initiation lag time (tlag) showing a slight increase in lag time at 0.78% IL and significantly extended lag time with 1.56 wt % IL treatment (FIG. 17C). Storage modulus (G') at 30 minutes following treatment with IL showing a ~20% decrease in storage modulus at 0.78% IL compared to 95% drop in modulus at 1.56 wt % IL and 100 wt % decrease at 3.12 wt % IL (FIG. 17D), suggesting concentration dependent anti-coagulation effect of IL. Hemolysis tests in pig blood treated with IL exhibited a significant increase in hemolysis FIG. 17E). Complete blood counts were performed on fresh blood aliquots treated with increasing concentrations of IL, and a concentration dependent decrease in the total counts of red blood cells (RBC, FIG. 17F) and white blood cells (WBCs, FIG. 17G) was observed that paralleled a similar decrease in granulocyte (FIG. 17J) and monocyte (FIG. 17I) counts. There was no change in lymphocyte count (FIG. 17H) in the same aliquots compared to control, suggesting resistance to IL treatment at the tested concentrations.

Figure 18A:
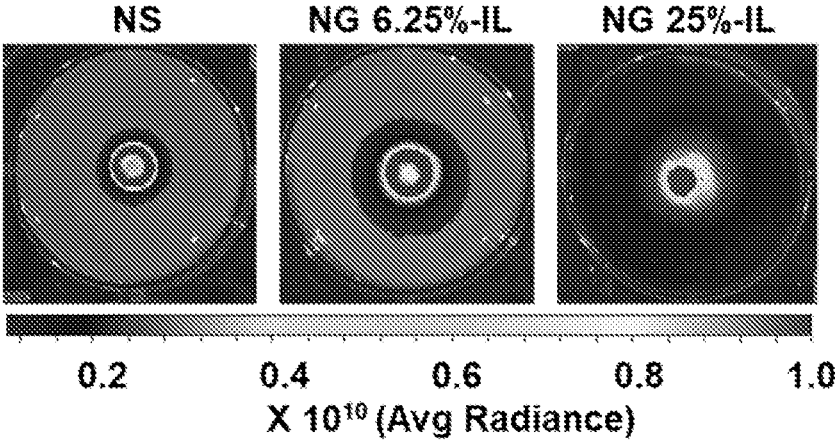
FIGS. 18A-18F. Assessing the Effect of NanoGel on Drug Diffusion and Stability in vitro.
Figure 18B:
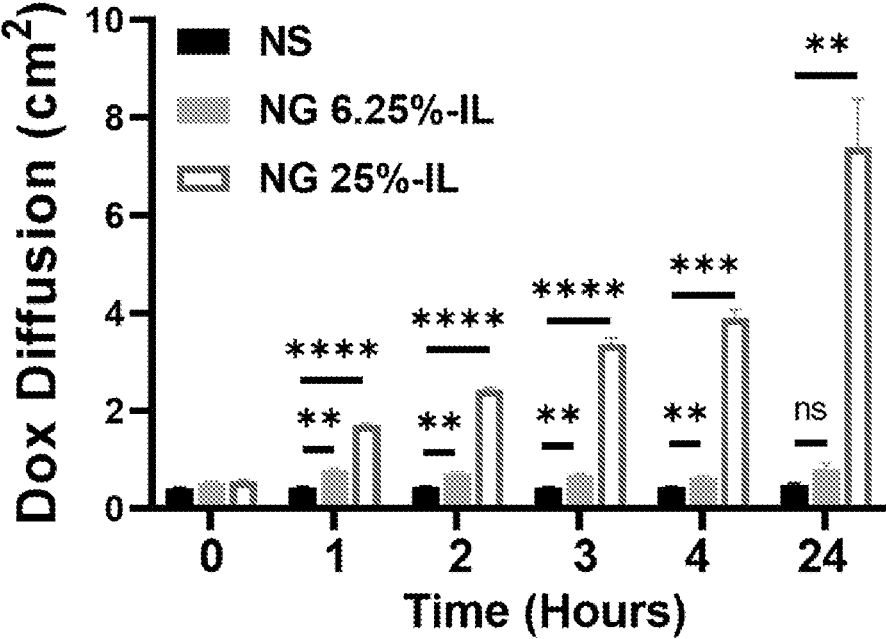
Figure 18C:
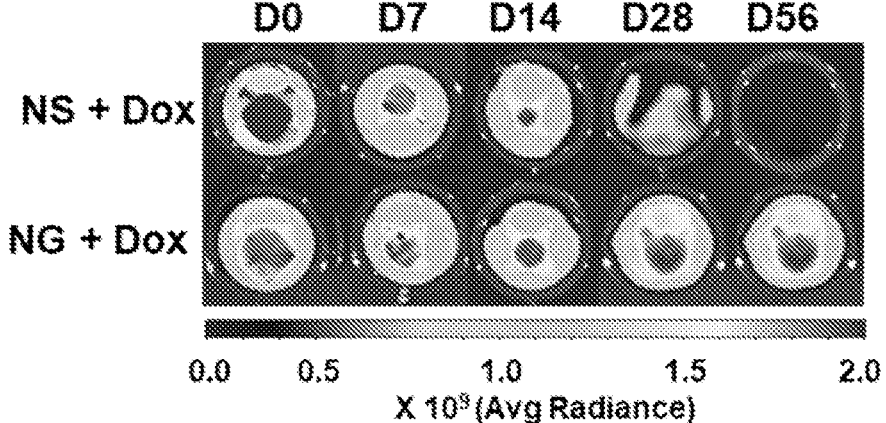
Figure 18D:
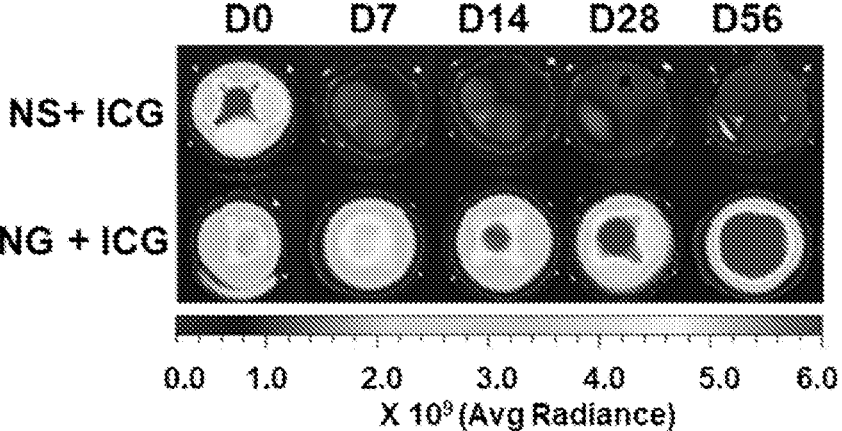
Figure 18E:
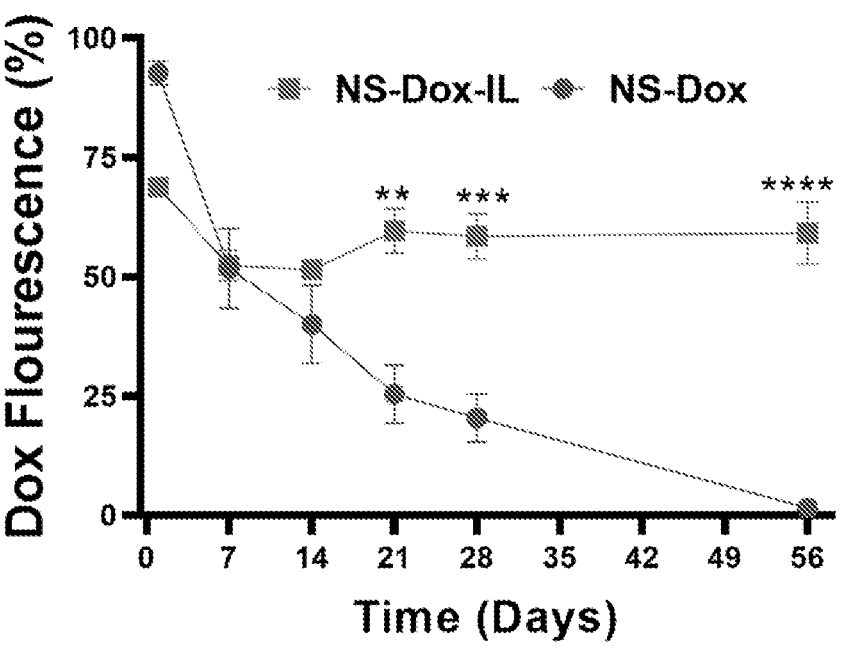
Figure 18F:
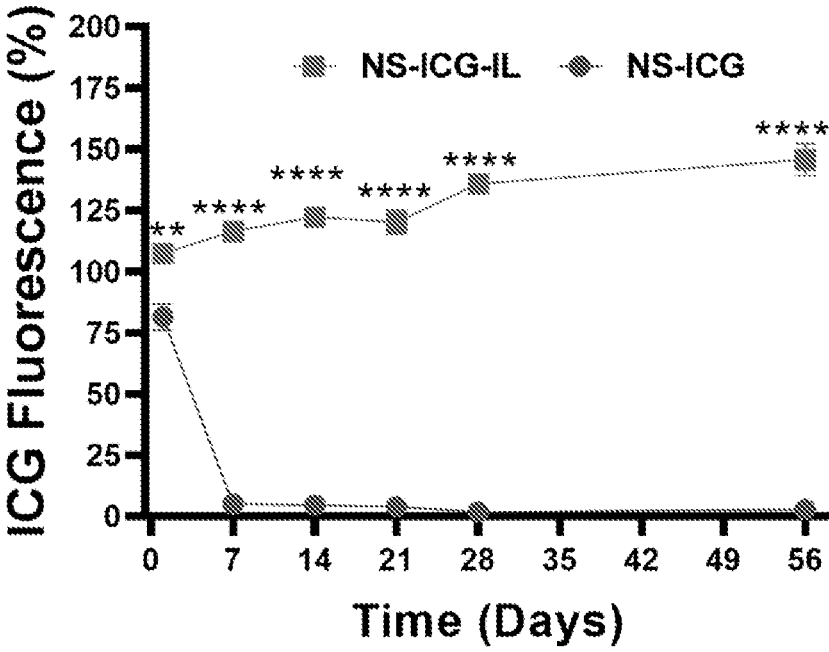

The effect of NG on drug diffusion and stability was assessed in vitro. (A) Fluorescent images showing radiant diffusion of the naturally fluorescent anticancer drug agent, Doxorubicin was incorporated into NS hydrogel (a control hydrogel without ionic liquid) or into NG containing 6.25%-IL or 25%-IL, equal aliquots were loaded to the center of designated wells of a 2% agarose casted within a multi-well plate, and fluorescent images were taken over a 24 hour period to assess radial diffusion (FIG. 18A). A consistently larger Dox diffusion area was observed in NG+Dox with 25 wt %-IL as compared to NG+Dox with 6.25%-IL (FIG. 18B). There was limited radial diffusion in the NS+Dox loaded wells throughout the 24 hour testing period (FIG. 18B). Fluorescence images and plots showing serial detection and measurements of Dox fluorescence (FIG. 18C) or ICG (FIG. 18D) incorporated into NG or into NS hydrogel showed persistent enhancement of Dox and ICG over a 56 days period compared to diminished detection in the NS hydrogel. These data demonstrated that IL mediated diffusion and enhanced stability of co-administered drug.

Figure 19A:
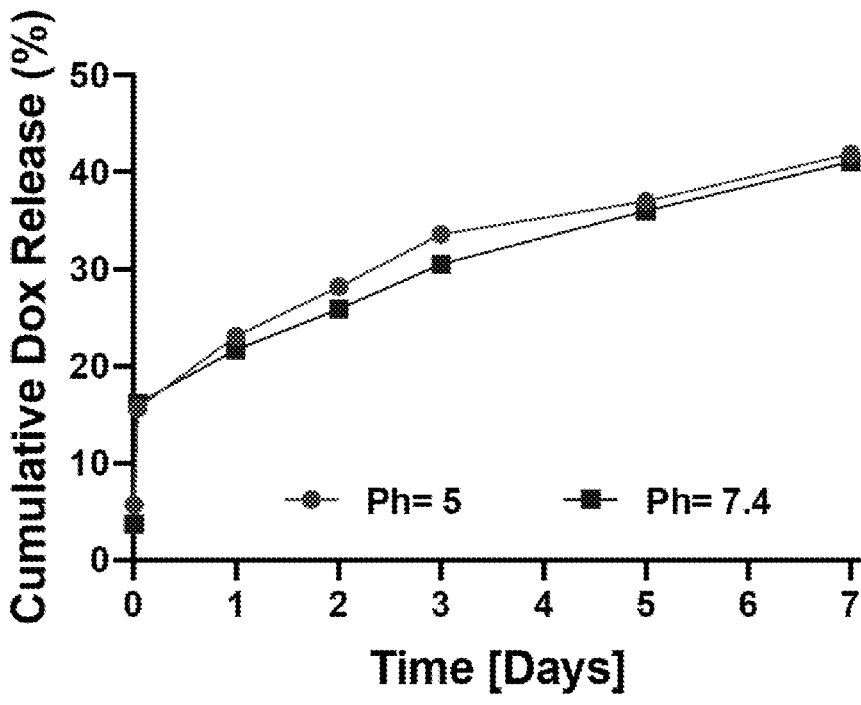
FIGS. 19A-19D. The effect of NanoGel on HepG2 cell viability, Dox diffusion and release.
Figure 19B:
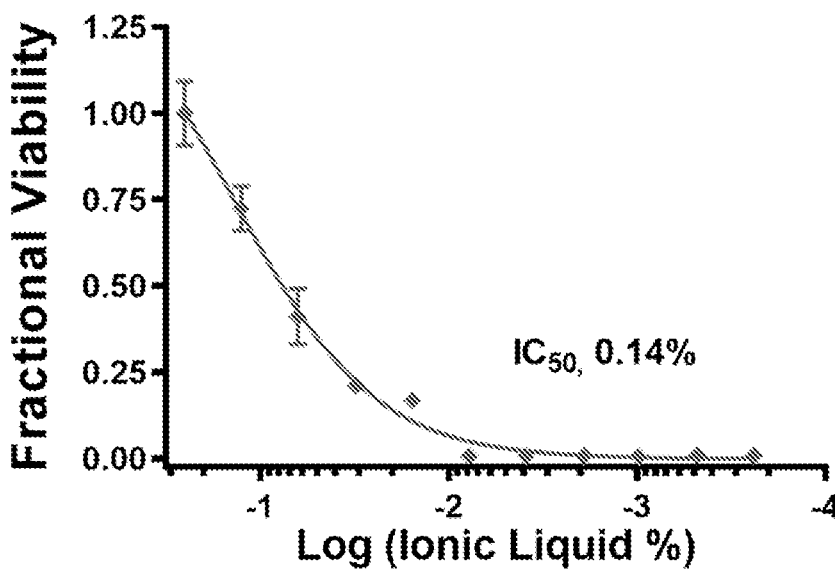
Figure 19C:
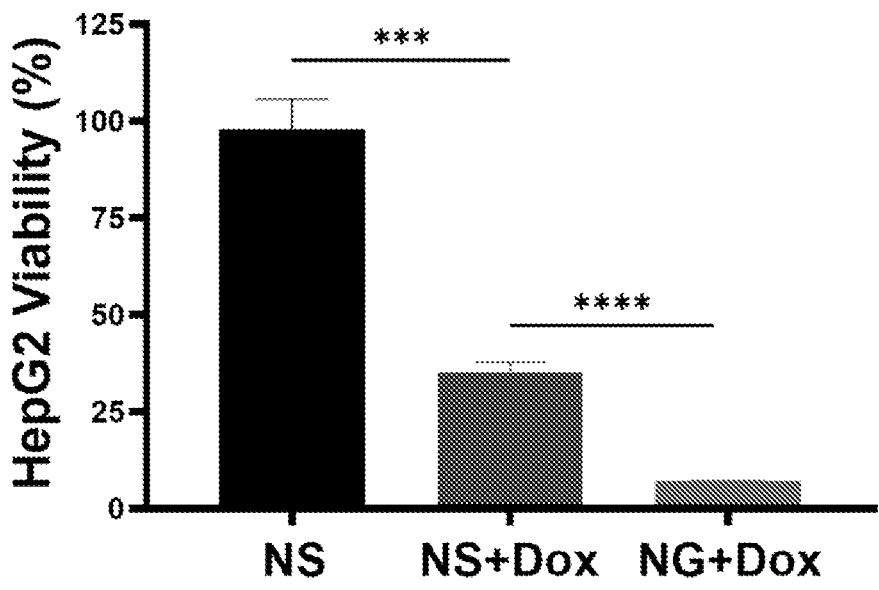
Figure 19D:
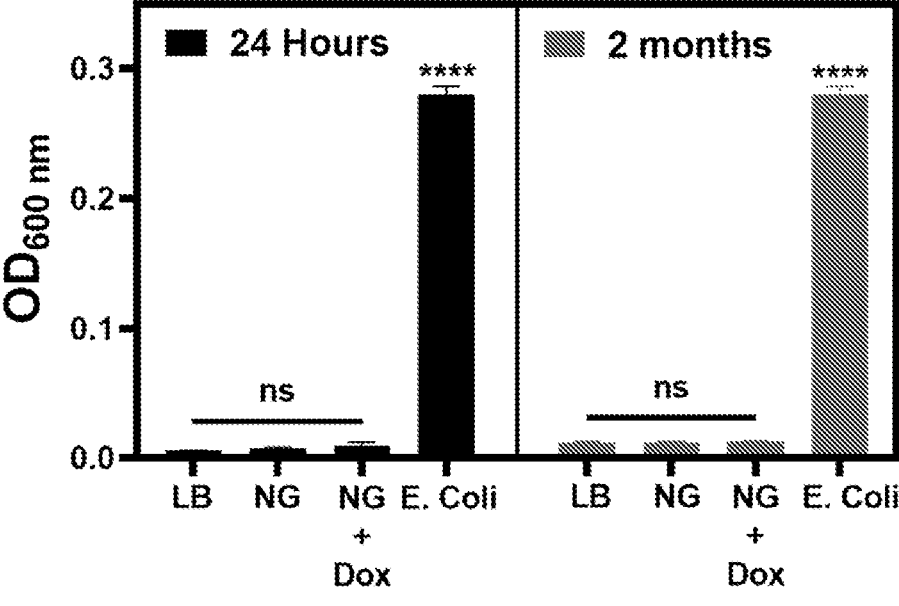

Drug release kinetics, cytotoxicity and sterility of NG were evaluated in vitro. The effect of NanoGel on HepG2 cell viability, Dox diffusion and release. Cumulative release of doxorubicin was observed from NG mixed with 0.25 mg/mL Dox that was incubated for 7 days under physiologic (pH=7.4) or acidic (pH=5.0) conditions, demonstrating sustained doxorubicin release (FIG. 19A). HepG2 cells were treated with serially diluted NG extracts, and fractional viability was observed at 24 hours post treatment resulting in an $IC_{50}$ at a IL concentration of 0.14%, suggesting preserved cytotoxic effect of NG (FIG. 19B). HepG2 cells also demonstrated enhanced cytotoxicity post treatment with NG extract containing 0.25 mg/mL Dox (NG+Dox) as compared to NS extract containing similar amount of doxorubicin (NS+Dox), suggesting a synergistic effect (FIG. 19C). NS alone did not show cytotoxic effect (FIG. 19C). NG and NG+Dox remained sterile post incubation for 24 hours or 2 months in LB broth (FIG. 19D). LB broth inoculated with *E. coli* bacteria was used as a positive control (FIG. 19D).

Together these data demonstrate that a NS hydrogel containing IL can be used to induce cancer cell ablation, to maintain and enhance the functionality of an anti-cancer agent such as Dox, and to synergistically maximize the anti-cancer response.

Example 6: Drug Distribution Capabilities Following NanoGel Injection

This Example describes ablation, and drug distribution capabilities following NanoGel injection into rat liver.

Methods

NanoGel Preparation

NanoGels were prepared as described in Example 5.

Experimental Design

Intraparenchymal injection of NanoGel formulations into normal rat liver was performed in 6 groups of Sprague Dawley rats (Charles River, 192 rats, 10-12 weeks, 250-300 g, 1:1 males and females). Rats in each experimental group received injection of NanoGel formulation which were compared to rats that received intraparenchymal injection of NS-IL, NS-Dox, and/or NS-ICI. 8 rats per data point were used to achieve statistical significance based on power analysis assuming a standard deviation of 30-40%, 90% confidence level, and 0.05 alpha level (p<0.05). Briefly, anesthetized rats were placed in a supine position on a warming platform. Following standard surgical preparation, the liver was exposed via laparotomy and the left lower liver lobe received three intraparenchymal injections of 50 μL of a NanoGel formulation, NS-IL, NS-Dox, or NS-ICI using a 27-gauge needle.

Outcome Analysis

To assess ExiTron diffusion, in vivo micro computed tomography (microCT) scanning was performed immediately after injection to obtain baseline volume as described elsewhere (Albadawi et al., *Sci. Transl. Med.,* 13(580) (2021)). Subsequently subgroups of rats had follow up microCT at 3, 7, 14, and 28 days after injection followed by euthanasia. At necropsy, the rat's liver was explanted and transected into two parts at the midline through each injection site for ex vivo fluorescent imaging to calculate Dox area of diffusion and fluorescence intensity at each injection site. Subsequently, tissues were incubated with triphenyl tetrazolium chloride (TTC, Sigma) reagent to assess tissue viability or processed for histological evaluation. To calculate the ablation area, freshly harvested tissues were incubated in 1% TTC solution to allow viable zone to be visually distinguished from dead/dying zone. Total ablation area and apoptotic vs. necrotic areas from transverse and longitudinal planes were used to calculate ablation areas and volumes as described elsewhere (Albadawi et al., *Sci. Transl. Med.,* 13(580) (2021); Bhonsle et al., J. *Vasc. Interv. Radiol.,* 27(12):1913-22 e2 (2016); Siddiqui et al., *HPB* (Oxford), 2016; 18(9):726-34 (2016); Stadlbauer et al., *Histol. Histopathol.,* 31(1):115-29 (2016)). Following fixation, serial sections were prepared and analyzed to confirm ablation area, evaluate vessel integrity, and evaluate biliary architecture. The extent of apoptosis was evaluated in sections immunostained for cleaved caspase-3 IgG and scored in the entire treated zone using ImageJ IHC profiler software. Additionally, assessing the local inflammatory response included quantitative analysis of T lymphocytes (CD3+, CD4+, CD8+), NK, and myeloid cell lineage infiltration. The systemic response was compared in blood samples using complete blood count and assessing markers of liver function (ALT, AST, GGT, LD, ALP, and bilirubin), markers of kidney function (creatinine and BUN), and markers of heart injury (CK, troponin, C-reactive protein, and lipids). In addition, serum samples were analyzed for the levels of cytokines and chemokines (Eve technology). Tissue specimens from brain, lung, kidney, liver, and spleen were harvested for histologic analysis to rule out any abnormalities.

Results

Figure 20A:
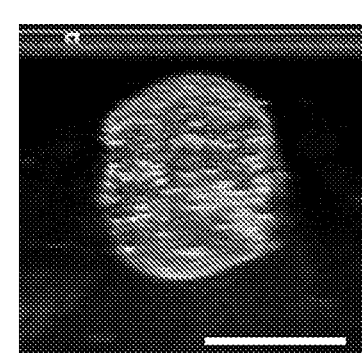
FIGS. 20A-20E. Demonstration of Percutaneous Ultrasound Guided Injection of NanoGel into Tissue and Enhanced Detection with Magnetic resonance Imaging.
Figure 20B:
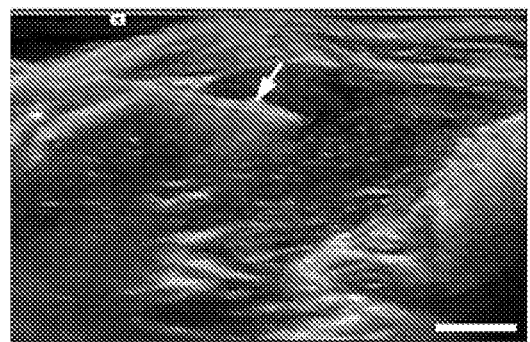
Figure 20C:
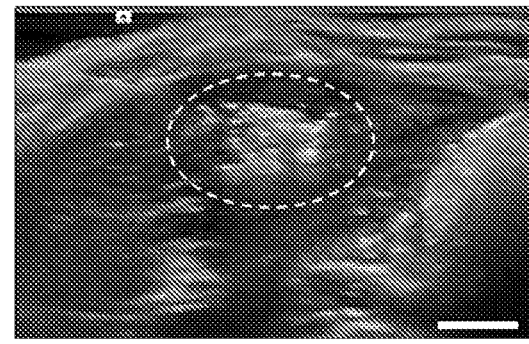
Figure 20D:
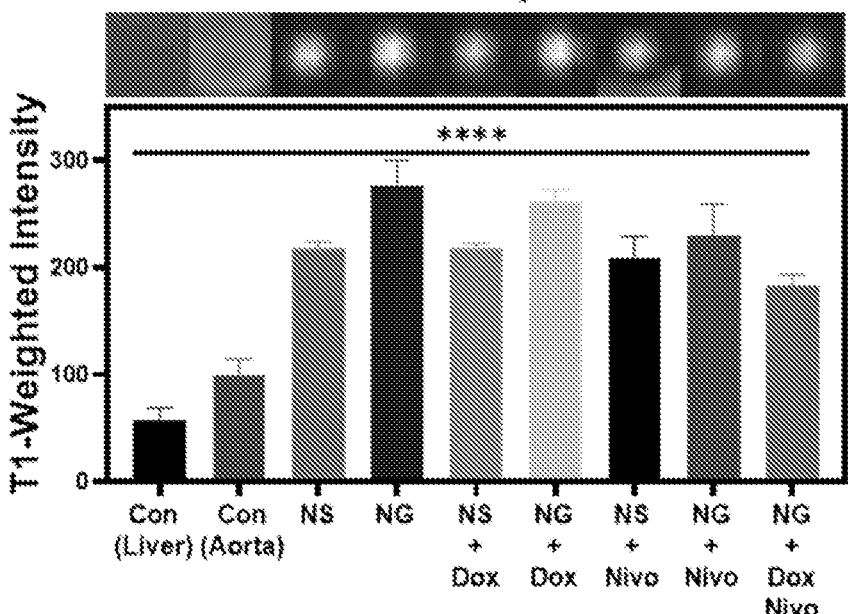
Figure 20E:
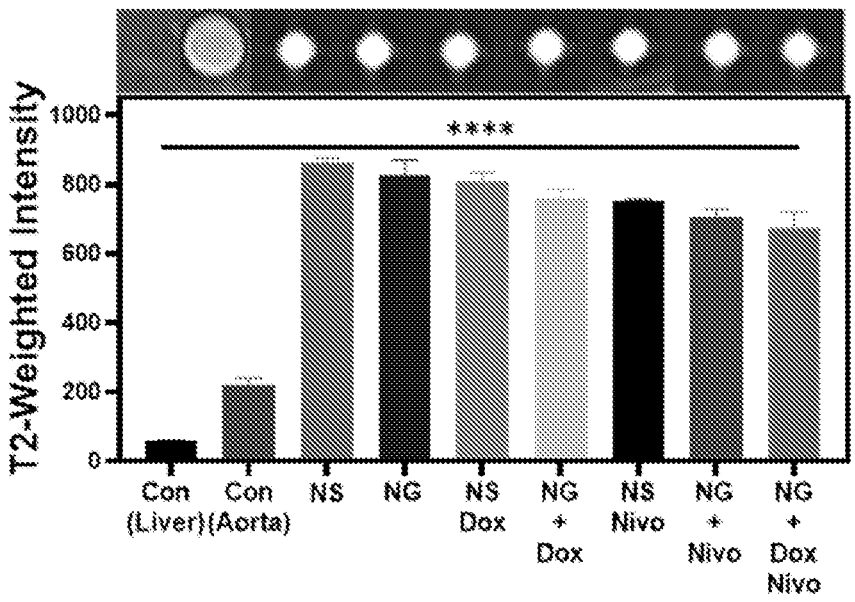

Image-guided intrahepatic injection was used to deliver 50 μL of different hydrogel formulations into normal rat livers all of which contained 0.25 mg/mL ICG. In vivo ultrasound imaging during direct injection of NanoGel into the liver parenchyma demonstrated the feasibility of percutaneous injection directly into targeted tissue (FIGS. 20A-20B). Neither Dox or Nivo affected signal enhancement on MRI (FIGS. 20D and 20E). These data demonstrate that NG can be used for real-time image guided injection using ultrasound or MRI.

Figure 21A:
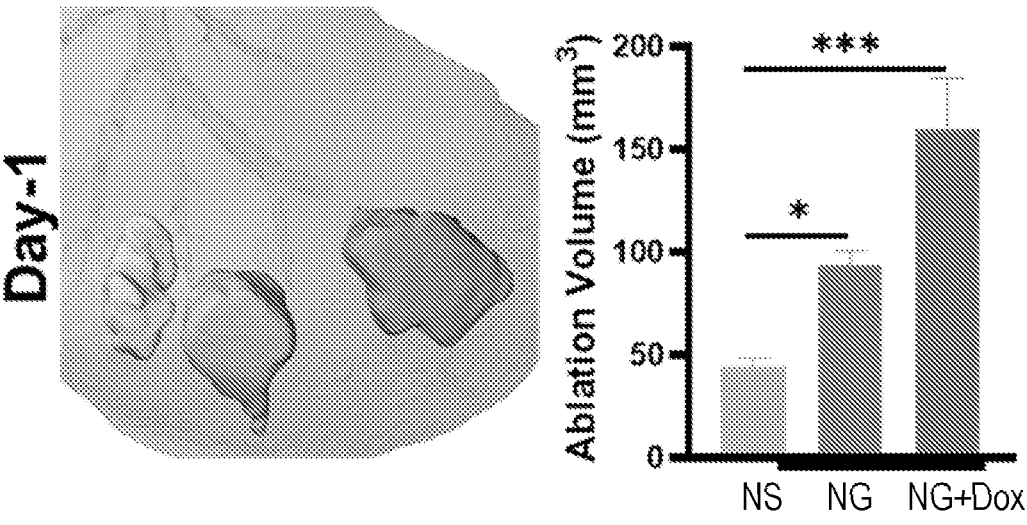
Figure 21B:
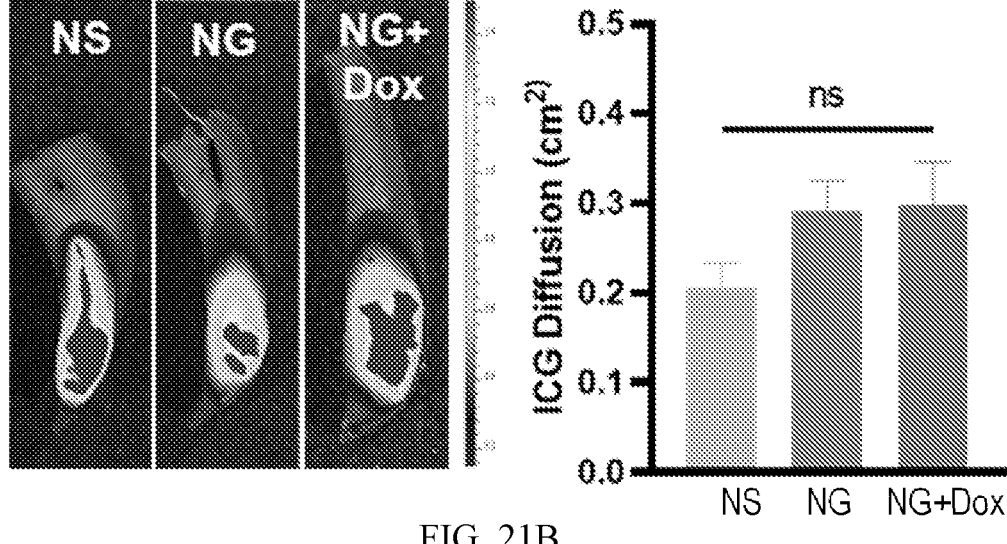
Figure 21C:
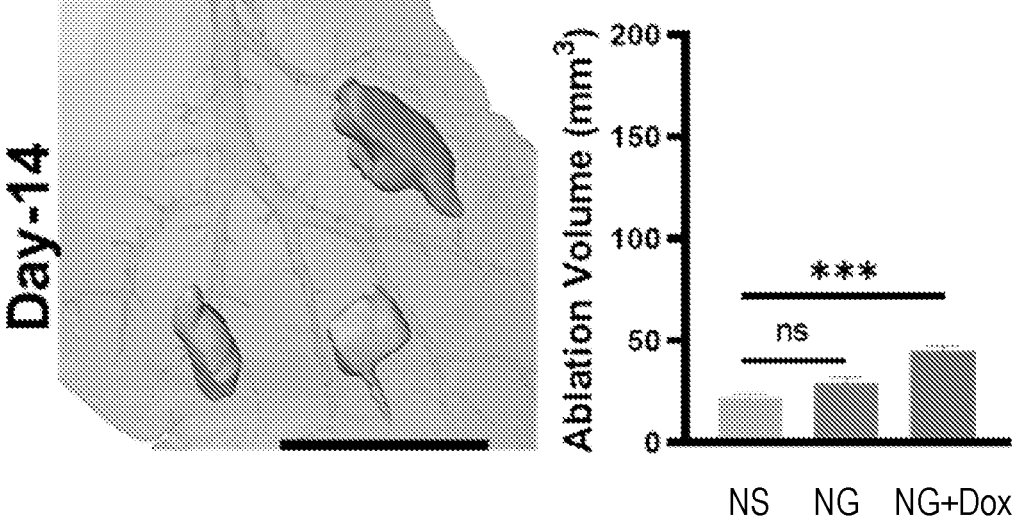
Figure 121D:
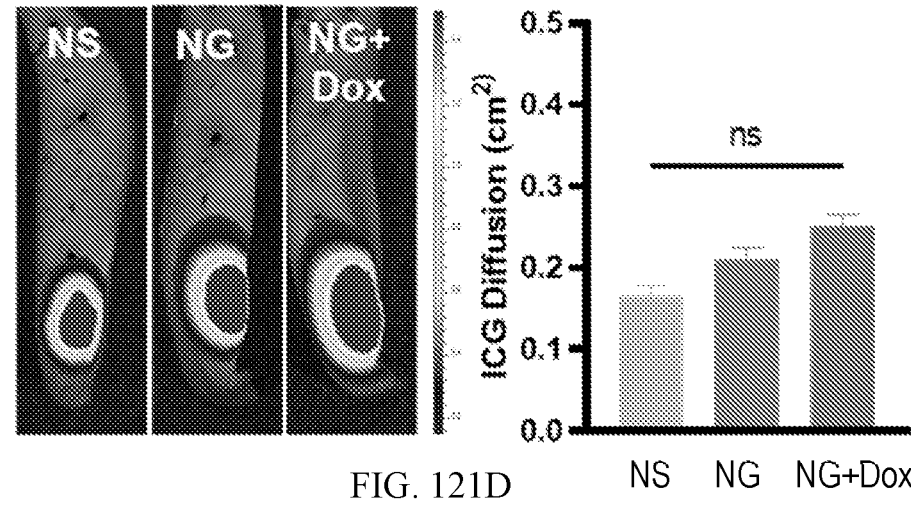
Figure 21E:
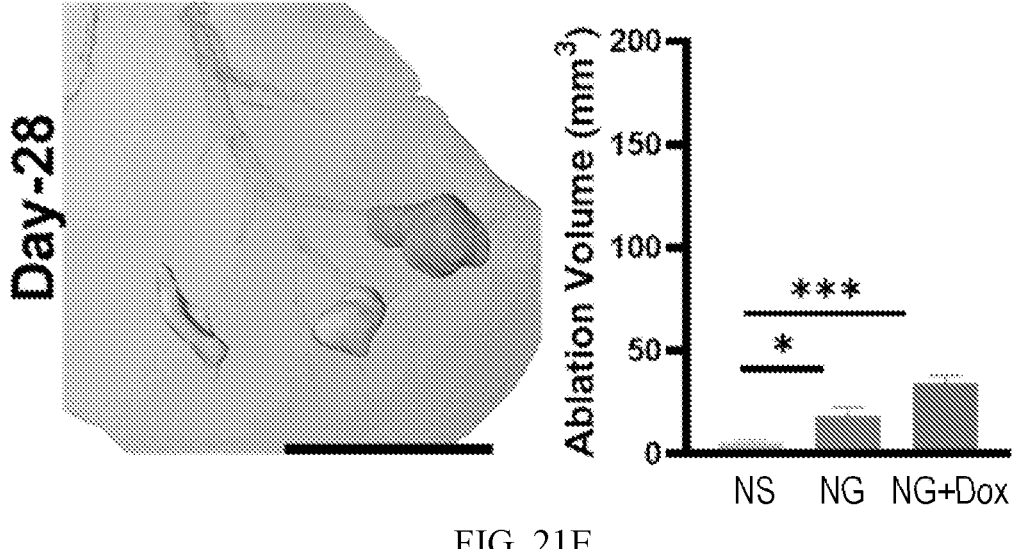
Figure 21F:
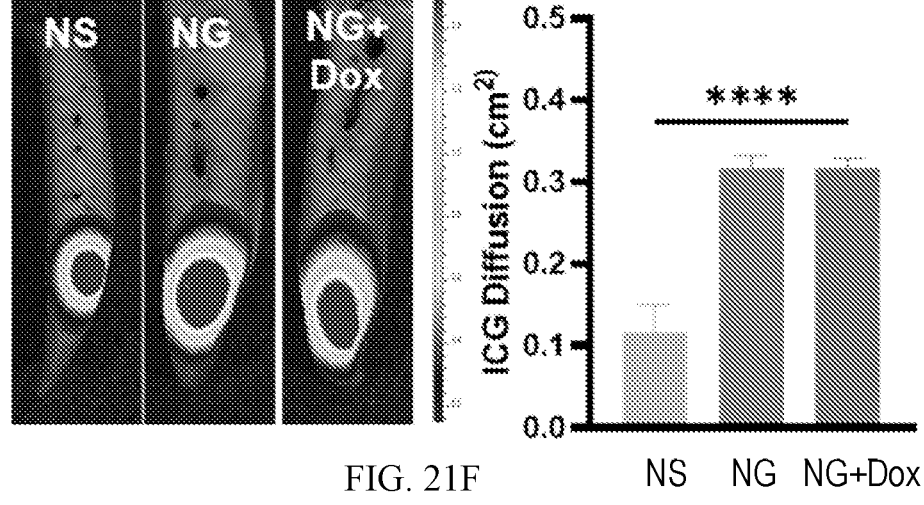
Figure 21G:
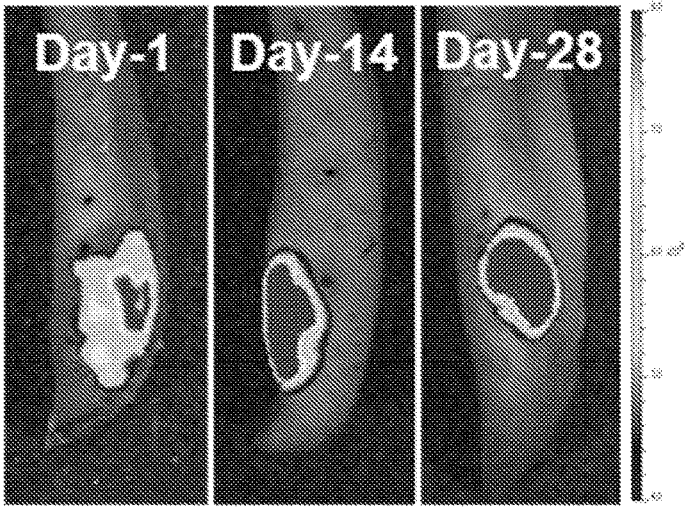
Figure 21H:
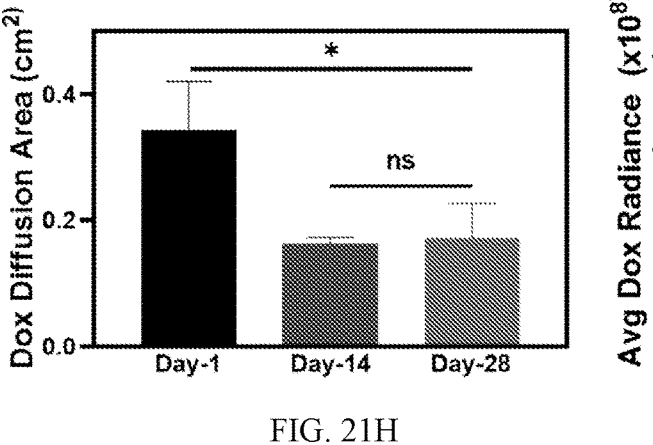
Figure 21I:
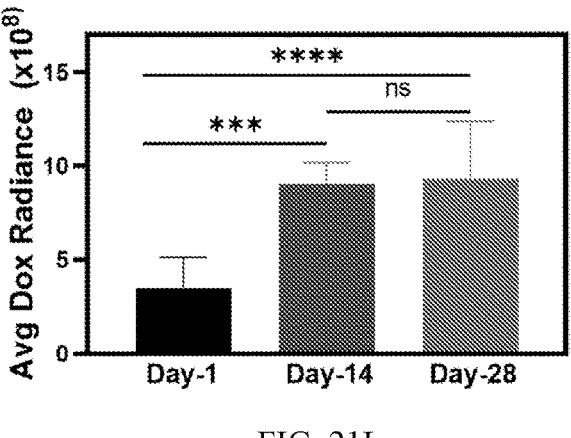

3D rendered reconstructed microCT and ICG fluorescence analysis of rat livers showing tissue ablation in each injection site that received NS, NG, or NG+Dox (FIGS. 21A, 21C, and 21E). There was a higher ablation volume induced by NG+Dox at all time points associated with time dependent decrease in ablation volume by day-28 post injection (FIGS. 21A, 21C, and 21E) reflecting normal healing of the ablated zone. Near infrared imaging of explanted rat liver showed the ICG-enhanced fluorescence area at each injection site following injection with NS, NG, or NG+Dox (FIGS. 21B, 21D, and 21F). A larger ICG diffusion area was observed at 28 days post injection with NG and NG+Dox compared to NS (FIGS. 21B, 21D, and 21F), suggesting higher diffusion and retention of ICG in the presence of IL in the NanoGel formulation. Dox enhanced fluorescence, diffusion area, and fluorescence intensity (average radiance) following injection with NG+Dox (FIGS. 21G-21I) suggesting enhanced diffusion and long-term retention of chemotherapy.

Figure 22A:
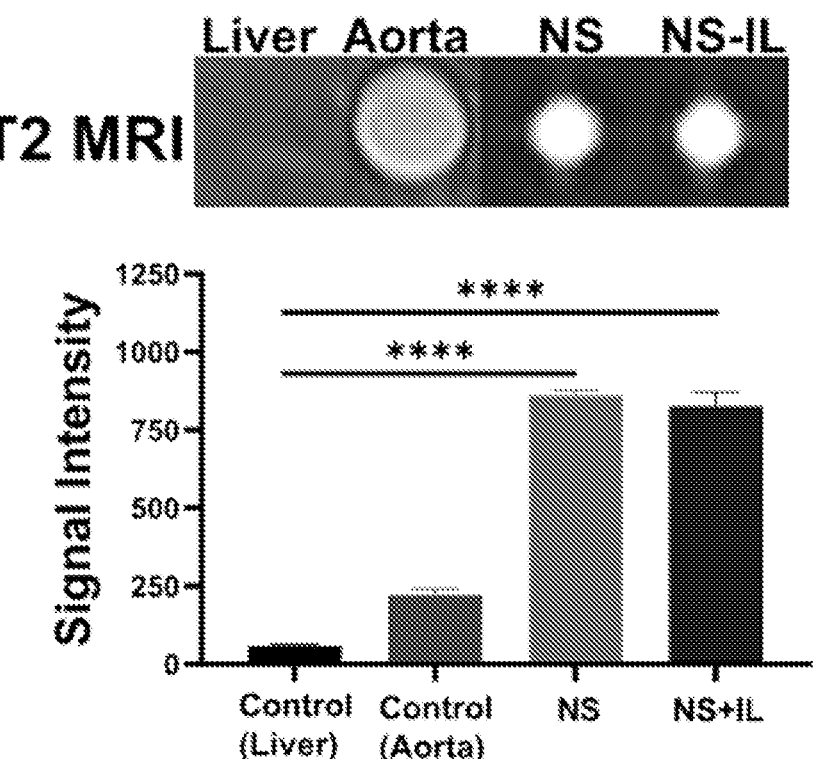
FIGS. 22A and 22B. NanoGel sterility and visibility on MRI.
Figure 22B:
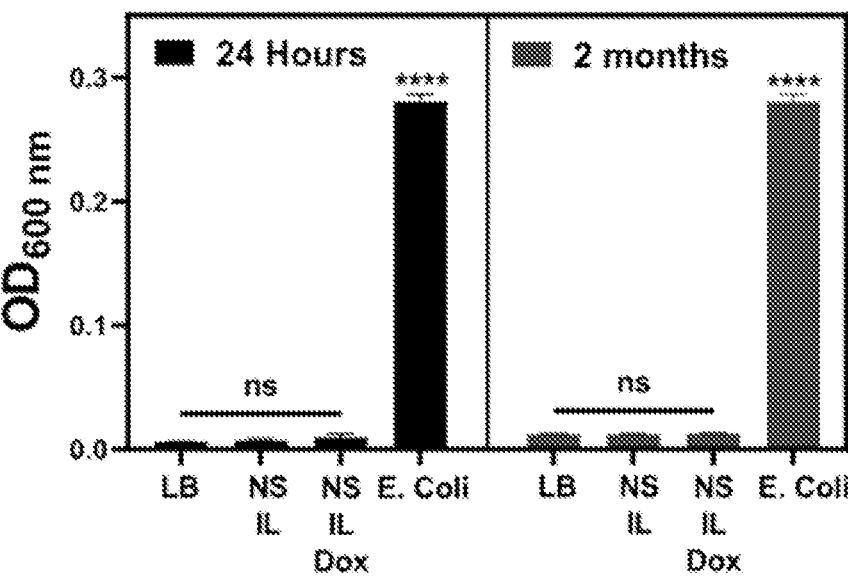

To assess the imaging characteristics on multiple imaging modalities, the visibility of a NS or NS-IL hydrogels loaded into syringes was assessed on magnetic resonance imaging (MRI), computerized tomography (CT), and ultrasound (US). Visibility using T2 based MRI is shown FIG. 22A. IL are known to have neutralizing properties against a wide range of pathogens. To verify whether NS hydrogel preserves IL antibacterial property when mixed with IL or Dox, sterility tests demonstrated no bacterial growth detection at 1 day and 2 months post incubation at 37° C. (FIG. 22B).

These data demonstrate that the combination of IL and Dox in a NS hydrogel can synergistically widens the treatment margin and expand the drug distribution zone.

Example 7: Time to Progression and Overall Survival Rate in Rodent Models of Solid Tumors This Example describes in vivo tumor response, ablation efficacy, imaging characteristics, drug distribution and retention, immune response, and survival rate of animal cancer models injected with NanoGel.

Methods

NanoGel Ablation Efficacy, Drug Distribution, Immune Response, and Survival Rate N1S1 rat model of liver hepatocellular carcinoma was induced in 160 Sprague Dawley rats (Envigo, CA) weighing 300-325 grams (males and females) as described elsewhere (Albadawi et al., *Sci. Transl. Med.,* 2021; 13(580) (2021)). The rat Novikoff hepatoma (N1S1) cells obtained from ATCC (CRL-1604, Manassas, VA) were propagated in Iscove's Modified Dulbecco's Medium (IMDM) containing 10% fetal bovine serum. The rat liver was surgically exposed under anesthesia via midline laparotomy followed by subcapsular inoculation of $1\times10^6$ N1S1 cell suspension in 100 µL volume injected into the left lower liver lobe using a 25-gauge syringe needle. Following recovery, serial ultrasound imaging was performed to confirm tumor formation, delineate tumor mass boundaries in grayscale (B-mode) to calculate volume and to assess vascularity in the color mode using ultrahigh frequency transducer (Vevo-3100, FUJIF-ILM). Four groups of rats bearing N1S1 tumor measuring 0.5 cm diameter on ultrasound were randomly divided to receive intratumoral injection of NanoGel (selected from aim 1.4), NS-IL, NS-Dox, NS-ICIs hydrogels all of which contain equal amount of ExiTron Nano 12000 contrast agent (Miltenyi Biotec). The injection volume was calculated based on 1.25-fold of tumor volume on ultrasound which will be calculated according to the following formula $v=4/3\pi[r+0.5]^3$. Time-dependent studies were performed by euthanizing subgroups of rats at 3, 7, 14, 28, or 42 days.

Figure 23A:
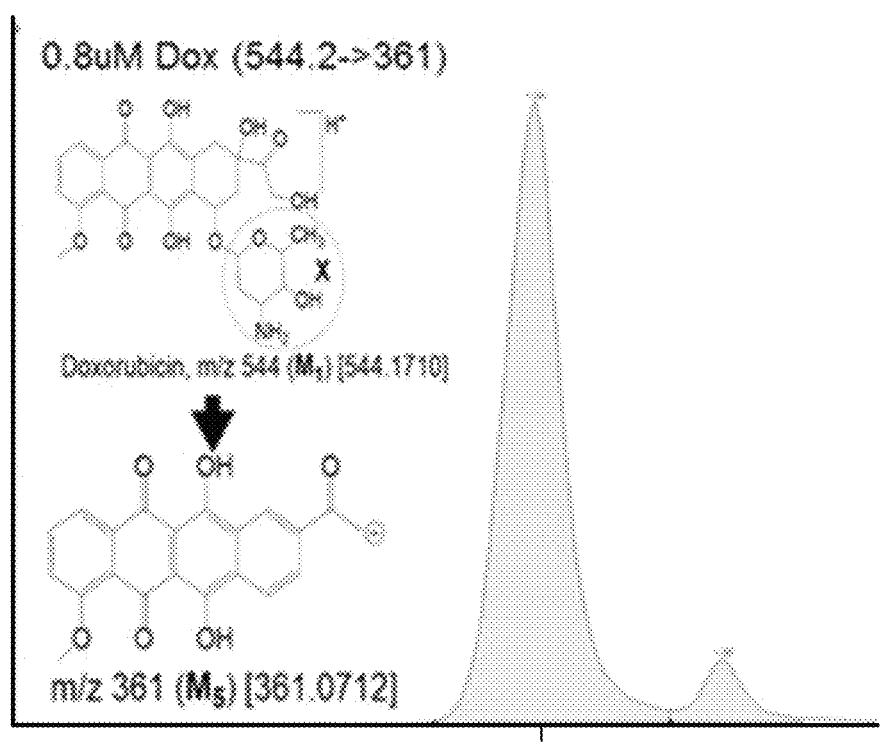
FIGS. 23A-23D. Liquid chromatography-tandem mass spectroscopy (LC-MS/MS) analysis of Dox levels in rat plasma.
Figure 23B:
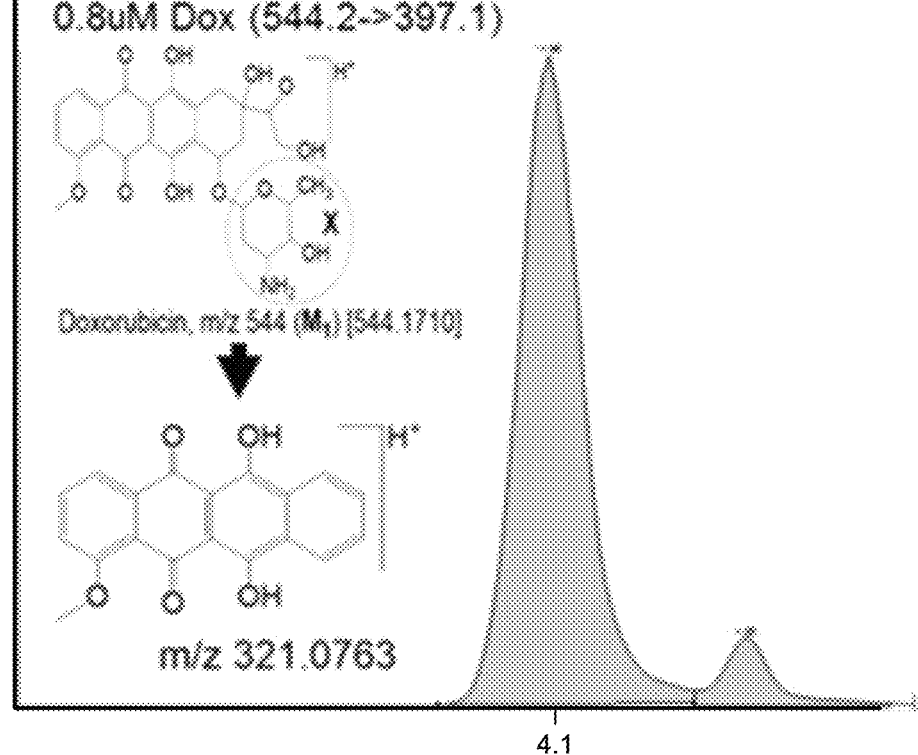
Figure 23C:
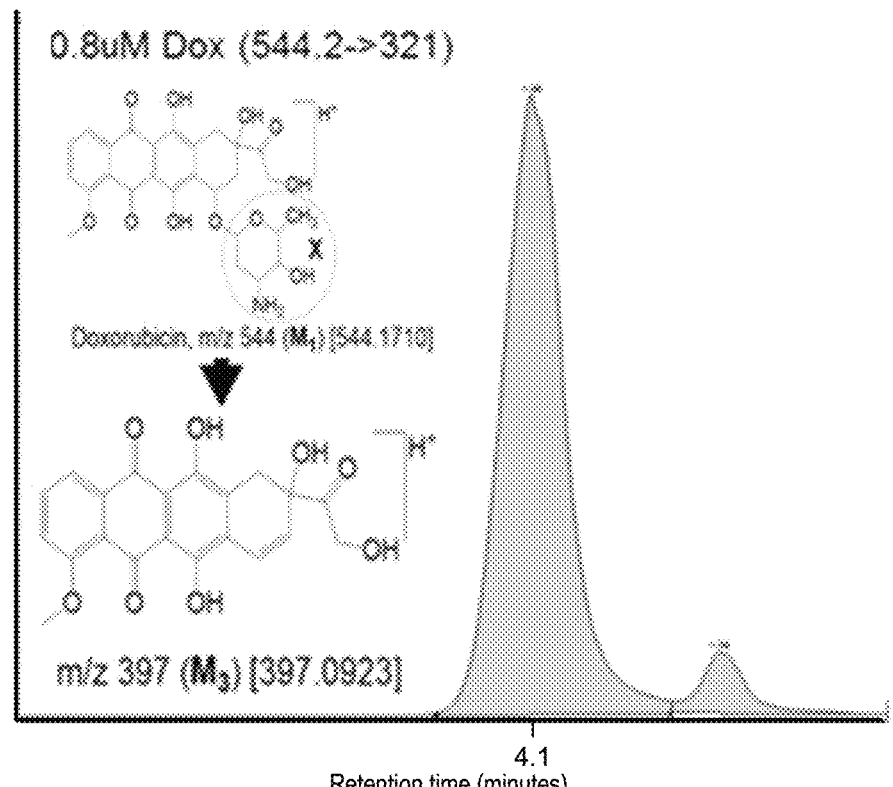
Figure 23D:
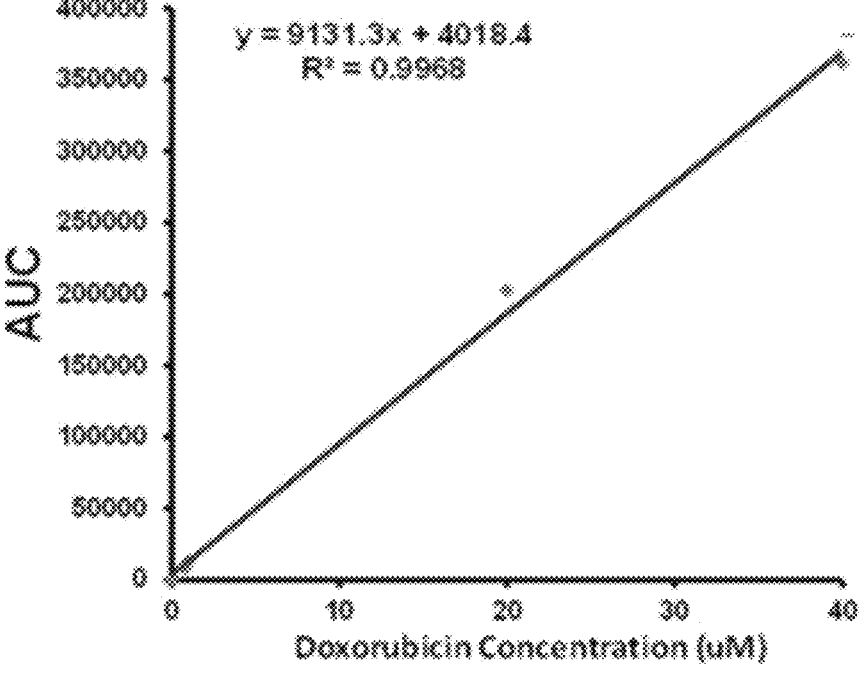
Figures 24A, 24B, 24C, 24D:
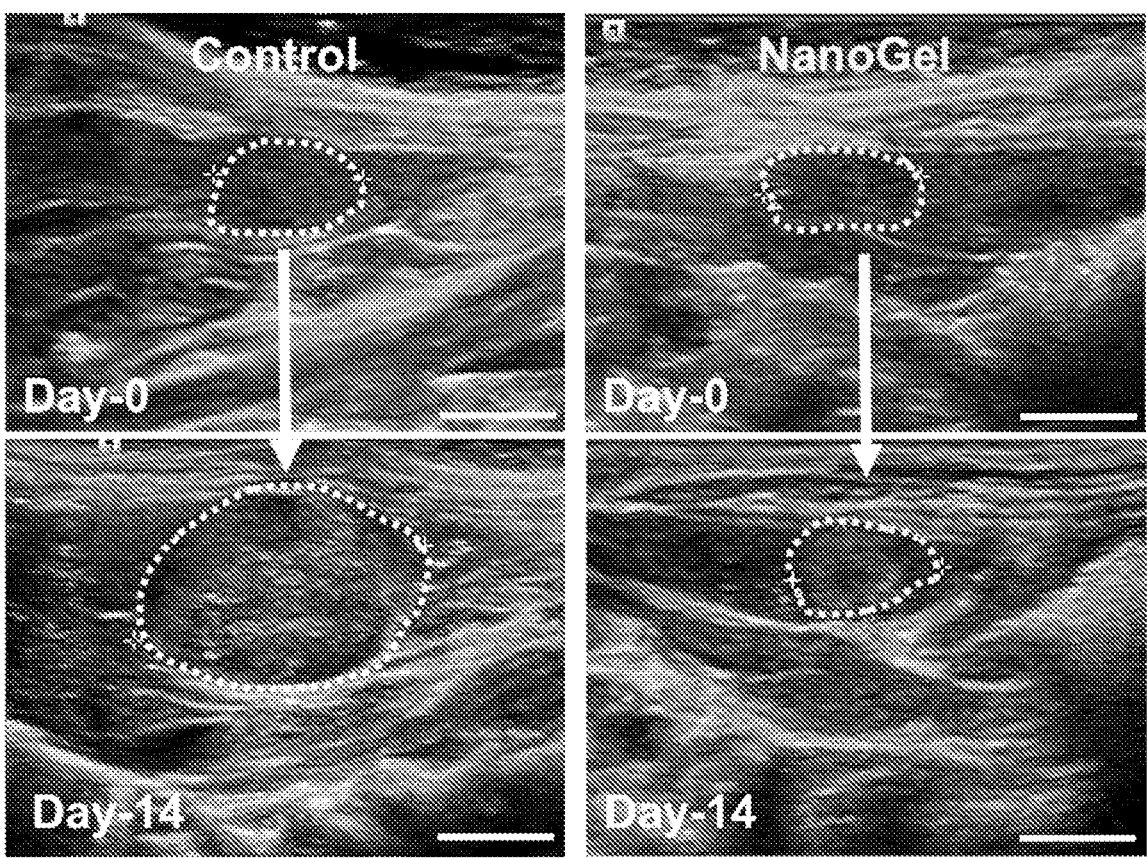
FIGS. 24A-24H. The effect of intratumoral injection of NanoGel into N1S1 rat HCC tumor.
Figure 24E:
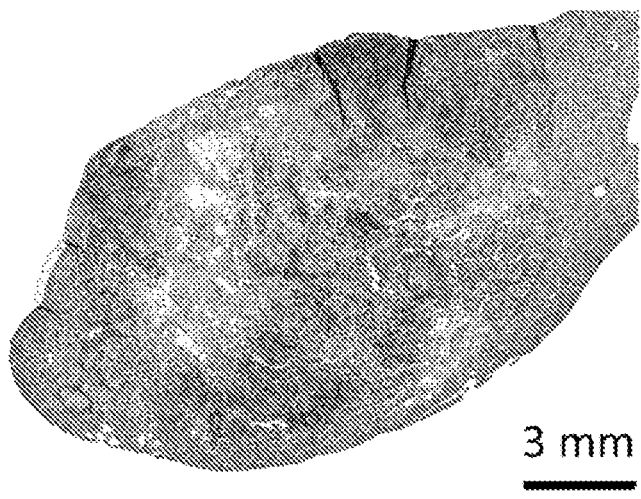
Figure 24F:
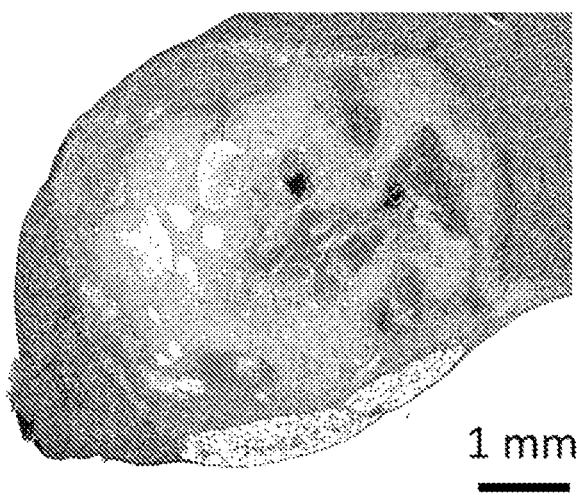
Figure 24G:
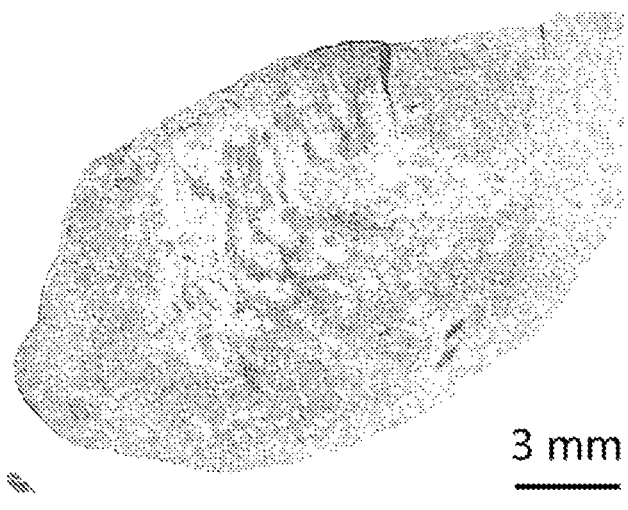
Figure 24H:
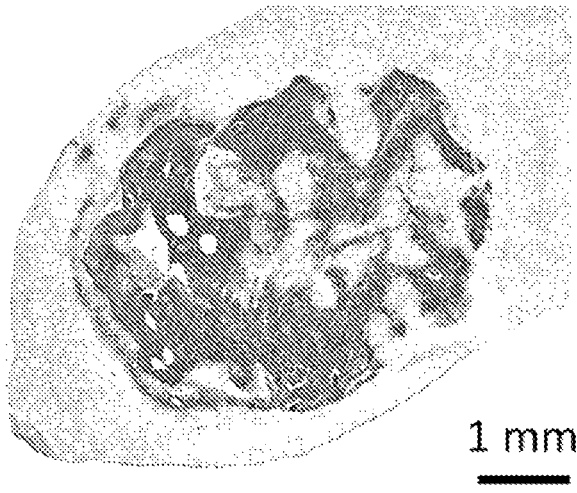

Tumor burden, Dox and ICIs distribution and retention, and the host response were evaluated and compared in N1S1 liver cancer bearing rats injected with NanoGel, NS-IL, NS-Dox, and NS-ICIs hydrogels. All rats were survived for predetermined time points of 3, 7, 14, 28, or 42 days and the tumor volume and vascularity were serially documented using ultrasound twice a week. To provide 3D rendering and tumor volume measurements and tissue structure on microscale level in vivo microCT analysis was performed using the SkyScan-1276 system (Bruker, Kontich, Belgium). Prior to necropsy, rat had laser speckle contrast analysis (LASCA, Perimed) directly over the exposed liver following by euthanasia. Rat livers were explanted and transected at midline for ex vivo fluorescence imaging to calculate Dox area of diffusion and measure fluorescence intensity of Dox within the core of each tumor using the IVIS 200 system (PerkinElmer, Inc. Waltham, MA). Subsequently the tumor tissues were either fixed or cryosectioned for H&E staining to assess tumor morphology, calculate ablation area and examine the tumor peripheral zone for residual viable tumor cells at the surgical margin of the treated tumors using specific pathologic staining for marker of active proliferation (Ki-67) and the marker of metastatic potential, cytokeratin-19 which is associated with poor prognosis after liver resection or ablation in HCC patients. Specimens from different region within and around the tumor lesion were analyzed using LC-MS/MS as demonstrated in FIG. 23. Representative chromatograms of rat plasma spiked with 0.8 µM Dox in three ionized channels; all demonstrate consistent retention time at 4.1 minutes confirmed Dox molecular structure (FIGS. 23A-23C). Quantitative analysis of Dox levels in the rat plasma showing linear relationship of the measured concentrations (r2=0.99, FIG. 23D). Immunostaining for PD-1 or PD-L1 antibodies was performed to assess tissue distribution and retention of ICIs (FIG. 24). The following in situ criteria were used to assess/confirm ablation, and drug distribution efficacy: 1) cellular uptake of Dox (quantified using LC-MS/MS); 2) the average transport distance of red-fluorescent Dox in segmented tumor margins (measured using confocal fluorescent microscopy); 3) number of actively proliferating cells in digitized microscopic fields obtained from tumor core, periphery, and peritumoral areas (measured using apoptosis rates (based on TUNEL and cleaved-Caspase-3 immunostaining) and proliferation rates (based on cytokeratin-19, Ki-67, and PCNA immunostaining)); and 4) ICI distribution (measure by immunostaining for anti-PD-1, and anti-PD-L1). Additionally, serially cut tissue sections were immunostained to elucidate the local immune response by counting the number of infiltrating lymphocytes lineage (CD3$^+$, CD4$^+$, CD8$^+$, and NK cells) and myeloid inflammatory cells (Granulocytes, monocytes, and macrophages). Blood samples be obtained at each endpoint were analyzed for blood chemistry as in Example 6.

Effect of Intratumoral Injection of NanoGel on Survival Rate and the Host Immune Response The immunocompetent mouse model of MC38 colorectal carcinoma was used to test the ablation efficacy of selected NanoGel formulations. MC38 colorectal carcinoma cells (about $1\times10^6$ cells) were subcutaneously inoculated in the lower right flank of 10-12 week old C57BL6 mice (200 mice). Mice bearing tumor volumes of ~200 mm$^3$ were randomly divided into three groups to receive direct intratumoral injection of 250 µL of NanoGel, whereas mice in the control groups received injection of NS-IL, NS-Dox, or NS-ICIs. ICIs evaluated include mouse specific PD-1 and PD-L1 inhibitors, anti-mPD-1-mIgGle3 InvivoFit™, and Anti-PD-L1-mIgGle3 InvivoFit™ mAbs (InvivoGen, San Diego, CA). Specific ELISA on serially diluted NanoGel extract containing the anti-PD-1 and anti-PD-L1 were used to assess binding. These antibodies were obtained sterile, endotoxin-free, preservative-free, and lyophilized, and were mixed to achieve 1 mg/mL concentrations. Following survival, subgroups of mice were euthanized at time points 1, 3, 7, 14, and 28 days after intratumoral injection to evaluate the immune response and survival rate.

The effect of intratumoral injection of NanoGel on tumor response and animal survival was assessed by serially measuring tumor volumes twice a week following treatment using ultrasound as shown in FIG. 26.

Tumor Model of Colorectal Carcinoma in Mice

Twelve-week-old female C57BL6/J mice (n=14, Jackson's Laboratories) were housed in the vivarium with 12 hours of light/dark cycle and ad libitum of food and water. The mice were anesthetized with continuous inhalation of isoflurane. The right flank received subcutaneous injection of $2\times10^6$ MC38 colorectal adenocarcinoma cells suspended in 0.1 mL of hanks balanced salt solution. Perpendicular tumor diameters were measured using a ultrasound and the tumor volume was calculated using the formula: $0.523\times$ (length$\times$width$\times$depth). When the tumor volume reached 150 mm$^3$, the tumor bearing mice were randomly divided into two groups to receive intratumoral injection of saline (Control, n=7), or NanoGel (n=7). The injection volume was calculated based on 1.25 of tumor volume. Tumor volume was serially assessed twice a week using US. Mice survival criteria was based on the number of days prior to reaching the maximally permissible tumor volume of 2,000 mm$^3$ or when tumors develop sever ulceration then tumors were considered progressed and individual mice were counted as dead in accordance with the Institutional Animal Care and Use Committee regulations. Tumor volume Prism Software was used to calculate log-rank survival to compare survival rate between the two groups. At the end-point mice were euthanized and tumors were harvested for histological examination.

Creation of the N1S1 Rat Model of Hepatocellular Carcinoma

Male Sprague-Dawley rats (Envigo, CA) weighing 300 to 325 g were used to induce N1S1 HCC. N1S1 rat hepatoma cells (CRL-1604, American Type Culture Collection, Manassas, VA) were cultured in Iscove's modified Dulbecco's medium, supplemented with 10% of heat-inactivated bovine calf serum (HyClone, UT). To prepare the cells for inoculation, N1S1 cell aliquots were rinsed and suspended in plain Iscove's modified Dulbecco's medium to yield $2\times10^6$ cells in 100 μL aliquot in a 1-ml syringe. The rat liver was surgically exposed under anesthesia through an upper midline laparotomy, followed by subcapsular inoculation of N1S1 cells into the left lower liver lobe using a 25-gauge syringe needle. Gentle compression was applied with gauze to achieve hemostasis and prevent cell reflux. Subsequently, the subcutaneous tissue and dermis layer were reapproximated with 5-0 vicryl suture (Ethicon, Somerville, NJ). After recovery, serial US imaging was performed to confirm tumor formation and assess tumor volume using an ACUSON 52000 system (Siemens Inc., Germany) and a multi-frequency linear transducer (9L4, 9.0 MHz) to delineate tumor mass boundaries in grayscale (B-mode). Two groups of rats bearing ~0.15 cm$^3$ of N1S1 tumor lesions measured with US received intratumoral injection of NG or NS hydrogel which contained 0.25% ICG and 1.25 mg/mL doxorubicin. The injection volume was calculated based on delivering 125% of the calculated tumor volume on US as previously described for chemical ablation procedures in human using ethanol injection. After intratumoral injection, treated rats were allowed to survive for 2 weeks, and tumor volume was documented using US.

Ex Vivo and In Vitro Fluorescence Imaging

Ex vivo spectral fluorescence imaging was performed on tissues to assess differences in Doxorubicin or ICG after intratumoral injection of NG or NS hydrogel using the IVIS 200 system (PerkinElmer Inc., Waltham, MA). Cross-sectional fluorescence images of Doxorubicin were acquired using an excitation wavelength of 460 nm and an emission wavelength of 560 nm. Near-infrared illumination at the excitation wavelength of 750 nm, and emission wavelength of 850 nm were used to visualize ICG. Fluorescent images in different experimental specimens were acquired using an identical setting of 1-s exposure time (f/stop=2) and displayed using the same scale in each group. Fluorescence intensities were quantified using radiance values in the region of interest and normalized to photons per second per square centimeter per steradian (p/s/cm$^2$/sr), and the area of fluorescence enhancement in each specimen was also calculated after applying a standardized threshold value.

Tumor size of <32 mm$^3$ was considered completely regressed, whereas tumors>2,000 mm$^3$ were considered progressed and animals were euthanized. Based on the survival outcome, survival rate and tumor volume are compared and calculated using statistical software (GraphPad Prism). At necropsy tumor tissues were excised and randomly divided for fluorescent imaging and histologic analysis, or evaluation of the host immune response, which were performed after the creation of single cell suspension from each tissue that is labeled and analyzed using the Helios mass cytometer system (Fluidigm) and the Hyperion imaging module to analyze tissue using antibody panels.

Results

These results demonstrate the feasibility of intratumoral injection of NanoGel formulation comprise 3 wt % NS, 25 wt % IL, 250 mg/mL Dox, and 1 mg/mL of anti-PD-1 antibody into rat N1S1 tumor which was compared to intratumoral injection a control hydrogel containing the same concentrations of NS, IL, Dox, and anti-PD-1 antibody without IL (FIG. 24). US examinations of the rat livers at baseline and at 2 weeks post injection revealed substantially smaller tumor in the NanoGel injected tumor compared to a larger tumor that received control hydrogel treatment (FIGS. 24A-24D). Histologic evaluation of harvested N1S1 tissues at 2 weeks showed extensive necrosis with a near absence of nuclear staining and loss of normal tissue architecture in the tumor injection with NanoGel compared to hypercellularity suggesting active proliferation (FIGS. 24E-24F). Immunostaining for anti PD-1 antibody revealed uniformly distributed ICI antibody throughout the ablated tumor at 2 weeks after NanoGel injection compared to diminished antibody detection in the control tumor (FIGS. 24G-24H). These results suggest that IL can be used for tumor ablation and for enabling ICI distribution and long-term retention in the tumor.

Figure 25A:
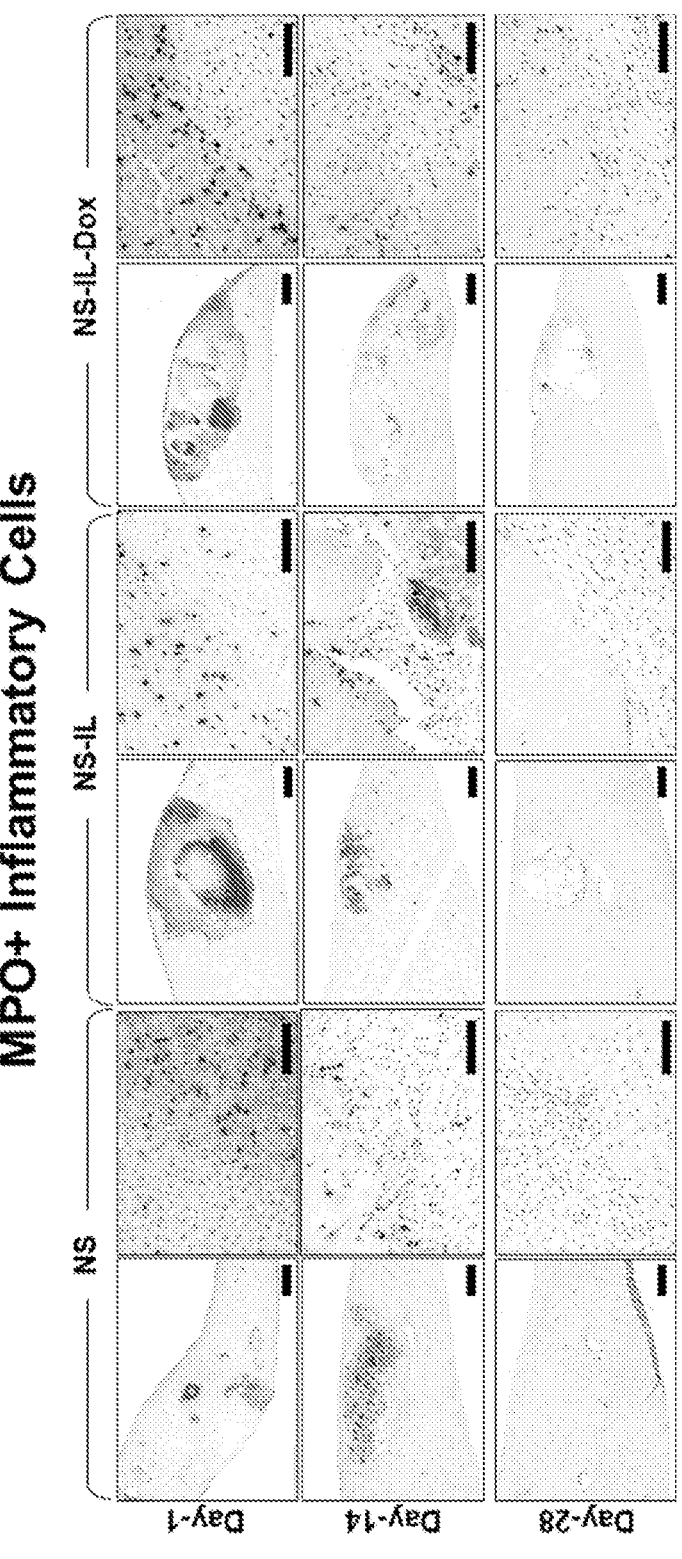
FIGS. 25A-25E. Assessing the Effect of NanoGel injection on inflammatory cell infiltration.
Figure 25B:
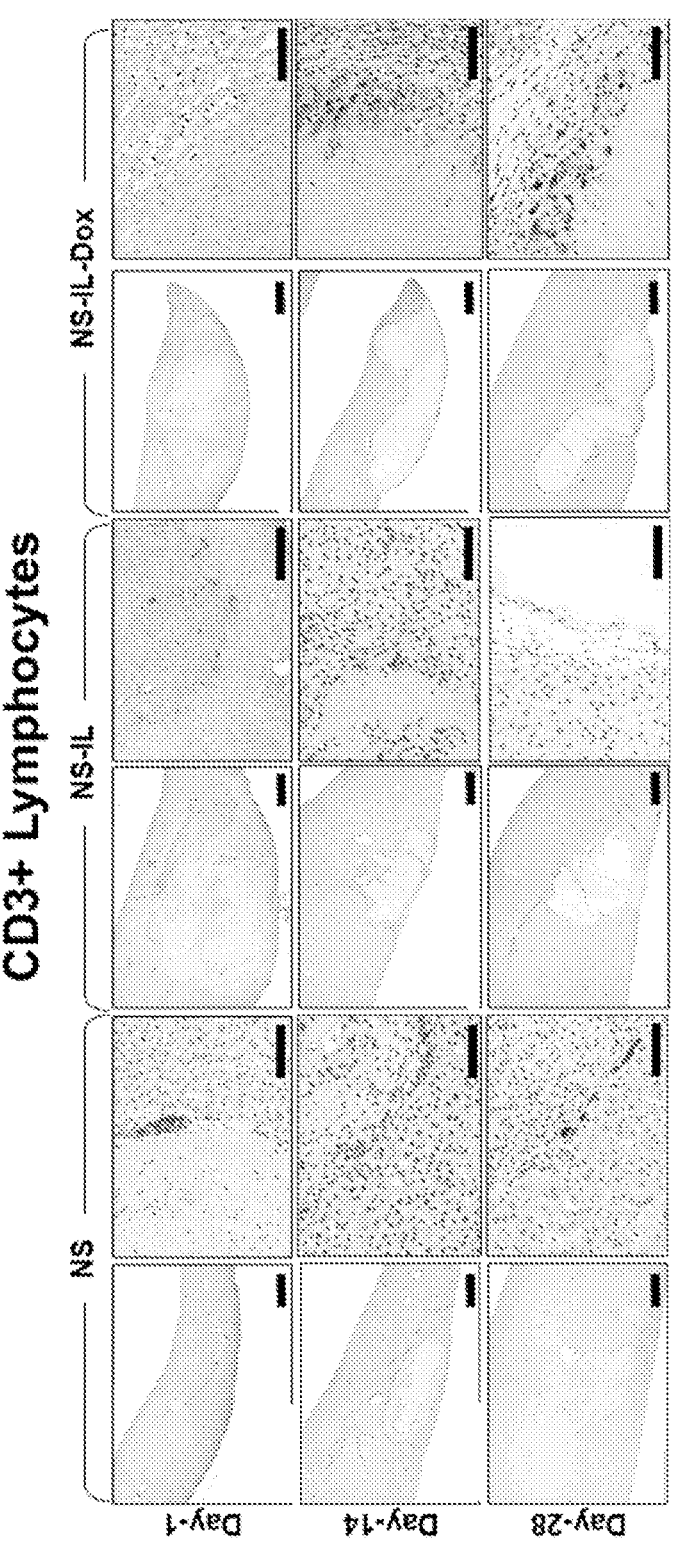
Figure 25C:
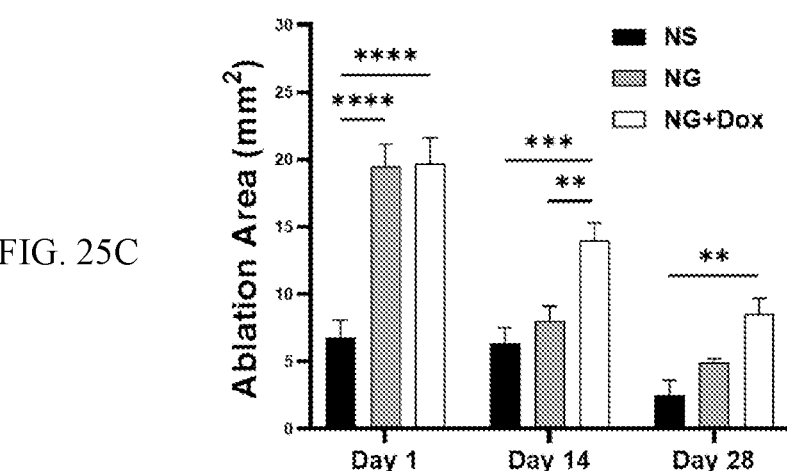
Figure 25D:
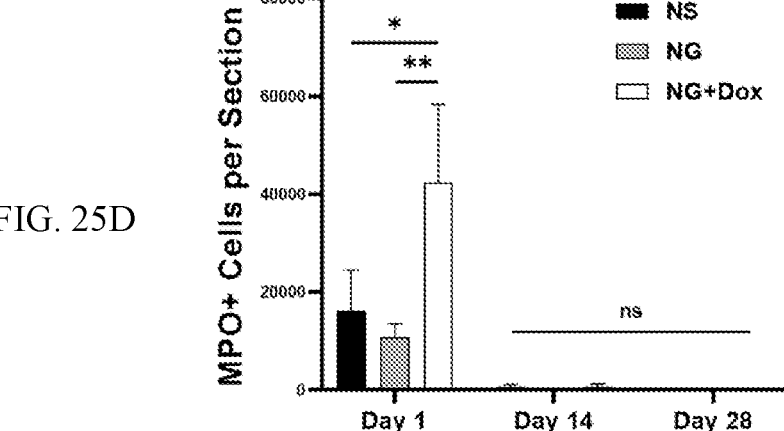
Figure 25E:
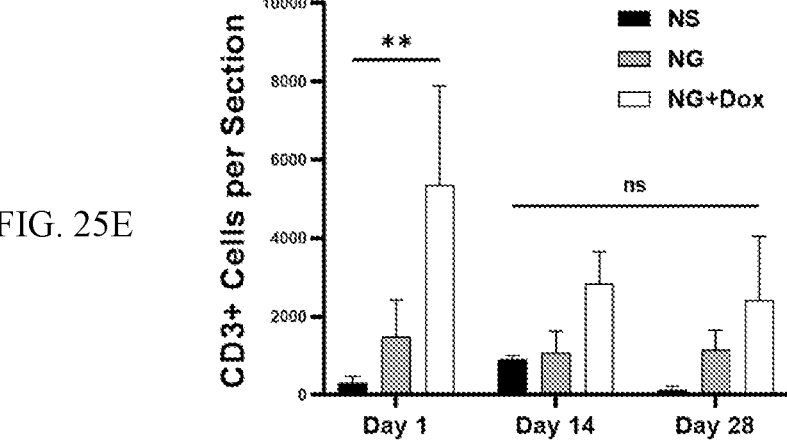

The effect of NanoGel injection on inflammatory cell infiltration was assessed. Histology sections of rat liver tissues were immunostained for myeloperoxidase (MPO) bearing inflammatory cells (FIG. 25A) or CD3+T-lympho- cytes (FIG. 25B) at Day-1, Day-14 or Day-28 following injection with NS hydrogel, NG, or NG+Dox. The area of ablation in the rat liver sections at Day-1, Day-14, and Day-28 after injection with NS, NG, or NG+Dox showed significantly larger ablation area in the NG and the NG+Dox injected sites compared to NS injected site at Day-1, Day-14 (FIG. 25C). A larger ablation area was measured in the NG+Dox injection site at Day-28 compared to NS. Mor- phometric analysis of MPO positive cells illustrated early MPO positive cells recruitment at Day-1 that gradually decreased by Day-14 and Day-28 (FIG. 25D), suggesting a transient acute pro-inflammatory response. Histologic analysis of the number of immunostained CD3+ cells counted within each injection site showed significantly higher CD3+ cells in the NG+Dox site compared to NS or NG injection sites, and showed a higher number of T-lym- phocytes recruitment in the NG+Dox injection site and a higher number of CD3+ cells up to 28 days after injection (FIG. 25E).

Figures 26A, 26B:
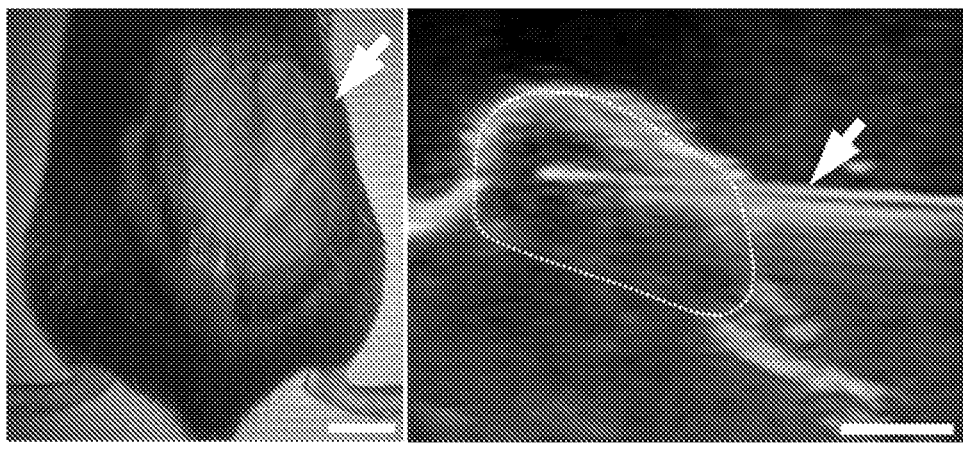
FIGS. 26A-26L. Ultrasound guided intratumoral injection of NanoGel into a mouse model of colorectal cancer.
Figures 26C, 26D:
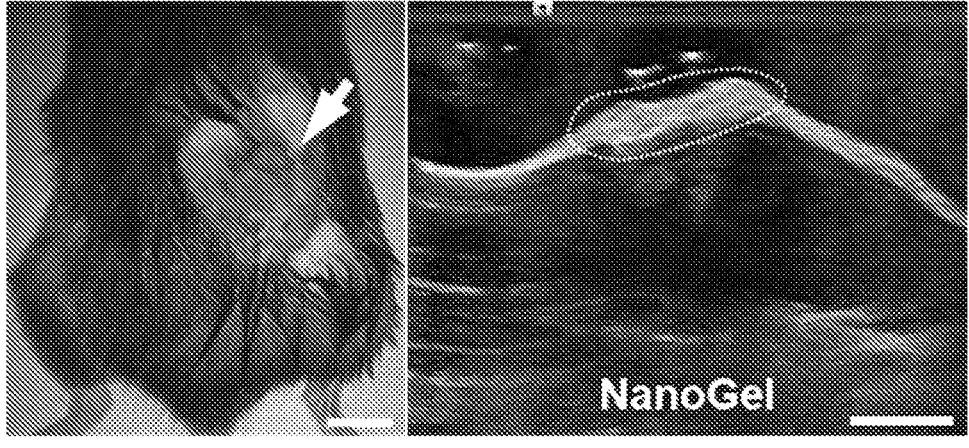
Figures 26E, 26F:
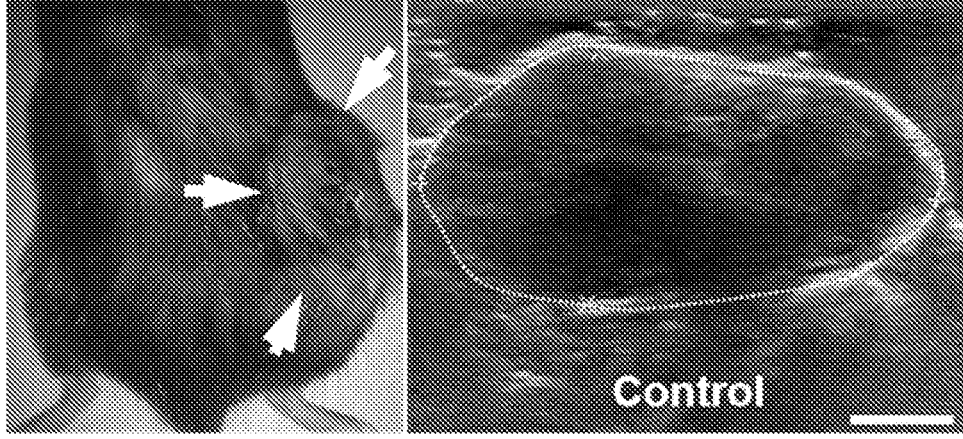
Figures 26G, 26H, 26I:
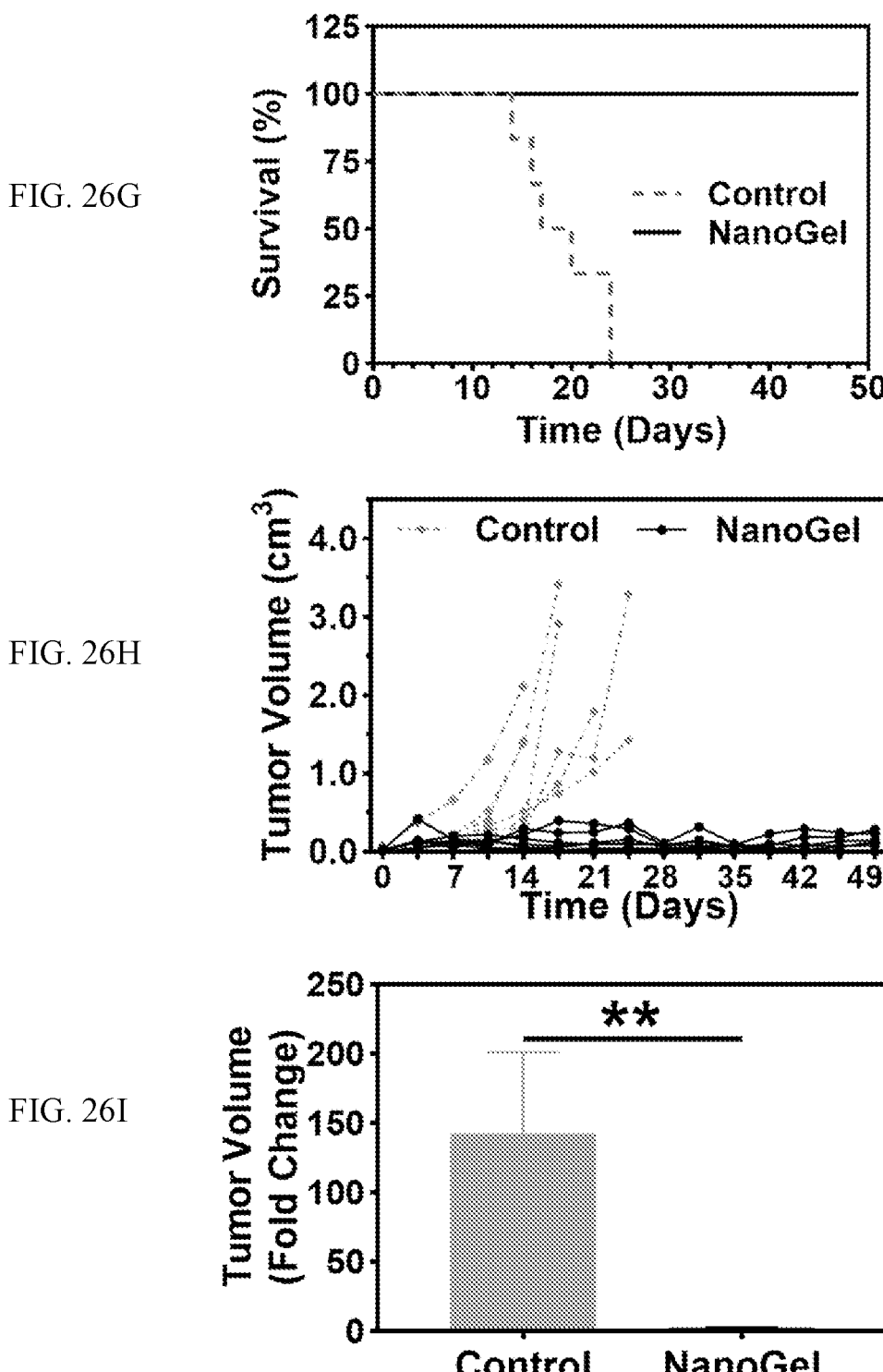
Figures 26J, 26K, 26L:
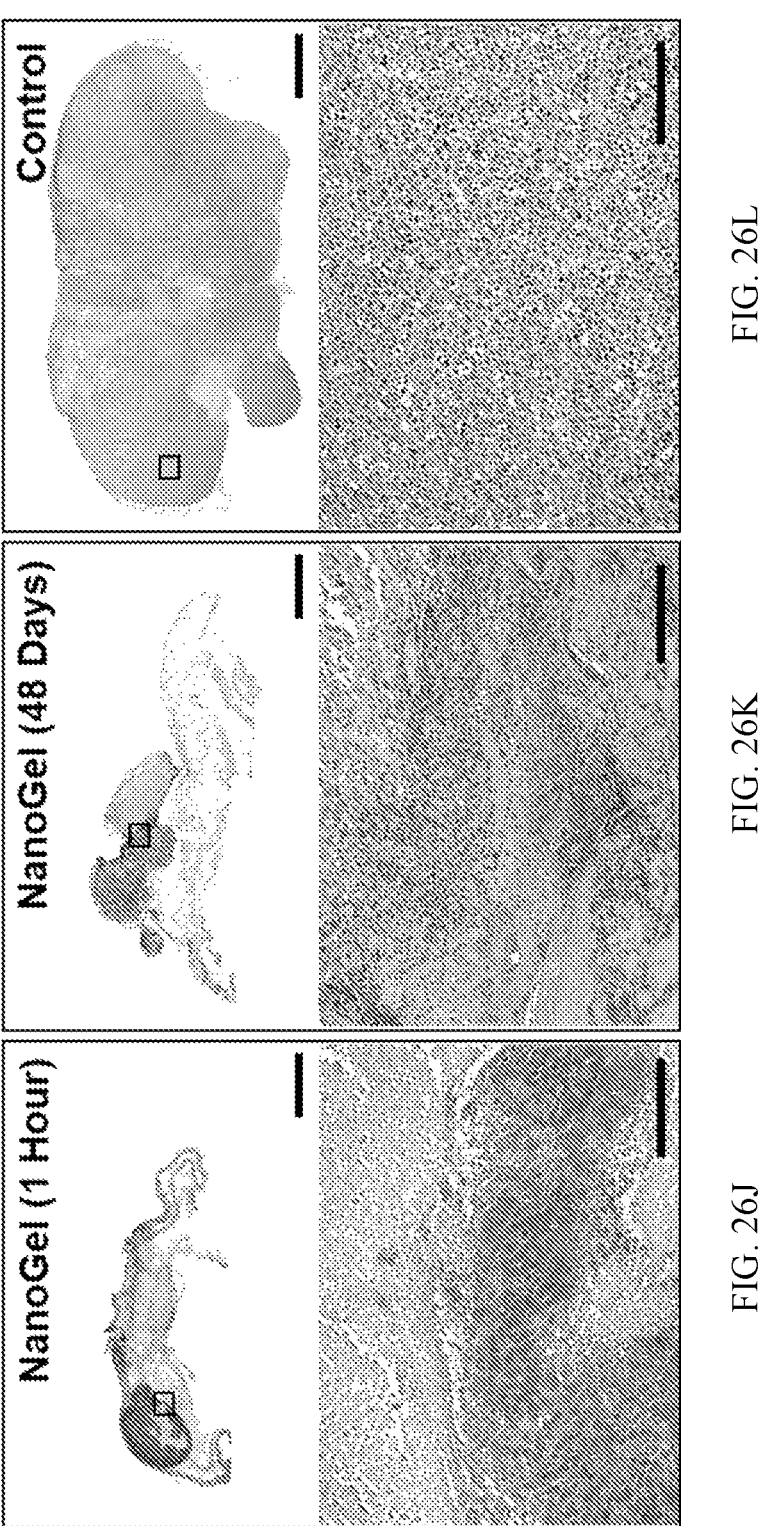
Figure 27G:
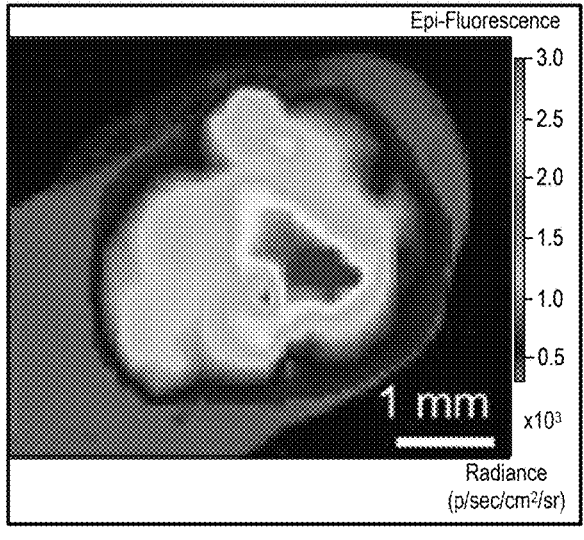
Figure 27H:
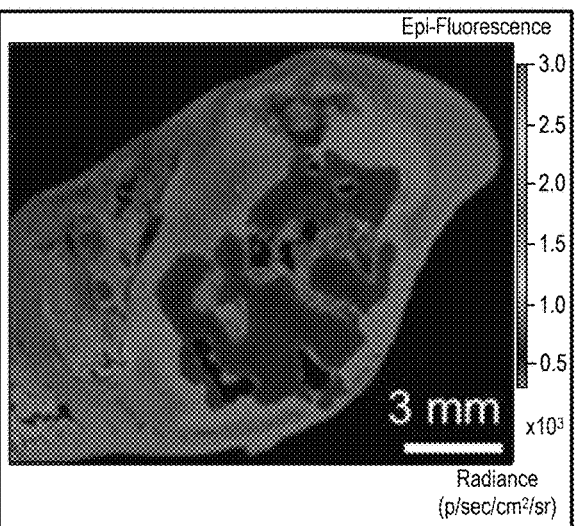
Figure 27I:
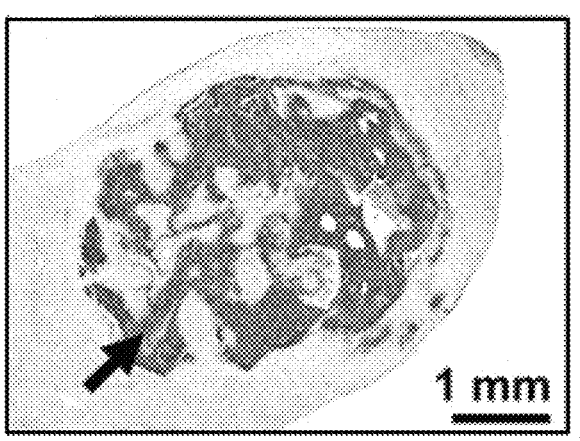
Figure 27J:
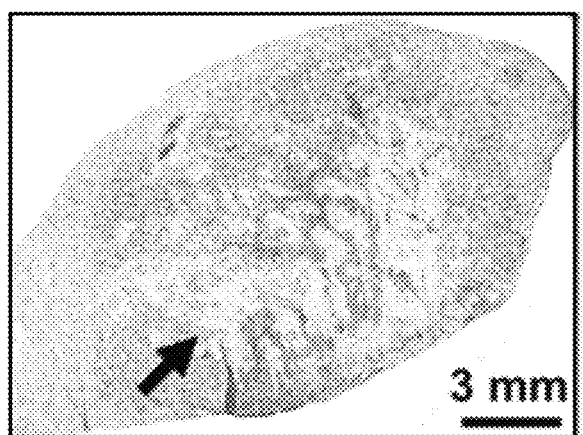
Figure 28A:
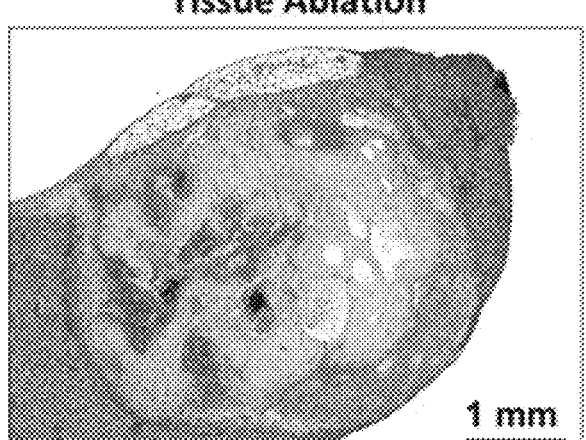
FIGS. 28A-28D. Intratumoral injection of NanoGel leads to effective deliver of anti-cancer immunotherapy and enhances T-lymphocytes recruitment in the N1S1 rat model of hepatocellular carcinoma.
Figure 28B:
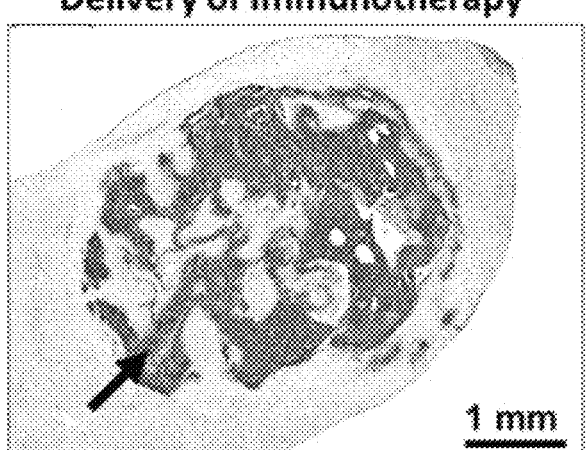
Figure 28C:
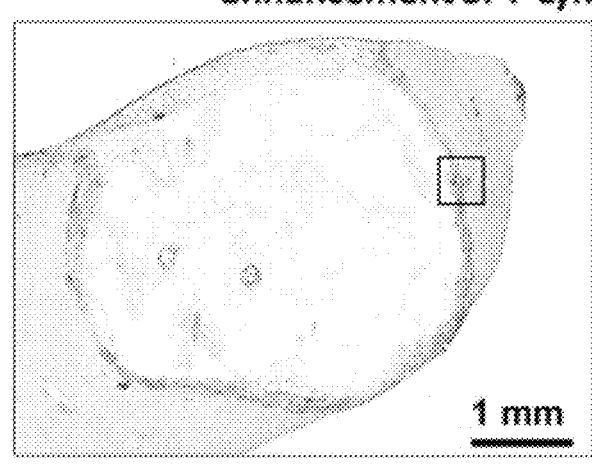
Figure 28D:
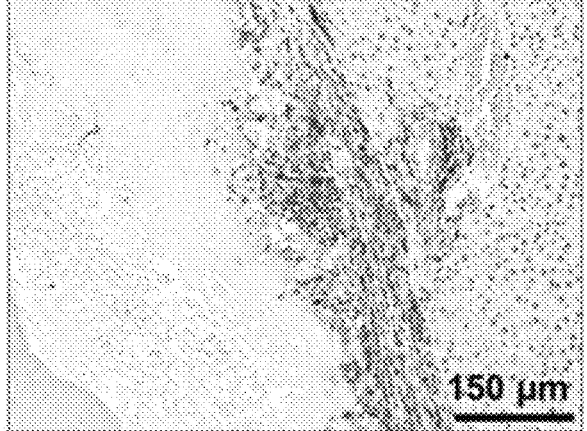

Ultrasound guided intratumoral injection was used to inoculate NanoGel into a mouse model of colorectal cancer. Subcutaneously inoculated MC38 colon adenocarcinoma cells form a tumor in the right lower flank of an immune competent C57BL6 mouse (FIG. 26A). Tumor growth was monitored twice a week by measuring tumor length, width, and depth on ultrasound imaging to calculate tumor volume. Ultrasound was used to image an MC38 tumor obtained during direct intratumoral injection of NanoGel showing high echogenic needle inside a hypoechogenic tumor lesion (FIG. 26B; dotted outline). NanoGel treated tumor at 49 days post Nanogel injection showing complete treatment response leaving a small scar on the mouse skin (FIG. 26C) that was visible on ultrasound (FIG. 26D). Gross view (FIG. 26E) and corresponding ultrasound (FIG. 26F) images of MC38 tumor bearing mouse showing tumor progression that reached cm$^2$ at 21 days post injection with saline. Mouse survival was based on the number of days prior to reaching the maximally permissible tumor volume of 2,000 mm$^3$ or when tumors develop severe ulceration then tumors were considered progressed and individual mice were counted as dead. Survival curves are shown in FIG. 26G. Tumor growth curves of individual tumors assessed by ultrasound showed early tumor progression in the control compared to consis- tently lower tumor volume in the NanoGel injected tumors (FIG. 26H), suggesting a tumor response to treatment. The average change in tumor volume was measured before intratumoral injection of NanoGel or Control and at the end of the survival period in each group (FIG. 26I). Average tumor volume showed significant increase in tumor volume in the control group, suggesting continuous tumor progres- sion compared to no change in tumor volume in the MC38 tumors that received NanoGel injection. Histology sections showed tumor cell ablation at 1 hour after injection with NanoGel (FIG. 26J), and showed reduced lesion size, cell ablation, and evidence of fibrous formation at 48 days after intratumoral injection of NanoGel (FIG. 26K). Histology sections of control, untreated, MC38 tumor showed substan- tially larger tumor area and evidence of actively proliferat- ing tumor cells (FIG. 26L).

Experiments were performed to see whether NG could also help deliver Nivolumab. NG was mixed with Nivo to see if it could also uniformly distribute, retain and deliver the drug throughout the tumor (FIGS. 27A-27J). The results indicated that NG has the capability to ablate tumors and uniformly deliver chemotherapy and immunotherapy throughout the ablation zone.

T-lymphocytes recruitment following intratumoral injec- tion of NanoGel containing an anti-cancer immunotherapy was evaluated (FIGS. 28A-28D). These images demon- strated that high levels of Nivo, tumor cell death, and high levels of CD3 within the ablation zone, suggesting that NanoGel containing an anti-cancer immunotherapy can achieve immunotherapy in solid tumors.

Example 8: Image-Guided Intratumoral Injection of Nanogel

This Example describes using intratumoral NanoGel injection to treat tumors.

Methods

Construction of the Rabbit VX2 Liver Cancer Model

New Zealand White rabbits (Charles River; 2.5-3.0 kg; male; 120 rabbits (males and females) were used for con- struction of the VX2 liver cancer model as described else- where (Albadawi et al., *Sci. Transl. Med.,* 13(580) (2021)). Power analysis showed an effective sample sizes for ANOVA (f=10; average SD=2, means=1-5) at approxi- mately 88% power and an alpha of 0.05 with 8 animals per data point in each group. Briefly, a cryopreserved VX2 slurry was expanded in vivo after intramuscular injection into the rabbit's thigh muscle. The formed muscle tumor was then aseptically isolated and minced and stored in cold DMEM. VX2 liver cancer was induced by implanting freshly a harvested piece of muscle tumor from the donor rabbit inside a deep pocket that was created in the medial left lobule of the recipient rabbit. Tumor size was monitored with US twice a week. Once VX2 tumor size reaches 1 cm$^3$, the rabbits were randomly divided into 3 treatment groups that were subjected to ultrasound-guided intratumoral injec- tion of 1.25 mL NanoGel, NS alone, or ethanol calculated based on the following formula: V=4/3π[r+0.5]$^3$. To mimic the clinical approach, intratumoral injection was performed using a standard 21-gauge access needle. The needle was inserted into the tumor and an aliquot of NanoGel, NS, or ethanol was slowly injected rendering the tumor tissue echogenic while the needle was slowly retracted to the proximal edge of the tumor.

Outcome Analysis

Serial US, as well as endpoint angiography, and CT imaging, histopathology, blood values, and molecular analy- sis data were used to assess, 1) technical success of intra- tumoral injection; 2) ablation efficacy, local tumor progres- sion and vascularity; 3) drug distribution and long-term retention of ICIs and Dox; and 4) survival rate; and were used to 5) rule out potential complications. Evaluation of the tumor burden was serially performed using ultrasound to compare changes in volume. At 1, 3, 7, 21, 28 days after intratumoral injection, subgroups of 10 rabbits had contrast enhanced angiography, and laser speckle scanning prior to euthanasia to assess tumor vascularity. At necropsy, livers bearing VX2 tumors were explanted for gross examination, ex vivo microCT, and fluorescence imaging to measure 3D tumor size following segmentation, Dox fluorescence inten- sity and distribution area. Whole blood samples were collected for CBC and markers of organ function (i.e., LFTs, BUN/Cr). In situ criteria as described in Example 7 used to assess/confirm ablation and drug distribution efficacy were evaluated as follows: 1) Dox chemotherapeutic levels were evaluated using LC-MS/MS; 2) Dox transport distance was measured using confocal fluorescent microscopy in six segmented tumor margins; 3) immunostaining was used to evaluate apoptosis (TUNEL and Caspase-3), proliferation rates (Ki-67 and PCNA), and local immune cell infiltration (lymphocytes, macrophages and granulocytes), in three different areas within the tumor boundaries (tumor core, periphery) as well as in peritumoral areas; and 4) immunostaining was used to assess ICI distribution (PD-1 and PD-L1).

Chemoembolization of the Renal Artery in Swine Using NanoGel

Healthy Yorkshire pigs (S&S Farms, Brentwood, CA) weighing 48 to 55 kg were acclimatized for at least 4 days under standard feeding conditions and suitable temperature. Pigs were anesthetized using intramuscular injection of 5 mg $kg^{-1}$ tiletamine-zolazepam (Telazol, Zoetis), 2 mg $mL^{-1}$ xylazine, and 0.02 mg $kg^{-1}$ glycopyrrolate. Pigs were then placed in a supine position and intubated on an X-ray compatible operating table (Pannomed Aeron, DRE, KY). Following intubation, anesthesia was maintained with inhalation of 1.5-3% isoflurane. During the procedure, electrocardiogram, transcutaneous oxyhemoglobin saturation (SpO2), end-tidal $CO_2$ concentration, inspired oxygen fraction, and core temperature were monitored. Percutaneous access to the carotid artery was obtained using ultrasound guidance (ACUSON 52000, Siemens) and fluoroscopy (OEC Elite C-Arm, GE Healthcare Systems, Chicago, IL). Access needle and wire were exchanged for a 5 French catheter (Cook Medical). Over a GT-glidewire (Terumo Medical), the tip of the catheter was advanced to the renal using contrast-enhanced fluoroscopy (350 mgI mL-1 Omnipaque, GE HealthCare, MA). Angiography of the renal artery was performed under real-time fluoroscopic guidance using an intravenous contrast agent (350 mgI mL-1 Omnipaque, GE HealthCare, MA). Syringes filled with the Nano-Gel, or NS embolic agent were connected directly to the catheter using the Luer-lock and 2 mL NanoGel or NS Hydrogel were delivered to the renal artery through the catheter. The radiopacity of NanoGel or NS hydrogel and vessel patency were assessed using digital subtraction angiography. Repeated angiography was performed to examine embolic efficacy. Pigs were sacrificed at 1-hour post-embolization (non-survival group; n=4), or at 1-week post-embolization (survival group; n=4). Angiograms were repeated prior to euthanasia to confirm embolization. At necropsy, the embolized kidneys were explanted for fluorescence imaging and histology.

Statistical Analysis

Animal survival was analyzed with the Kaplan-Meier method and the log-rank test to compare survival between groups. The statistical analysis with a two-way repeat-measured analysis of variance (ANOVA) was performed to assess tumor response using serial ultrasound. Kruskal-Wallis analysis was used to test total ablation, apoptotic, and necrotic areas among the groups, and Wilcoxon signed rank tests will be used for pairwise testing. Ablation area, volume, and apoptotic vs. necrotic areas/volumes were presented as mean values±SEM, along with median, minimum, and maximum values. Statistical analysis was performed using Prism software. A p value<0.05 will be considered statistically significant.

Results

Figure 29C:
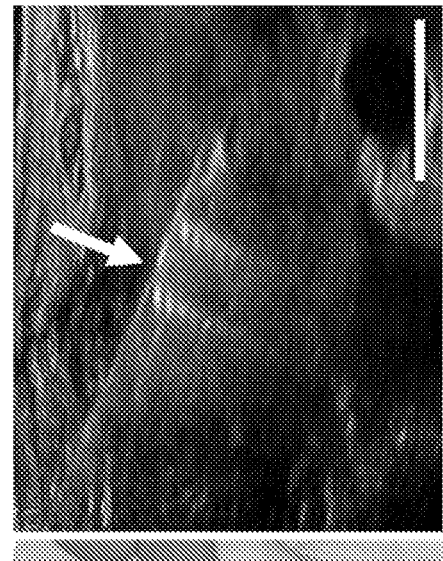
Figure 29B:
Figure 29A:
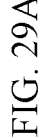
Figure 29D:
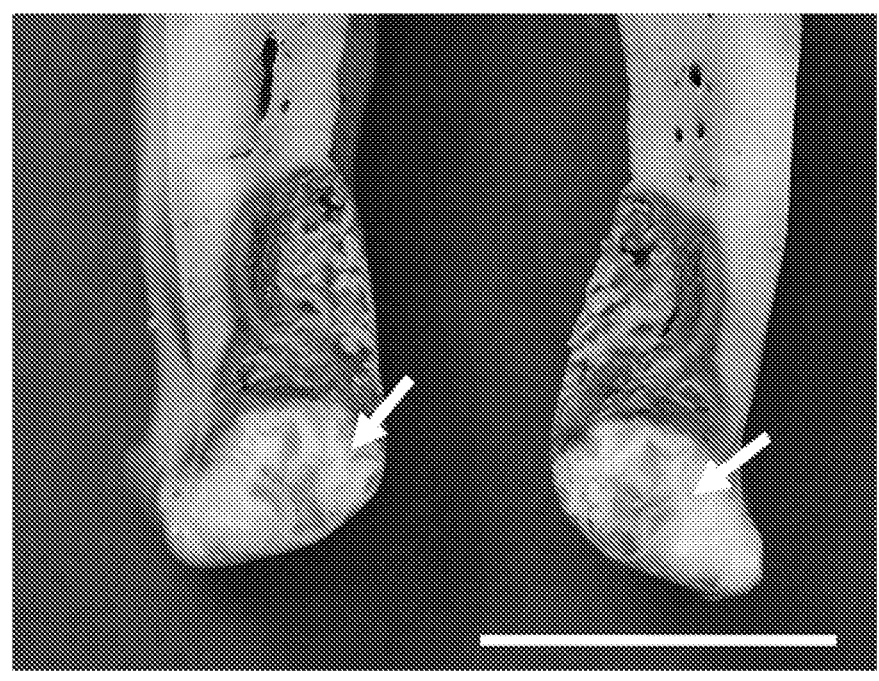
Figure 29E:
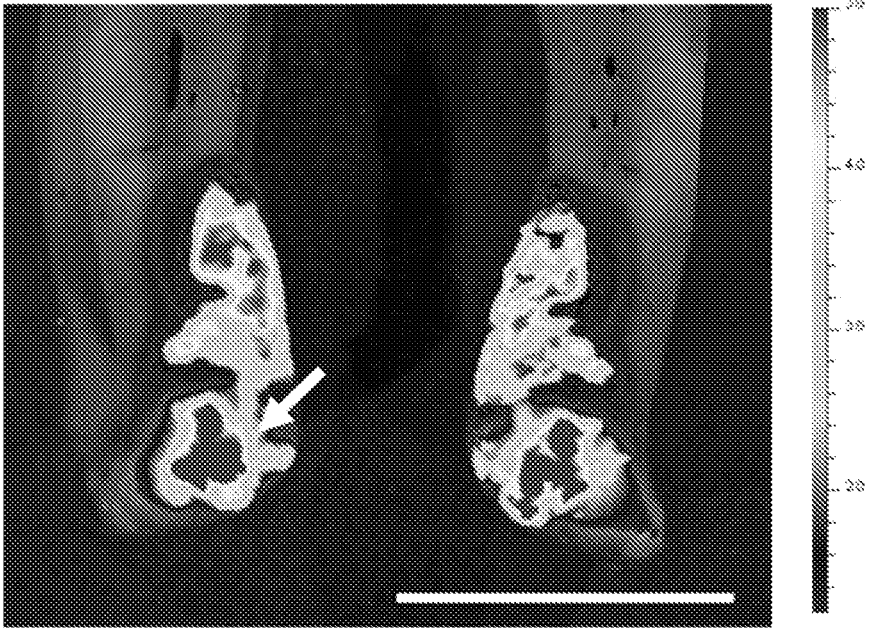
Figure 31:
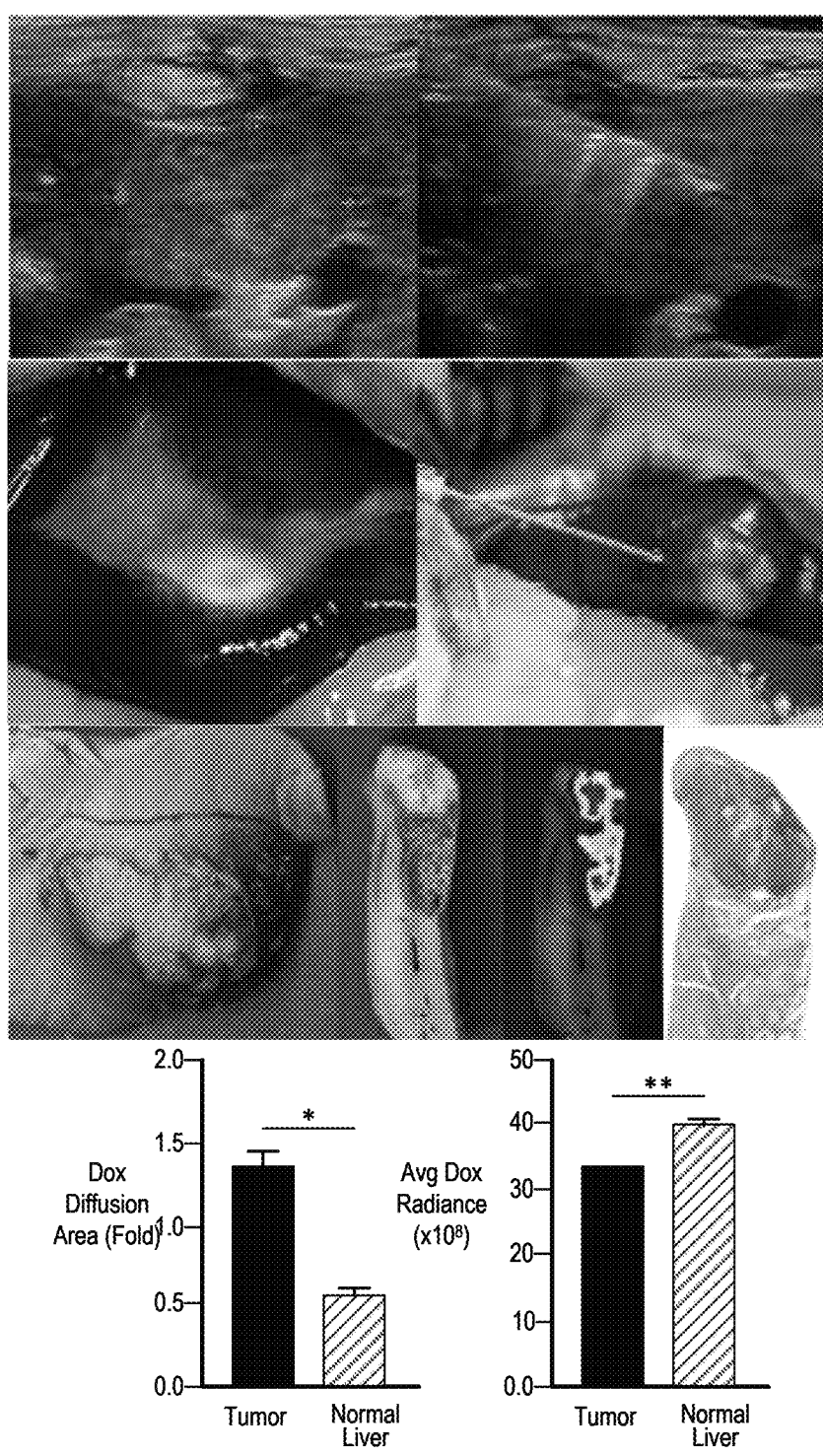
FIG. 31. VX2-tumor treated with NG+Dox+Nivo. Images demonstrate ablation and diffusion of Dox.

Non survival experiments were performed to demonstrate the feasibility of ultrasound-guided intratumoral injection of NanoGel. NanoGel containing 25 wt %-IL mixed with 1.25 mg/mL Dox and 1 mg/mL anti-PD-1 antibody into a VX2 tumor using a 21-gauge standard access needle (FIGS. 29A-29C). At 1 hour after injection, animals were euthanized, and the liver tissues were harvested for fluorescent imaging. Gross examination and fluorescent imaging of the transected VX2 tumor showed uniformly distributed Dox fluorescence encompassing the ablation zone (FIGS. 29D and 29E). H&E histologic sections revealed extensive tumor ablation at 1 hour after injection (FIG. 29F). Furthermore, immunostaining for PD-1 antibody showed extensive areas of positive staining that localized to the area of complete tissue ablation (FIG. 29G). These results suggest that Nano-Gel can induce rapid tumor ablation associated with uniform Dox and ICI distribution throughout the treatment zone.

Figure 32C:
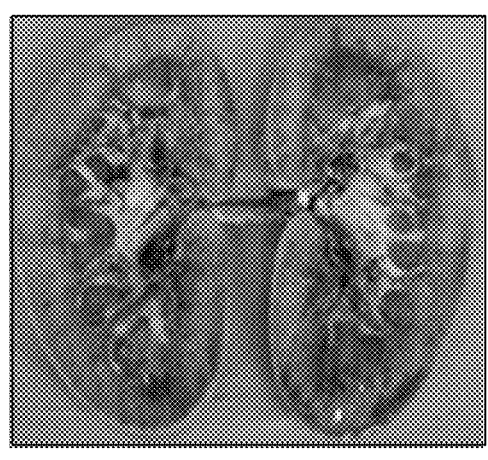
Figure 32D:
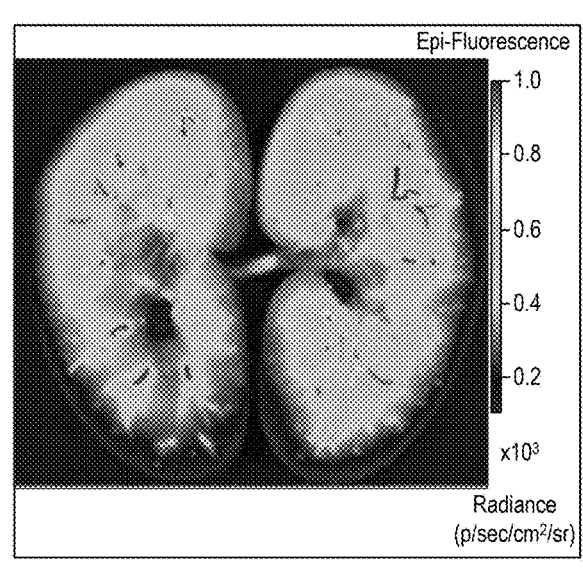
Figure 32E:
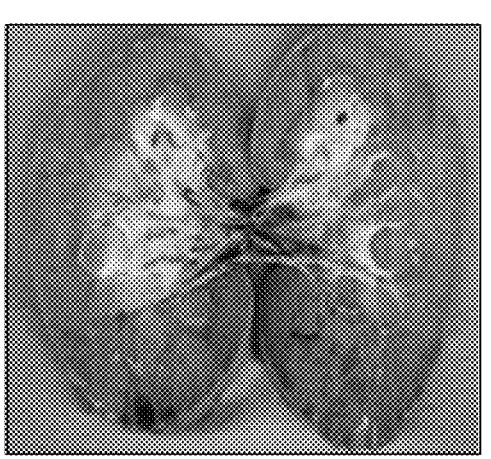
Figure 32F:
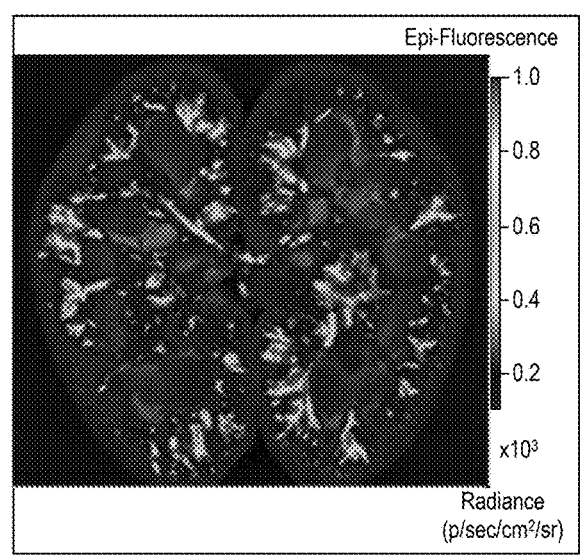
Figure 32G:
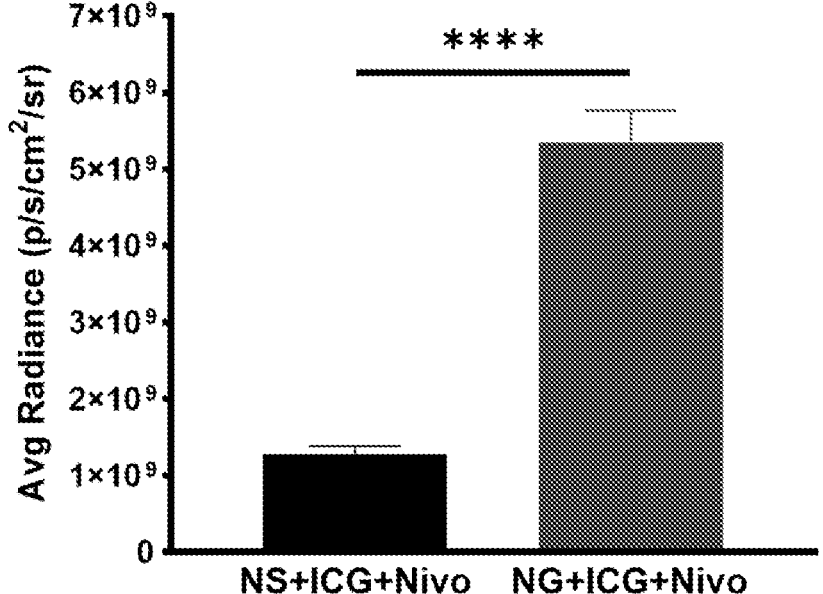

Example 9: NanoGel Formulations for Effective Tissue Ablation and Drug Delivery Whether NG and its components delivered via catheters into the arteries of an organ, (e.g., a kidney), in a large animal model would traverse the vessel wall to achieve parenchymal delivery was explored. There was a complete absence of renal arterial flow to the kidney (white arrow) at 1 hour after embolization as shown in the digitally subtracted angiogram (FIGS. 32A-32C), suggesting successful embolization. Diffuse fluorescence enhancement of ICG throughout the renal cortex and medulla was observed at 1 hour post embolization (FIG. 32D). Diminished fluorescence enhancement of ICG that was limited to the vascular network of the renal was observed one hour post embolization with NS hydrogel containing 0.25 mg/mL ICG, and 20% iohexol (FIGS. 32E and 32F). These results suggest time that NG could be used to achieve vascular embolization and drug delivery such as ICG into the parenchyma of highly vascular organ such as the kidneys. Moreover, this delivery is not transient—ICG was retained indicating sustained delivery of the drug/therapeutic.

Whether a components contained in NG could be delivered across the vessel wall was also examined. H&E-staining of renal artery branches at the renal cortex region showed complete casting of the artery at one hour following renal artery embolization with NanoGel demonstrating the ability of the NG to reach smaller arterial branches (FIG. 33A). Immunohistochemistry detection of nivolumab showed that Nivo was localized inside the renal artery and in the surrounding area suggesting transarterial drug delivery (FIG. 33B). Diminished nuclear staining in the arterial wall was observed suggesting successful transarterial delivery of IL and ablation following embolization with NG (FIGS. 33C and 33D). These results demonstrate the capability of sustained drug delivery across the arterial wall. In addition, these results demonstrate that embolization with NG is capable of ablating all layers of the vessel wall.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for ablating at least a portion of a tissue within a mammal, wherein said method comprises percutaneously injecting a composition comprising an ionic liquid into said tissue within said mammal, wherein said ionic liquid comprises:

(a) a cationic component comprising choline; and (b) an anionic component comprising geranate;

wherein the composition does not comprise any additional therapeutic agent, wherein the choline and geranate are in a ratio of 1:1, wherein said composition is in the form of an aqueous solution or a hydrogel comprising a nanosilicate and is effective to create an ablation zone within said tissue, wherein when the composition is aqueous, the composition comprises 10-90% (w/w) of the choline geranate, and wherein said composition is effective to reduce the number of cells within said ablation zone.

2. The method of claim 1, wherein said mammal is a human.

3. The method of claim 1, wherein said tissue is selected from the group consisting of fat tissue, cardiac tissue, connective tissue, bone tissue, synovial tissue, abscess tissue, and cysts.

4. The method of claim 3, wherein said percutaneously injecting step comprises a guided injection.

5. The method of claim 4, wherein said composition comprising an ionic liquid further comprises a contrast agent.

6. The method of claim 5, wherein said contrast agent is selected from the group consisting of indocyanine green, a radiodense contrast agent, iohexol, tantalum nanoparticles, tantalum microparticles, gold nanoparticles, gadolinium, indium[111], and microbubbles.

7. The method of claim 1, wherein said ablation zone is from about 0.1 cm to about 4 cm.

8. A method for treating a mammal having cancer, wherein said method comprises percutaneously injecting a composition comprising an ionic liquid into a tumor tissue within said mammal, wherein said ionic liquid comprises:

(a) a cationic component comprising choline; and (b) an anionic component comprising geranate;

wherein the composition does not comprise any additional therapeutic agent, wherein the choline and geranate are in a ratio of 1:1, wherein said composition is in the form of an aqueous solution or a hydrogel comprising a nanosilicate and is effective to create an ablation zone within said tumor tissue, wherein when the composition is aqueous, the composition comprises 10-90% (w/w) of the choline geranate, and wherein said composition is effective to reduce the number of cancer cells within said ablation zone.

9. The method of claim 8, wherein said mammal is a human.

10. The method of claim 8, wherein said cancer is selected from the group consisting of a liver cancer, a bile duct cancer, a pancreatic cancer, a colorectal cancer, a renal cancer, an ovarian cancer, a breast cancer, a prostate cancer, a colon cancer, a bladder cancer, a lung cancer, a thyroid cancer, a melanoma, a brain cancer, a stomach cancer, a cervical cancer, a uterine cancer, a skin cancer, a synovial cancer, an appendiceal cancer, and an adrenal cancer.

11. The method of claim 8, wherein said percutaneously injecting step comprises a guided injection, and wherein said composition comprises a contrast agent.

12. The method of claim 11, wherein said contrast agent is selected from the group consisting indocvanine green, a radiodense contrast agent, iohexol, tantalum nanoparticles, tantalum microparticles, gold nanoparticles, gadolinium, indium[111], and microbubbles.

13. The method of claim 11, wherein said ionic liquid choline geranate.

14. The method of claim 11, wherein said method is effective to maintain said ionic liquid within said ablation zone for from about 1 day to about 30 days.

15. The method of claim 8, wherein said method is effective to reduce the size of said cancer by at least 2-fold.

16. The method of claim 8, said method comprising identifying said mammal as having said cancer.

17. The method of claim 1, wherein said composition is in the form of a hydrogel.

18. The method of claim 17, wherein said hydrogel comprises from about 1% (w/v) to about 10% (w/v) of said nanosilicate.

19. The method of claim 18, wherein said nanosilicate comprises a smectite clay.

20. The method of claim 1, wherein said composition is in the form of an aqueous solution.

* * * * *